(12) United States Patent
Dillon et al.

(10) Patent No.: US 7,563,880 B2
(45) Date of Patent: Jul. 21, 2009

(54) COMPOSITIONS AND METHODS FOR THE THERAPY AND DIAGNOSIS OF BREAST CANCER

(75) Inventors: Davin C Dillon, Issaquah, WA (US); Yuqiu Jiang, San Diego, CA (US)

(73) Assignee: Corixa Corporation, Wilmington, DE (US)

( * ) Notice: Subject to any disclaimer, the term of this patent is extended or adjusted under 35 U.S.C. 154(b) by 403 days.

(21) Appl. No.: 10/714,389

(22) Filed: Nov. 13, 2003

(65) Prior Publication Data

US 2004/0101899 A1 May 27, 2004

Related U.S. Application Data

(60) Division of application No. 09/778,320, filed on Feb. 6, 2001, now abandoned, which is a continuation-in-part of application No. 09/571,025, filed on May 15, 2000, now abandoned, which is a continuation-in-part of application No. 09/545,068, filed on Apr. 7, 2000, now abandoned, which is a continuation-in-part of application No. 09/523,586, filed on Mar. 10, 2000, now abandoned, which is a continuation-in-part of application No. 09/510,662, filed on Feb. 22, 2000, now abandoned, which is a continuation-in-part of application No. 09/451,651, filed on Nov. 30, 1999, now Pat. No. 6,489,101.

(51) Int. Cl.
C07H 21/02 (2006.01)
C07H 21/04 (2006.01)
C12Q 1/68 (2006.01)
C12P 19/34 (2006.01)

(52) U.S. Cl. .................. 536/23.1; 536/24.3; 435/6; 435/91.2

(58) Field of Classification Search ............... None
See application file for complete search history.

(56) References Cited

U.S. PATENT DOCUMENTS

| | | | |
|---|---|---|---|
| 4,962,187 A | 10/1990 | Pant | 530/350 |
| 5,215,926 A | 6/1993 | Etchells, III et al. | 436/501 |
| 5,240,856 A | 8/1993 | Goffe et al. | 435/299 |
| 5,478,556 A | 12/1995 | Elliott et al. | 424/852 |
| 5,654,172 A | 8/1997 | Li et al. | 435/69.1 |
| 5,668,267 A | 9/1997 | Watson et al. | 536/23.5 |
| 5,843,435 A | 12/1998 | Slavin | 424/93.71 |
| 5,855,889 A | 1/1999 | Watson et al. | 424/185.1 |
| 5,861,381 A | 1/1999 | Chambon et al. | 514/44 |
| 5,891,857 A | 4/1999 | Holt et al. | 514/44 |
| 5,922,836 A | 7/1999 | Watson et al. | 530/300 |
| 5,968,754 A | 10/1999 | Watson et al. | 435/7.23 |
| 5,981,731 A | 11/1999 | Monia | 536/24.5 |
| 5,986,170 A | 11/1999 | Subjeck | 800/2 |
| 6,004,756 A | 12/1999 | Watson et al. | 435/6 |
| 6,153,386 A | 11/2000 | Lalouel et al. | 435/6 |
| 6,365,348 B1 | 4/2002 | Reed et al. | |
| 6,379,951 B1 | 4/2002 | Reed et al. | 435/325 |
| 6,387,697 B1 | 5/2002 | Yuqiu et al. | 435/325 |
| 6,528,054 B1 | 3/2003 | Jiang et al. | 424/130.1 |
| 6,579,973 B1 | 6/2003 | Yuqiu et al. | 530/806 |
| 6,586,572 B2 | 7/2003 | Jiang et al. | 530/350 |
| 6,590,076 B1 | 7/2003 | Yuqiu et al. | 530/350 |
| 6,844,325 B2 | 1/2005 | Jiang et al. | 514/44 |
| 2002/0009738 A1 | 1/2002 | Houghton et al. | 435/6 |
| 2002/0150581 A1 | 10/2002 | Jiang et al. | 424/155.1 |
| 2003/0022334 A1 | 1/2003 | Glucksmann | 435/189 |
| 2003/0027988 A1 | 2/2003 | Baker et al. | 530/350 |

FOREIGN PATENT DOCUMENTS

| | | |
|---|---|---|
| WO | WO 89/06280 | 7/1989 |
| WO | WO 91/16116 | 10/1991 |
| WO | WO 91/16629 | 10/1991 |
| WO | WO 92/07243 | 4/1992 |
| WO | 95/19783 | 7/1995 |
| WO | WO 96/06862 | 3/1996 |
| WO | WO 96/29430 | 9/1996 |
| WO | WO 97/02280 | 1/1997 |
| WO | WO 97/22349 | 6/1997 |
| WO | WO 97/25426 | 7/1997 |
| WO | WO 97/25431 | 7/1997 |
| WO | WO 98/21331 | 5/1998 |
| WO | WO 98/33915 | 8/1998 |
| WO | WO 98/45328 | 10/1998 |
| WO | WO 98/54963 | 12/1998 |
| WO | WO 99/00408 | 1/1999 |

(Continued)

OTHER PUBLICATIONS

GenBank Accession No. AA193450, May 19, 1997.*
Stratagene Catalog, p. 39 (1988).*
Burger et al., "Breast Cancer Genome Anatomy: Correlation of Morphological Changes in Breast Carcinomas with Expression of the Novel Gene Product Di12," *Oncogene* 16:327-333, 1998.
Diatchenko et al., "Suppression subtractive Hybridization: A Method for Generating Differentially Regulated or Tissue-Specific cDNA Probes and Libraries," *PNAS* 93:6025-6030, Jun. 1996.
Hara et al., "Characterization of cell phenotype by a novel cDNA library subtraction system: expression of CD8α in a mast cell-derived interleukin-4-dependent cell line," *Blood* 84(1):189-199, Jul. 1, 1994.

(Continued)

*Primary Examiner*—Teresa E Strzelecka
(74) *Attorney, Agent, or Firm*—Seed IP Law Group PLLC

(57) ABSTRACT

Compositions and methods for the therapy and diagnosis of cancer, particularly breast cancer, are disclosed. Illustrative compositions comprise one or more breast tumor polypeptides, immunogenic portions thereof, polynucleotides that encode such polypeptides, antigen presenting cell that expresses such polypeptides, and T cells that are specific for cells expressing such polypeptides. The disclosed compositions are useful, for example, in the diagnosis, prevention and/or treatment of diseases, particularly breast cancer.

5 Claims, No Drawings

FOREIGN PATENT DOCUMENTS

| WO | WO 99/09155 | 2/1999 |
|----|----|----|
| WO | WO 99/14230 | 3/1999 |
| WO | WO 99/25877 | 5/1999 |
| WO | WO 99/37775 | 7/1999 |
| WO | WO 99/33869 | 9/1999 |
| WO | WO 00/08210 | 2/2000 |
| WO | WO 00/12758 | 3/2000 |
| WO | WO 00/36107 | 6/2000 |
| WO | WO 00/37643 | 6/2000 |
| WO | WO 00/43420 | 7/2000 |
| WO | WO 00/60076 | 10/2000 |
| WO | WO 00/61756 | 10/2000 |
| WO | 00/078960 | 12/2000 |
| WO | WO 00/73801 | 12/2000 |
| WO | WO 01/37779 | 5/2001 |
| WO | WO 01/40269 | 6/2001 |
| WO | WO 01/47959 | 7/2001 |
| WO | WO 01/51628 | 7/2001 |
| WO | WO 01/51638 | 7/2001 |
| WO | WO 01/57270 | 8/2001 |
| WO | WO 01/79286 | 10/2001 |
| WO | WO 01/90334 | 11/2001 |
| WO | WO 01/93983 | 12/2001 |
| WO | WO 02/059377 | 8/2002 |

OTHER PUBLICATIONS

Hedblom and Kirkness, "A novel class of GABA$_A$ receptor subunit in tissues of the reproductive system," *The Journal of Biological Chemistry* 272(24):15346-15350, Jun. 13, 1997.

Lee et al., "Positive Selection of Candidate Tumor-Suppressor Genes by Subtractive Hybridization," *PNAS* 88:2825-2829, Apr. 1991.

Porter-Jordan and Lippman, "Overview of the biologic markers of breast cancer," *Breast Cancer* 8(1):73-100, Feb. 1994.

Schlom et al., "Strategies for the development of recombinant vaccines for the immunotherapy of breast cancer," *Breast Cancer Research and Treatment* 38(1):27-39, 1996.

GenBank Database, Accession No. AF100759, Jul. 8, 1999.
GenBank Database, Accession No. AJ131016, Feb. 4, 2000.
GenBank Database, Accession No. AL135960, Feb. 3, 2000.
GenBank Database, Accession No. AL356793, Nov. 29, 2001.
Genseq Database (Thomason Derwent), Accession No. AAL08649, Dec. 7, 2001.
Genseq Database (Thomason Derwent), Accession No. AAL18673, Dec. 7, 2001.
Genseq Database (Thomason Derwent), Accession No. AAL23934, Dec. 7, 2001.
Genseq Database (Thomason Derwent), Accession No. AAL24582, Dec. 7, 2001.
Genseq Database (Thomason Derwent), Accession No. AAW92654, Apr. 30, 1999.

Xu, J. et al., "Identification of differentially expressed genes in human breast tumor using subtraction and microarray," *Proceedings of the American Association for Cancer Research 40*: 319, Abstract #2115, Mar. 1999.

GenBank Database, Accession No. AI820775, Jul. 9, 1999.
GenBank Database, Accession No. BI772715, Sep. 24, 2001.

Jiang, Y. et al., "Discovery of differentially expressed genes in human breast cancer using subtracted cDNA libraries and cDNA microarrays," *Oncogene* 21:2270-2282, 2002.

Feng et al., "Molecular Biomarkers for Cancer Detection in Blood and Bodily Fluids," Critical Reviews in Clinical Laboratory Sciences 43(5-6):497-560, 2006.

Mitas et al., "Quantitative Real-Time RT-PCR Detection of Breast Cancer Micrometastasis Using Multigene Marker Panel," International Journal of Cancer 93:162-171, 2001.

Srinivas et al., "Trends in Biomarker Research for Cancer Detection," The Lancet Oncology 2:698-704, Nov. 2001.

GenBank Accession No. AA003705, Jul. 22 1996.
GenBank Accession No. AY262056, Apr. 9, 2004.
GenBank Accession No. AAE14447, Sep. 29, 1999.
GenBank Accession No. H21976, Jul. 6, 1995.
GenBank Accession No. H21977, Jul. 6, 1995.
GenBank Accession No. H25577, Jul. 10, 1995.
GenBank Accession No. H25624, Jul. 10, 1995.

Rieger, M.A. et al., "Identification of a Novel Mammary-Restricted Cytochrome P450, CYP4Z1, with Overexpression in Breast Carcinoma," Cancer Research 64:2357-2364, Apr. 1, 2004.

Ji, H. et al., "Identification of a Breast Cancer-specific Gene, *BCSG1*, by Direct Differential cDNA Sequencing," *Cancer Research* 57:759-764, Feb. 15, 1997.

Liang, P. et al., "Differential Display and Cloning of Messenger RNAs from Human Breast Cancer vs. Mammary Epithelial Cells," *Cancer Research* 52:6966-6968, Dec. 15, 1992.

Watson, M.A. et al., "Mammaglobin, a Mammary-specific Member of the Uteroglobin Gene Family, Is Overexpressed in Human Breast Cancer," *Cancer Research* 56:860-865, Feb. 15, 1996.

* cited by examiner

COMPOSITIONS AND METHODS FOR THE THERAPY AND DIAGNOSIS OF BREAST CANCER

CROSS REFERENCE TO RELATED APPLICATIONS

This application is a divisional of U.S. patent application Ser. No. 09/778,320 filed Feb. 6, 2001, now abandoned, which is a continuation-in-part of U.S. patent application Ser. No. 09/571,025, filed May 15, 2000, now abandoned, which is a continuation-in-part of U.S. patent application Ser. No. 09/545,068, filed Apr. 7, 2000, now abandoned, which is a continuation-in-part of U.S. patent application Ser. No. 09/523,586, filed Mar. 10, 2000, now abandoned, which is a continuation-in-part of U.S. patent application Ser. No. 09/510,662, filed Feb. 22, 2000, now abandoned, which is a continuation-in-part of U.S. patent application Ser. No. 09/451,651, filed Nov. 30, 1999, now issued as U.S. Pat. No. 6,489,101, which are incorporated by reference in their entireties.

TECHNICAL FIELD OF THE INVENTION

The present invention relates generally to therapy and diagnosis of cancer, such as breast cancer. The invention is more specifically related to polypeptides, comprising at least a portion of a breast tumor protein, and to polynucleotides encoding such polypeptides. Such polypeptides and polynucleotides are useful in pharmaceutical compositions, e.g., vaccines, and other compositions for the diagnosis and treatment of breast cancer.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are now one in eight. relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73-100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for therapy and diagnosis of breast cancer. The present invention fulfills these needs and further provides other related advantages.

SUMMARY OF THE INVENTION

In one aspect, the present invention provides polynucleotide compositions comprising a sequence selected from the group consisting of:

(a) sequences provided in SEQ ID NO: 1-38, 42-204, 205, 207, 210-290, 293, 296, 297 and 300;

(b) complements of the sequences provided in SEQ ID NO: 1-38, 42-204, 205, 207, 210-290, 293, 296, 297 and 300;

(c) sequences consisting of at least 20 contiguous residues of a sequence provided in SEQ ID NO: 1-38, 42-204, 205, 207, 210-290, 293, 296, 297 and 300;

(d) sequences that hybridize to a sequence provided in SEQ ID NO: 1-38, 42-204, 205, 207, 210-290, 293, 296, 297 and 300, under moderately stringent conditions;

(e) sequences having at least 75% identity to a sequence of SEQ ID NO: 1-38, 42-204, 205, 207, 210-290, 293, 296, 297 and 300;

(f) sequences having at least 90% identity to a sequence of SEQ ID NO: 1-38, 42-204, 205, 207, 210-290, 293, 296, 297 and 300; and (g) degenerate variants of a sequence provided in SEQ ID NO: 1-38, 42-204, 205, 207, 210-290, 293, 296, 297 and 300.

In one preferred embodiment, the polynucleotide compositions of the invention are expressed in at least about 20%, more preferably in at least about 30%, and most preferably in at least about 50% of breast tumors samples tested, at a level that is at least about 2-fold, preferably at least about 5-fold, and most preferably at least about 10-fold higher than that for normal tissues.

The present invention, in another aspect, provides polypeptide compositions comprising an amino acid sequence that is encoded by a polynucleotide sequence described above.

The present invention further provides polypeptide compositions comprising an amino acid sequence selected from the group consisting of sequences recited in SEQ ID NO: 39-41, 206, 208, 209, 294, 295 and 301.

In certain preferred embodiments, the polypeptides and/or polynucleotides of the present invention are immunogenic, i.e., they are capable of eliciting an immune response, particularly a humoral and/or cellular immune response, as further described herein.

The present invention further provides fragments, variants and/or derivatives of the disclosed polypeptide and/or polynucleotide sequences, wherein the fragments, variants and/or derivatives preferably have a level of immunogenic activity of at least about 50%, preferably at least about 70% and more preferably at least about 90% of the level of immunogenic activity of a polypeptide sequence set forth in SEQ ID NOs: 39-41, 206, 208, 209, 294, 295 and 301 or a polypeptide sequence encoded by a polynucleotide sequence set forth in SEQ ID NOs: 1-38, 42-204, 205, 207, 210-290, 293, 296, 297 and 300.

The present invention further provides polynucleotides that encode a polypeptide described above, expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, the pharmaceutical compositions, e.g., vaccine compositions, are provided for prophylactic or therapeutic applications. Such compositions generally comprise an immunogenic polypeptide or polynucleotide of the invention and an immunostimulant, such as an adjuvant.

The present invention further provides pharmaceutical compositions that comprise: (a) an antibody or antigen-binding fragment thereof that specifically binds to a polypeptide of the present invention, or a fragment thereof; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Illustrative antigen presenting cells include dendritic cells, macrophages, monocytes, fibroblasts and B cells.

Within related aspects, pharmaceutical compositions are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier and/or an immunostimulant. The fusions proteins may comprise multiple immunogenic polypeptides or portions/variants thereof, as described herein, and may further comprise one or more polypeptide segments for facilitating the expression, purification and/or immunogenicity of the polypeptide(s).

Within further aspects, the present invention provides methods for stimulating an immune response in a patient, preferably a T cell response in a human patient, comprising administering a pharmaceutical composition described herein. The patient may be afflicted with breast cancer, in which case the methods provide treatment for the disease, or patient considered at risk for such a disease may be treated prophylactically.

Within further aspects, the present invention provides methods for inhibiting the development of a cancer in a patient, comprising administering to a patient a pharmaceutical composition as recited above. The patient may be afflicted with breast cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a polypeptide of the present invention, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a polypeptide of the present invention, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of polypeptide disclosed herein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer, preferably a breast cancer, in a patient comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a polypeptide of the present invention; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a polypeptide of the present invention; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description. All references disclosed herein are hereby incorporated by reference in their entirety as if each was incorporated individually.

Sequence Identifiers

SEQ ID NO: 1 is the determined cDNA sequence for clone 26915.

SEQ ID NO: 2 is the determined cDNA sequence for clone 26914.

SEQ ID NO: 3 is the determined cDNA sequence for clone 26673.

SEQ ID NO: 4 is the determined cDNA sequence for clone 26672.

SEQ ID NO: 5 is the determined cDNA sequence for clone 26671.

SEQ ID NO: 6 is the determined cDNA sequence for clone 26670.

SEQ ID NO: 7 is the determined cDNA sequence for clone 26669.

SEQ ID NO: 8 is a first determined cDNA sequence for clone 26668.

SEQ ID NO: 9 is a second determined cDNA sequence for clone 26668.

SEQ ID NO: 10 is the determined cDNA sequence for clone 26667.

SEQ ID NO: 11 is the determined cDNA sequence for clone 26666.

SEQ ID NO: 12 is the determined cDNA sequence for clone 26665.

SEQ ID NO: 13 is the determined cDNA sequence for clone 26664.

SEQ ID NO: 14 is the determined cDNA sequence for clone 26662.

SEQ ID NO: 15 is the determined cDNA sequence for clone 26661.

SEQ ID NO: 16 is the determined cDNA sequence for clone 26660.

SEQ ID NO: 17 is the determined cDNA sequence for clone 26603.

SEQ ID NO: 18 is the determined cDNA sequence for clone 26601.

SEQ ID NO: 19 is the determined cDNA sequence for clone 26600.

SEQ ID NO: 20 is the determined cDNA sequence for clone 26587.

SEQ ID NO: 21 is the determined cDNA sequence for clone 26586.

SEQ ID NO: 22 is the determined cDNA sequence for clone 26584.

SEQ ID NO: 23 is the determined cDNA sequence for clone 26583.

SEQ ID NO: 24 is the determined cDNA sequence for clone 26580.

SEQ ID NO: 25 is the determined cDNA sequence for clone 26579.

SEQ ID NO: 26 is the determined cDNA sequence for clone 26577.

SEQ ID NO: 27 is the determined cDNA sequence for clone 26575.

SEQ ID NO: 28 is the determined cDNA sequence for clone 26574.

SEQ ID NO: 29 is the determined cDNA sequence for clone 26573.

SEQ ID NO: 30 is the determined cDNA sequence for clone 25612.

SEQ ID NO: 31 is the determined cDNA sequence for clone 22295.

SEQ ID NO: 32 is the determined cDNA sequence for clone 22301.

SEQ ID NO: 33 is the determined cDNA sequence for clone 22298.

SEQ ID NO: 34 is the determined cDNA sequence for clone 22297.

SEQ ID NO: 35 is the determined cDNA sequence for clone 22303.

SEQ ID NO: 36 is the determined cDNA sequence for a first $GABA_A$ receptor clone.

SEQ ID NO: 37 is the determined cDNA sequence for a second $GABA_A$ receptor clone.

SEQ ID NO: 38 is the determined cDNA sequence for a third $GABA_A$ receptor clone.

SEQ ID NO: 39 is the amino acid sequence encoded by SEQ ID NO: 36.

SEQ ID NO: 40 is the amino acid sequence encoded by SEQ ID NO: 37.

SEQ ID NO: 41 is the amino acid sequence encoded by SEQ ID NO: 38.

SEQ ID NO: 42 is the determined cDNA sequence for contig 1.

SEQ ID NO: 43 is the determined cDNA sequence for contig 2.

SEQ ID NO: 44 is the determined cDNA sequence for contig 3.

SEQ ID NO: 45 is the determined cDNA sequence for contig 4.

SEQ ID NO: 46 is the determined cDNA sequence for contig 5.

SEQ ID NO: 47 is the determined cDNA sequence for contig 6.

SEQ ID NO: 48 is the determined cDNA sequence for contig 7.

SEQ ID NO: 49 is the determined cDNA sequence for contig 8.

SEQ ID NO: 50 is the determined cDNA sequence for contig 9.

SEQ ID NO: 51 is the determined cDNA sequence for contig 10.

SEQ ID NO: 52 is the determined cDNA sequence for contig 11.

SEQ ID NO: 53 is the determined cDNA sequence for contig 12.

SEQ ID NO: 54 is the determined cDNA sequence for contig 13.

SEQ ID NO: 55 is the determined cDNA sequence for contig 14.

SEQ ID NO: 56 is the determined cDNA sequence for contig 15.

SEQ ID NO: 57 is the determined cDNA sequence for contig 16.

SEQ ID NO: 58 is the determined cDNA sequence for contig 17.

SEQ ID NO: 59 is the determined cDNA sequence for contig 18.

SEQ ID NO: 60 is the determined cDNA sequence for contig 19.

SEQ ID NO: 61 is the determined cDNA sequence for contig 20.

SEQ ID NO: 62 is the determined cDNA sequence for contig 21.

SEQ ID NO: 63 is the determined cDNA sequence for contig 22.

SEQ ID NO: 64 is the determined cDNA sequence for contig 23.

SEQ ID NO: 65 is the determined cDNA sequence for contig 24.
SEQ ID NO: 66 is the determined cDNA sequence for contig 25.
SEQ ID NO: 67 is the determined cDNA sequence for contig 26.
SEQ ID NO: 68 is the determined cDNA sequence for contig 27.
SEQ ID NO: 69 is the determined cDNA sequence for contig 28.
SEQ ID NO: 70 is the determined cDNA sequence for contig 29.
SEQ ID NO: 71 is the determined cDNA sequence for contig 30.
SEQ ID NO: 72 is the determined cDNA sequence for contig 31.
SEQ ID NO: 73 is the determined cDNA sequence for contig 32.
SEQ ID NO: 74 is the determined cDNA sequence for contig 33.
SEQ ID NO: 75 is the determined cDNA sequence for contig 34.
SEQ ID NO: 76 is the determined cDNA sequence for contig 35.
SEQ ID NO: 77 is the determined cDNA sequence for contig 36.
SEQ ID NO: 78 is the determined cDNA sequence for contig 37.
SEQ ID NO: 79 is the determined cDNA sequence for contig 38.
SEQ ID NO: 80 is the determined cDNA sequence for contig 39.
SEQ ID NO: 81 is the determined cDNA sequence for contig 40.
SEQ ID NO: 82 is the determined cDNA sequence for contig 41.
SEQ ID NO: 83 is the determined cDNA sequence for contig 42.
SEQ ID NO: 84 is the determined cDNA sequence for contig 43.
SEQ ID NO: 85 is the determined cDNA sequence for contig 44.
SEQ ID NO: 85 is the determined cDNA sequence for contig 45.
SEQ ID NO: 85 is the determined cDNA sequence for contig 46.
SEQ ID NO: 88 is the determined cDNA sequence for contig 47.
SEQ ID NO: 89 is the determined cDNA sequence for contig 48.
SEQ ID NO: 90 is the determined cDNA sequence for contig 49.
SEQ ID NO: 91 is the determined cDNA sequence for contig 50.
SEQ ID NO: 92 is the determined cDNA sequence for contig 51.
SEQ ID NO: 93 is the determined cDNA sequence for contig 52.
SEQ ID NO: 94 is the determined cDNA sequence for contig 53.
SEQ ID NO: 95 is the determined cDNA sequence for contig 54.
SEQ ID NO: 96 is the determined cDNA sequence for contig 55.
SEQ ID NO: 97 is the determined cDNA sequence for contig 56.
SEQ ID NO: 98 is the determined cDNA sequence for contig 57.
SEQ ID NO: 99 is the determined cDNA sequence for contig 58.
SEQ ID NO: 100 is the determined cDNA sequence for contig 59.
SEQ ID NO: 101 is the determined cDNA sequence for contig 60.
SEQ ID NO: 102 is the determined cDNA sequence for contig 61.
SEQ ID NO: 103 is the determined cDNA sequence for contig 62.
SEQ ID NO: 104 is the determined cDNA sequence for contig 63.
SEQ ID NO: 105 is the determined cDNA sequence for contig 64.
SEQ ID NO: 106 is the determined cDNA sequence for contig 65.
SEQ ID NO: 107 is the determined cDNA sequence for contig 66.
SEQ ID NO: 108 is the determined cDNA sequence for contig 67.
SEQ ID NO: 109 is the determined cDNA sequence for contig 68.
SEQ ID NO: 110 is the determined cDNA sequence for contig 69.
SEQ ID NO: 111 is the determined cDNA sequence for contig 70.
SEQ ID NO: 112 is the determined cDNA sequence for contig 71.
SEQ ID NO: 113 is the determined cDNA sequence for contig 72.
SEQ ID NO: 114 is the determined cDNA sequence for contig 73.
SEQ ID NO: 115 is the determined cDNA sequence for contig 74.
SEQ ID NO: 116 is the determined cDNA sequence for contig 75.
SEQ ID NO: 117 is the determined cDNA sequence for contig 76.
SEQ ID NO: 118 is the determined cDNA sequence for contig 77.
SEQ ID NO: 119 is the determined cDNA sequence for contig 78.
SEQ ID NO: 120 is the determined cDNA sequence for contig 79.
SEQ ID NO: 121 is the determined cDNA sequence for contig 80.
SEQ ID NO: 122 is the determined cDNA sequence for contig 81.
SEQ ID NO: 123 is the determined cDNA sequence for contig 82.
SEQ ID NO: 124 is the determined cDNA sequence for contig 83.
SEQ ID NO: 125 is the determined cDNA sequence for contig 84.
SEQ ID NO: 126 is the determined cDNA sequence for contig 85.
SEQ ID NO: 127 is the determined cDNA sequence for contig 86.
SEQ ID NO: 128 is the determined cDNA sequence for contig 87.
SEQ ID NO: 129 is the determined cDNA sequence for contig 88.
SEQ ID NO: 130 is the determined cDNA sequence for contig 89.

SEQ ID NO: 131 is the determined cDNA sequence for contig 90.
SEQ ID NO: 132 is the determined cDNA sequence for contig 91.
SEQ ID NO: 133 is the determined cDNA sequence for contig 92.
SEQ ID NO: 134 is the determined cDNA sequence for contig 93.
SEQ ID NO: 135 is the determined cDNA sequence for contig 94.
SEQ ID NO: 136 is the determined cDNA sequence for contig 95.
SEQ ID NO: 137 is the determined cDNA sequence for contig 96.
SEQ ID NO: 138 is the determined cDNA sequence for clone 47589.
SEQ ID NO: 139 is the determined cDNA sequence for clone 47578.
SEQ ID NO: 140 is the determined cDNA sequence for clone 47602.
SEQ ID NO: 141 is the determined cDNA sequence for clone 47593.
SEQ ID NO: 142 is the determined cDNA sequence for clone 47583.
SEQ ID NO: 143 is the determined cDNA sequence for clone 47624.
SEQ ID NO: 144 is the determined cDNA sequence for clone 47622.
SEQ ID NO: 145 is the determined cDNA sequence for clone 47649.
SEQ ID NO: 146 is the determined cDNA sequence for clone 48955.
SEQ ID NO: 147 is the determined cDNA sequence for clone 48962.
SEQ ID NO: 148 is the determined cDNA sequence for clone 48964.
SEQ ID NO: 149 is the determined cDNA sequence for clone 48987.
SEQ ID NO: 150 is the determined cDNA sequence for clone 49002.
SEQ ID NO: 151 is the determined cDNA sequence for clone 48950.
SEQ ID NO: 152 is the determined cDNA sequence for clone 48934.
SEQ ID NO: 153 is the determined cDNA sequence for clone 48960.
SEQ ID NO: 154 is the determined cDNA sequence for clone 48931.
SEQ ID NO: 155 is the determined cDNA sequence for clone 48935.
SEQ ID NO: 156 is the determined cDNA sequence for clone 48940.
SEQ ID NO: 157 is the determined cDNA sequence for clone 48936.
SEQ ID NO: 158 is the determined cDNA sequence for clone 48930.
SEQ ID NO: 159 is the determined cDNA sequence for clone 48956.
SEQ ID NO: 160 is the determined cDNA sequence for clone 48959.
SEQ ID NO: 161 is the determined cDNA sequence for clone 48949.
SEQ ID NO: 162 is the determined cDNA sequence for clone 48965.
SEQ ID NO: 163 is the determined cDNA sequence for clone 48970.
SEQ ID NO: 164 is the determined cDNA sequence for clone 48984.
SEQ ID NO: 165 is the determined cDNA sequence for clone 48969.
SEQ ID NO: 166 is the determined cDNA sequence for clone 48978.
SEQ ID NO: 167 is the determined cDNA sequence for clone 48968 (also referred to as B863P).
SEQ ID NO: 168 is the determined cDNA sequence for clone 48929.
SEQ ID NO: 169 is the determined cDNA sequence for clone 48937.
SEQ ID NO: 170 is the determined cDNA sequence for clone 48982.
SEQ ID NO: 171 is the determined cDNA sequence for clone 48983.
SEQ ID NO: 172 is the determined cDNA sequence for clone 48997.
SEQ ID NO: 173 is the determined cDNA sequence for clone 48992.
SEQ ID NO: 174 is the determined cDNA sequence for clone 49006.
SEQ ID NO: 175 is the determined cDNA sequence for clone 48994.
SEQ ID NO: 176 is the determined cDNA sequence for clone 49013.
SEQ ID NO: 177 is the determined cDNA sequence for clone 49008.
SEQ ID NO: 178 is the determined cDNA sequence for clone 48990.
SEQ ID NO: 179 is the determined cDNA sequence for clone 48989.
SEQ ID NO: 180 is the determined cDNA sequence for clone 49014.
SEQ ID NO: 181 is the determined cDNA sequence for clone 48988.
SEQ ID NO: 182 is the determined cDNA sequence for clone 49018.
SEQ ID NO: 183 is the determined cDNA sequence for clone 6921.
SEQ ID NO: 184 is the determined cDNA sequence for clone 6837.
SEQ ID NO: 185 is the determined cDNA sequence for clone 6840.
SEQ ID NO: 186 is the determined cDNA sequence for clone 6844.
SEQ ID NO: 187 is the determined cDNA sequence for clone 6854.
SEQ ID NO: 188 is the determined cDNA sequence for clone 6872.
SEQ ID NO: 189 is the determined cDNA sequence for clone 6906.
SEQ ID NO: 190 is the determined cDNA sequence for clone 6908.
SEQ ID NO: 191 is the determined cDNA sequence for clone 6910.
SEQ ID NO: 192 is the determined cDNA sequence for clone 6912.
SEQ ID NO: 193 is the determined cDNA sequence for clone 6913.
SEQ ID NO: 194 is the determined cDNA sequence for clone 6914.
SEQ ID NO: 195 is the determined cDNA sequence for clone 6916.
SEQ ID NO: 196 is the determined cDNA sequence for clone 6918.

SEQ ID NO: 197 is the determined cDNA sequence for clone 6924.

SEQ ID NO: 198 is the determined cDNA sequence for clone 6928.

SEQ ID NO: 199 is the determined cDNA sequence for clone 6978A.

SEQ ID NO: 200 is the determined cDNA sequence for clone 6978B.

SEQ ID NO: 201 is the determined cDNA sequence for clone 6982A.

SEQ ID NO: 202 is the determined cDNA sequence for clone 6982B.

SEQ ID NO: 203 is the determined cDNA sequence for clone 6850.

SEQ ID NO: 204 is the determined cDNA sequence for clone 6860.

SEQ ID NO: 205 is the determined cDNA sequence for O772P.

SEQ ID NO: 206 is the amino acid sequence encoded by SEQ ID NO: 205.

SEQ ID NO: 207 is the full-length cDNA sequence for O8E.

SEQ ID NO: 208 is a first amino acid sequence encoded by SEQ ID NO: 207.

SEQ ID NO: 209 is a second amino acid sequence encoded by SEQ ID NO: 209.

SEQ ID NO: 210-290 are determined cDNA sequences of breast-tumor specific clones.

SEQ ID NO: 291 and 292 are PCR primers.

SEQ ID NO: 293 is the determined cDNA sequence of a truncated portion of the GABA clone expressed in *E. coli*.

SEQ ID NO: 294 is the amino acid sequence of a truncated portion of the GABA clone expressed in *E. coli*.

SEQ ID NO: 295 is the full-length amino acid sequence of B863P.

SEQ ID NO: 296 is the cDNA sequence of the coding region of B863P.

SEQ ID NO: 297 is the full-length cDNA sequence of B863P.

SEQ ID NO: 298 and 299 are PCR primers

SEQ ID NO: 300 is the determined cDNA sequence of B863P expressed in *E. coli*.

SEQ ID NO: 301 is the amino acid sequence of a truncated form of B863P expressed in *E. coli*.

DETAILED DESCRIPTION OF THE INVENTION

The present invention is directed generally to compositions and their use in the therapy and diagnosis of cancer, particularly breast cancer. As described further below, illustrative compositions of the present invention include, but are not restricted to, polypeptides, particularly immunogenic polypeptides, polynucleotides encoding such polypeptides, antibodies and other binding agents, antigen presenting cells (APCs) and immune system cells (e.g., T cells).

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Polypeptide Compositions

As used herein, the term "polypeptide" "is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

Particularly illustrative polypeptides of the present invention comprise those encoded by a polynucleotide sequence set forth in any one of SEQ ID NOs: 1-38, 42-204, 205, 207, 210-290, 293, 296, 297 and 300, or a sequence that hybridizes under moderately stringent conditions, or, alternatively, under highly stringent conditions, to a polynucleotide sequence set forth in any one of SEQ ID NOs: 1-38, 42-204, 205, 207, 210-290, 293, 296, 297 and 300. Certain other illustrative polypeptides of the invention comprise amino acid sequences as set forth in any one of SEQ ID NOs: 39-41, 206, 208, 209, 294, 295 and 301.

The polypeptides of the present invention are sometimes herein referred to as breast tumor proteins or breast tumor polypeptides, as an indication that their identification has been based at least in part upon their increased levels of expression in breast tumor samples. Thus, a "breast tumor polypeptide" or "breast tumor protein," refers generally to a polypeptide sequence of the present invention, or a polynucleotide sequence encoding such a polypeptide, that is expressed in a substantial proportion of breast tumor samples, for example preferably greater than about 20%, more preferably greater than about 30%, and most preferably greater than about 50% or more of breast tumor samples tested, at a level that is at least two fold, and preferably at least five fold, greater than the level of expression in normal tissues, as determined using a representative assay provided herein. A breast tumor polypeptide sequence of the invention, based upon its increased level of expression in tumor cells, has particular utility both as a diagnostic marker as well as a therapeutic target, as further described below.

In certain preferred embodiments, the polypeptides of the invention are immunogenic, i.e., they react detectably within an immunoassay (such as an ELISA or T-cell stimulation assay) with antisera and/or T-cells from a patient with breast cancer. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology*, 3rd ed., 243-247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1-30 amino acids, preferably 5-15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotide sequences disclosed herein, or immunogenic fragments or variants thereof, or to one or more nucleic acid sequences which hybridize to one or more of these sequences under conditions of moderate to high stringency.

The present invention, in another aspect, provides polypeptide fragments comprising at least about 5, 10, 15, 20, 25, 50, or 100 contiguous amino acids, or more, including all intermediate lengths, of a polypeptide compositions set forth herein, such as those set forth in SEQ ID NOs: 39-41, 206, 208, 209, 294, 295 and 301, or those encoded by a polynucleotide sequence set forth in a sequence of SEQ ID NOs: 1-38, 42-204, 205, 207, 210-290, 293, 296, 297 and 300.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In one preferred embodiment, the polypeptide fragments and variants provide by the present invention are immunologically reactive with an antibody and/or T-cell that reacts with a full-length polypeptide specifically set for the herein.

In another preferred embodiment, the polypeptide fragments and variants provided by the present invention exhibit a level of immunogenic activity of at least about 50%, preferably at least about 70%, and most preferably at least about 90% or more of that exhibited by a full-length polypeptide sequence specifically set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein and/or using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., 1-30 amino acids, preferably 5-15 amino acids) has been removed from the N- and/or C-terminal of the mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos.4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.,* 336:86-91, 1997).

In one preferred embodiment, the immunological fusion partner is derived from a Mycobacterium sp., such as a Mycobacterium tuberculosis-derived Ra12 fragment. Ra12 compositions and methods for their use in enhancing the expression and/or immunogenicity of heterologous polynucleotide/polypeptide sequences is described in U.S. Patent Application 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. Patent Application 60/158, 585; see also, Skeiky et al., *Infection and Immun.* (1999) 67:3998-4007, incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798, 1992). Within a preferred embodiment, a repeat portion of LYTA may be incorporated into a fusion polypeptide. A repeat portion is found in the C-terminal region starting at residue 178. A particularly preferred repeat portion incorporates residues 188-305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of CD4$^+$ T-cells specific for the polypeptide.

Polypeptides of the invention are prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

Polynucleotide Compositions

The present invention, in other aspects, provides polynucleotide compositions. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be also recognized by the skilled artisan, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof) or may comprise a sequence that encodes a variant or derivative, preferably and immunogenic variant or derivative, of such a sequence.

Therefore, according to another aspect of the present invention, polynucleotide compositions are provided that comprise some or all of a polynucleotide sequence set forth in any one of SEQ ID NOs: 1-38, 42-204, 205, 207, 210-290, 293, 296, 297 and 300, complements of a polynucleotide sequence set forth in any one of SEQ ID NOs: 1-38, 42-204, 205, 207, 210-290, 293, 296, 297 and 300, and degenerate variants of a polynucleotide sequence set forth in any one of SEQ ID NOs: 1-38, 42-204, 205, 207, 210-290, 293, 296, 297 and 300. In certain preferred embodiments, the polynucleotide sequences set forth herein encode immunogenic polypeptides, as described above.

In other related embodiments, the present invention provides polynucleotide variants having substantial identity to the sequences disclosed herein in SEQ ID NOs: 1-38, 42-204, 205, 207, 210-290, 293, 296, 297 and 300, for example those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In certain preferred embodiments, the polynucleotides described above, e.g., polynucleotide variants, fragments and hybridizing sequences, encode polypeptides that are immunologically cross-reactive with a polypeptide sequence specifically set forth herein. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Tax-*

*onomy,* Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment of the invention, a mutagenesis approach, such as site-specific mutagenesis, is employed for the preparation of immunogenic variants and/or derivatives of the polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention having, for example, enhanced immunogenic activity.

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15-25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequences set forth herein, or to any continuous portion of the sequences, from about 15-25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

According to another embodiment of the present invention, polynucleotide compositions comprising antisense oligonucleotides are provided. Antisense oligonucleotides have been demonstrated to be effective and targeted inhibitors of protein synthesis, and, consequently, provide a therapeutic approach by which a disease can be treated by inhibiting the synthesis of proteins that contribute to the disease. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. Nos. 5,739, 119 and 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., Science. 1988 Jun. 10;240(4858):1544-6; Vasanthakumar and Ahmed, Cancer Commun. 1989;1(4):225-32; Peris et al., Brain Res Mol Brain Res. 1988 Jun. 15;57(2):310-20; U.S. Pat. Nos. 5,801,154; 5,789,573; 5,718,709 and 5,610, 288). Antisense constructs have also been described that inhibit and can be used to treat a variety of abnormal cellular proliferations, e.g. cancer (U.S. Pat. Nos. 5,747,470; 5,591, 317 and 5,783,683).

Therefore, in certain embodiments, the present invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein. Selection of antisense compositions specific for a given gene sequence is based upon analysis of the chosen target sequence and determination of secondary structure, $T_m$, binding energy, and relative stability. Antisense compositions may be selected based upon their relative inability to form dimers, hairpins, or other secondary structures that would reduce or prohibit specific binding to the target mRNA in a host cell. Highly preferred target regions of the mRNA, are those which are at or near the AUG translation initiation codon, and those sequences which are substantially complementary to 5' regions of the mRNA. These secondary structure analyses and target site selection considerations can be performed, for example, using v.4 of the OLIGO primer analysis software and/or the BLASTN 2.0.5 algorithm software (Altschul et al., Nucleic Acids Res. 1997, 25(17):3389-402).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., Nucleic Acids Res. 1997 Jul. 15;25(14):2730-6). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane.

According to another embodiment of the invention, the polynucleotide compositions described herein are used in the design and preparation of ribozyme molecules for inhibiting expression of the tumor polypeptides and proteins of the present invention in tumor cells. Ribozymes are RNA-protein complexes that cleave nucleic acids in a site-specific fashion. Ribozymes have specific catalytic domains that possess endonuclease activity (Kim and Cech, Proc Natl Acad Sci USA. 1987 December;84(24):8788-92; Forster and Symons, Cell. 1987 Apr. 24;49(2):211-20). For example, a large number of ribozymes accelerate phosphoester transfer reactions with a high degree of specificity, often cleaving only one of several phosphoesters in an oligonucleotide substrate (Cech et al., Cell. 1981 December;27(3 Pt 2):487-96; Michel and Westhof, J Mol Biol. 1990 Dec. 5;216(3):585-610 Reinhold-Hurek and Shub, Nature. 1992 May 14;357(6374):173-6). This specificity has been attributed to the requirement that the substrate bind via specific base-pairing interactions to the internal guide sequence ("IGS") of the ribozyme prior to chemical reaction.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., Proc Natl Acad Sci USA. 1992 Aug. 15;89(16): 7305-9). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. Nucleic Acids Res. 1992 Sep. 11;20(17):4559-65. Examples of hairpin motifs are described by Hampel et al. (Eur. Pat. Appl. Publ. No. EP 0360257), Hampel and Tritz, Biochemistry 1989 Jun. 13;28

(12):4929-33; Hampel et al., Nucleic Acids Res. 1990 Jan. 25;18(2):299-304 and U.S. Pat. No. 5,631,359. An example of the hepatitis δ virus motif is described by Perrotta and Been, Biochemistry. 1992 Dec. 1;31(47):11843-52; an example of the RNaseP motif is described by Guerrier-Takada et al., Cell. 1983 December;35(3 Pt 2):849-57; Neurospora VS RNA ribozyme motif is described by Collins (Saville and Collins, Cell. 1990 May 18;61(4):685-96; Saville and Collins, Proc Natl Acad Sci USA. 1991 Oct. 1;88(19):8826-30; Collins and Olive, Biochemistry. 1993 Mar. 23;32(11):2795-9); and an example of the Group I intron is described in (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells Ribozymes expressed from such promoters have been shown to function in mammalian cells. Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

In another embodiment of the invention, peptide nucleic acids (PNAs) compositions are provided. PNA is a DNA mimic in which the nucleobases are attached to a pseudopeptide backbone (Good and Nielsen, Antisense Nucleic Acid Drug Dev. 1997 7(4) 431-37). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (*Trends Biotechnol* 1997 June;15(6): 224-9). As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., *Science* 1991 Dec. 6;254(5037):1497-500; Hanvey et al., Science. 1992 Nov. 27;258(5087):1481-5; Hyrup and Nielsen, Bioorg Med Chem. 1996 January;4(1):5-23). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc or Fmoc protocols for solid-phase peptide synthesis, although other methods, including a modified Merrifield method, have been used.

PNA monomers or ready-made oligomers are commercially available from PerSeptive Biosystems (Framingham, Mass.). PNA syntheses by either Boc or Fmoc protocols are straightforward using manual or automated protocols (Norton et al., Bioorg Med Chem. 1995 April;3(4):437-45). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., Bioorg Med Chem. 1995 April;3(4):437-45; Petersen et al., J Pept Sci. 1995 May-June;1(3):175-83; Orum et al., Biotechniques. 1995 September;19(3):472-80; Footer et al., Biochemistry. 1996 Aug. 20;35(33):10673-9; Griffith et al., Nucleic Acids Res. 1995 Aug. 11;23(15):3003-8; Pardridge et al., Proc Natl Acad Sci USA. 1995 Jun. 6;92(12):5592-6; Boffa et al., Proc Natl Acad Sci USA. 1995 Mar. 14;92(6):1901-5; Gambacorti-Passerini et al., Blood. 1996 Aug. 15;88(4):1411-7; Armitage et al., Proc Natl Acad Sci USA. 1997 Nov. 11;94(23):12320-5; Seeger et al., Biotechniques. 1997 September; 23(3):512-7). U.S. Pat. No. 5,700,922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (Anal Chem. 1993 Dec. 15;65 (24):3545-9) and Jensen et al. (Biochemistry. 1997 Apr. 22;36 (16):5072-7). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Polynucleotide Identification, Characterization and Expression

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references). For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using the microarray technology of Affymetrix, Inc. (Santa Clara, Calif.) according to the manufacturer's instructions (and essentially as described by Schena et al., *Proc. Natl. Acad. Sci. USA* 93:10614-10619, 1996 and Heller et al., *Proc. Natl. Acad. Sci. USA* 94:2150-2155, 1997). Alternatively, polynucleotides may be amplified from cDNA prepared from cells expressing the proteins described herein, such as tumor cells.

Many template dependent processes are available to amplify a target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

An amplified portion of a polynucleotide of the present invention may be used to isolate a full length gene from a suitable library (e.g., a tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$P) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then be assembled into a single contiguous sequence. A full length cDNA molecule can be generated by ligating suitable fragments, using well known techniques.

Alternatively, amplification techniques, such as those described above, can be useful for obtaining a full length coding sequence from a partial cDNA sequence. One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111-19, 1991) and walking PCR (Parker et al., *Nucl. Acids. Res.* 19:3055-60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215-223, Horn, T. et al. (1980) *Nucl. Acids Res. Symp. Ser.* 225-232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202-204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503-5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) *Methods Enzymol.* 153:516-544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307-311. Alternatively, plant promoters such as the small subunit of RUBISCO or heat shock promoters may be used (Coruzzi, G. et al. (1984) *EMBO J.* 3:1671-1680; Broglie, R. et al. (1984) *Science* 224:838-843; and Winter, J. et al. (1991) *Results Probl. Cell Differ.* 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae.* The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard, E. K. et al. (1994) *Proc. Natl. Acad. Sci.* 91:3224-3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al.

(1977) Cell 11:223-32) and adenine phosphoribosyltransferase (Lowy, I. et al. (1990) Cell 22:817-23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567-70); npt, which confers resistance to the aminoglycosides, neomycin and G-418 (Colbere-Garapin, F. et al (1981) J. Mol. Biol. 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121-131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; J. Exp. Med. 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263-281) while the enterokinase cleavage site provides a means for purifying the desired polypeptide from the fusion protein. A discussion of vectors which contain fusion proteins is provided in Kroll, D. J. et al. (1993; DNA Cell Biol. 12:441-453).

In addition to recombinant production methods, polypeptides of the invention, and fragments thereof, may be produced by direct peptide synthesis using solid-phase techniques (Merrifield J. (1963) J. Am. Chem. Soc. 85:2149-2154). Protein synthesis may be performed using manual techniques or by automation. Automated synthesis may be achieved, for example, using Applied Biosystems 431 A Peptide Synthesizer (Perkin Elmer). Alternatively, various fragments may be chemically synthesized separately and combined using chemical methods to produce the full length molecule.

Antibody Compositions, Fragments Thereof and Other Binding Agents

According to another aspect, the present invention further provides binding agents, such as antibodies and antigen-binding fragments thereof, that exhibit immunological binding to a tumor polypeptide disclosed herein, or to a portion, variant or derivative thereof. An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439-473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Binding agents may be further capable of differentiating between patients with and without a cancer, such as breast cancer, using the representative assays provided herein. For example, antibodies or other binding agents that bind to a tumor protein will preferably generate a signal indicating the presence of a cancer in at least about 20% of patients with the disease, more preferably at least about 30% of patients. Alternatively, or in addition, the antibody will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. Preferably, a statistically significant number of samples with and without the disease will be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual,* Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) Proc. Nat. Acad. Sci. USA 69:2659-2662; Hochman et al. (1976) Biochem 15:2706-2710; and Ehrlich et al. (1980) Biochem 19:4091-4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349:293-299; Lobuglio et al. (1989) Proc. Nat. Acad. Sci. USA 86:4220-4224; Shaw et al. (1987) J Immunol. 138:4534-4538; and Brown et al. (1987) Cancer Res. 47:3577-3583), rodent CDRs grafted into a human supporting FR prior to fusion with an appropriate human antibody constant domain (Riechmann et al. (1988) Nature 332:323-327; Verhoeyen et al. (1988) Science 239:1534-1536; and Jones et al. (1986) Nature 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439-473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

In another embodiment of the invention, monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671, 958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

T Cell Compositions

The present invention, in another aspect, provides T cells specific for a tumor polypeptide disclosed herein, or for a variant or derivative thereof. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. Nos. 5,240,856; 5,215,926; WO 89/06280; WO 91/16116 and WO 92/07243). Alternatively, T cells may be derived from related or unrelated humans, non-human mammals, cell lines or cultures.

T cells may be stimulated with a polypeptide, polynucleotide encoding a polypeptide and/or an antigen presenting cell (APC) that expresses such a polypeptide. Such stimulation is performed under conditions and for a time sufficient to permit the generation of T cells that are specific for the polypeptide of interest. Preferably, a tumor polypeptide or polynucleotide of the invention is present within a delivery vehicle, such as a microsphere, to facilitate the generation of specific T cells.

T cells are considered to be specific for a polypeptide of the present invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a tumor polypeptide (100 ng/ml-100 µg/ml, preferably 200 ng/ml-25 µg/ml) for 3-7 days will typically result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a tumor polypeptide, polynucleotide or polypeptide-expressing APC may be CD4$^+$ and/or CD8$^+$. Tumor polypeptide-specific T cells may be expanded using standard techniques. Within preferred embodiments, the T cells are derived from a patient, a related donor or an unrelated donor, and are administered to the patient following stimulation and expansion.

For therapeutic purposes, CD4$^+$ or CD8$^+$ T cells that proliferate in response to a tumor polypeptide, polynucleotide or APC can be expanded in number either in vitro or in vivo. Proliferation of such T cells in vitro may be accomplished in a variety of ways. For example, the T cells can be re-exposed to a tumor polypeptide, or a short peptide corresponding to an immunogenic portion of such a polypeptide, with or without the addition of T cell growth factors, such as interleukin-2, and/or stimulator cells that synthesize a tumor polypeptide. Alternatively, one or more T cells that proliferate in the presence of the tumor polypeptide can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclosed herein in pharmaceutically-acceptable carriers for administration to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide, antibody, and/or T-cell compositions described herein in combination with a physiologically acceptable carrier. In certain preferred embodiments, the pharmaceutical compositions of the invention comprise immunogenic polynucleotide and/or polypeptide compositions of the invention for use in prophylactic and theraputic vaccine applications. Vaccine preparation is generally described in, for example, M. F. Powell and M. J. Newman, eds., "Vaccine Design (the subunit and adjuvant approach)," Plenum Press (NY, 1995). Generally, such compositions will comprise one or more polynucleotide and/or polypeptide compositions of the present invention in combination with one or more immunostimulants.

It will be apparent that any of the pharmaceutical compositions described herein can contain pharmaceutically acceptable salts of the polynucleotides and polypeptides of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

In another embodiment, illustrative immunogenic compositions, e.g., vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, Crit. Rev. Therap. Drug Carrier Systems 15:143-198, 1998, and references cited therein. Appropriate polynucleotide expression systems will, of course, contain the necessary regulatory DNA regulatory sequences for expression in a patient (such as a suitable promoter and terminating signal). Alternatively, bacterial delivery systems may involve the administration of a bacterium (such as *Bacillus-Calmette-Guerrin*) that expresses an immunogenic portion of the polypeptide on its cell surface or secretes such an epitope.

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; and Rich et al. (1993) Human Gene Therapy 4:461-476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

Additional viral vectors useful for delivering the polynucleotides encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(-) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al. Proc. Natl. Acad. Sci. USA (1986) 83:8122-8126.

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866-6869 and Wagner et al. Proc. Natl. Acad. Sci. USA (1992) 89:6099-6103, can also be used for gene delivery under the invention.

Additional illustrative information on these and other known viral-based delivery systems can be found, for example, in Fisher-Hoch et al., Proc. Natl. Acad. Sci. USA 86:317-321, 1989; Flexner et al., Ann. N.Y. Acad. Sci. 569: 86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

According to another embodiment, the pharmaceutical compositions described herein will comprise one or more immunostimulants in addition to the immunogenic polynucleotide, polypeptide, antibody, T-cell and/or APC compositions of this invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an immune response predominantly of the Th1 type. High levels of Th1-type cytokines (e.g., IFN-$\gamma$, TNF$\alpha$, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses.

Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145-173, 1989.

Certain preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol® to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the pharmaceutical compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Enhanzyn®) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other preferred adjuvants include adjuvant molecules of the general formula $$HO(CH_2CH_2O)_n\text{---}A\text{---}R, \qquad (I):$$

wherein, n is 1-50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4-24, most preferably 9; the R component is $C_{1-50}$, preferably $C_4$-$C_{20}$ alkyl and most preferably $C_{12}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245-251, 1998) and have been shown to be effective as a physiological adjuvant for eliciting prophylactic or therapeutic antitumor immunity (see Timmerman and Levy, *Ann. Rev. Med.* 50:507-529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and cell Biology 75:456-460, 1997. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems. such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature 1997 Mar. 27;386(6623):410-4; Hwang et al., Crit Rev Ther Drug Carrier Syst 1998;15(3):243-84; U.S. Pat. Nos. 5,641,515; 5,580,579 and 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. Nos. 5,543,158; 5,641,515 and 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. Nos. 5,756,353 and 5,804,212. Likewise, the delivery of drugs using intranasal microparticle resins (Takenaga et al., J Controlled Release 1998 Mar. 2;52(1-2):81-7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July;16(7):307-21; Takakura, Nippon Rinsho 1998 March;56(3):691-5; Chandran et al., Indian J Exp Biol. 1997 August;35(8):801-9; Margalit, Crit Rev Ther Drug Carrier Syst. 1995;12(2-3):233-61; U.S. Pat. Nos. 5,567,434; 5,552,157; 5,565,213; 5,738,868 and 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol Chem. 1990 Sep. 25;265(27):16337-42; Muller et al., DNA Cell Biol. 1990 April;9(3):221-9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December;24(12): 1113-28). To avoid side effects due to intracellular polymeric overloading, such ultrafine particles (sized around 0.1 µm) may be designed using polymers able to be degraded in vivo. Such particles can be made as described, for example, by Couvreur et al., Crit Rev Ther Drug Carrier Syst. 1988;5(1):1-20; zur Muhlen et al., Eur J Pharm Biopharm. 1998 March;45(2): 149-55; Zambaux et al. J Controlled Release. 1998 Jan. 2;50 (1-3):31-40; and U.S. Pat. No. 5,145,684.

Cancer Therapeutic Methods

In further aspects of the present invention, the pharmaceutical compositions described herein may be used for the treatment of cancer, particularly for the immunotherapy of breast cancer. Within such methods, the pharmaceutical compositions described herein are administered to a patient, typically a warm-blooded animal, preferably a human. A patient may or may not be afflicted with cancer. Accordingly, the above pharmaceutical compositions may be used to prevent the development of a cancer or to treat a patient afflicted with a cancer. Pharmaceutical compositions and vaccines may be administered either prior to or following surgical removal of primary tumors and/or treatment such as administration of radiotherapy or conventional chemotherapeutic drugs. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10-50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 µg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnostic Compositions, Methods and Kits

In general, a cancer may be detected in a patient based on the presence of one or more breast tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as breast cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a breast tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length breast tumor proteins and polypeptide portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as breast cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, p. 106-7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use tumor polypeptides to detect antibodies that bind to such polypeptides in a biological sample. The detection of such tumor protein specific antibodies may correlate with the presence of a cancer.

A cancer may also, or alternatively, be detected based on the presence of T cells that specifically react with a tumor protein in a biological sample. Within certain methods, a biological sample comprising $CD4^+$ and/or $CD8^+$ T cells isolated from a patient is incubated with a tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2-9 days (typically 4 days) at 37° C. with polypeptide (e.g., 5-25 µg/ml). It may be desirable to incubate another aliquot of a T cell sample in the absence of tumor polypeptide to serve as a control. For $CD4^+$ T cells, activation is preferably detected by evaluating proliferation of the T cells. For CD8+ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a tumor protein in a biological sample. For example, at least two oligonucleotide primers may be employed in a polymerase chain reaction (PCR) based assay to amplify a portion of a tumor cDNA derived from a biological sample, wherein at least one of the oligonucleotide primers is specific for (i.e., hybridizes to) a polynucleotide encoding the tumor protein. The amplified cDNA is then separated and detected using techniques well known in the art, such as gel electrophoresis. Similarly, oligonucleotide probes that specifically hybridize to a polynucleotide encoding a tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a tumor protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10-40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24-72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a tumor protein in a biological sample. Such kits generally comprise at least one oligonucleotide probe or primer, as described above, that hybridizes to a polynucleotide encoding a tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a tumor protein.

The following Examples are offered by way of illustration and not by way of limitation.

EXAMPLE 1

Identification of Breast Tumor Protein cDNAs Using Subtraction Methodology

This Example illustrates the identification of cDNA molecules encoding breast tumor proteins.

A human metastatic breast tumor cDNA expression library was constructed from metastatic breast tumor poly A+ RNA using a Superscript Plasmid System for cDNA Synthesis and Plasmid Cloning kit (BRL Life Technologies, Gaithersburg, Md. 20897) following the manufacturer's protocol. Specifically, breast tumor tissues were homogenized with polytron (Kinematica, Switzerland) and total RNA was extracted using Trizol reagent (BRL Life Technologies) as directed by the manufacturer. The poly A+ RNA was then purified using a Qiagen oligotex spin column mRNA purification kit (Qiagen, Santa Clarita, Calif. 91355) according to the manufacturer's protocol. First-strand cDNA was synthesized using the NotI/Oligo-dT18 primer. Double-stranded cDNA was synthesized, ligated with EcoRI/BstX I adaptors (Invitrogen, Carlsbad, Calif.) and digested with NotI. Following size fractionation with Chroma Spin-1000 columns (Clontech, Palo Alto, Calif. 94303), the cDNA was ligated into the EcoRI/NotI site of pCDNA3.1 (Invitrogen, Carlsbad, Calif.) and transformed into ElectroMax *E. coli* DH10B cells (BRL Life Technologies) by electroporation.

Using the same procedure, a normal human breast cDNA expression library was prepared from a pool of four normal breast tissue specimens. The cDNA libraries were characterized by determining the number of independent colonies, the percentage of clones that carried insert, the average insert size and by sequence analysis. Sequencing analysis showed both libraries to contain good complex cDNA clones that were synthesized from mRNA, with minimal rRNA and mitochondrial DNA contamination sequencing.

A cDNA subtracted library (referred to as BS3) was prepared using the above metastatic breast tumor and normal breast cDNA libraries, as described by Hara et al. (*Blood*, 84:189-199, 1994) with some modifications. Specifically, a breast tumor-specific subtracted cDNA library was generated as follows. Normal breast cDNA library (70 µg) was digested with EcoRI, NotI, and SfuI, followed by a filling-in reaction with DNA polymerase Klenow fragment. After phenol-chloroform extraction and ethanol precipitation, the DNA was dissolved in 100 µl of H$_2$O, heat-denatured and mixed with 100 µl (100 µg) of Photoprobe biotin (Vector Laboratories, Burlingame, Calif.), the resulting mixture was irradiated with a 270 W sunlamp on ice for 20 minutes. Additional Photoprobe biotin (50 µl) was added and the biotinylation reaction was repeated. After extraction with butanol five times, the DNA was ethanol-precipitated and dissolved in 23 µl H$_2$O to form the driver DNA.

To form the tracer DNA, 10 µg breast tumor cDNA library was digested with BamHI and XhoI, phenol chloroform extracted and passed through Chroma spin-400 columns (Clontech). Following ethanol precipitation, the tracer DNA was dissolved in 5 µl H$_2$O. Tracer DNA was mixed with 15 µl driver DNA and 20 µl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 µl H$_2$O, mixed with 8 µl driver DNA and 20 µl of 2×hybridization buffer, and subjected to a hybridization at 68° C. for 2 hours (short hybridization [SH]). After removal of biotinylated double-stranded DNA, subtracted cDNA was ligated into BamHI/XhoI site of chloramphenicol resistant pBCSK$^+$ (Stratagene, La Jolla, Calif. 92037) and transformed into ElectroMax *E. coli* DH10B cells by electroporation to generate a breast tumor specific subtracted cDNA library.

To analyze the subtracted cDNA library, plasmid DNA was prepared from independent clones, randomly picked from the subtracted breast tumor specific library and characterized by DNA sequencing with a Perkin Elmer/Applied Biosystems Division Automated Sequencer Model 373A (Foster City, Calif.).

A second cDNA subtraction library containing cDNA from breast tumor subtracted with normal breast cDNA, and known as BT, was constructed as follows. Total RNA was extracted from primary breast tumor tissues using Trizol reagent (Gibco BRL Life Technologies, Gaithersburg, Md.) as described by the manufacturer. The polyA+ RNA was purified using an oligo(dT) cellulose column according to standard protocols. First strand cDNA was synthesized using the primer supplied in a Clontech PCR-Select cDNA Subtraction Kit (Clontech, Palo Alto, Calif.). The driver DNA consisted of cDNAs from two normal breast tissues with the tester cDNA being from three primary breast tumors. Double-stranded cDNA was synthesized for both tester and driver, and digested with a combination of endonucleases (MluI, MscI, PvuII, SalI and StuI) which recognize six base pairs DNA. This modification increased the average cDNA size dramatically compared with cDNAs generated according to the protocol of Clontech. The digested tester cDNAs were ligated to two different adaptors and the subtraction was performed according to Clontech's protocol. The subtracted cDNAs were subjected to two rounds of PCR amplification, following the manufacturer's protocol. The resulting PCR products were subcloned into the TA cloning vector, pCRII (Invitrogen, San Diego, Calif.) and transformed into ElectroMax *E. coli* DH10B cells (Gibco BRL Life, Technologies) by electroporation. DNA was isolated from independent clones and sequenced using a Perkin Elmer/Applied Biosystems Division (Foster City, Calif.) Automated Sequencer Model 373A.

Two additional subtracted cDNA libraries were prepared from cDNA from breast tumors subtracted with a pool of cDNA from six normal tissues (liver, brain, stomach, small intestine, kidney and heart; referred to as 2BT and BC6) using the PCR-subtraction protocol of Clontech, described above. A fourth subtracted library (referred to as Bt-Met) was prepared using the protocol of Clontech from cDNA from metastatic breast tumors subtracted with cDNA from five normal tissues (brain, lung, PBMC, pancreas and normal breast).

cDNA clones isolated in the breast subtractions BS3, BT, 2BT, BC6 and BT-Met, described above, were colony PCR amplified and their mRNA expression levels in breast tumor, normal breast and various other normal tissues were determined using microarray technology. Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity.

The determined cDNA sequences of 131 clones determined to be over-expressed in breast tumor tissue compared to other tissues tested by a visual analysis of the microarray data are provided in SEQ ID NO: 1-35 and 42-137. Comparison of these cDNA sequences with known sequences in the gene bank using the EMBL and GenBank databases revealed no significant homologies to the sequences provided in SEQ ID NO: 7, 10, 21, 26, 30, 63, 81 and 104. The sequences of SEQ ID NO: 2-5, 8, 9, 13, 15, 16, 22, 25, 27, 28, 33, 35, 72, 73, 103, 107, 109, 118, 128, 129 134 and 136 showed some homology to previously isolated expressed sequences tags (ESTs), while the sequences of SEQ ID NO: 1, 6, 11, 12, 14, 17-20, 23, 24, 29, 31, 32, 34, 42-62, 64-71, 74-80, 82-102, 105, 106, 108, 110-117, 119-127, 130-133, 135 and 137 showed some homology to previously identified genes.

The determined cDNA sequences of an additional 45 clones isolated from the BT-Met library as described above and found to be over-expressed in breast tumors and metastatic breast tumors compared to other tissues tested, are provided in SEQ ID NO: 138-182. Comparison of the sequences of SEQ ID NO: 159-161, 164 and 181 revealed no significant homologies to previously identified sequences. The sequences of SEQ ID NO: 138-158, 162, 163, 165-180 and 182 showed some homology to previously identified genes.

Further studies resulted in the isolation of the full-length sequence of clone 48968 (also referred to as B863P). The full length amino acid sequence of B863P is provided in SEQ ID NO: 295, with the cDNA sequence of the coding region being provided in SEQ ID NO: 296 and the full-length cDNA sequence being provided in SEQ ID NO: 297.

In further studies, suppression subtractive hybridization (Clontech) was preformed using a pool of cDNA from 3 unique human breast tumors as the tester and a pool of cDNA from 6 other normal human tissues (liver, brain, stomach, small intestine, heart and kidney) as the driver. The isolated cDNA fragments were subcloned and characterized by DNA sequencing. The determined cDNA sequences of 22 isolated clones are provided in SEQ ID NO: 183-204. Comparison of these sequences with those in the public databases revealed no significant homologies to previously identified sequences.

The determined cDNA sequences of 71 additional breast-specific genes isolated during characterization of breast tumor cDNA libraries are provided in SEQ ID NO: 210-290. Comparison of these sequences with those in the GenBank and Geneseq databases revealed no significant homologies.

EXAMPLE 2

Identification of Breast Tumor Protein cDNAs By RT-PCR $GABA_A$ receptor clones were isolated from human breast cancer cDNA libraries by first preparing cDNA libraries from breast tumor samples from different patients as described above. PCR primers were designed based on the $GABA_A$ receptor subunit sequences described by Hedblom and Kirkness (*Jnl. Biol. Chem.* 272:15346-15350, 1997) and used to amplify sequences from the breast tumor cDNA libraries by RT-PCR. The determined cDNA sequences of three $GABA_A$ receptor clones are provided in SEQ ID NO: 36-38, with the corresponding amino acid sequences being provided in SEQ ID NO: 39-41.

The clone with the longest open reading frame (ORF; SEQ ID NO: 36) showed homology to the $GABA_A$ receptor of Hedblom and Kirkness, with four potential transmembrane regions at the C-terminal part of the protein, while the clones of SEQ ID NO: 37 and 38 retained either no transmembrane region or only the first transmembrane region. Some patients were found to have only the clones with the shorter ORFs while others had both the clones with longer and shorter ORFs.

EXAMPLE 3

Expression of Ovarian Tumor-Derived Antigens in Breast

Isolation of the antigens O772P and O8E from ovarian tumor tissue is described in U.S. patent application Ser. No. 09/338,933, filed Jun. 23, 1999. The determined cDNA sequence for O772P is provided in SEQ ID NO: 205, with the corresponding amino acid sequence being provided in SEQ ID NO: 206. The full-length cDNA sequence for O8E is provided in SEQ ID NO: 207. Two protein sequences may be translated from the full length O8E. Form "A" (SEQ ID NO: 208) begins with a putative start methionine. A second form "B" (SEQ ID NO: 209) includes 27 additional upstream residues to the 5' end of the nucleotide sequence.

The expression levels of O772P and O8E in a variety of tumor and normal tissues, including metastatic breast tumors, were analyzed by real time PCR. Both genes were found to have increased mRNA expression in 30-50% of breast tumors. For O772P, elevated expression was also observed in normal trachea, ureter, uterus and ovary. For O8E, elevated expression was also observed in normal trachea, kidney and ovary. Additional analysis employing a panel of tumor cell lines demonstrated increased expression of O8E in the breast tumor cell lines SKBR3, MDA-MB-415 and BT474, and increased expression of O772P in SKBR3. Collectively, the data indicate that O772P and O8E may be useful in the diagnosis and therapy of breast cancer.

EXAMPLE 4

Protein Expression of Breast Tumor Antigens

This example describes the expression of breast tumor antigens in *E. coli*.

a) Expression of GABA in *E. coli*

The GABA receptor clone of SEQ ID NO: 39 was expressed in *E. coli* as follows. The open reading frame of the GABA clone was PCR amplified from amino acids 19-241 using the primers PDM-625 (SEQ ID NO: 291) and PDM-626 (SEQ ID NO: 292). DNA amplification was performed using 10 µl 10×Pfu buffer, 1 µl 10 mM dNTPs, 2 µl each of the PCR primers at 10 µM concentration, 83 µl water, 1.5 µl Pfu DNA polymerase (Stratagene, La Jolla, Calif.) and 0.5 µl DNA at 100 ng/µl. Denaturation at 96° C. was performed for 2 min, followed by 40 cycles of 96° C. for 20 sec, 62° C. for 15 sec and 72° C. for 1.5 min, and lastly by 1 cycle of 72° C. for 4 min. The resulting PCR product was digested with EcoRI and cloned into a modified pET28 vector with a His tag inframe on the 5' end which had been digested with Eco72I and EcoRI. The construct was confirmed by sequence analysis and transformed into BLR (DE3) pLysS and BLR (DE3) CodonPlus RIL *E. coli* (Stratagene).

The determined cDNA sequence encoding the recombinant GABA protein is provided in SEQ ID NO: 293, with the amino acid sequence being provided in SEQ ID NO: 294.

b) Expression of B863P in *E. coli*

The B863P clone (amino acid sequence provided in SEQ ID NO: 295) was expressed in *E. coli* as follows.

The open reading frame of B863P (SEQ ID NO: 296) minus the signal sequence was PCR amplified using the primers PDM-623 (SEQ ID NO: 298) and PDM-624 (SEQ ID NO: 299). DNA amplification was performed using 10 µl 10×Pfu buffer, 1 µl 10 mM dNTPs, 2 µl each of the PCR primers at 10 µM concentration, 83 µl water, 1.5 µl Pfu DNA polymerase (Stratagene, La Jolla, Calif.) and 0.5 µl DNA at 100 ng/µl. Denaturation at 96° C. was performed for 2 min, followed by 40 cycles of 96° C. for 20 sec, 62° C. for 15 sec and 72° C. for 30 sec, and lastly by 1 cycle of 72° C. for 4 min. The resulting PCR product was digested with EcoRI and cloned into a modified pET28 vector with a His tag in frame on the 5' end, which had been digested with Eco72I and EcoRI. The construct was confirmed to be correct by sequence analysis and transformed into BLR (DE3) pLysS and BLR (DE3) Codon-Plus RIL *E. coli* cells (Stratagene). The determined cDNA sequence of the recombinant protein is provided in SEQ ID NO: 300, with the corresponding amino acid sequence being provided in SEQ ID NO: 301.

EXAMPLE 5

Synthesis of Polypeptides

Polypeptides may be synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%-60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing it will be appreciated that, although specific embodiments of the invention have been described herein for purposes of illustration, various modifications may be made without deviating from the spirit and scope of the invention. Accordingly, the invention is not limited except as by the appended claims.

---

What is claimed:

1. An isolated polynucleotide consisting of SEQ ID NO:52, the complement thereof, or a fragment thereof wherein the sequence of the fragment consists of at least 20 contiguous residues of SEQ ID NO:52, or the complement thereof, and wherein the fragment detects the presence of the sequence provided in SEQ ID NO:52, or the complement thereof, in a biological sample.

2. An expression vector comprising a polynucleotide of claim 1 operably linked to an expression control sequence.

3. A host cell transformed or transfected with an expression vector according to claim 2.

4. A composition comprising a first component selected from the group consisting of physiologically acceptable carriers and immunostimulants, and a second component comprising a polynucleotide according to claim 1.

5. A diagnostic kit comprising a polynucleotide according to claim 1.

* * * * *

SEQUENCE LISTING

<160> NUMBER OF SEQ ID NOS: 301

<210> SEQ ID NO 1
<211> LENGTH: 298
<212> TYPE: DNA
<213> ORGANISM: Homo sapien

<400> SEQUENCE: 1

```
ctgaacagtg tcagctccgt gctggagaca gtcctgctga tcacctgaat gctgaacatg      60
cttcgtgggg ctatcttttg ttttctctgt agtctctttg gtgatctcat ctgcttttct     120
gctcgagtga tgacagcctt gaaccttgtc cttccttgtc tcagagggga aaaaggaatt     180
ggatttcctc agggtctggg gcctgggctg tggcttgagg ttccgagact gatgaatcca     240
agcatgcttg agggcctggt ccggggtcat gcgaagagaa ggttcccata ccaaacac       298
```

<210> SEQ ID NO 2
<211> LENGTH: 276
<212> TYPE: DNA
<213> ORGANISM: Homo sapien

<400> SEQUENCE: 2

```
tggaaggtgt ggtgactaag ggccacggtt attgggtgaa atttgagatt gtaggccaac      60
tgtattttca agcttctgaa cttaggcaaa atattcatcg caaagtctct agcgtcatat     120
ttttctcacc taaattacgt ttccacgaga ttatttatat atagttggtc tatctctgca     180
gtccttgaag gtgaagttgt gtgttactag gctgtgtttt gggatgtcag cagtggcctg     240
aagtgagttg tgcaataaat gttaagttga aacctc                                276
```

<210> SEQ ID NO 3
<211> LENGTH: 405
<212> TYPE: DNA
<213> ORGANISM: Homo sapien
<220> FEATURE:
<221> NAME/KEY: misc_feature
<222> LOCATION: (1)...(405)
<223> OTHER INFORMATION: n = A,T,C or G

<400> SEQUENCE: 3

```
tcacatggct atttcattta tttagtagtt ttgaaatgtt agcaaatata aggtatttgt      60
aaagcatctt tcattataaa gagattagta atattcacca atcatgccaa tgagattata     120
cactctgcca aagactacta naaaaatttg atcattatta aattcaatgt tatttgacag     180
tgtgaactct atgtaacagc acaaattctg gactttgaat ctggctgctg tcctcacctg     240
aaccattaaa atgaccttgt taacaaggaa ggaatcaatg gggaaatatc acaaccagag     300
attggctgtg tgtccaaggg tgctttgtct tgttgccagg atcagactgt gaaatcacag     360
```

-continued aggcaagctg atgtcatcag aggtgactct gcccccaaca caatg      405

<210> SEQ ID NO 4
<211> LENGTH: 696
<212> TYPE: DNA
<213> ORGANISM: Homo sapien

<400> SEQUENCE: 4
cattgtgttg ggcactgtta cagtgaaacg gaaacgtgga aaatcacagc caaactgtgc      60
tctgaaagaa cactctatgt ctaatatagc cagcgtcaag agtccttatg aggcggagaa     120
ctccggggaa gagctggatc agaggtattc caaggccaag ccaatgtgta acacatgtgg     180
gaaagtgttt tcagaagcca gcagtttgag aaggcacatg agaatacata aaggagtcaa     240
accttacgtc tgccacttat gtggaaaggc atttacccaa tgtaaccagc tgaaaacgca     300
tgtaagaact catacaggtg agaagccata caatgtgaa ttgtgtgata aggatttgc      360 tcagaaatgt cagctagtct tccatagtcg catgcatcat ggtgaagaaa acccctataa     420
atgtgatgta tgcaacttac agtttgcaac ttctagcaat ctcaagattc atgcaaggaa     480
gcatagtgga gagaagccat atgtctgtga taggtgtgga cagagatttg ctcaagccag     540
cacactgacc tatcatgtcc gtaggcatac tggagaaaag ccttatgtat gtgatacctg     600
tgggaaggca tttgctgtct ctagttctct tatcactcat tctcgaaaac atacaggtaa     660
gtttgacagg gagagactgc ttaaaataaa gttata                              696

<210> SEQ ID NO 5
<211> LENGTH: 580
<212> TYPE: DNA
<213> ORGANISM: Homo sapien
<220> FEATURE:
<221> NAME/KEY: misc_feature
<222> LOCATION: (1)...(580)
<223> OTHER INFORMATION: n = A,T,C or G

<400> SEQUENCE: 5
acatcaaaaa ggaaatattt ttgacttgct tttcttctgt aaatcctccc atctcactaa      60
tatttacaac aatccagagt agcgtttatg agacactgaa aaagacaggg aggaaatcct     120
ttttcaagat atgaagtcag aacctgaatg tagacatcgg acagagaagt cctcaaccac     180
aaacctgtcc tccagctcta gagagagtaa ggctgtattt ccaaccttga gatttttcat     240 tacatttttcc ccttttttggg tgttaaattc tttccaagaa tgctgtactt gtaaaaatga     300
ttttattcta gctacaaaac atttcattta anaaaccgc attttatatc cttgtgtgaa     360
atgctcccaa aagccatcaa gatatggaga caacagattt taaaaacata aatctaatca     420
tatgggcttg aaacagtatg aacatttaac agagtgacac gatatcatta ttatatttgt     480
ttgtcatgag atgaaaggcc tggaggcaga tggtgattaa tcataattcc tgagcttcta     540
cagaaatttt aaaatgaaat tactaactgc ttaaaattat                            580

<210> SEQ ID NO 6
<211> LENGTH: 557
<212> TYPE: DNA
<213> ORGANISM: Homo sapien

<400> SEQUENCE: 6
attacattca agataaaaga tttattcaca ccacaaaaag ataatcacaa caaaatatac      60
actaacttaa aaaacaaaag attatagtga cataaaatgt tatattctct ttttaagtgg     120

```
gtaaaagtat tttgttttgct tctacataaa tttctattca tgagagaata acaaatatta    180
aaatacagtg atagtttgca tttcttctat agaatgaaca tagacataac cctgaagctt    240
ttagtttaca gggagtttcc atgaagccac aaactaaact aattatcaaa cacattagtt    300
atttccagac tcaaatagat acacattcaa ccaataaact gagaaagaag catttcatgt    360
tctctttcat tttgctataa agcatttttt cttttgacta aatgcaaagt gagaaattgt    420
attttttctc cttttaattg acctcagaag atgcactatc taattcatga gaaatacgaa    480
atttcaggtg tttatcttct tccttacttt tggggtctac aaccagcata tcttcatggc    540
tgtgaaattc atggctg                                                    557

<210> SEQ ID NO 7
<211> LENGTH: 653
<212> TYPE: DNA
<213> ORGANISM: Homo sapien

<400> SEQUENCE: 7
cattgtgttg ggggaagtag ggaatatatt tgaggcaggg taagaaatgg tttacaattc     60
tgaaaggatg atcaaagaaa aactcattgt tgagaaagta atatgagtag agacctgaaa    120
taagtgaggg agtgacgggt tatgtccagg gcaataatgt ttctgacaga ggggagagtc    180
atttcagaag cctagaggca tgtgtaaagc tgttagaatg ccagacagtc accaggccaa    240
gatgtgcaga tatccataag tgaaggggaa agaaatacaa aatgaaggca gagaaatcac    300
aaaattggat aagtggtgcc ttgtaggcca tgatgatttt agttcatact aaaattgagt    360
taggctgcca ttgtagggtt tgtgagctca gggataacat ggtctgaatt ttatttctaa    420
aaggatcact ccaagtgtta cattgcaaag aataacgtaa ggtggctggt gtagtagact    480
aaagtggaat atagtaacag tgaaatacat tttgtggtaa agcttggtag atttgaccac    540
acaaaattgt gaaattacct gtggcacaaa aaatatcaaa ggtacataca gacagaagaa    600
ccttgcgatt gtttattaat gtccttaatt tataatgtta ataccagtag aag            653

<210> SEQ ID NO 8
<211> LENGTH: 456
<212> TYPE: DNA
<213> ORGANISM: Homo sapien

<400> SEQUENCE: 8
cattgtgttg ggctaatcct tggtctctat ccaccctgcc tagcaattta tctcaaagct     60
tcaagttcct gccatctaca tgtgcccagg tcaaccaatc aatggctcag acagataagc    120
caacatgcat cccgccggag ctgccgaaaa tgctgaagga gtttgccaaa gccgccattc    180
gggcgcagcc gcaggacctc atccagtggg ggccgattat ttttgaggcc ctgtcccgtg    240
gagagacgcc tccggtgaga gagcggtctg agcgagtcgc tttgtgtaac tgggcagagc    300
taacacctga gctgttaaag atcctgcatt ctcaggttgc tggcagactg atcatccgtg    360
cagaggagct ggcccagatg tggaaagtgg tgaatctccc aacagatctg tttaatagtg    420
tgatgaatgt gggtcgcttc acggaggaga tcgagt                               456

<210> SEQ ID NO 9
<211> LENGTH: 512
<212> TYPE: DNA
<213> ORGANISM: Homo sapien

<400> SEQUENCE: 9 gttttttgatt cattttattt taacaatgtt taacaatgta agtccacata taagataccc     60
```

```
aagctttaaa tatctataca tataaactga tttcaacatc tttggcttca aaacagtaaa    120 attgttttc caatatcaaa caagtcaaat ttggaaaagg cataaatctg tatgaacatc     180
ctgtatccat ggagatgtca tgactaaatt cagaaatagc ctcatctctc tttgtttttg   240
ctttcttatg tctgagttct gcatccaatt ctgtttatta catagttttc tataagattg   300 taccccttt aaacagtgtc tattgatata tattctaggt gtctggaagt ctttttctat    360
agtcggctct tggttgtctc tgggaatatg aatggaagga gcagagtgaa aataaatctg   420
agggcaatat tcataaataa tccaagagct acactgtagt caactctccc cagagcctga   480
ccacagtgtt tccctctctc ctcctcccaa cc                                 512
```

<210> SEQ ID NO 10
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 10

```
atgtttatga agacctttaa atatttatat agaaacaaaa tgtcattgca acctaacatc    60
atccattaaa aataaaagga aaggaaaacg gcagggaaaa gtgcagtaat aacaaatggt   120
gacatgcttg gtcttaagca tcatagcaaa ctcattattt ccaatgaaac aaggattttt   180
agacccatct ttggaaatga ttcccaaatt aganaaccat caggtctcaa aaaaggaagg   240
gtcatcaaag tccatccagc ccagccaccc tgaggngcct gtatctcctc aacaagccca   300
acacaatg                                                            308
```

<210> SEQ ID NO 11
<211> LENGTH: 510
<212> TYPE: DNA
<213> ORGANISM: Homo sapien
<220> FEATURE:
<221> NAME/KEY: misc_feature
<222> LOCATION: (1)...(510)
<223> OTHER INFORMATION: n = A,T,C or G

<400> SEQUENCE: 11

```
attatatgaa tattttaatg caaaatgctt aacacttaaa attagcaaag cgtcatttaa    60
attaaaattc catttaacta aagatggtta accccaanaa attgtacagt agttgatttc   120
tgctatataa tgccagtcct atgccataca ataagaactg caacattagc tgtcacttcc   180
tccattgctc ttctggaccc taagggatga gggaggggac tcagacacaa aacacaaccc   240
aaataaactg tgcagtgatt cctaatagtt ataaacccaa tctaagttgt ccaaacagct   300
gaagaataac tgcaggtatt gttccanagc tgatacgagg ttttgctttt acagcctggt   360
aaaagttctg cactaggtga gaagtcacag tttaaggatg catgttctgt aaatagttac   420
tacatataca catttactgt ctgtaaacac tagaaatata cattagacag agtaccctca   480
caagttgggt acagttttaaa aaagaagatg                                   510
```

<210> SEQ ID NO 12
<211> LENGTH: 611
<212> TYPE: DNA
<213> ORGANISM: Homo sapien
<220> FEATURE:
<221> NAME/KEY: misc_feature
<222> LOCATION: (1)...(611)

<223> OTHER INFORMATION: n = A,T,C or G

<400> SEQUENCE: 12

```
agttttataa aatatttat ttacagtaga gctttacaaa aatagtctta aattaataca      60
aatcccttt gcaatataac ttatatgact atcttctcaa aaacgtgaca ttcgattata     120
acacataaac tacatttata gttgttaagt caccttgtag tataaatatg ttttcatctt     180
tttttgtaa taaggnacat accaataaca atgaacaatg gacaacaaat cttattttgt     240
tattcttcca atgtaaaatt catctctggc caaaacaaaa ttaaccaaag aaaagtaaaa     300
caattgtccc tctgttcaac aatacagtcc tttttaatta tttgagagtt tatctgacag     360
agacacagca ttaaactgaa agcaccatgg cataaagtct agtaacatta tcctcaaaag     420
cttttccaa tgtctttcct tcaactgttt attcagtatt tggccagtac aaataaagat     480
tggtctcaac tctctctttc attagtctca agtgttccta ttatgcactg agttttcaga     540
ccttcccaac tggcatgtgt tttaagtgtg agtttctttc tttggcttca agtggagttt     600
cacaacattt a                                                          611
```

<210> SEQ ID NO 13
<211> LENGTH: 394
<212> TYPE: DNA
<213> ORGANISM: Homo sapien
<220> FEATURE:
<221> NAME/KEY: misc_feature
<222> LOCATION: (1)...(394)
<223> OTHER INFORMATION: n = A,T,C or G

<400> SEQUENCE: 13

```
caatgtttag attcatttta ttagtggcat atacaaagca ccatataata tatgaaacgt      60
anaacaatca tgactatgta attaactgta naaataactg ctaanaaaat atagcaatat     120
ttaacacagg atttctaaaa ccattatatt ttcattactt ttcccaaagc taatgtccca     180
tgttttattt tatanacttt gtttatcaag atttatatgc atttggcacc ttttgggct      240
gaaaatagtt gatgtactct gtacagtaat gttacagttt tatacaaaat tcanaaatat     300
tgcatttgga atagtcttta tggtcctctt ccaagtattc agtttcacac aacagcaaac     360
actctgaatg cctttcctcc tgcccaacac aatg                                 394
```

<210> SEQ ID NO 14
<211> LENGTH: 361
<212> TYPE: DNA
<213> ORGANISM: Homo sapien
<220> FEATURE:
<221> NAME/KEY: misc_feature
<222> LOCATION: (1)...(361)
<223> OTHER INFORMATION: n = A,T,C or G

<400> SEQUENCE: 14

```
agcaggnact ataattttat aattaatttt acaattcatg tagcaaatgg aaaatcatac      60
agagaggcca atgtatataa ataagagttt atacagaaac tgccaattca caaacagca      120
ctgcatggtt tctatattgc aagcacaaga catggtcaca tggttccact gtacaggtag     180
aaacaagccc acagacaata catagagtac cacctgaaac gaggcccttg gagctgctca     240
gcttcttana aaatagnaaa cttttcaatgg tcataataca ttttgattca aaatgtcttc     300
taaaatgttt tcattgtggg agaaaattaa gaagggcaa aaatccatct atggaacttc      360
t                                                                     361
```

```
<210> SEQ ID NO 15
<211> LENGTH: 537
<212> TYPE: DNA
<213> ORGANISM: Homo sapien
<220> FEATURE:
<221> NAME/KEY: misc_feature
<222> LOCATION: (1)...(537)
<223> OTHER INFORMATION: n = A,T,C or G

<400> SEQUENCE: 15
acttacaaaa ttaattttat tttgcaaaac tcaacaaata cacgttcaga tctggtttct      60
cttcaaaaca tgtgtttgtt tttttaacaa acatgcaagt taatttggca tgccaaacat     120 cttttctctct agctcgcctt ggaaaaattt ttttcataac acaaacaagg gtgcaaatat    180
tgtccaaacc tatttacatt tttaccctct agaattacat acattaatat ttattgggag     240
gaaagcaaaa ctgcaaaaca tagtctttgg cattcacatt tgcttcagca gtataattaa    300
aaccttatat ttgttttaaa gataaacagt ttgaaggaaa tttaataaat cttgttttgg    360
ctctgcaaag gagccactat atcaaagcat ttaactggag ctgttgagtt cctgctggta    420
gaatattact tccagcctat ttattagctt gtcttccggn ggcccaatac atgcttttt     480 ccctctacac tgaatgaaag tacaaaaga aaaccatttc ttttcccccaa cacaatg      537

<210> SEQ ID NO 16
<211> LENGTH: 547
<212> TYPE: DNA
<213> ORGANISM: Homo sapien
<220> FEATURE:
<221> NAME/KEY: misc_feature
<222> LOCATION: (1)...(547)
<223> OTHER INFORMATION: n = A,T,C or G

<400> SEQUENCE: 16
gggtgtggng atgtatttat tcataatata ttttcagaac acattaataa tggagaataa     60
cacttattca tatactgaat ataacttttc ctggagcact ctagagcttg tttggagttg    120
gagaatactg ccaggctttt cctaatctct ttggtctttg gaagtgggca gggtttctca    180
aaccaagtgt cttccatggg ccattggcaa aggcttccct tcatcagctt ggaggggcag    240
aaagaccatg gcttcagcac ttccattttg gaaagaagta acaaaaagt gaattaatga    300 gcaatcggaa agactcaaag cattttgtac tccacagttc atttcttcac acaaacgtcc    360
attactgcag cgggcatgaa aaccggcagg gtgttaggct catggcctga agagaagtca    420
catcaccagc cgatgttttc atgcaaaagg caatcgtgat gattcanaac ctggttctga    480
atttctccag gtgtgctcgt gagctgaagg tcatgcccat tctgtgcatc ctgtgcccaa    540
cacaatg                                                              547

<210> SEQ ID NO 17
<211> LENGTH: 342
<212> TYPE: DNA
<213> ORGANISM: Homo sapien

<400> SEQUENCE: 17
acattaagaa gctcctcttc tagcatgtcc ttaagaagcc tgtcttgcag cactttcata     60
tcttctttca tcaaacacat ctcggatgta aaaacagttt cttcactatc agtattacag    120
aagacacttt tagccaatga agttttcaaa agaagaaagc ctctgttgtt cgctttttg    180 atatgcactg aacttctgaa atatctttc ccaaaagtcc acaaattcct tttccaaatc    240 tttttaaagac tgtgaatctt tttcaaaatt ctccagctcc tctatgataa tgaattggaa    300
```

```
tttatcaagt tttttaatcc tagagtcctg actttggatg at                         342

<210> SEQ ID NO 18
<211> LENGTH: 279
<212> TYPE: DNA
<213> ORGANISM: Homo sapien

<400> SEQUENCE: 18
catcataagg ttttattcat atatatacag ggtattaaga attaagagga tgctgggctc       60
tgttcttggc ttggaagatt ctatttaatt gaaactctct gttcagaaag caataacttt      120
gtctcgttcc tgttgggctg aaccctaagg tgagtgtgca gtacagtgtg tgtgggtgaa      180
atggagattt ggaattgaac tctctgcctg taaatgttcc ccaaataatt gttgtgtgta      240
tgatacgtgt ataataaaag tattcttgtt agaatctga                             279

<210> SEQ ID NO 19
<211> LENGTH: 239
<212> TYPE: DNA
<213> ORGANISM: Homo sapien

<400> SEQUENCE: 19
ctgccagcgt ttttgtgtgg ctgcagtgtg cctgggccca gctcacgggc agtgggtgga       60
cctaactgcc caggcaggcg agagctactt ccagagcctt ccagtgcatg ggagggcagg      120
gctaggtgta gcggtgtctc ctctttgaaa ttaagaacta tctttcttgt agcaaagctg      180
cacctgatga tgctgcctct cctctctgtg ttgtctgggc ccttgtttac aagcacgcg       239

<210> SEQ ID NO 20
<211> LENGTH: 527
<212> TYPE: DNA
<213> ORGANISM: Homo sapien

<400> SEQUENCE: 20
ctgaaccatt atgggataaa ctggtgcaaa ttctttgcct tctctacttc tcactgattg       60
aacataagct tccagggctc ccctgatgag gaggagcctg tccttttcag atggatggtc      120
atccagccac tgagagaagc gtgtgtggga ccactctgcc ctctggaaag agatttcag       180 ttcagcgggt gctctcgtga acaaaaactg aataatgatg ctgaacggaa tcacatcccc      240
caatgcagga ctactggcta catgttcact tgcctggaag agcagaggtc tgaatgatct      300
cagcatccga taggactttc ctaaatcaga tactcgtcta cagaatgaac ccacagccaa      360
ctccatctgt gcaaaatcag cagcaagtcg cattttccca ccttcaccaa gaggtcttat      420
gagactggca tggcggataa aaagttcaac agctctttgg caataaccct cagtgttgtc      480
aaagacaaaa tccaagcatt caagtgtttt aaaatagtca ctcataa                    527

<210> SEQ ID NO 21
<211> LENGTH: 399
<212> TYPE: DNA
<213> ORGANISM: Homo sapien

<400> SEQUENCE: 21
ctgcaatggt tgcaagtgct atttccacct agctctgact ctccacttct aaccagacaa       60
acagccaacc aaccaatcaa catgtattta ataaccacct atggggtgca agcacaaaa       120 gggcactcat cttgaaaagg aaagaccaag aatgtgctag agtaaagaga cagagaccag      180
accctactct caagatcaag agacttcagt ctcggagaca tctgccattt ctctcttctt      240
aataaaccct atttgccttt aaaaatacat ttgctttggg ggcccagaat caagaaagga      300
```

```
aactttacaa agtaaacaga agttactccc cacagggagg cagaagcaga ttaaccccaa    360
cagcagacat ctgcccggaa gagcaaactc cacatctgg                           399
```

<210> SEQ ID NO 22
<211> LENGTH: 532
<212> TYPE: DNA
<213> ORGANISM: Homo sapien

<400> SEQUENCE: 22

```
ccagaaggtg aagaaaagtt atctgataat gctcaaagtg cagtagaaat acttttaacc    60
attgatgata caagagagc tggaatgaaa gagctaaaac gtcatcctct cttcagtgat    120
gtggactggg aaaatctgca gcatcagact atgcctttca tccccagcc agatgatgaa    180 acagataccct cctatttga agccaggaat actgctcagc acctgaccgt atctggattt    240
agtctgtagc acaaaaattt tccttttagt ctagcctcgt gttatagaat gaacttgcat    300
aattatatac tccttaatac tagattgatc taaggggaa agatcattat ttaacctagt    360
tcaatgtgct tttaatgtac gttacagctt cacagagtt aaaaggctga aggaatata    420 gtcagtaatt tatcttaacc tcaaaactgt atataaatct tcaaagcttt tttcatctat    480
ttattttgtt tattgcactt tatgaaaact gaagcatcaa taaaattaga gg            532
```

<210> SEQ ID NO 23
<211> LENGTH: 215
<212> TYPE: DNA
<213> ORGANISM: Homo sapien

<400> SEQUENCE: 23

```
tgcaaataag ggctgctgtt tcgacgacac cgttcgtggg gtcccctggt gcttctatcc    60
taataccatc gacgtccctc cagaagagga gtgtgaattt tagacacttc tgcagggatc   120
tgcctgcatc ctgacacggt gccgtcccca gcacggtgat tagtcccaga gctcggctgc   180
cacctccacc ggacacctca gacacgcttc tgcag                              215
```

<210> SEQ ID NO 24
<211> LENGTH: 215
<212> TYPE: DNA
<213> ORGANISM: Homo sapien

<400> SEQUENCE: 24

```
cctgaggctc caggctaaga agtagccaag tttcacctgg agagaagagt agagggactt    60
cccaaatttc ttcctgaact cagctctgat actcagaagg tcagtctcac atcgagagat   120
aaggatgcga atcaggactt ggtaattggg ctcagtttcc tagtagggga agaaagagat   180
ggggggtagt tagtgagagt ctcactgaga gtagg                              215
```

<210> SEQ ID NO 25
<211> LENGTH: 530
<212> TYPE: DNA
<213> ORGANISM: Homo sapien

<400> SEQUENCE: 25

```
ttttttttct agtaagacta gatttattca atacccctagt aaaagttttg attataagta    60
tccaacagta taaaaagtac aaaacagatc tgtagatttc taatatatta atacaaagtg   120
catgactaca tacagtacat cctacaggca aagagaggtg gaaggggaaa agaagactg    180 tggttgaggt ctagtaataa ataaataaat acagaagtag agatgatcca tattatagta   240
```

```
tattctacca ccaatactgc agccaaaatg tacaaaaaaa atcatttcaa ataactcagg    300
aggatgataa tggctggact tttgtaattc acctcaaaga ctgtgggaga gccaactcaa    360
ctcactgtat agtctgtgca tatggtggct tgtagcatgt aggttttttc caaaagaagg    420
aaatataaaa tgtttagatt aagaactata aaactacagg gtgcctataa aaggtggctt    480
actccttatt gttattatac tatccaattt ttaaaatgca gtttaaaaaa                530
```

```
<210> SEQ ID NO 26
<211> LENGTH: 366
<212> TYPE: DNA
<213> ORGANISM: Homo sapien

<400> SEQUENCE: 26
ccagcagttc tcggacctcc tctgggggca gggagaggcc attgggtcag gggctggacc     60
caggaggagt tggaatgggt gaaagatggg gagcaagttt ttagggtaca gggtgggcct    120
aagatgggtc agtagacaga tgggagcaca gagcagggca gggggtgagg tcaagtgagg    180
gccacaggat gtgctgaggg ctcccaggga gccctaccca ggctcacgtc ctcctggtca    240
ccacctgtac tgtctggggt ccacaggggtg tgggcgttgc cagggagcac tgggagggcc    300
tcggtagggt ccacctgtag ggagaggatg tcaggaccac tagcctctgg gcaagggcag    360
aggagg                                                              366
```

```
<210> SEQ ID NO 27
<211> LENGTH: 331
<212> TYPE: DNA
<213> ORGANISM: Homo sapien
<220> FEATURE:
<221> NAME/KEY: misc_feature
<222> LOCATION: (1)...(331)
<223> OTHER INFORMATION: n = A,T,C or G

<400> SEQUENCE: 27
ccaaactcag agatggtacc agccaggggc aagcatgacc agagccaggg accctgtggc     60
tctgatcccc catttatcca ccccatgtgc ctcaggacta gagtgagcaa tcatacctta    120
taaatgactt ttgtgccttt ctgctccagt ctcaaaattt cctacacctg ccagttcttt    180
acatttttcc aaggaaagga aaacggaagc agggttcttg cctggtagct ccaggaccca    240
nctctgcagg cacccaaaga ccctctgtgt ccagcctctt ccttgagttc tcggaacctc    300
ctccctaatt ctcccttcct tccccacaag g                                   331
```

```
<210> SEQ ID NO 28
<211> LENGTH: 530
<212> TYPE: DNA
<213> ORGANISM: Homo sapien

<400> SEQUENCE: 28
ccatgaatgc ccaacaagat aatattctat accagactgt tacaggattg aagaaagatt     60
tgtcaggagt tcagaaggtc cctgcactcc tagaaaatca agtggaggaa aggacttgtt    120
ctgattcaga agatattgga agctctgagt gctctgacac agattctgaa gagcagggag    180
accatgcccg ccccaagaaa cacaccacgg accctgacat tgataaaaaa gaaagaaaaa    240
agatggtcaa ggaagcccag agagagaaaa gaaaaaacaa aattcctaaa catgtgaaaa    300
aagaaaagga gaagacagcc aagacgaaaa aaggcaaata gaatgagaac catattatgt    360
acagtcattt tcctcagttc cttttctcgc ctgaactctt aagctgcatc tggaagatgg    420
cttattggtt ttaaccagat tgtcatcgtg gcactgtctg tgaagacgga ttcaaatgtt    480
```

<210> SEQ ID NO 29
<211> LENGTH: 571
<212> TYPE: DNA
<213> ORGANISM: Homo sapien
<220> FEATURE:
<221> NAME/KEY: misc_feature
<222> LOCATION: (1)...(571)
<223> OTHER INFORMATION: n = A,T,C or G

<400> SEQUENCE: 29

```
ccataatatt ctgatgatca aggagcacac atatacaaaa gttattggat tactgcaatt      60
ctcagaggca caaacctga catggtgtga tatagtatat aatcagtcac ggggggaaa      120
agaacattaa gtctttaaaa aggcttagga agacataaac agtaaatctt tgttttcta     180
ccttcctttg gacagtgtta tatttcactt tcttctttgc aaaatgttc caaattcatt     240
tgctcaggat ttatttaaga taataactta aaacaactaa cagttgttta tgctatatgc    300
atatcatgca tgttctactg gttcaaggac aaaattaaaa caagatcttc tctgtaaagc    360
aaatatattt attatgcact tcatataca cagggatttt ttgagtacca angggataaa    420
ataaaacttt tacaatgtga aattcaatgt acattttgg ctatttacat acctcaaacc    480
aagggaaaaa taaaagaaa gcatttgttt gcaactacac ttgctgagaa gtgtaaatgg    540
aggacattaa gcaaaacaaa tatttgcata g                                   571
```

<210> SEQ ID NO 30
<211> LENGTH: 917
<212> TYPE: DNA
<213> ORGANISM: Homo sapien

<400> SEQUENCE: 30

```
actgccagag agtatgattt gaaggagatg ggagcagatg taattcttgg ctggaatctc      60
tcatttcaaa atcacttcac ataatggtgt catcatttaa acacttaaca gtcagtgcaa    120
ctgccactgt aacatctagt tggacaaaac cacaaggagg gggaggagaa atgccatca    180
ctattatgtt aacaaacatt taatttaaat ggttgctgca ctagtaaatt tctgcagaaa    240
acagttttac ccgccccctt tcacagttcc aaattaatca aggatgcttt tctataatct    300
gatgcttagc aaattagctc atgattcaaa ttttgccctc ttgaagcaca tatacctttt    360
attttaaaag tccattatag agaattgga atatataagg tatttgaatt gcagaacacc    420
cctctaattc tgttaatata gcaaagacaa acagtatca tatacatcaa gatcatactt    480
ttaaagtaag tttaaaggtc tcaattgccc agatattaaa tttatatttt ccttctatta    540
aaaaatatta catttcaatt ttgtaatatt gtaacatatt ttaagatgac cagcaagacc    600
tagtcaattt gaaatacccc ttgcattcca tacacaagct ataccataag taataaccca    660
agtatatgat gtgtaaaagt tggtgaaggt cataatactg aatttttttg caaatgtaaa    720
ctgctttcca agtaatcagc accatttttt actagactac attttaatca cttccttagc    780
tgcttacaac ctctacttag gcataaataa aagaatctga aattggtata tttccccttc    840
ctgctgtgtt aaccaaaaat actatttgac ttaaagatca aagagtcttt ttcctgaagg    900
tttttgtttt taaatgt                                                    917
```

<210> SEQ ID NO 31
<211> LENGTH: 367
<212> TYPE: DNA

<213> ORGANISM: Homo sapien
<220> FEATURE:
<221> NAME/KEY: misc_feature
<222> LOCATION: (1)...(367)
<223> OTHER INFORMATION: n = A,T,C or G

<400> SEQUENCE: 31

| | | | | | |
|---|---|---|---|---|---|
| tcttttcttt | ctgtatttcc | caaattacag | ggagctatgc | ccttggtatt | gcacacagta | 60 |
| cactgcaaaa | gattcacaag | gttagttgaa | agtcattttt | gccctggtga | ttcaaagctc | 120 |
| aaanaatttt | ctagcataaa | gtcttattaa | aaattttaat | caaaatatta | tttgagttta | 180 |
| agtttaataa | aacaatacca | ctatatatac | tctcaacaac | ttcattatat | aatcagtcct | 240 |
| atgaggttgt | acttgctttt | catatcacac | tgattaagga | caaaaataat | tttgatgtac | 300 |
| atgtaccata | cactgatatg | caatctacac | actgatgcat | ttacatacat | acaaccccaa | 360 |
| cacaatg | | | | | | 367 |

<210> SEQ ID NO 32
<211> LENGTH: 847
<212> TYPE: DNA
<213> ORGANISM: Homo sapien

<400> SEQUENCE: 32

| | | | | | |
|---|---|---|---|---|---|
| cattgtgttg | ggctggcagg | atagaagcag | cggctcactt | ggacttttc | accagggaaa | 60 |
| tcagagacaa | tgatggggct | cttccccaga | actacagggg | ctctggccat | cttcgtggta | 120 |
| agtcctggat | tttcctaata | atcacaaact | tccctgcttc | ctcccttgtt | aaagaatatt | 180 |
| atatttgatt | gcacaatctt | tattataaat | tctaaaagga | gtgcagtgga | aatcaacact | 240 |
| ttgaaatgaa | atcgtgaaga | ttaccaattt | ccttctttttg | ttgtttttta | tgttgtattt | 300 |
| tacatagaaa | aataaaccag | aaagaaatga | gttttaaaaa | ccatttagaa | ttttttttag | 360 |
| ttaatgaatt | aagtaatctt | aatcacaggt | tatattttcc | acaacatttt | cactttcttt | 420 |
| aaagttatgc | ttttactagt | ttttctaacc | cacaaacaag | aacacaggag | ccacttctat | 480 |
| tttccaagat | tacatgtctc | ttagcatata | gctaagaact | ctacacgcct | gggcttgata | 540 |
| cctgacacgc | ttttaaaagt | aaaaaatcgc | agaattaaaa | tcaaagcagt | gtttgactct | 600 |
| agagaagttg | ggaggattat | taagtaagta | tttatgttta | gctattatgt | gccaaaagaa | 660 |
| aatgtcagcc | tttggggatg | gggggaaaga | catacaacat | tttaaagcca | ttttttttcag | 720 |
| aaaagtaata | cttctgttga | ttgagaaagt | cgtacatagt | attatctaaa | agagaaacgg | 780 |
| aatgttacag | actgttttaaa | acctggatgt | tacagactaa | cttactcctt | aactgtgttc | 840 |
| ttatagc | | | | | | 847 |

<210> SEQ ID NO 33
<211> LENGTH: 863
<212> TYPE: DNA
<213> ORGANISM: Homo sapien
<220> FEATURE:
<221> NAME/KEY: misc_feature
<222> LOCATION: (1)...(863)
<223> OTHER INFORMATION: n = A,T,C or G

<400> SEQUENCE: 33

| | | | | | |
|---|---|---|---|---|---|
| cattgtgttg | ggcttttatt | tgagtttatg | aacagaaata | gaaagtatgg | tgcttgggtt | 60 |
| ttgccctttc | ttactcctga | aagttaaatc | agaagacact | gatttcattt | tgtgaaattt | 120 |
| agctcagaga | ctattgatct | tttgtttcat | taatatgaac | aactattagt | aaaaaatagc | 180 |
| tttaacagca | tttctgctga | tatctagtaa | tctattcttt | taatgtgaaa | ataagataaa | 240 |

```
atgtcctgga gctaattcta gcttaaattt gccagtattt ctgtatgtca ttaagttttt    300
ttcctctaag gttggtaata naattttgtt aatctttgca tacctgatgg catctatgtc    360
aatgctgatt gggtaattat aaattctgtg ctaatttaaa acttaatttg cctcttaagg    420
tgattgtcct ctgagtaatg attgtagtta aatgaagtat agcttgcaac tatactatca    480
catgggtcgt taagtaaaaa taaataaacc aaatttgtct gagacaggct aagatcaatc    540
ttctcatcaa accaattttt ctntaagagc aatttcactt tcagttttag ggtggacatt    600
nttgaatgcc tcaaattaaa cgttatctat ttaatcttcc tggaatagtc tgtgaccaaa    660
aaggagggtg tgatatattt aggtgtaaat atatcacata tatggtgtga tatatttggg    720
atttatatat tcagctcatt ctctgtgaag aagtcttcct gactaaaatt ggtttcaaga    780
taaactaatt tctgttagta tttctactct gcctaccatg tatgcctttt tgttagaaac    840
taataaatgt atcagtcnct agc                                           863

<210> SEQ ID NO 34
<211> LENGTH: 432
<212> TYPE: DNA
<213> ORGANISM: Homo sapien

<400> SEQUENCE: 34
agtgcatttc ctcttgattt gtctgggtta aaaccattcc ttttgtatga aatgttttga     60
cttaggaatc atttatgta cttgttctac ctggattgtc aacaactgaa agtcatatt     120 tcatccaaat caagctaaaa tgtatttaag ttgattctga gagtacaggt cagtaagcct    180
cattatttgg aatttgagag aaggtatagg tgatcggatc tgtttcattt ataaaaggtc    240 cagttttag gactagtaca ttcctgttat tttctgggtt ttatcatttt gcctaaaata    300
ggatataaaa gggacaaaaa ataagtagac tgttttatg tgtgaattat atttctacta    360 aatgttttg tatgactgtg ttatacttga taatatatat atatatatat atatatatca    420
acttgttaaa tt                                                       432

<210> SEQ ID NO 35
<211> LENGTH: 350
<212> TYPE: DNA
<213> ORGANISM: Homo sapien

<400> SEQUENCE: 35
ccagaggggt gtttatctta gggttggaat gtttctgatt atgctgacaa tagccattag     60
gctgatgttt tggggctgga tttaggcagt ttttaaataa aagagaactt aaaatggtgg    120
tgtttgtcca agatggtgat gttcctgctg tcaattagca taaacaaaag agaattctga    180
taccctgttg gaatgtcctc attcctctga gcttctccac tcacaggata aatgcaggag    240
tggcttcccc tcatggacac ctgcaaatgc agagtgtggg ggctctcctg gccctgcatc    300
actagcaaga gcaaaagctg ctccgagtct tgtttttaga acctggtcga                350

<210> SEQ ID NO 36
<211> LENGTH: 1082
<212> TYPE: DNA
<213> ORGANISM: Homo sapien

<400> SEQUENCE: 36
atgaactaca gcctccactt ggccttcgtg tgtctgagtc tcttcactga gaggatgtgc     60
atccagggga gtcagttcaa cgtcgaggtc ggcagaagtg acaagctttc cctgcctggc    120
```

```
tttgagaacc tcacagcagg atataacaaa tttctcaggc ccaattttgg tggagaaccc      180
gtacagatag cgctgactct ggacattgca agtatctcta gcatttcaga gagtaacatg      240
gactacacag ccaccatata cctccgacag cgctggatgg accagcggct ggtgtttgaa      300
ggcaacaaga gcttcactct ggatgcccgc ctcgtggagt tcctctgggt gccagatact      360
tacattgtgg agtccaagaa gtccttcctc catgaagtca ctgtgggaaa caggctcatc      420
cgcctcttct ccaatggcac ggtcctgtat gccctcagaa tcacgacaac tgttgcatgt      480
aacatggatc tgtctaaata ccccatggac acacagacat gcaagttgca gctggaaagc      540
tggggctatg atggaaatga tgtggagttc acctggctga gagggaacga ctctgtgcgt      600
ggactggaac acctgcggct tgctcagtac accatagagc ggtatttcac cttagtcacc      660
agatcgcagc aggagacagg aaattacact agattggtct tacagtttga gcttcggagg      720
aatgttctgt atttcatttt ggatctctct cgattcagtc cctgcaagaa cctgcattgg      780
ggacaacaaa ggaagtagaa gaagtcagta ttactaatat catcaacagc tccatctcca      840
gctttaaacg gaagatcagc tttgccagca ttgaaatttc cagcgacaac gttgactaca      900
gtgacttgac aatgaaaacc agcgacaagt taaagtttgt cttccgagaa agatgggca      960 ggattgttga ttatttcaca attcaaaacc ccagtaatgt tgatcactat tccaaactac     1020
tgtttccttt gattttatg ctagccaatg tattttactg ggcatactac atgtatttt     1080 ga                                                                   1082

<210> SEQ ID NO 37
<211> LENGTH: 1135
<212> TYPE: DNA
<213> ORGANISM: Homo sapien

<400> SEQUENCE: 37
atgaactaca gcctccactt ggccttcgtg tgtctgagtc tcttcactga gaggatgtgc       60
atccagggga gtcagttcaa cgtcgaggtc ggcagaagtg acaagctttc cctgcctggc      120
tttgagaacc tcacagcagg atataacaaa tttctcaggc ccaattttgg tggagaaccc      180
gtacagatag cgctgactct ggacattgca agtatctcta gcatttcaga gagtaacatg      240
gactacacag ccaccatata cctccgacag cgctggatgg accagcggct ggtgtttgaa      300
ggcaacaaga gcttcactct ggatgcccgc ctcgtggagt tcctctgggt gccagatact      360
tacattgtgg agtccaagaa gtccttcctc catgaagtca ctgtgggaaa caggctcatc      420
cgcctcttct ccaatggcac ggtcctgtat gccctcagaa tcacgacaac tgttgcatgt      480
aacatggatc tgtctaaata ccccatggac acacagacat gcaagttgca gctggaaagc      540
tggggctatg atggaaatga tgtggagttc acctggctga gagggaacga ctctgtgcgt      600
ggactggaac acctgcggct tgctcagtac accatagagc ggtatttcac cttagtcacc      660
agatcgcagc aggagacagg aaattacact agattggtct tacagtttga gcttcggagg      720
aatgttctgt atttcatttt ggaaacctac gttccttcca ctttcctggt ggtgttgtcc      780
tgggtttcat tttggatctc tctcgattca gtccctgcaa gaacccgcat tggggacaac      840
aaaggaagta gaagaagtca gtattactaa tatcatcaac agctccatct ccagctttaa      900
acggaagatc agctttgcca gcattgaaat tccagcgac aacgttgact acagtgactt      960
gacaatgaaa accagcgaca gttaaagtt tgtcttccga gaaagatgg gcaggattgt     1020 tgattatttc acaattcaaa accccagtaa tgttgatcac tattccaaac tactgtttcc     1080
tttgattttt atgctagcca atgtatttta ctgggcatcc tacatgtatt tttga          1135
```

<210> SEQ ID NO 38
<211> LENGTH: 1323
<212> TYPE: DNA
<213> ORGANISM: Homo sapien

<400> SEQUENCE: 38

```
atgaactaca gcctccactt ggccttcgtg tgtctgagtc tcttcactga gaggatgtgc      60
atccagggga gtcagttcaa cgtcgaggtc ggcagaagtg acaagctttc cctgcctggc     120
tttgagaacc tcacagcagg atataacaaa tttctcaggc ccaattttgg tggagaaccc     180
gtacagatag cgctgactct ggacattgca agtatctcta gcatttcaga gagtaacatg     240
gactacacag ccaccatata cctccgacag cgctggatgg accagcggct ggtgtttgaa     300
ggcaacaaga gcttcactct ggatgcccgc ctcgtggagt tcctctgggt gccagatact     360
tacattgtgg agtccaagaa gtccttcctc catgaagtca ctgtgggaaa caggctcatc     420
cgcctcttct ccaatggcac ggtcctgtat gccctcagaa tcacgacaac tgttgcatgt     480
aacatggatc tgtctaaata ccccatggac acacagacat gcaagttgca gctgaaaagc     540
tggggctatg atggaaatga tgtggagttc acctggctga gagggaacga ctctgtgcgt     600
ggactggaac acctgcggct tgctcagtac accatagagc ggtatttcac cttagtcacc     660
agatcgcagc aggagacagg aaattacact agattggtct tacagtttga gcttcggagg     720
aatgttctgt atttcatttt ggaaacctac gttccttcca ctttcctggt ggtgttgtcc     780
tgggtttcat tttggatctc tctcgattca gtccctgcaa gaacctgcat ggagtgacg     840
accgtgttat caatgaccac actgatgatc gggtcccgca cttctcttcc caacaccaac     900
tgcttcatca aggccatcga tgtgtacctg gggatctgct ttagctttgt gtttgggcc     960
ttgctagaat atgcagttgc tcactacagt tccttacagc agatggcagc caaagatagg    1020
gggacaacaa aggaagtaga agaagtcagt attactaata tcatcaacag ctccatctcc    1080
agctttaaac ggaagatcag ctttgccagc attgaaattt ccagcgacaa cgttgactac    1140
agtgacttga atgaaaac cagcgacaag ttcaagtttg tcttccgaga aaagatgggc    1200
aggattgttg attatttcac aattcaaaac cccagtaatg ttgatcacta ttccaaacta    1260
ctgtttcctt tgattttat gctagccaat gtatttact gggcatacta catgtatttt    1320
tga                                                                 1323
```

<210> SEQ ID NO 39
<211> LENGTH: 440
<212> TYPE: PRT
<213> ORGANISM: Homo sapien

<400> SEQUENCE: 39

```
Met Asn Tyr Ser Leu His Leu Ala Phe Val Cys Leu Ser Leu Phe Thr
  1               5                  10                  15

Glu Arg Met Cys Ile Gln Gly Ser Gln Phe Asn Val Glu Val Gly Arg
             20                  25                  30

Ser Asp Lys Leu Ser Leu Pro Gly Phe Glu Asn Leu Thr Ala Gly Tyr
         35                  40                  45

Asn Lys Phe Leu Arg Pro Asn Phe Gly Gly Glu Pro Val Gln Ile Ala
     50                  55                  60

Leu Thr Leu Asp Ile Ala Ser Ile Ser Ser Ile Ser Glu Ser Asn Met
 65                  70                  75                  80

Asp Tyr Thr Ala Thr Ile Tyr Leu Arg Gln Arg Trp Met Asp Gln Arg
```

```
                    85                  90                  95
Leu Val Phe Glu Gly Asn Lys Ser Phe Thr Leu Asp Ala Arg Leu Val
            100                 105                 110
Glu Phe Leu Trp Val Pro Asp Thr Tyr Ile Val Glu Ser Lys Lys Ser
            115                 120                 125
Phe Leu His Glu Val Thr Val Gly Asn Arg Leu Ile Arg Leu Phe Ser
            130                 135                 140
Asn Gly Thr Val Leu Tyr Ala Leu Arg Ile Thr Thr Thr Val Ala Cys
145                 150                 155                 160
Asn Met Asp Leu Ser Lys Tyr Pro Met Asp Thr Gln Thr Cys Lys Leu
                165                 170                 175
Gln Leu Glu Ser Trp Gly Tyr Asp Gly Asn Asp Val Glu Phe Thr Trp
            180                 185                 190
Leu Arg Gly Asn Asp Ser Val Arg Gly Leu Glu His Leu Arg Leu Ala
            195                 200                 205
Gln Tyr Thr Ile Glu Arg Tyr Phe Thr Leu Val Thr Arg Ser Gln Gln
            210                 215                 220
Glu Thr Gly Asn Tyr Thr Arg Leu Val Leu Gln Phe Glu Leu Arg Arg
225                 230                 235                 240
Asn Val Leu Tyr Phe Ile Leu Glu Thr Tyr Val Pro Ser Thr Phe Leu
                245                 250                 255
Val Val Leu Ser Trp Val Ser Phe Trp Ile Ser Leu Asp Ser Val Pro
            260                 265                 270
Ala Arg Thr Cys Ile Gly Val Thr Thr Val Leu Ser Met Thr Thr Leu
            275                 280                 285
Met Ile Gly Ser Arg Thr Ser Leu Pro Asn Thr Asn Cys Phe Ile Lys
290                 295                 300
Ala Ile Asp Val Tyr Leu Gly Ile Cys Phe Ser Phe Val Phe Gly Ala
305                 310                 315                 320
Leu Leu Glu Tyr Ala Val Ala His Tyr Ser Ser Leu Gln Gln Met Ala
                325                 330                 335
Ala Lys Asp Arg Gly Thr Thr Lys Glu Val Glu Glu Val Ser Ile Thr
            340                 345                 350
Asn Ile Ile Asn Ser Ser Ile Ser Ser Phe Lys Arg Lys Ile Ser Phe
            355                 360                 365
Ala Ser Ile Glu Ile Ser Ser Asp Asn Val Asp Tyr Ser Asp Leu Thr
            370                 375                 380
Met Lys Thr Ser Asp Lys Phe Lys Phe Val Phe Arg Glu Lys Met Gly
385                 390                 395                 400
Arg Ile Val Asp Tyr Phe Thr Ile Gln Asn Pro Ser Asn Val Asp His
                405                 410                 415
Tyr Ser Lys Leu Leu Phe Pro Leu Ile Phe Met Leu Ala Asn Val Phe
            420                 425                 430
Tyr Trp Ala Tyr Tyr Met Tyr Phe
            435                 440

<210> SEQ ID NO 40
<211> LENGTH: 289
<212> TYPE: PRT
<213> ORGANISM: Homo sapien

<400> SEQUENCE: 40

Met Asn Tyr Ser Leu His Leu Ala Phe Val Cys Leu Ser Leu Phe Thr
1               5                   10                  15
```

```
Glu Arg Met Cys Ile Gln Gly Ser Gln Phe Asn Val Glu Val Gly Arg
            20                  25                  30

Ser Asp Lys Leu Ser Leu Pro Gly Phe Glu Asn Leu Thr Ala Gly Tyr
        35                  40                  45

Asn Lys Phe Leu Arg Pro Asn Phe Gly Gly Glu Pro Val Gln Ile Ala
    50                  55                  60

Leu Thr Leu Asp Ile Ala Ser Ile Ser Ser Ile Ser Glu Ser Asn Met
65                  70                  75                  80

Asp Tyr Thr Ala Thr Ile Tyr Leu Arg Gln Arg Trp Met Asp Gln Arg
                85                  90                  95

Leu Val Phe Glu Gly Asn Lys Ser Phe Thr Leu Asp Ala Arg Leu Val
            100                 105                 110

Glu Phe Leu Trp Val Pro Asp Thr Tyr Ile Val Glu Ser Lys Lys Ser
        115                 120                 125

Phe Leu His Glu Val Thr Val Gly Asn Arg Leu Ile Arg Leu Phe Ser
    130                 135                 140

Asn Gly Thr Val Leu Tyr Ala Leu Arg Ile Thr Thr Thr Val Ala Cys
145                 150                 155                 160

Asn Met Asp Leu Ser Lys Tyr Pro Met Asp Thr Gln Thr Cys Lys Leu
                165                 170                 175

Gln Leu Glu Ser Trp Gly Tyr Asp Gly Asn Asp Val Glu Phe Thr Trp
            180                 185                 190

Leu Arg Gly Asn Asp Ser Val Arg Gly Leu Glu His Leu Arg Leu Ala
        195                 200                 205

Gln Tyr Thr Ile Glu Arg Tyr Phe Thr Leu Val Thr Arg Ser Gln Gln
    210                 215                 220

Glu Thr Gly Asn Tyr Thr Arg Leu Val Leu Gln Phe Glu Leu Arg Arg
225                 230                 235                 240

Asn Val Leu Tyr Phe Ile Leu Glu Thr Tyr Val Pro Ser Thr Phe Leu
                245                 250                 255

Val Val Leu Ser Trp Val Ser Phe Trp Ile Ser Leu Asp Ser Val Pro
            260                 265                 270

Ala Arg Thr Arg Ile Gly Asp Asn Lys Gly Ser Arg Arg Ser Gln Tyr
        275                 280                 285

Tyr

<210> SEQ ID NO 41
<211> LENGTH: 265
<212> TYPE: PRT
<213> ORGANISM: Homo sapien

<400> SEQUENCE: 41

Met Asn Tyr Ser Leu His Leu Ala Phe Val Cys Leu Ser Leu Phe Thr
1               5                   10                  15

Glu Arg Met Cys Ile Gln Gly Ser Gln Phe Asn Val Glu Val Gly Arg
            20                  25                  30

Ser Asp Lys Leu Ser Leu Pro Gly Phe Glu Asn Leu Thr Ala Gly Tyr
        35                  40                  45

Asn Lys Phe Leu Arg Pro Asn Phe Gly Gly Glu Pro Val Gln Ile Ala
    50                  55                  60

Leu Thr Leu Asp Ile Ala Ser Ile Ser Ser Ile Ser Glu Ser Asn Met
65                  70                  75                  80

Asp Tyr Thr Ala Thr Ile Tyr Leu Arg Gln Arg Trp Met Asp Gln Arg
                85                  90                  95
```

```
Leu Val Phe Glu Gly Asn Lys Ser Phe Thr Leu Asp Ala Arg Leu Val
                100                 105                 110

Glu Phe Leu Trp Val Pro Asp Thr Tyr Ile Val Glu Ser Lys Lys Ser
            115                 120                 125

Phe Leu His Glu Val Thr Val Gly Asn Arg Leu Ile Arg Leu Phe Ser
        130                 135                 140

Asn Gly Thr Val Leu Tyr Ala Leu Arg Ile Thr Thr Val Ala Cys
145                 150                 155                 160

Asn Met Asp Leu Ser Lys Tyr Pro Met Asp Thr Gln Thr Cys Lys Leu
                165                 170                 175

Gln Leu Glu Ser Trp Gly Tyr Asp Gly Asn Asp Val Glu Phe Thr Trp
            180                 185                 190

Leu Arg Gly Asn Asp Ser Val Arg Gly Leu Glu His Leu Arg Leu Ala
        195                 200                 205

Gln Tyr Thr Ile Glu Arg Tyr Phe Thr Leu Val Thr Arg Ser Gln Gln
    210                 215                 220

Glu Thr Gly Asn Tyr Thr Arg Leu Val Leu Gln Phe Glu Leu Arg Arg
225                 230                 235                 240

Asn Val Leu Tyr Phe Ile Leu Asp Leu Ser Arg Phe Ser Pro Cys Lys
                245                 250                 255

Asn Leu His Trp Gly Gln Gln Arg Lys
            260                 265

<210> SEQ ID NO 42
<211> LENGTH: 574
<212> TYPE: DNA
<213> ORGANISM: Homo sapien
<220> FEATURE:
<221> NAME/KEY: misc_feature
<222> LOCATION: (1)...(574)
<223> OTHER INFORMATION: n = A,T,C or G

<400> SEQUENCE: 42
accaacanag cttagtaatt tctaaaaaga aaaatgatc tttttccgac ttctaaacaa     60
gtgactatac tagcataaat cattcttcta gtaaaacagc taaggtatag acattctaat    120
aatttgggaa aacctatgat tacaagtaaa aactcagaaa tgcaaagatg ttggtttttt    180
gtttctcagt ctgctttagc ttttaactct ggaaacgcat gcacactgaa ctctgctcag    240
tgctaaacag tcaccagcag gttcctcagg gtttcagccc taaaatgtaa aacctggata    300
atcagtgtat gttgcaccag aatcagcatt ttttttttaa ctgcaaaaaa tgatggtctc    360
atctctgaat ttatatttct cattcttttg aacatactat agctaatata ttttatgttg    420
ctaaattgct tctatctagc atgttaaaca aagataaat actttcgatg aaagtaaatt    480
ataggaaaaa aattaactgt tttaaaaaga acttgattat gttttatgat ttcaggcaag    540
tattcatttt taacttgcta cctactttta aata                                574

<210> SEQ ID NO 43
<211> LENGTH: 467
<212> TYPE: DNA
<213> ORGANISM: Homo sapien
<220> FEATURE:
<221> NAME/KEY: misc_feature
<222> LOCATION: (1)...(467)
<223> OTHER INFORMATION: n = A,T,C or G

<400> SEQUENCE: 43
tttttttttt ttttttattg ccatcaattt attaaaataa acatgtatag caggtttcaa     60
```

```
caattgtctt gtagtttgta gtaaaaagac ataagaaaga gaaggtgtgg tttgcagcaa      120
tccgtagctg gtttctcacc ataccctgca gttctgtgag ccaaaggtct tgcagaaagt      180
taaaataaat cacaaagact gctgtcatat attaattgca taaacacctc aacattgctc      240
anagtttcat ccgtttggtt aanaaaacat tccttcaatt catctatggc atttgtagtg      300
gcattgtcgt ctatgaactc ttgaagaagt tctttgtatt cagtcttaga cacttgtgga      360
ttgattgtct tggaaatcac attctccaat aaggggcagc cagagcctgc gtagcagtgc      420
tgggagaggg ccgccagcat gaggaccatc agcaacttca tggtgag                   467
```

```
<210> SEQ ID NO 44
<211> LENGTH: 613
<212> TYPE: DNA
<213> ORGANISM: Homo sapien
<220> FEATURE:
<221> NAME/KEY: misc_feature
<222> LOCATION: (1)...(613)
<223> OTHER INFORMATION: n = A,T,C or G

<400> SEQUENCE: 44
```

```
tttttttttt ttttttttag ttttaaaata ttttcacttt attattatgc ttataatatt       60
attccaacag actgtattaa aggcagtgat cactaacaca gaacacgaca gggcgaagag      120
gcagccgggc cgattgcagg acgtggcctg tcgggccagg gtcgctgaca tgcacgctgg      180
tagctcatac actgctaccc tcagcacagg ctgcaggaat agggacaaga cagatgccgc      240
cggactctta gaagctattt aataaatatc atccaaaaac aaaatggaaa agaaacaaga      300
aaccctccga gcacaaccac cttaggccaa ctgaatgtaa tctagtttat tcaaccaaaa      360
attgagagag aaggaaaata ttgaaacaaa caaacgaaag aaagcagttc ttaagactag      420
cagtaaataa atttatacaa cagttcggtc tgtataatat gatgaaataa atctacatct      480
tttcttattt tggngctttg aattatacat acaaacaaca attacaggga cttgttcaca      540
aagcatgtag gcctanaaaa aggctctctg aaaccctcaa tggcaactgg tgaacggtaa      600
cactgattgc cca                                                         613
```

```
<210> SEQ ID NO 45
<211> LENGTH: 334
<212> TYPE: DNA
<213> ORGANISM: Homo sapien
<220> FEATURE:
<221> NAME/KEY: misc_feature
<222> LOCATION: (1)...(334)
<223> OTHER INFORMATION: n = A,T,C or G

<400> SEQUENCE: 45
```

```
accagaccaa gtgaatgcga cagggaatta tttcctgtgt tgataattca tgaagtagaa       60
cagtataatc aaaatcaatt gtatcatcat tagttttcca ctgcctcaca ctagtgagct      120
gtgccaagta gtagtgtgac acctgtgttg tcatttccca catcacgtaa gagcttccaa      180
ggaaagccaa atcccagatg agtctcagag agggatcaat atgtccatga ttatcaggta      240
tgctgactat ttccaagggg ttttttcagtt gcttcatttg cttgtaaagc aggtaatcct      300
cttgttgtnt tttcttttttc tcgatgagcc gtgt                                 334
```

```
<210> SEQ ID NO 46
<211> LENGTH: 429
<212> TYPE: DNA
<213> ORGANISM: Homo sapien
<220> FEATURE:
<221> NAME/KEY: misc_feature
```

```
<222> LOCATION: (1)...(429)
<223> OTHER INFORMATION: n = A,T,C or G

<400> SEQUENCE: 46 acaatttttnt taaacaagca gaatagcact aggcagaata aaaaattgca cagacgtatg      60
caattttcca agatagcatt ctttaaattc agtattcagc ttccaaagat tggttgccca     120
taatagactt aaacatataa tgatggctaa aaaaaataag tatacgaaaa tgtaaaaaag     180
gaaatgtaag tccactctca atctcataaa aggtgagagt aaggatgcta aagcaaaata     240
aatgtaggtt cttttttttct atttccgttt atcatgcagt ctgcttcttt gatatgcctt     300
agggttaccc atttaagtta gaggttgtaa tgcaatggtg ggaatgaaaa ttgatcaaat     360
atacaccttg tcatttcatt tcaaattgcg gntggaaact tccaaaaaaa gggtaggcat     420
gaagaaaaa                                                              429

<210> SEQ ID NO 47
<211> LENGTH: 394
<212> TYPE: DNA
<213> ORGANISM: Homo sapien
<220> FEATURE:
<221> NAME/KEY: misc_feature
<222> LOCATION: (1)...(394)
<223> OTHER INFORMATION: n = A,T,C or G

<400> SEQUENCE: 47
acgcgaantt gtgttatgac tgatagcctt cagctacaaa angataggac tgacctggtt      60
taaagtgttc tattttgtaa atcattccat ttgagtcttt ctgatgaact tggctatact     120
gaaatctgtt attttagtga ggctccaaaa tgagcaaagc taggcctgat tagagtagag     180
tgactattaa aaaacataac tttctaggag ctataaatca aagttttaaa aagatgtttg     240
gatatatttg agtattccga tcatgaaaac agaaattgcc ctgcctacta caaggacaga     300
ctgatgggaa attatgcacc tggtcaactt agcttttaag cagacgatgc tgtaaaaaca     360
aacggcttct ctgatatttta ttgtaagttt tagt                                 394

<210> SEQ ID NO 48
<211> LENGTH: 486
<212> TYPE: DNA
<213> ORGANISM: Homo sapien

<400> SEQUENCE: 48
acaaaggaac cgaggggtga ccacctctga gatgtccttg actttgtcat agcctggggc      60
atattgagca tctctctcac agctgccttt cttatcccca ttcttgatgt agacctcctt     120
ccgagtcagc ttttttctcct cctcagacac aaacagagct tgatatcct gtgcagggag     180 cagctcttcc ttttgttgct ggcaagtggt agttggagga agcctcaaag ctcgagttgt     240
tccctcggtg caggggagac aaatgggcct gatagtctgg ccatatttca gcttattctt     300
gagcttgatc agggcaacgt catagtcata aaattcagga attcctgctt cttttttccc     360
attaatgttg tagttggggt gaaataggac tacttctatc tccaggtccc gcttctcccc     420
tcccttgatt gagtgttcct tgtcatccac agtgaaacaa tgtgctgctg tcagcacaaa     480
gtacct                                                                 486

<210> SEQ ID NO 49
<211> LENGTH: 487
<212> TYPE: DNA
<213> ORGANISM: Homo sapien
```

<400> SEQUENCE: 49

```
acgggctgac agagaagatt cccgagagta aatcatcttt ccaatccaga ggaacaagca    60
tgtctctctg ccaagatcca tctaaactgg agtgatgtta gcagacccag cttagagttc   120
ttctttcttt cttaagccct tgctctggag gaagttctc cagcttcagc tcaactcaca    180
gcttctccaa gcatcaccct gggagttttcc tgagggtttt ctcataaatg agggctgcac   240
attgcctgtt ctgcttcgaa gtattcaata ccgctcagta ttttaaatga agtgattcta   300
agatttggtt tgggatcaat aggaaagcat atgcagccaa ccaagatgca atgttttga    360
aatgatatga ccaaaatttt aagtaggaaa gtcacccaaa cacttctgct ttcacttaag   420
tgtctggccc gcaatactgt aggaacaagc atgatcttgt tactgtgata ttttaaatat   480
ccacagt                                                             487
```

<210> SEQ ID NO 50
<211> LENGTH: 460
<212> TYPE: DNA
<213> ORGANISM: Homo sapien
<220> FEATURE:
<221> NAME/KEY: misc_feature
<222> LOCATION: (1)...(460)
<223> OTHER INFORMATION: n = A,T,C or G

<400> SEQUENCE: 50

```
acatattttg gttgaagaca ccagactgaa gtaaacagct gtgcatccaa tttattatag    60
ttttgtaagt aacaatatgt aatcaaactt ctaggtgact tgagagtgga acctcctata   120
tcattattta gcaccgttta tgacagtaac catttcagtg tattgtttat tataccactt   180
atatcaactt attttccacc aggttaaaat tttaatttct acaaaataac attctgaatc   240
aagcacactg tatgttcagt aggttgaact atgaacactg tcatcaatgt tcagttcaaa   300
agcctgaaag tttagatcta gaagctggta aaaatgacaa tatcaatcac attaggggaa   360
ccattgttgt cttcacttaa tccatttagc actattgaaa ataagcacac caagntatat   420
gactaatata acttgaaaat tttttatact gaggggtng                          460
```

<210> SEQ ID NO 51
<211> LENGTH: 529
<212> TYPE: DNA
<213> ORGANISM: Homo sapien

<400> SEQUENCE: 51

```
acacttgaaa ccaaatttct aaaacttgtt tttcttaaaa aatagttgtt gtaacattaa    60
accataaccct aatcagtgtg ttcactatgc ttccacacta gccagtcttc tcacacttct   120
tctggtttca agtctcaagg cctgacagac agaagggctt ggagattttt tttctttaca   180
attcagtctt cagcaacttg agagctttct tcatgttgtc aagcaacaga gctgtatctg   240
caggttcgta agcatagaga cggtttgaat atcttccagt gatatcggct ctaactgtca   300
gagatgggtc aacaaacata atcctgggga catactggcc atcaggagaa aggtgtttgt   360
cagttgtttc ataaaccaga ttgaggagga caaactgctc tgccaatttc tggatttctt   420
tattttcagc aaacactttc tttaaagctt gactgtgtgg gcactcatcc aagtgatgaa   480
taaatcatca agggtttgtt gcttgtcttg gatttatata gagcttctt                529
```

<210> SEQ ID NO 52
<211> LENGTH: 379
<212> TYPE: DNA
<213> ORGANISM: Homo sapien

<400> SEQUENCE: 52

```
actttgccaa gcagtaaagg atccaggaga tagcactgga tgtggtgtca tgtcctgcaa    60
acatgaacgt tttcacttca gcctggagat ctgcttcaga gaaatctttg gtgttttcgc   120
ttttggcact caaaagtatg tccagaaaat cccagcgcct tttctgagta gtatcttgtt   180
ttagcttatc cttaagagac tccttccggt cctggattac tttctctgtg aactgatgaa   240
gttcttggtt aaatttagaa aagatttggc cttgagagct gaatttgaaa accaggtcgt   300
tgtgatgtag aaaattgttc atgcgctggt tggagatttt gctaaggttg aacactgctt   360
tcaggtatga gtccagggt                                                379
```

<210> SEQ ID NO 53
<211> LENGTH: 380
<212> TYPE: DNA
<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 53

```
acttttatct taaagggtg gtagttttcc ctaaaatact tattatgtaa gggtcattag    60
acaaatgtct tgaagtagac atggaattta tgaatggttc tttatcattt ctcttccccc   120
tttttggcat cctggcttgc ctccagtttt aggtccttta gtttgcttct gtaagcaacg   180
ggaacacctg ctgaggggc tctttccctc atgtatactt caagtaagat caagaatctt   240
ttgtgaaatt atagaaattn actatgtaaa tgcttgatgg aatnntttcc tgctagtgta   300
gcttctgaaa ggcgctttct ccatttattt aaaactaccc atgcaattaa aaggtacctt   360
gccgcgacca cnctaanggc                                              380
```

<210> SEQ ID NO 54
<211> LENGTH: 245
<212> TYPE: DNA
<213> ORGANISM: Homo sapien

<400> SEQUENCE: 54

```
gcgcggcgct tcacttcttc aacttccggt ccggctcgcc cagcgcgctg cgagtgctgg    60
ccgaggtgca ggagggccgc gcgtggatta atccaaaaga gggatgtaaa gttcacgtgg   120
tcttcagcac agagcgctac aacccagagt ctttacttca ggaaggtgag ggacgtttgg   180
ggaaatgttc tgctcgagtg ttttttcaaga atcagaaacc cagaccaacc atcaatgtaa   240
cttgt                                                              245
```

<210> SEQ ID NO 55
<211> LENGTH: 556
<212> TYPE: DNA
<213> ORGANISM: Homo sapien

<400> SEQUENCE: 55

```
acagaagatg aataataatg aaaaactgtg atttttttgac tatcacatac attgtgttaa    60
aaaacaggta aatataatga ctattactgt taagaaagac aaggaggaaa actgtttcaa   120
tgttcaggtt taaatactaa gcacaaaaat ataacaaatt ctgtgtctac aataattttt   180
gaagtgtata caagtgcatt gcaaatgagc tctttaaaat ttaaagtcca tttccccttt   240
agccaagcat atgtctacat ttatgatttc tttctcttat tttaaagtct cttctggttt   300
```

```
agtttttaa aaagtttcat catggctgtc atcttggaat ctagcctcca gctcaaagct        360
gagacttcac gcatacatat tctcctttct ggttgcatct tcacctagtt tctccaagta        420
ttcagagtta aatagcacaa cttcttttat atgttcactt ttgtccacat gtagtggcag        480
tgctgctgct tcagtaggct ttctcacaca ccctttccct tctttcaaca gcagtcacca        540
aacgttcaca acacaa                                                       556
```

<210> SEQ ID NO 56
<211> LENGTH: 166
<212> TYPE: DNA
<213> ORGANISM: Homo sapien
<220> FEATURE:
<221> NAME/KEY: misc_feature
<222> LOCATION: (1)...(166)
<223> OTHER INFORMATION: n = A,T,C or G

<400> SEQUENCE: 56

```
atgggccctg attacatcat tatgaactac tcaggnnaac atcccaaata ccgacctngg        60
gaaagacttg gtccgagatg tgttcatcca tacaggctac ctcttccaga gcncaggncc       120
caagagctgc ntnatcacct acctggccca ggtggacccc anaggg                      166
```

<210> SEQ ID NO 57
<211> LENGTH: 475
<212> TYPE: DNA
<213> ORGANISM: Homo sapien
<220> FEATURE:
<221> NAME/KEY: misc_feature
<222> LOCATION: (1)...(475)
<223> OTHER INFORMATION: n = A,T,C or G

<400> SEQUENCE: 57

```
acatccncat gttcctccaa atgacgtttg gggtcctgct tgccaacatt ctttattgcc        60
agctgttcag gtgtcatctt atcttcttct tctacagcct tattgtaatt cttggctaat       120
tccaacatct cttttaccac tgattcattg cgtttacaat gttcactgta gtcctgaagt       180
gtcaaacctt ccatccaact cttcttatgc aaatttagca acatcttctg ttccagttca       240
tttttccgat agttaatagt aatggagtaa taatgtctgt ttagtccatg aattaatgcc       300
tggatagatg gcttgtttaa gtgacccaga ttcgaagttg tttgtcttgg ttcatgtcct       360
aagaccatca tattagcatt gatcaatctg aaggcatcaa taacaacctt tccttttaca       420
ctctgaatgg gatccacaac cactgccaca gntctctccg ataaggcttc aaagc           475
```

<210> SEQ ID NO 58
<211> LENGTH: 520
<212> TYPE: DNA
<213> ORGANISM: Homo sapien
<220> FEATURE:
<221> NAME/KEY: misc_feature
<222> LOCATION: (1)...(520)
<223> OTHER INFORMATION: n = A,T,C or G

<400> SEQUENCE: 58

```
actgttnatg tgctacttgc atttgtccct cttcctgtgc actaaagacc ccactcactt        60
ccctagtgtt cagcagtgga tgacctctag tcaagacctt tgcactagga tagttaatgt       120
gaaccatggc aactgatcac aacaatgtct ttcagatcag atccatttta tcctccttgt       180
tttacagcaa gggatattaa ttacctatgt tacctttccc tgggactatg aatgtgcaaa       240
attccaatgt tcatggtctc tccctttaaa cctatattct accccttta cattatagaa        300 aggaatgctg gaaacccaga gtccttctct tgggactctt aatgtgtatt tctaattatc       360
```

```
catgactctt aatgtgcata ttttcaattg cctaatngat ttcaattgtc taagacattt      420
caaatgtcta attggggaga actgagtctt ttatatcaag ctaatatcta gcttttatat      480
caagctaata tcttgacttc tcagcatcat agaaggggt                             520
```

<210> SEQ ID NO 59
<211> LENGTH: 214
<212> TYPE: DNA
<213> ORGANISM: Homo sapien
<220> FEATURE:
<221> NAME/KEY: misc_feature
<222> LOCATION: (1)...(214)
<223> OTHER INFORMATION: n = A,T,C or G

<400> SEQUENCE: 59

```
ctggcaggaa atgcatcaaa agacttaaag gtanagcgta ttacccctcg tcacttgcaa       60
cttgctattc gtggagatga agaattggat tctctcatca aggctacaat tgctggtggn      120
ggtgtcattc cacacatcca caaatctctg atngggaana aaggacaaca naagactgnc     180
taanggatgc ctgnatncct tggaatctca tgac                                  214
```

<210> SEQ ID NO 60
<211> LENGTH: 360
<212> TYPE: DNA
<213> ORGANISM: Homo sapien
<220> FEATURE:
<221> NAME/KEY: misc_feature
<222> LOCATION: (1)...(360)
<223> OTHER INFORMATION: n = A,T,C or G

<400> SEQUENCE: 60

```
gcatacaaca tggcagcagg gcctcgggaa gangggtagg aggaccgagc agcattctct       60
gtagaggaag acaggaaagg agaccctctt ggcacacatt tatggagggt tgtccctgaa      120
gagaagggca ggtgggagag gttccctgtt acttaagaga aggcaccagt ggcaaagagc     180
acaatgaaga ggatgatgat aaaaacaatc acgcagataa ggacaatcat cttcacgttc     240
ttccaccaga atttttcgagc caccttctgc gatgtcgtct tgaagtgctc agatgtggct    300
tccagatcct ctgtcttgtt gcggagatgt tccaagtttt cccccgggc caggatccgc     360
```

<210> SEQ ID NO 61
<211> LENGTH: 391
<212> TYPE: DNA
<213> ORGANISM: Homo sapien
<220> FEATURE:
<221> NAME/KEY: misc_feature
<222> LOCATION: (1)...(391)
<223> OTHER INFORMATION: n = A,T,C or G

<400> SEQUENCE: 61

```
tntgggatcg tactcgatta aacagagcca cctttgttcc tgaggcaatg cataantcan       60 cattttcaa tgactgcttc ttttggaag gnttggagat gacttttatc cgcttgctga      120
ggaacacacc aatgncatca ctgttgccat agaacatctt tacagacaac atgaantgct     180
ttcgcttgtc tgagtcagat atatacaatg ttttggctgt gcaatagttc tttccttcca     240
agtttagctg ctgcatttct tggncactat ttcctatccc aataaatgca cacggttgag     300
actcttgntc agaacaacca tcncgttcca tttgttcttt ttttntcttc catccactgc     360
ccataagata tacacannga ggtgggcaaa a                                     391
```

<210> SEQ ID NO 62

```
<211> LENGTH: 324
<212> TYPE: DNA
<213> ORGANISM: Homo sapien
<220> FEATURE:
<221> NAME/KEY: misc_feature
<222> LOCATION: (1)...(324)
<223> OTHER INFORMATION: n = A,T,C or G

<400> SEQUENCE: 62
acaattttat tttaacagat ttcaagagtc cattttttaa aaaatgagca ataaagaacc    60
tctatcagtg agacttctca ttttatagca aatacatttt tgcagcttaa attttcttga   120
attcatatac gcttctgtca tttaaacaaa cttccagaga aaactggtct ctatatattt   180
aagtaacaaa tttgacaaaa tacatattta tacatatata ganctctaat ataaatatta   240
aatttgaaaa aatcaaatgt gaagcagaaa ctgctataca agtatattgt ntaatatcta   300
tntnatacat taaagnnttc cggg                                         324

<210> SEQ ID NO 63
<211> LENGTH: 360
<212> TYPE: DNA
<213> ORGANISM: Homo sapien
<220> FEATURE:
<221> NAME/KEY: misc_feature
<222> LOCATION: (1)...(360)
<223> OTHER INFORMATION: n = A,T,C or G

<400> SEQUENCE: 63
acaganncct tgaatatgtt gtggttccct cattatggcc cttcattccc ttctgtgtta    60
atagtaaagc atgttgccta ataactacaa ccctgaccaa atttgggcct ggatctcatg   120
ggtcacgtgg agttttaaat acgatttta atttacttgg gtaattgagc tgaatcttta   180
gttttcagat tactttttta aacagatagg ctcttagaac aaattattaa aaacataata   240
ccccattgga ggggaatctg gattaactac ccactgttcc caccccccc aacttttgaa   300 aaattttggc catatagaat gcatgaaaaa tcaggtatga tcttatgagg actttatagt   360

<210> SEQ ID NO 64
<211> LENGTH: 491
<212> TYPE: DNA
<213> ORGANISM: Homo sapien
<220> FEATURE:
<221> NAME/KEY: misc_feature
<222> LOCATION: (1)...(491)
<223> OTHER INFORMATION: n = A,T,C or G

<400> SEQUENCE: 64
nctgactgtg atgtccactt gttccctgat ttttacacat catgtcaaag ataacagctg    60
ttcccaccca ccagttcctc taagcacata ctctgctttt ctgtcaacat cccattttgg   120
ggaaaggaaa agtcatattt attcccgcac cccagttttt taacttgttc tcccagttgt   180 cccctcttc tctgggtgta agaagggaaa ttggaaaaaa attatatata tattctcctt   240
ttaatggtgg ggggctactg gagaggagag acagcaagtc caccctaact tgttacacag   300
cacataccac aggttctgga attctcatct tcgaacctag agaataggt gctataaaca   360 gggaattaag caaaatgctg gatgctatag atctttaat tgncttaatt tttttttctat   420 tattaaacta caggctgtag atntcttagg tctcacagaa cttntatcat tttaaactga   480
cttgtatatt t                                                        491

<210> SEQ ID NO 65
<211> LENGTH: 484
```

<212> TYPE: DNA
<213> ORGANISM: Homo sapien
<220> FEATURE:
<221> NAME/KEY: misc_feature
<222> LOCATION: (1)...(484)
<223> OTHER INFORMATION: n = A,T,C or G

<400> SEQUENCE: 65

| | | | | | |
|---|---|---|---|---|---|
| accagcacac | cggcgccgtc | ctggactgcg | ccttctacga | tccaacgcat | gcctggagtg | 60 |
| gaggactaga | tcatcaattg | aaaatgcatg | atttgaacac | tgatcaagaa | aatcttgttg | 120 |
| ggacccatga | tgccctatc | agatgtgttg | aatactgtcc | agaagtgaat | gtgatggtca | 180 |
| ctggaagttg | ggatcagaca | gctaaactgt | gggatccag | aactccttgt | aatgctggga | 240 |
| ccttctctca | gcctgaaaag | gtatatacccc | tctcagtgtc | tggagaccgg | ctgattgtgg | 300 |
| gaacagcagg | ccgcagagng | ttggtgtggg | acttacggaa | catgggttac | gtgcagcagc | 360 |
| gcagggagtc | cagcctgaaa | taccagactc | gctgcatacg | agcgtttcca | aacaagcagg | 420 |
| gttatgtatt | aagctctatt | gaaggccgag | tggcagttga | gtatttggac | ccaagccctg | 480 |
| aggt | | | | | | 484 |

<210> SEQ ID NO 66
<211> LENGTH: 355
<212> TYPE: DNA
<213> ORGANISM: Homo sapien
<220> FEATURE:
<221> NAME/KEY: misc_feature
<222> LOCATION: (1)...(355)
<223> OTHER INFORMATION: n = A,T,C or G

<400> SEQUENCE: 66

| | | | | | |
|---|---|---|---|---|---|
| ngaagaaagt | atgggtggag | gtgaaggtaa | tcacagagct | gctgattctc | aaaacagtgg | 60 |
| tgaaggaaat | acaggtgctg | cagaatcttc | tttttctcag | gaggtttcta | gagaacaaca | 120 |
| gccatcatca | gcatctgaaa | gacaggcccc | tcgagcacc | cagtcaccga | gacgccacc | 180 |
| acatccactt | cccccaagac | tgaccattca | tgccccacct | caggagttgg | gaccaccagt | 240 |
| tcagagaatt | cagatgaccc | gaaggcagtc | tgtaggacgt | ggccttcagt | tgactccagg | 300 |
| aataggtggc | acgcaacagc | atttttttga | tgatgaagac | agaacagttc | caagt | 355 |

<210> SEQ ID NO 67
<211> LENGTH: 417
<212> TYPE: DNA
<213> ORGANISM: Homo sapien

<400> SEQUENCE: 67

| | | | | | |
|---|---|---|---|---|---|
| acgacacccc | tcaagaggtg | gccgaagctt | tcctgtcttc | cctgacagag | accatagaag | 60 |
| gagtcgatgc | tgaggatggg | cacagcccag | gggaacaaca | gaagcggaag | atcgtcctgg | 120 |
| acccttcagg | ctccatgaac | atctacctgg | tgctagatgg | atcagacagc | attggggcca | 180 |
| gcaacttcac | aggagccaaa | agtgtctag | tcaacttaat | tgagaaggtg | gcaagttatg | 240 |
| gtgtgaagtc | aagatatggt | ctagtgacat | atgccacata | ccccaaaatt | tgggtcaaag | 300 |
| tgtctgaagc | agacagcagt | aatgcagact | gggtcacgaa | gcagctcaat | gaaatcaatt | 360 |
| atgaagacca | caagttgaag | tcagggacta | acaccaagaa | ggccctccag | gcagtgt | 417 |

<210> SEQ ID NO 68
<211> LENGTH: 223
<212> TYPE: DNA
<213> ORGANISM: Homo sapien
<220> FEATURE:

```
<221> NAME/KEY: misc_feature
<222> LOCATION: (1)...(223)
<223> OTHER INFORMATION: n = A,T,C or G

<400> SEQUENCE: 68
cacttgcaag cttgcttaca gagacctgnt aaacaaagaa cagacagatt ctataaaatc    60
agttatatca acatataaag gagtgtgatt ttcagtttgt ttttttaagt aaatatgacc   120
aaactgacta aataagaagg caaaacaaaa aattatgctt ccttgacaag gcctttggag   180
taaacaaaat gctttaaggc tcctggtgaa tggggttgca agg                     223

<210> SEQ ID NO 69
<211> LENGTH: 396
<212> TYPE: DNA
<213> ORGANISM: Homo sapien

<400> SEQUENCE: 69 acctttttc tctccaaagg aacagtttct aaagttttct gggggaaaa aaaacttaca      60 tcaaatttaa accatatgtt aaactgcata ttagttgtgt tacaccaaaa aattgcctca   120
gctgatctac acaagtttca aagtcattaa tgcttgatat aaatttactc aacattaaat   180
tatcttaaat tattaattaa aaaaaaaact ttctaaggaa aaataaacaa atgtagaccg   240
tgattatcaa aggattatta aagaatcttt accaaaaatt tcaaccctac aacctaaaac   300
cgcaaatttc tattttttaaa catcagaaaaa taactcttgg ttcattactt atgacccaaa   360 gttttattt cactattcaa tatctgaaaa gtatca                              396

<210> SEQ ID NO 70
<211> LENGTH: 402
<212> TYPE: DNA
<213> ORGANISM: Homo sapien
<220> FEATURE:
<221> NAME/KEY: misc_feature
<222> LOCATION: (1)...(402)
<223> OTHER INFORMATION: n = A,T,C or G

<400> SEQUENCE: 70
acccannccc acccaggcaa acagctccga catgtttngt aagtgagaca agccagtgca    60 agttttttt ttttttcct ttttctttt tttgtctttt gcttaccttc ttgcttaatg     120
gaattgttat ggctaagcac atagaaggcc aaaaaaggag ttttcaaac ccagcaaatc    180 aagtgcttgg attctgaact gccaaaagaa aactgcactt cccctcttaa gtaaaacgaa   240
atgagtttct taggtaaatg tattcatcag cccagataaa aaaaaaacca gttatgtgag   300
cgttagtcac tgctcatttc caggaanatc aaacaaaata ccagcccagc cagactcaca   360
tgtgggnata tatatataaa gcaagagagc cacacccaca ag                      402

<210> SEQ ID NO 71
<211> LENGTH: 385
<212> TYPE: DNA
<213> ORGANISM: Homo sapien
<220> FEATURE:
<221> NAME/KEY: misc_feature
<222> LOCATION: (1)...(385)
<223> OTHER INFORMATION: n = A,T,C or G

<400> SEQUENCE: 71
accagtagag agtggcccct gcaggccact tataaacagg aagctctctc ctgagctcac    60
tgatcaacct gccctggca cagacagaac ctaccagaaa agaacaagta caaaacacta   120
tcattatctg ttttctcaag acagtcccaa atgtccttgt gcgatcgcca caaactcagt   180
```

```
gattggccca agtcattccc gggtgccata acagtaact ggtgtgcanc attagaacaa    240
ggggacacgg ccttgattct cttctgagca acatgaactg ggatttctgc cnccccggat    300
ctcggctgcc acctccgaag aagtcgtgac cagccacctc cacagtaaaa gattcctccc    360
gtgagtatga tttggaatgc gncct                                          385
```

<210> SEQ ID NO 72
<211> LENGTH: 538
<212> TYPE: DNA
<213> ORGANISM: Homo sapien
<220> FEATURE:
<221> NAME/KEY: misc_feature
<222> LOCATION: (1)...(538)
<223> OTHER INFORMATION: n = A,T,C or G

<400> SEQUENCE: 72

```
caattaatta acagaggtat aattgtctca ctttcagaag tgatcattta tttttattta    60
gcacaggtca taagaaaaat atatagaaaa ataatcaatt tcatatataa aaggattatt   120
tctccacctt taattattgg cctatcattt gttagtgtta tttggtcata ttattgaact   180
aatgtattat tccattcaaa gtctttctag atttaaaaat gtatgcaaaa gcttaggatt   240
atatcatgtg taactattat agataacatc ctaaaccttc agtttagata tataattgac   300
tgggtgtaat ctcttttgta atctgntttg acagatttct taaattatgt tagcataatc   360
aaggaagatt taccttgaag cactttccaa attgatactt tcaaacttat tttaaagcag   420
tagaaccttt tctatgaact aagtcacatg caaaactcca acctgtaagt atacataaaa   480
tggacttact tattcctctc accttctcca ggcctaggaa tattcttctc tggagccc    538
```

<210> SEQ ID NO 73
<211> LENGTH: 405
<212> TYPE: DNA
<213> ORGANISM: Homo sapien
<220> FEATURE:
<221> NAME/KEY: misc_feature
<222> LOCATION: (1)...(405)
<223> OTHER INFORMATION: n = A,T,C or G

<400> SEQUENCE: 73

```
actttatnna tggaattttc ttctacttgt atccatttnc cggggcttat ggacccattc    60
atactctcca tatttagaat caaaggttcc tttctgaaga gaccttaatt ttaaggtaaa   120
acgtggtcca agttcctgaa ttcccacttt cttttcactc ctgaatatgt atctgtgaaa   180
tctgaagaat atgtaatccc gttgattgtg gaatgtggca acctgccttc cgataaattg   240
aggattatga ggaaagagag atgcaaacat acgtccaatt gaatgaccca gccgtgttgt   300
aaaattattc agaattattt caggtatgtg ttctgtgggg tccttgcctc ttctcttaat   360
ttctttacga agacgaacac tgctcatttt aaaatgagca gttgg                   405
```

<210> SEQ ID NO 74
<211> LENGTH: 498
<212> TYPE: DNA
<213> ORGANISM: Homo sapien
<220> FEATURE:
<221> NAME/KEY: misc_feature
<222> LOCATION: (1)...(498)
<223> OTHER INFORMATION: n = A,T,C or G

<400> SEQUENCE: 74

```
tgagccctgc acctgttcc tgcaccccct gccnactggt tctatggcca caaggagttt    60
```

```
tacccagtaa aggagtttga ggtgtattat aagctgatgg aaaaataccc atgtgctgtt      120
cccttgtggg ttggacccctt tacgatgttc ttcagtgtcc atgacccaga ctatgccaag     180
attctcctga aaagacaaga tcccaaaagt gctgttagcc acaaaatcct tgaatcctgg      240
gttggtcgag gacttgtgac cctggatggt tctaaatgga aaaagcaccg ccagattgtg      300
aaacctggct tcaacatcag cattctgaaa atattcatca ccatgatgtc tgagagtgtt      360
cggatgatgc tgaacaaatg ggaggaacac attgcccaaa actcacgtct ggagctcttt      420
caacatgtct ccctgatgac cctggacagc atcatgaagt gtgccttcag ccaccagggc      480
agcatccagt tggacagt                                                   498

<210> SEQ ID NO 75
<211> LENGTH: 458
<212> TYPE: DNA
<213> ORGANISM: Homo sapien

<400> SEQUENCE: 75
agccttgcac atgatactca gattcctcac ccttgcttag gagtaaaaca atatactttta    60 cagggtgata taatctcca tagttatttg aagtggcttg aaaaaggcaa gattgacttt      120
tatgacattg gataaaatct acaaatcagc cctcgagtta ttcaatgata actgacaaac     180
taaattattt ccctagaaag gaagatgaaa ggagtggagt gtggtttggc agaacaactg     240
catttcacag cttttccagt taaattggag cactgaacgt tcagatgcat accaaattat     300
gcatgggtcc taatcacaca taaggctg gctaccagct ttgacacagc actgttcatc      360
tggccaaaca actgtggtta aaaacacatg taaaatgctt tttaacagct gatactgtat     420
aagacaaagc caagatgcaa aattaggctt tgattggc                             458

<210> SEQ ID NO 76
<211> LENGTH: 340
<212> TYPE: DNA
<213> ORGANISM: Homo sapien
<220> FEATURE:
<221> NAME/KEY: misc_feature
<222> LOCATION: (1)...(340)
<223> OTHER INFORMATION: n = A,T,C or G

<400> SEQUENCE: 76
accttatacc aaanaatgc ttattccaaa atatttttg tagctagtag ttctttcctt       60
ggaggtaaag aaaatacacc caaactttta attaccagga ttcagaatat ttaagagaac    120
aattttagtt aagaatcaaa tatactgaga ttcaaagagg ggaaaaaaag gaaatattat    180
agaagacaaa ggtcaaactg gcattccaga tctggagcaa ttttgtaaag caggaaaaca    240
actatgacaa tctgnagctt cttagatcat tatagtgaat gtncccattt actataaggg    300
tttttataat ggtgtttcct aaataaagga acataaatgt                          340

<210> SEQ ID NO 77
<211> LENGTH: 405
<212> TYPE: DNA
<213> ORGANISM: Homo sapien

<400> SEQUENCE: 77
actccatttg tggaactcgt gtcggagtct ggtaaacagc cgaatgtctt cctcccctac     60
agtttcctct ccttgcatga gagcagtgat gtcctgatta aaggcattaa ttttatctat    120
caggaagaac attttttcat tttcgtcttc cggtatgtcg acaccatact tttgtagctc    180
ctctgttatt ctctggtgag tctccttgat ttgattttct aacaggggca gagatttaca    240
```

```
gatatgtgtg atgagctcgc tggtaagttt ttctgccagg cagggaaccg tggcctttcc      300
ttcctccagc agatccctga aatatgggtg gttctcaaag aagatcttct ctctctgcag      360
ggcttcggac aggctcagct ggtcctggat ctcctgctgg ccccg                      405

<210> SEQ ID NO 78
<211> LENGTH: 410
<212> TYPE: DNA
<213> ORGANISM: Homo sapien
<220> FEATURE:
<221> NAME/KEY: misc_feature
<222> LOCATION: (1)...(410)
<223> OTHER INFORMATION: n = A,T,C or G

<400> SEQUENCE: 78
acagcagntn tagatggctg caacaacctt cctcctaccc cagcccagaa aatatttctg       60
ccccacccca ggatccggga ccaaaataaa gagcaagcag gccccccttca ctgaggtgct     120 gggtagggct cagtgccaca ttactgtgct ttgagaaaga ggaaggggat ttgtttggca     180
ctttaaaaat agaggagtaa gcaggactgg agaggccaga gaagatacca aaattggcag     240
ggagagacca tttggcgcca gtcccctagg agatgggagg agggagatag gtatgagggt     300
aggcgctaag aagagtagga ggggtccact ccaagtggca gggtgctgaa atgggctagg     360
accaacagga cactgactct aggtttatga cctgtccata cccgttccac              410

<210> SEQ ID NO 79
<211> LENGTH: 512
<212> TYPE: DNA
<213> ORGANISM: Homo sapien
<220> FEATURE:
<221> NAME/KEY: misc_feature
<222> LOCATION: (1)...(512)
<223> OTHER INFORMATION: n = A,T,C or G

<400> SEQUENCE: 79
acagtgaaaa acaaactaat ataaagcatt ccagnngata aaaacctcct caggcttatg       60
gtttgttttc caaggaaatt atgtttcaat gtaaagtttg aaatactcca gacatacatt     120
ccatgtaggt tttgggtgcc aatgttaaaa tttcaaattt tgcatgcaag gcttagcaaa     180
gaaacactgg cagaattcca gcatttgcaa aattctaagt tttggtgaat attgtaaata     240
ttacaattgg tattagaaag ccatgatgaa tccagaatta agagaaaacc catttcataa     300
atattttgtt tgattaaaaa ataccaggct taccatgttc taaataacac aagaaaatat     360 cttttaaaaaa aaaaggactg caatttaaca gtaatctgta tatctttagc tgccattaaa     420
aaaagaaaaa agaacaacca aaaacaatga aaatgttaca actggtataa agtnacccna     480
tgatgctccc cttacgagaa aacaaaactg tc                                    512

<210> SEQ ID NO 80
<211> LENGTH: 174
<212> TYPE: DNA
<213> ORGANISM: Homo sapien
<220> FEATURE:
<221> NAME/KEY: misc_feature
<222> LOCATION: (1)...(174)
<223> OTHER INFORMATION: n = A,T,C or G

<400> SEQUENCE: 80
tgattcccca gacctcaaat gggctaacac gcttctcttc tncagcagnc ttcctgtccg       60
tgaagntncc ttccagattg gtacatggaa ctgaaaacaa agggagcctc agctggattg     120
```
aaatctggag catgccacaa agncttgcac tnggcatttt cnagaagaac ccat      174

<210> SEQ ID NO 81
<211> LENGTH: 274
<212> TYPE: DNA
<213> ORGANISM: Homo sapien
<220> FEATURE:
<221> NAME/KEY: misc_feature
<222> LOCATION: (1)...(274)
<223> OTHER INFORMATION: n = A,T,C or G

<400> SEQUENCE: 81
ttgcaacaag cacattaaat taaggcctgc tngaatttct tcctccccaa tcaggtaaac      60
tttctttgcc aataaagttt gaggaggtgg catttgaaaa tctctttaaa aaagaagtct     120
tcatctattc acnagaaaac tcaaaaataa ttttcattat caacacacaa actaactcaa     180
tctctgcttt aagtttctat tggccaattt ttctgattna tacgagaatt attntcagnt     240
ntagaaaatc ctggtctttg gtcattacaa gntg                                 274

<210> SEQ ID NO 82
<211> LENGTH: 101
<212> TYPE: DNA
<213> ORGANISM: Homo sapien
<220> FEATURE:
<221> NAME/KEY: misc_feature
<222> LOCATION: (1)...(101)
<223> OTHER INFORMATION: n = A,T,C or G

<400> SEQUENCE: 82
atggagaaga tcgaacctga gcctnntgag aattgcctgc tacngcctgg cagccctgcc      60
cgagtggccc agcnncattt cacnagntgg gcatgatttg n                        101

<210> SEQ ID NO 83
<211> LENGTH: 182
<212> TYPE: DNA
<213> ORGANISM: Homo sapien

<400> SEQUENCE: 83
tattatgggg aaagataact gagaataaag ctatcatgca gatatttgca gagataaaag      60
taatgcagat actgagtgga gttttgatca aactatgctt gaaagccact ctaccactag     120
ttacacaaac caataatttc ccttcgcagt ggaagtcagc ttgagttttt tcaggtgttt     180
tt                                                                    182

<210> SEQ ID NO 84
<211> LENGTH: 229
<212> TYPE: DNA
<213> ORGANISM: Homo sapien
<220> FEATURE:
<221> NAME/KEY: misc_feature
<222> LOCATION: (1)...(229)
<223> OTHER INFORMATION: n = A,T,C or G

<400> SEQUENCE: 84
actgtttgta gctgcactac aacagattct taccgtctcc acaaaggtca gagattgtaa      60
atggtcaata ctgactttt ttttattccc ttgactcaag acagctaact tcattttcag     120
aactgtttta aacctttgtg tgctggttta taaaataatg tgngtaatcc ttgttgcttt     180
cctgatacca nactgtttcc cgnggttggt tagaatatat tnngttcng               229

<210> SEQ ID NO 85
<211> LENGTH: 500

```
<212> TYPE: DNA
<213> ORGANISM: Homo sapien
<220> FEATURE:
<221> NAME/KEY: misc_feature
<222> LOCATION: (1)...(500)
<223> OTHER INFORMATION: n = A,T,C or G

<400> SEQUENCE: 85
ggggagtang tgatttatta aagcaagacg ttgaaacctt tacnttctgc agtgaagatc        60
agggtgtcat tgaaagacag tggaaaccag gatgaaagtt tttacatgtc acacactaca      120
tttcttcaat attttcacca ggacttccgc aatgaggctt cgtttctgaa gggacatctg      180
atccgagcat ctcttcactc ctaacttggc tgcaacagct tccagagggg catcaaattt      240
ggcaagactt aacttgaaca gaggttcact aatgaagaag aagtctaaca gctcagaaac      300
aagagctggg cagaactcgg cattggcctg gtagcagcag agggccagcg tgaccagcag      360
gagacacacc gacagcttca tggtggcttg ttttgctgtg agctcagctt tcacaaacaa      420
tgagtgattt ggactccacc ccaggagcct gtggagctgc agagcccagg gctatttgta      480
cctgcccggg cggncgctcg                                                   500

<210> SEQ ID NO 86
<211> LENGTH: 323
<212> TYPE: DNA
<213> ORGANISM: Homo sapien
<220> FEATURE:
<221> NAME/KEY: misc_feature
<222> LOCATION: (1)...(323)
<223> OTHER INFORMATION: n = A,T,C or G

<400> SEQUENCE: 86
ccgccagtgt gctggaattc gcccttgccg cccgggcagg tactcagaag tcatttgtta       60
tttacaattg ggtttgtgtg ggatgggatn tanggcggat gagccagtgc ttttgcaatg      120
aagatgcaat antcattgtc ctctcccact gtctcctctt tcctcacccc atggcagctn      180
tcatgaccca ttcccaaagg gtccaccgag tcctgaactc agcttcatca ccaacattcc      240
tcgccttcag ttgaattcaa cactgncaan ggagnagang caaagacttg ggtcagggag      300
agggngggaa acacanaaca aac                                              323

<210> SEQ ID NO 87
<211> LENGTH: 230
<212> TYPE: DNA
<213> ORGANISM: Homo sapien

<400> SEQUENCE: 87
gcagcattga gccaccccct tggcaggcga tacggcagct ctgtgccctt ggccagcatg       60
tggagtggag gagatgctgc ccctgtggtt ggaacatcct ggggtgaccc ccgacccagc      120
ctcgctgggc tgtcccctgt ccctatctct cactctggac ccagggctga catcctaata      180
aaataactgt tggattagac aaaaaaaaaa aaaaaaaaa aaaaaaaagg                  230

<210> SEQ ID NO 88
<211> LENGTH: 249
<212> TYPE: DNA
<213> ORGANISM: Homo sapien
<220> FEATURE:
<221> NAME/KEY: misc_feature
<222> LOCATION: (1)...(249)
<223> OTHER INFORMATION: n = A,T,C or G

<400> SEQUENCE: 88
```

```
atgtgaccag gtctaggtct ggagtttcag nttggacact gagccaagca gacaagcaaa    60
gcaagccagg acacaccatc ctgccccagg cccagcttct ctcctgcctt ccaacgccat   120
ggggagcaat ctcagccccc aactctgcct gatgccettt atcttgggcc tcttgtctgg   180
aggtgtgacc accactccnt ggtctttggc ccggccccat ggatcctgct ctctggaggg   240 ggtntagat                                                          249
```

```
<210> SEQ ID NO 89
<211> LENGTH: 203
<212> TYPE: DNA
<213> ORGANISM: Homo sapien
<220> FEATURE:
<221> NAME/KEY: misc_feature
<222> LOCATION: (1)...(203)
<223> OTHER INFORMATION: n = A,T,C or G

<400> SEQUENCE: 89
tgtttacact gtcaaggatg acaaggaaag tgttcntatc tntgatacca tcatcccagc    60
tgttcctcct cccactgacc tgcgattcac caacattggt ccagacacca tgcgtgtcac   120
ctgggctcca cccccatcta ttgatttaac taacttcctg gtgcgnnact cacctgtgaa   180
aaatgangaa gatgttgcag agt                                          203
```

```
<210> SEQ ID NO 90
<211> LENGTH: 455
<212> TYPE: DNA
<213> ORGANISM: Homo sapien

<400> SEQUENCE: 90
ctctaagggg gctggcaaca tggctcagca ggcttgcccc agagccatgg caaagaatgg    60
acttgtaatt tgcatcctgg tgatcacctt actcctggac cagaccacca gccacacatc   120
cagattaaaa gccaggaagc acagcaaacg tcgagtgaga gacaaggatg gagatctgaa   180
gactcaaatt gaaaagctct ggacagaagt caatgccttg aaggaaattc aagccctgca   240
gacagtctgt ctccgaggca ctaaagttca caagaaatgc taccttgctt cagaaggttt   300
gaagcatttc catgaggcca atgaagactg catttccaaa ggaggaatcc tggttatccc   360
caggaactcc gacgaaatca acgccctcca agactatggt aaaaggagcc tgccaggtgt   420
caatgacttt tggctgggca tcaatgacat ggtca                             455
```

```
<210> SEQ ID NO 91
<211> LENGTH: 488
<212> TYPE: DNA
<213> ORGANISM: Homo sapien

<400> SEQUENCE: 91
actttgcttg ctcatatgca tgtagtcact ttataagtca ttgtatgtta ttatattccg    60
taggtagatg tgtaacctct tcaccttatt catggctgaa gtcacctctt ggttacagta   120
gcgtagcgtg gccgtgtgca tgtcctttgc gcctgtgacc accacccaa caaaccatcc    180 agtgacaaac catccagtgg aggtttgtcg ggcaccagcc agcgtagcag ggtcgggaaa   240
ggccacctgt cccactccta cgatacgcta ctataaagag aagacgaaat agtgacataa   300
tatattctat ttttatactc ttcctatttt tgtagtgacc tgtttatgag atgctggttt   360
tctacccaac ggccctgcag ccagctcacg tccaggttca acccacagct acttggtttg   420
tgttcttctt catattctaa aaccattcca tttccaagca ctttcagtcc aataggtgta   480
ggaaatag                                                           488
```

<210> SEQ ID NO 92
<211> LENGTH: 420
<212> TYPE: DNA
<213> ORGANISM: Homo sapien
<220> FEATURE:
<221> NAME/KEY: misc_feature
<222> LOCATION: (1)...(420)
<223> OTHER INFORMATION: n = A,T,C or G

<400> SEQUENCE: 92

```
tctccggcag gctctgcccc ggtcgtagcn agnnaaccta taatcctgac cttttttgta      60
gacaaccttg gtgctgaggt taactccatc cattgtagtg gcctgtatat caatgggacg     120
attgcatatt tttcctgggt gagctttcca gaggtctgaa attttctccc cacctttagt     180
ctgagatact ttatcatgat cganccactc cgtccactcc acgtnttgaa cccactcact     240
ggacaaagaa acattgaaat attcgccatg ctctgtctgg aacaatttga atacccgggc     300
agcagcagag cctcgatgnc caggatattc aatatggtct tccactgaag atgatggatt     360
tcctttcaca gntagaaaac ttncnagggn gtctaaatcc aaggtgcagg aagngngngc     420
```

<210> SEQ ID NO 93
<211> LENGTH: 241
<212> TYPE: DNA
<213> ORGANISM: Homo sapien
<220> FEATURE:
<221> NAME/KEY: misc_feature
<222> LOCATION: (1)...(241)
<223> OTHER INFORMATION: n = A,T,C or G

<400> SEQUENCE: 93

```
accacgaatt ncaacatcca gatccaccac tatcctaatg ggattgtaac tgngaactgt      60
gcccggctcc tgaaagccga ccaccatgca accaacgggg tggtgcacct catcgataag     120
gtcatctcca ccatcaccaa caacatccag cagatcattg agatcganga cacctttgag     180
acccttcggg ctgctgnggc tgcatcaggg ctcaacacga tgcttgaagg naacggncag     240
t                                                                    241
```

<210> SEQ ID NO 94
<211> LENGTH: 395
<212> TYPE: DNA
<213> ORGANISM: Homo sapien
<220> FEATURE:
<221> NAME/KEY: misc_feature
<222> LOCATION: (1)...(395)
<223> OTHER INFORMATION: n = A,T,C or G

<400> SEQUENCE: 94

```
actctattnt aattctgcct ttttatactt aattctaaat ttttcccctc taatttacaa      60
caaattttgt gatttttata agaatctatg cctccccaat tctcagattc ttctcttttc     120
tcctttattt ctttgcttaa attcagtata agctttcttg gtattttagg cttcatgcac     180
attcttattc ctaaacacca gcagttcttc agagacctaa aatccagtat aggaataact     240
gtgttagttc ttgaaaaagc attaaagaca ttttccctg aaacatacag aacatgtcat     300
gccaaatctc ttgtttacat aataaactgg taataccggt gaattgcaca tacagatttt     360
atctccaaga tagaataact taaatattaa aacgt                                395
```

<210> SEQ ID NO 95
<211> LENGTH: 304
<212> TYPE: DNA

```
<213> ORGANISM: Homo sapien
<220> FEATURE:
<221> NAME/KEY: misc_feature
<222> LOCATION: (1)...(304)
<223> OTHER INFORMATION: n = A,T,C or G

<400> SEQUENCE: 95
cgaggtacag tgatngctcc ccctgggcaa tacaatacaa gaacngnggg ttttgtcaaa     60
ttggaacaag gaaacagaac cacagaaata aatacattgg ttaacatcag attagttcag    120 gttactttt tgtaaaagtt aaagtacgag gggacttctg tattatgcta actcaagtan    180
actggaatct cctgttttct ttttttttt taaatnggtt ttaatttttt ttaattggat    240
ctatcttctt ccttaacatt tcagttggag tatgtagcat ttagcaccac tggctnaaac    300
ctgt                                                                 304

<210> SEQ ID NO 96
<211> LENGTH: 506
<212> TYPE: DNA
<213> ORGANISM: Homo sapien

<400> SEQUENCE: 96
acactgtcag cagggactgt aaacacagac agggtcaaag tgttttctct gaacacattg     60
agttggaatc actgtttaga acacacacac ttacttttc tggtctctac cactgctgat    120
attttctcta ggaaatatac ttttacaagt aacaaaata aaaactctta taaatttcta    180
tttttatctg agttacagaa atgattactg aggaagatta ctcagtaatt tgtttaaaaa    240
gtaataaaat tcaacaaaca tttgctgaat agctactata tgtcaagtgc tgtgcaaggt    300 attcactct gtaattgaat attattcctc aaaaaattgc acatagtaga acgctatctg    360
ggaagctatt tttttcagtt ttgatatttc tagcttatct acttccaaac taattttat    420 ttttgctgag actaatctta atcattttct ctaatatggc aaccattata accttaattt    480
attattaacc atacccctaag aagtac                                         506

<210> SEQ ID NO 97
<211> LENGTH: 241
<212> TYPE: DNA
<213> ORGANISM: Homo sapien
<220> FEATURE:
<221> NAME/KEY: misc_feature
<222> LOCATION: (1)...(241)
<223> OTHER INFORMATION: n = A,T,C or G

<400> SEQUENCE: 97
attttctttt taattacttt agagagctag ggatgcaaat gttttcagtt agaaagcctt     60
tatttacttt tggaaattga acaagaaatg catctgtctt agaaactgga gattatttga    120
tgttaggtaa aacatgtaat tgtntctctg gcaaatttgt atcantnatt ngaaaatgag    180
atattangaa aaaccaattc ttcttaaatc tagnncatct ttctttanaa gaacattana    240
t                                                                    241

<210> SEQ ID NO 98
<211> LENGTH: 79
<212> TYPE: DNA
<213> ORGANISM: Homo sapien
<220> FEATURE:
<221> NAME/KEY: misc_feature
<222> LOCATION: (1)...(79)
<223> OTHER INFORMATION: n = A,T,C or G

<400> SEQUENCE: 98
```

```
ggcaaacana cttatgctgn ancngggttt tancaaggtt ttcaaagnaa aaancccatt    60
ngactttatg gaaaatatt                                                79
```

<210> SEQ ID NO 99
<211> LENGTH: 316
<212> TYPE: DNA
<213> ORGANISM: Homo sapien
<220> FEATURE:
<221> NAME/KEY: misc_feature
<222> LOCATION: (1)...(316)
<223> OTHER INFORMATION: n = A,T,C or G

<400> SEQUENCE: 99

```
ccacatatgt aaaacccaga aagaccngnt tngcactttc actgagagtt gagtcatctg    60
ggctgtcnac aggtgtctga cgtgtaaact tggaatcaaa ctgacttaca tcctcttcag   120
attgcaacag aggtttaaag gggggctcca cctttcgagc cagaagttct tcccagttaa   180
tgtgtctaaa gaatggatga gcttgaactt ctccagcgtc cccaggacca gctcccagac   240
gagaagcagc atttcttttc agcagctttt taagcagatc tctggcttct tgngtgaggt   300
agggaggcaa attgag                                                   316
```

<210> SEQ ID NO 100
<211> LENGTH: 425
<212> TYPE: DNA
<213> ORGANISM: Homo sapien
<220> FEATURE:
<221> NAME/KEY: misc_feature
<222> LOCATION: (1)...(425)
<223> OTHER INFORMATION: n = A,T,C or G

<400> SEQUENCE: 100

```
accgctttca gaaagtttat atgggttatt cttcagcctc tcttttatgc ctttcgacct    60
ctgtttatca accccaaacc aattacgtat ctggaagtta tcaataccgt ggcacaggtc   120
acttttgaca ttttaattta ttactttttg ggaattaaat ccttagtcta catgttggca   180
gcatctttac ttggcctggg tttgcaccca atttctggac attttatagc tgagcattac   240
atgttcttaa agggncatga aacttactca tattatgggc ctctgaattt acttaccttc   300
aatgtgggtt atcataatga acatcatgat ttccccaaca ttcctggaaa agtcttccca   360
ctggtgagga aaatagcagc tgaatactat gacaacctgc ctcactacaa tttctggata   420
aaagg                                                               425
```

<210> SEQ ID NO 101
<211> LENGTH: 156
<212> TYPE: DNA
<213> ORGANISM: Homo sapien
<220> FEATURE:
<221> NAME/KEY: misc_feature
<222> LOCATION: (1)...(156)
<223> OTHER INFORMATION: n = A,T,C or G

<400> SEQUENCE: 101

```
actgacttgg gaatgtcaaa attctttatt atgatcttcc gagtgttgtc ctgagctttg    60
ttggccctca actgcaggca gagaaccagg agcagggtgg cagggctggc cctgaacagg   120
agctggagca agcgcatgct ngagaaaaca gaaggc                             156
```

<210> SEQ ID NO 102
<211> LENGTH: 230
<212> TYPE: DNA

```
<213> ORGANISM: Homo sapien
<220> FEATURE:
<221> NAME/KEY: misc_feature
<222> LOCATION: (1)...(230)
<223> OTHER INFORMATION: n = A,T,C or G

<400> SEQUENCE: 102
actccaggcc gggnctcagg ttatcaaaag tgcaggagct ctgatcagca tggaccactt    60
cttccaaaga atttccctgc tggccgtttg taggggttgt ggtaattcta taaccagtaa   120
tgtctggggt ggtgctcctc tcccaggaga ctgtgagcac tccagtgtca gggtttgcct   180
ccagatgcaa gntngtnggt ggagacaatg gtgncaccac tttgtnnaca              230

<210> SEQ ID NO 103
<211> LENGTH: 404
<212> TYPE: DNA
<213> ORGANISM: Homo sapien
<220> FEATURE:
<221> NAME/KEY: misc_feature
<222> LOCATION: (1)...(404)
<223> OTHER INFORMATION: n = A,T,C or G

<400> SEQUENCE: 103
actgtgaacc ctgnggnttc nangcgacct acctggagct ggccagtgct gtgaaggagc    60
agtatccggg catcgagatc gagtcgcgcc tcggggcac aggtgccttt gagatagaga    120
taaatggaca gctggtgttc tccaagctgg agaatggggg ctttccctat gagaaagatc   180
tcattgaggc catccgaaga gccagtaatg gagaaaccct agaaaagatc accaacagcc   240
gtcctccctg cgtcatcctg tgactgcaca ggactctggg ttcctgctct gttctggggt   300
ccaaaccttg gtctcccttt ggtcctgctg ggagctcccc ctgcctcttt cccctactta   360
gctccttagc aaagagaccc tggcctccac tttgcccttt gggt                    404

<210> SEQ ID NO 104
<211> LENGTH: 404
<212> TYPE: DNA
<213> ORGANISM: Homo sapien
<220> FEATURE:
<221> NAME/KEY: misc_feature
<222> LOCATION: (1)...(404)
<223> OTHER INFORMATION: n = A,T,C or G

<400> SEQUENCE: 104
accaggttat ataatagtat aacactgcca aggagcggat tatctcatct tcatcctgta    60
attccagtgt ttgtcacgtg gttgttgaat aaatgaataa agaatgagaa aaccagaagc   120
tctgatacat aatcataatg ataattattt caatgcacaa ctacgggtgg tgctgaacta   180
gaatctatat tttctgaaac tggctcctct aggatctact aatgatttaa atctaaaaga   240
tgaagttagt aaagcatcag aaaaaaaagt gggtattcct acaagtcagg acattctacg   300
tgactataat ataatctcac agaaatttaa cattaatacn ttctaagatt taattcttag   360
antctnggta aacaaagtag ctcctgtgga natgattggc atca                    404

<210> SEQ ID NO 105
<211> LENGTH: 325
<212> TYPE: DNA
<213> ORGANISM: Homo sapien
<220> FEATURE:
<221> NAME/KEY: misc_feature
<222> LOCATION: (1)...(325)
<223> OTHER INFORMATION: n = A,T,C or G

<400> SEQUENCE: 105
```

```
acagcagaag ccagtctang atggtgtgat tcaatttctg cctctagtat ttctttgtct      60 tgttttcct tcaatttaga agtgagcatt gtgttctcag ctatcagaac tttaagctgc      120
ccactatatt gagatgccct tttagctaat gattcctctt tcagttttag ggtcatctga     180
agttcagcat tcttttcttt taaaatctta atgtcctcaa agtatttatt ttccttttcc     240
tggtattggn gtttcagngt ggctatttcc agttttagca tggcaattnc cttttcaac     300 atgcaatttt catgtaagag ataat                                            325

<210> SEQ ID NO 106
<211> LENGTH: 444
<212> TYPE: DNA
<213> ORGANISM: Homo sapien
<220> FEATURE:
<221> NAME/KEY: misc_feature
<222> LOCATION: (1)...(444)
<223> OTHER INFORMATION: n = A,T,C or G

<400> SEQUENCE: 106
actgtcttca atnctatgcg tgcaggtgtc taccacaggc aaacagtttt ctccccattt     60
tgtagtaatg tgatttttcct attagcaaaa agaggtcacc agcccctgta gacttaaggg    120
actcaagtca caggatgggg atttcctctt aatatttttt atttngttgt ttgaactctt    180
gatgcaacat tgtagagcag ggtgttcagg acctgctgtg cccaagggac tgataaagga    240
aaaagctcta tttattcttt ttgtgatttg atgcacagat gaaaaactta acacacaata    300
acagaagttg gncgttaata aatcacatcc taggcttttca gcgcttncgt aagcagacga    360
catcttcagt tttctagctc ttgnagnttc aacacngnaa catcaatgat gcatatgtnc    420
agaatcagtt acaaagacca tccg                                            444

<210> SEQ ID NO 107
<211> LENGTH: 287
<212> TYPE: DNA
<213> ORGANISM: Homo sapien
<220> FEATURE:
<221> NAME/KEY: misc_feature
<222> LOCATION: (1)...(287)
<223> OTHER INFORMATION: n = A,T,C or G

<400> SEQUENCE: 107
acctgcactc gnacntcagg cantaggcct ccacgtcatg gccaggcact ggcatgggct    60
ccaccacgtg caggcagttg cagtccttct gggatacatt ctggttgtaa atgtgcccac    120
tgatgttcct ataaggtggg acagatgcat ttgcaccgga tatcttcana actcttgttg    180
gctncagctg ggggcaccaa caaacacccg accacagcca ccaaagataa nagcttcatg    240
cttatcangc ttgctgggcc agnaaagccg gacacctaca agcccnc                  287

<210> SEQ ID NO 108
<211> LENGTH: 478
<212> TYPE: DNA
<213> ORGANISM: Homo sapien

<400> SEQUENCE: 108
acatgtgcaa gaatttggaa aagcagggca ttttcccctca tctctcctag agggaatatc    60
acagcatctg tctctactgg tccacactgg actgcagaca atgtcaaaac tctggatttg    120
gaatgcggct gatttccttt cccctttaag gagttttcca agaatttcat aaccatcagt    180
tgttatattt ccagcttcct tgatgtcttt ttctataatt tcatagcagt caatgtaaat    240
```

```
cttaacacctt tttgaggtca ctacaatatg aaccttgtga aaacttccat aaaataatgt    300 cttttacttct tctgtgtcaa atgtaacagt ttgcacctcg cctcttgtat ccttgttaaa    360
gaatgataac gtcttgctag aaggatctgc aatcactcca acttgtggtt tgtagtctct    420
gtctgtgatt tgccaaattg caaaagggtc actgggagtt tctgggagaa gtctgaat     478

<210> SEQ ID NO 109
<211> LENGTH: 361
<212> TYPE: DNA
<213> ORGANISM: Homo sapien
<220> FEATURE:
<221> NAME/KEY: misc_feature
<222> LOCATION: (1)...(361)
<223> OTHER INFORMATION: n = A,T,C or G

<400> SEQUENCE: 109
gaatttttct tctanaataa gtattctgtt gacacagact attggtaaga ttttcaacat     60
aaggtaatgc taggactggc ctcctagcat gagttgtgag taaagatctg gtctgttgtt    120
tctccaaaag aagnttctta ctgcttgtct ctcatgagtt ttctgtttct gctttctctt    180
tttcatattg atatatacgg ntttttaaat ggtnattgta attaaatatc tcctcatttt    240
tctcttttag gagatgatgt tgcattttcc tctcaagaaa atgaatatca attgttatct    300
tgcttttgnt gncagctttc ttatgtgcat gaactaattg ctgttgaagc cacatatttt    360
t                                                                    361

<210> SEQ ID NO 110
<211> LENGTH: 305
<212> TYPE: DNA
<213> ORGANISM: Homo sapien
<220> FEATURE:
<221> NAME/KEY: misc_feature
<222> LOCATION: (1)...(305)
<223> OTHER INFORMATION: n = A,T,C or G

<400> SEQUENCE: 110
acataatgac tnncanagtg aagctgattg gctgcggttc tggagtaaat ataagctctc     60
cgttcctggg aatccgcact acttgagtca cgtgcctggc ctaccaaatn cttgccaaaa    120
ctatgtgcct tatcccacct tnnaatctgn ctcctcattt ntcagctgtt ggatcagaca    180
atgacattcc tntagatntg gcgatcaagc attccanacc tgngccaact gcaaacggtg    240
cctncaagga gaaaacgaag gcnccaccaa atgnaaaaaa tgaangnccc ttgaatgtac    300
taaaa                                                                305

<210> SEQ ID NO 111
<211> LENGTH: 371
<212> TYPE: DNA
<213> ORGANISM: Homo sapien
<220> FEATURE:
<221> NAME/KEY: misc_feature
<222> LOCATION: (1)...(371)
<223> OTHER INFORMATION: n = A,T,C or G

<400> SEQUENCE: 111
cgggggccag ccgggggtat tcagccatcg atcaaactca aaacctggaa tgatatccac     60 tctcttttc ttaagctcag ggaaatattc caagtagaag tccagaaagt catcggctaa    120
gatgcttcgg aatttgaatt catgcacata ggccttgaga aaactgtcaa actgatcctg    180
atcacccacc aagtgggcca ggtatgagac aaagcagaaa cctttctcgt agggggtctc    240
attataggtg tcgtccgggt caacgcctgg ttcaatcttc acgcggagct tgttgagtgg    300
```

```
gttttcctct ccagtgatgt ccatgtgctg acgcagcaga ncccgccccg ttgcagcctc    360
caagcaggng t                                                         371

<210> SEQ ID NO 112
<211> LENGTH: 460
<212> TYPE: DNA
<213> ORGANISM: Homo sapien
<220> FEATURE:
<221> NAME/KEY: misc_feature
<222> LOCATION: (1)...(460)
<223> OTHER INFORMATION: n = A,T,C or G

<400> SEQUENCE: 112
acatcttagg tttttnttcc tttantgtga agaggcgttt ccaccaaccc acagctctgc     60
gtcgagtttt tactagattg ctgcaaattt catggaatct ttgctgttgt tcagtggtcc    120
atttattgga gccaaaaatt ctagggcgct agaatgggaa caaggtagtc agccaagcac    180
aaaaacataa caaaacagga aacgccggac agaacagatg gatctagata gtagataatc    240
agaaacacca agaaaccac acccatgatg gcaggtggaa accaggctct ttctcatcgg     300
aggactttat cagccatcag catcacttct ccccatcctt gcagctgttc ttccagactt    360
gcagtctctg cagccagcag gttgggtgct gcgattacct ccctccgcca tcgtctcggg    420
gatgcagtct ctacaagcgc aggccacctc cccaacgagt                          460

<210> SEQ ID NO 113
<211> LENGTH: 204
<212> TYPE: DNA
<213> ORGANISM: Homo sapien

<400> SEQUENCE: 113
gagaagacag cagagctgct ttccgcctct ttgagaccaa gatcacccaa gtcctgcact     60
tcaccaagga tgtcaaggcc gctgctaatc agatgcgcaa cttcctggtt cgagcctcct    120
gccgccttag cttggaacct gggaaagaat atttgatcat gggtctagat ggggccacct    180
atgacctcga gggacacccc cagt                                           204

<210> SEQ ID NO 114
<211> LENGTH: 137
<212> TYPE: DNA
<213> ORGANISM: Homo sapien
<220> FEATURE:
<221> NAME/KEY: misc_feature
<222> LOCATION: (1)...(137)
<223> OTHER INFORMATION: n = A,T,C or G

<400> SEQUENCE: 114
accgcaagaa atgggacagc aacgtcattg agactttga catcgnccgc tngacagtca      60
acgctgacgt gggctattac tcctggaggt gtcccaagcc cctgaagaac cgtgatgtca    120
tcaccctccg ntccctg                                                   137

<210> SEQ ID NO 115
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 115
```

```
gcgggcggct ttntggactc gctcatttac agagcatgcg tggtcttcac ccttggcatg    60
ttctccgccg gcctctcgga cctcaggcac atgcgaatga cccggagtgt ggacaacgtc   120
cagntcctgc cctttctcac cacggangtc aacaacctgg gctggctgan ttatggggct   180
ttgaagggag acgggatcct catcgtcanc aacacagtgg gtgctgcgct tcanaccctg   240
tatatctttg gcatatctgc attactgccc tcggaagc                          278
```

<210> SEQ ID NO 116
<211> LENGTH: 178
<212> TYPE: DNA
<213> ORGANISM: Homo sapien
<220> FEATURE:
<221> NAME/KEY: misc_feature
<222> LOCATION: (1)...(178)
<223> OTHER INFORMATION: n = A,T,C or G

<400> SEQUENCE: 116

```
acaccgtcat angtcaaaag tncagtgctg gccatcttgc atcaaatgtt cttaaggcag    60
tgactggcta tcaaccacag nttctgtctc cccagntgca aacacaggat ccatgcaac   120 gttctgagac catacactta gaaaccacng ggagatgcgg atcanatgca naactnnc    178
```

<210> SEQ ID NO 117
<211> LENGTH: 360
<212> TYPE: DNA
<213> ORGANISM: Homo sapien
<220> FEATURE:
<221> NAME/KEY: misc_feature
<222> LOCATION: (1)...(360)
<223> OTHER INFORMATION: n = A,T,C or G

<400> SEQUENCE: 117

```
actccccaat ggnggattta ttactattaa agaaaccagg gaaaatatta attttaatat    60
tataacaacc tgaaaataat ggaaaagagg ttttttgaatt ttttttttaa ataaacacct   120
tcttaagtgc atgagatggt tgatggtttt gctgcattaa aggtatttgg gcaaacaaaa   180
ttggagggca agtgactgca gttttgagaa tcagttttga ccttgatgat ttttgtttc   240 cactgtggaa ataaatgttt gtaaataagt gtaataaaaa tccctttgca ttctttctgg   300
accttaaatg gtagaggaaa aggctcgtga gccatttgtt tcttttgctg gttatagttg   360
```

<210> SEQ ID NO 118
<211> LENGTH: 125
<212> TYPE: DNA
<213> ORGANISM: Homo sapien
<220> FEATURE:
<221> NAME/KEY: misc_feature
<222> LOCATION: (1)...(125)
<223> OTHER INFORMATION: n = A,T,C or G

<400> SEQUENCE: 118

```
gcgtcgtgct atgaccggac ttngtcttga aaggggatga cagcatggga ggcaatggnt    60
ncacatgtaa accccacact gaaagacaag gcactctctc cacagcagcc ccaacaacta   120
gccct                                                              125
```

<210> SEQ ID NO 119
<211> LENGTH: 490
<212> TYPE: DNA
<213> ORGANISM: Homo sapien
<220> FEATURE:
<221> NAME/KEY: misc_feature
<222> LOCATION: (1)...(490)
<223> OTHER INFORMATION: n = A,T,C or G

<400> SEQUENCE: 119

```
nacaaagaaa agcaaaaaga atttacgaag attgtgatct cttattaaat caattgttac      60
tgatcatgaa tgttagttag aaaatgttag gttttaactt aaanaaaatn gtattgngat     120
tttcaatntt atgttgaaat cngngtaata tcctgangtt nttttccccc cagaagataa     180
agaggataga caacctctta aaatattttt acaatttaat ganaaaaagn ttaaaattct     240
caatacnaat caaacaattt aaatatttta agaaaaaagg aaaagtagat agtgatactg     300
agggtaaaaa aaaattgatt caattttatg gtaaaggaaa cccatgcaat tttacctaga     360
cagccttaaa tatgtctggt tttccatctg ctagcatttc agacatttta tgttcctctt     420
actcaattga taccaacaga aatatcaact tctggagtct attanatgtg ttgtcacctt     480
tctnaagctt                                                            490
```

<210> SEQ ID NO 120
<211> LENGTH: 361
<212> TYPE: DNA
<213> ORGANISM: Homo sapien
<220> FEATURE:
<221> NAME/KEY: misc_feature
<222> LOCATION: (1)...(361)
<223> OTHER INFORMATION: n = A,T,C or G

<400> SEQUENCE: 120

```
caggtacagt aaaattaaca cttccgttac aggaaatgta tgacgcaaat aatataaaat      60
taaaaggtga aaaaaaggtg acactggttt cctaagatac aatttactct ttacaaccag     120
ggtccacagg tccaggctgc anagcgggca tcaggaagca gagcctncca cctgcttctg     180
ggggacctgg taataaaaat cagcccatga tggcgctatg gcctctcaga cacccacgc     240
tgcctaaaca cctagagctc tggaaatagt caacaggaga gtgatttcca tgggggaaat     300
tttaaanaag atgcacatgg gacaggcaat agaaagtttg ccaaggntaa atttggtacc     360
t                                                                     361
```

<210> SEQ ID NO 121
<211> LENGTH: 405
<212> TYPE: DNA
<213> ORGANISM: Homo sapien
<220> FEATURE:
<221> NAME/KEY: misc_feature
<222> LOCATION: (1)...(405)
<223> OTHER INFORMATION: n = A,T,C or G

<400> SEQUENCE: 121

```
acacaaaacc ttttnacata ttgggggctt accgctccaa attgctactg atcctttaag      60
ttcacaatat agaatttctt caccaattaa gtaataaccc tcattacaaa taaagtgcat     120
ctgataacca aactcgtaag tcccatttgc agggactgct tggccatta aaggatcccg      180
tatatatgga catgtttctc tataacaggc gtcatctgag acaggtagcc atgtatgatt     240
ccgatcacaa atagtatggg tggcaagagg aggtatatag aagtatcctt ttttacactt     300
ataatctact cgttcaccaa tctcatagta gggttttggt ttaccaatga gcctccatan     360
cttcaaatgt tgggtggctn ctcacaggca tcnggcanaa ngagt                     405
```

<210> SEQ ID NO 122
<211> LENGTH: 152
<212> TYPE: DNA
<213> ORGANISM: Homo sapien
<220> FEATURE:

```
<221> NAME/KEY: misc_feature
<222> LOCATION: (1)...(152)
<223> OTHER INFORMATION: n = A,T,C or G

<400> SEQUENCE: 122
accccgctcc gttgncacag atcgctgtct gcccactcca tcggccattc acttggcagg      60
tgcgattggc agagccccgg agagtgtaac cgtcatagca gtggaaagag atctcatcac    120
tcacattgta gtagggagac cggggccaan ta                                  152

<210> SEQ ID NO 123
<211> LENGTH: 336
<212> TYPE: DNA
<213> ORGANISM: Homo sapien

<400> SEQUENCE: 123
acatctgaca tatttatata gcacataaat tagggagtgc tctgacccct gcccgtggag     60
cccaagcact gagcagggag gtgaacgcca gtccagaaag aaggtgctgg agccccctgct  120 ctgtcctctc catcacgggg ctcccctagg gcctccccag gcctccttgg ctcagtccag    180
gtgtctgcag gaggaaggtg ttgtctgcat ttagtgtctg agactgggtt tgaggaggca    240
ccagataaaa ggagatacac ttgcagctat aaagtcagct tcaaacccca gggcttgtaa    300
ttccaagagg agggtgggga ggcgaggcca tagtct                               336

<210> SEQ ID NO 124
<211> LENGTH: 253
<212> TYPE: DNA
<213> ORGANISM: Homo sapien
<220> FEATURE:
<221> NAME/KEY: misc_feature
<222> LOCATION: (1)...(253)
<223> OTHER INFORMATION: n = A,T,C or G

<400> SEQUENCE: 124
ctgcaagagc ccagatcacc cattccgggt tcactccccg cctccccaag tcagcagtcc     60 tagcccccaaa ccagcccaga gcagggtctc tctaaagggg acttgagggc ctgagcagga  120
aagactggcc ctctagcttc taccctttgt ccctgtagcc tatacagttt agaatattta    180
tttgttaatt ttattaaaat gctttaaaaa aacaaaaaaa aaaaaaaaaa aaaaaaaaaa    240
aaaaaagntt gtn                                                         253

<210> SEQ ID NO 125
<211> LENGTH: 522
<212> TYPE: DNA
<213> ORGANISM: Homo sapien

<400> SEQUENCE: 125
acaactgcaa gtctaagata atgttcattc attcccatca taaatgtaac attctaaata     60
ggtgtcttct gatgtcatct gtcagaattt cttttaaact ttttcttcat cttcaacatt    120
atcaaagttc atccttattc ctcttgcctt gatttcggag agtttccaat ttttcactta    180
ttaaggcagc gattgctttt gcatctctgg tatttatctg ctcttcttga aaatttctct    240
ttgctctttc gtagaaataa aacttaacag ttggataggc cctgatccca gctttctggc    300
atgtctgagc ataagcctga cagtctactt ttccagcttt cacttttcct ttaatcatcc    360
tagccaagag ctcaaattct ggagcaaaat tctggcaagg tccacaccaa ggagcataga    420
aatcaatcac ccaatgattt ttcccttgta gaacttttc actgaaagtc tgaggtgtta    480
gatctgtgga tacttgaggt aaaaatccta gaccccagat tc                       522
```

<210> SEQ ID NO 126
<211> LENGTH: 374
<212> TYPE: DNA
<213> ORGANISM: Homo sapien
<220> FEATURE:
<221> NAME/KEY: misc_feature
<222> LOCATION: (1)...(374)
<223> OTHER INFORMATION: n = A,T,C or G

<400> SEQUENCE: 126

```
tttttaagat attaacttta cctttataaa tctttgtgtg aaatgaaaaa aaaaatcaag      60
gcatacaaat ttcattgtgt tctacatttt taaataccat cctttgtctc cgttaaaaga    120
ttttcatcca tttattcaaa aaccttttaa gttcaactgt ccaatttaag acagagtgaa    180
gacattttg agtatctgaa ctaagcattg tcttgactga aacgaagtaa gaactcaatg     240
agagtccttg tgggcctccc aggcatgcct ttccgtagat agggaacttc atctttgttg    300
gncatcacgc ctgctatgtc taaatgtgcc cacttaggat gagttacgaa ttcttttcagg   360
aatgctgcag ctgt                                                     374
```

<210> SEQ ID NO 127
<211> LENGTH: 130
<212> TYPE: DNA
<213> ORGANISM: Homo sapien
<220> FEATURE:
<221> NAME/KEY: misc_feature
<222> LOCATION: (1)...(130)
<223> OTHER INFORMATION: n = A,T,C or G

<400> SEQUENCE: 127

```
aaagccaaga cngccattgg cactgctatg gtaaggncac agggcancca gggccttctg     60
gcaaaaggng atacnaccag cactatnaac agacaggaca tggttgagag gnagnctaca   120
caantcctaa                                                          130
```

<210> SEQ ID NO 128
<211> LENGTH: 350
<212> TYPE: DNA
<213> ORGANISM: Homo sapien
<220> FEATURE:
<221> NAME/KEY: misc_feature
<222> LOCATION: (1)...(350)
<223> OTHER INFORMATION: n = A,T,C or G

<400> SEQUENCE: 128

```
acactgattt ccgntnaaaa gaancatcat ctttaccttg acttttcagg gaattactga     60
actttcttct cagaagatag ggcacagcca ttgccttggc ctcacttgaa gggtctgcat    120
ttgggtcctc tggtctcttg ccaagnttcc cagccactcg agggagaaat atcgggaggt    180
ttgacttcct ccggggcttt cccgagggct tcaccgtgag ccctgcggcc tcagggctg     240
caatcctgga ttcaatgtct gaaacctcgc tctctgcctg ctggacttct gaggccgtca    300
ctgccactct gtcctccagc tctgacagct cctcatctgt ggcctgttga               350
```

<210> SEQ ID NO 129
<211> LENGTH: 505
<212> TYPE: DNA
<213> ORGANISM: Homo sapien
<220> FEATURE:
<221> NAME/KEY: misc_feature
<222> LOCATION: (1)...(505)
<223> OTHER INFORMATION: n = A,T,C or G

```
<400> SEQUENCE: 129
acaataccaa agcttcataa tgctaaagaa aaccaaaaca aaagacaatg gtttacacag      60
ggaaataacc ctaaggcaat atgaaaacag tcataattta ttactgataa agagtaaagg     120
catccttccc atagagggg ggaattcaca gggaacacta attatatcag atgaaccacg      180
gggatagaaa ataggcccat ttttaaaatt cattgagaaa ttattacttt ttctccacaa     240
ctgtgattct atacaaaata taaaccctgc aaaccttatg tgctacctga cagataaaag    300
tagcaggagc cagactcttg aagcacttga gactgatttc tacaaagtcc aggaagagca    360
atgattccag tgtgcagtgc tgatgcatgt gtgagcctaa catgttattc agctctggtt    420
gcagccccat ctacatgggg cccagttagt ttttagggag tcacagatta ngcaggcaac    480
cgaggggcat gatttaaaaa gcaca                                           505

<210> SEQ ID NO 130
<211> LENGTH: 526
<212> TYPE: DNA
<213> ORGANISM: Homo sapien

<400> SEQUENCE: 130 acaaagagc ctgattcttt ttaattccac aaatacctag catctcaaag taacatgtaa      60
acaaacttct atgctgctca atgaatcctt ccaatttcga taataaacta atagtattg     120 gatctagtat atgactttca tgtgtaagtt atggttctat ccattacttt aacaatatta    180
ctgatgtaac agagaaaaat tttcaactat tgtacttatt taaaacaaac tgacaagttc    240
aagcacctgt cttcagaaaa gccagcagca ttttttttttt tttaacatac tcaaagtaag  300
atttggccta agcccttaat acctttctga acagccatgc aactaaacac cctcaggaga    360
tgttacataa gggagagaag aacatggagc aatttgcact ttttcccta gataatatta    420 acaaggtaaa gcaaatccag atctttatga atgaatggct gtcatgttta atacacttgg   480
agctctataa aactagagcc actatcatat atgtttatat agatat                   526

<210> SEQ ID NO 131
<211> LENGTH: 477
<212> TYPE: DNA
<213> ORGANISM: Homo sapien

<400> SEQUENCE: 131
ctcagttttc ccagcaacag atgctcctga gcaatttatt agtcaagtga cggtgctgaa     60 atactttct cattacatgg aggagaacct catggatggt ggagatctgc ctagtgttac    120
tgatattcga agacctcggc tctacctcct tcagtggcta aaatctgata aggccctaat   180
gatgctcttt aatgatggca cctttcaggt gaatttctac catgatcata caaaaatcat   240
catctgtagc caaaatgaag aataccttct cacctacatc aatgaggata ggatatctac   300
aactttcagg ctgacaactc tgctgatgtc tggctgttca tcagaattaa aaaattgaat   360
ggaatatgcc ctgaacatgc tcttacaaag atgtaactga aagacttttc gaatggaccc  420
tatgggactc ctctttttcca ctgtgagatc tacagggaac ccaaaagaat gatctag     477

<210> SEQ ID NO 132
<211> LENGTH: 404
<212> TYPE: DNA
<213> ORGANISM: Homo sapien
<220> FEATURE:
<221> NAME/KEY: misc_feature
<222> LOCATION: (1)...(404)
<223> OTHER INFORMATION: n = A,T,C or G
```

<400> SEQUENCE: 132

```
accacacgan cgggnatcnt ttgnacatag tgagacccgg ctgattccca tacatgaatc    60
cattcatgga gtgcatttta ttagatncct gaaagtcttc atcttcctta tccacctgat   120
caggngcagt tgtaaacatn cctaatatta tcttccagga gtaaactctc attctcatca   180
aatactgtag gaaacaaata gaattccttg tctacatctt tctgtctccc atttgcatat   240
aaacttcctt tcttgcatat tttcattggc ccaataagcc cagtgaatat atctttagtg   300
ggatccacag cagaataata catcttagct agacacacag ggatctgcat tacgngggtc   360
ctacttcttt ggggacagcc cttcatacgn gaatgttttnt gtgg                   404
```

<210> SEQ ID NO 133
<211> LENGTH: 552
<212> TYPE: DNA
<213> ORGANISM: Homo sapien
<220> FEATURE:
<221> NAME/KEY: misc_feature
<222> LOCATION: (1)...(552)
<223> OTHER INFORMATION: n = A,T,C or G

<400> SEQUENCE: 133

```
accccaaatt atctctctcc tgaagtcctc aacaaacaag gacatggctg tgaatcagac    60
atttgggccc tgggctgtgt aatgtataca atgttactag ggaggccccc atttgaaact   120
acaaatctca agaaacttta taggtgcata agggaagcaa ggtatacaat gccgtcctca   180
ttgctggctc ctgccaagca cttaattgct agtatgttgt ccaaaaaccc agaggatcgt   240
cccagtttgg atgacatcat tcgacatgac tttttttgc agggcttcac tccggacaga   300
ctgtcttcta gctgttgtca tacagttcca gatttccact tatcaagccc agctaagaat   360
ttctttaaga aagcagctgc tgctctttt ggtggcaaaa aagacaaagc aagatatatt   420
gacacacata atagagtgtc taaagaagat gaagacatct acaagcttag gcatgatttg   480
aaaaagactt caataactca gcaacccagc aaacacaggg acagatgang agctccacca   540
cctaccacca ca                                                       552
```

<210> SEQ ID NO 134
<211> LENGTH: 496
<212> TYPE: DNA
<213> ORGANISM: Homo sapien

<400> SEQUENCE: 134

```
acattgatgg gctggagagc agggtggcag cctgttctgc acagaaccaa gaattacaga    60
aaaaagtcca ggagctggag aggcacaaca tctccttggt agctcagctc cgccagctgc   120
agacgctaat tgctcaaact tccaacaaag ctgcccagac cagcacttgt gttttgattc   180
ttctttttc cctggctctc atcatcctgc ccagcttcag tccattccag agtcgaccag   240
aagctgggtc tgaggattac cagcctcacg gagtgacttc cagaaatatc ctgacccaca   300
aggacgtaac agaaaatctg gagacccaag tggtagagtc cagactgacg gagccacctg   360
gagccaagga tgcaaatggc tcaacaagga cactgcttga gaagatggga gggaagccaa   420
gacccagtgg gcgcatccgg tccgtgctgc atgcagatga gatgtgagct ggaacagacc   480
ttttctgggc cacttt                                                   496
```

<210> SEQ ID NO 135
<211> LENGTH: 560
<212> TYPE: DNA

<213> ORGANISM: Homo sapien

<400> SEQUENCE: 135

```
actgggagtg atcactaaca ccatagtaat gtctaatatt cacaggcaga tctgcttggg      60
gaagctagtt atgtgaaagg caaatagagt catacagtag ctcaaaaggc aaccataatt     120
ctctttggtg caggtcttgg gagcgtgatc tagattacac tgcaccattc ccaagttaat     180
cccctgaaaa cttactctca actggagcaa atgaactttg gtcccaaata tccatctttt     240
cagtagcgtt aattatgctc tgtttccaac tgcatttcct ttccaattga attaaagtgt     300
ggcctcgttt ttagtcattt aaaattgttt tctaagtaat tgctgcctct attatggcac     360
ttcaattttg cactgtcttt tgagattcaa gaaaaatttc tattctttttt tttgcatcca     420
attgtgcctg aacttttaaa atatgtaaat gctgccatgt tccaaaccca tcgtcaagtg     480
tgtgtgttta gagctgtgca ccctagaaac aacatattgc ccatgagcag gtgcctgaac     540
acagacccct ttgcattcac                                                 560
```

<210> SEQ ID NO 136
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 136

```
accagcaaat ctccattagc atttctcagg tttcatgatc cttttcagat atgttggttg      60
attttatgta tatattgctt agaaacaaaa atccacctga tattaaaaca aaccaaaaaa     120
aatcataaaa gcaagcaaat gaacaaaaaa ccctagtttt gttgtgcttt tctttcacat     180
ttcctacagg gagatttgta tatctcagat acttttcaaaa tctaataggt aagtaaaatt     240
agtgccttaa ccaaacagta agataccaaa gaatcctcca tcacaagtta ctgaatcaaa     300
cttctcatga catttgcggt atattcagat ttgaagattt tttaaattta gaatttaaaa     360
caaactttag actgctgatt ttccatattt caaagactgt agctgtntgc agcatataaa     420
tgga                                                                  424
```

<210> SEQ ID NO 137
<211> LENGTH: 392
<212> TYPE: DNA
<213> ORGANISM: Homo sapien
<220> FEATURE:
<221> NAME/KEY: misc_feature
<222> LOCATION: (1)...(392)
<223> OTHER INFORMATION: n = A,T,C or G

<400> SEQUENCE: 137

```
tgcggggntg aaggctagca aaccgagcga tcatgtcgca caaacaaatt tactattcgg      60
acaaatacga cgacgaggag tttgagtatc gacatgtcat gctgcccaag gacatagcca     120
agctgggccc taaaacccat ctgatgtctg aatctgaatg gaggaatctt ggcgatcagc     180
anagtcaggg atgggtccat tatatgatcc atgaaccaga acctcacatc ttgctgttcc     240
ggcgcccact acccaagaaa ccaaagaaat gaagctggca agctactttt cancctcaag     300
ctttacacag ctgnccttac ttcctaacat cttttctgata acattattat gctgccttcc     360
tgttctcact ctganatnta aaagatgttc aa                                   392
```

<210> SEQ ID NO 138
<211> LENGTH: 284
<212> TYPE: DNA
<213> ORGANISM: Homo sapiens
<220> FEATURE:
<221> NAME/KEY: misc_feature
<222> LOCATION: (1)...(284)
<223> OTHER INFORMATION: n = A,T,C or G

<400> SEQUENCE: 138

```
tgcctgtgca cctctttgct tgaaatatgg caagacttgg aaaaatgttt gcccttagaa      60
tctatctcac tactttagtt agttgtctcc tttgggcctg gcacagttc tggccctgat      120 ctggaacaga ctccctttc taaaactgaa cttgaccaca tcaaaagntt gnaaaacaat      180
ctccatggta attaaacttg cattcaacac catatggnaa cagaagatgg caggaggata      240
anatncagat cttatgatct ttccangnan ggcatgttac atga                      284
```

<210> SEQ ID NO 139
<211> LENGTH: 249
<212> TYPE: DNA
<213> ORGANISM: Homo sapiens
<220> FEATURE:
<221> NAME/KEY: misc_feature
<222> LOCATION: (1)...(249)
<223> OTHER INFORMATION: n = A,T,C or G

<400> SEQUENCE: 139

```
gaggaagggg ggactgaatc tancaccntg acngaactag agacagccat gggcatgatc      60
atagacnnct ttacccgata ntcgggcagc gagggcagca cgcagaccct gaccaagggg     120
gagctcaagg ggctgatgga gaaggagcta ccaggcttcc ngcagagngg aaaanacaag     180
gangccgtgg ataaattgct caaggaccta dacgccnatg gaggatgccc aggtggactc     240 cagcgagnt                                                              249
```

<210> SEQ ID NO 140
<211> LENGTH: 390
<212> TYPE: DNA
<213> ORGANISM: Homo sapiens
<220> FEATURE:
<221> NAME/KEY: misc_feature
<222> LOCATION: (1)...(390)
<223> OTHER INFORMATION: n = A,T,C or G

<400> SEQUENCE: 140

```
tcataatggt tggggcagct ataatnnact acaanaatca natgtttcac atctagacct      60
cgggcagcaa cagaggtagc cacaagaagt ttgcangtcc cattcttaaa gtcatttatg     120
atgctatctc tgtcatattg atcaatgcct ccatgaagag acatgcaagg ataagatgct     180
ctcattaaat ccttaagaag accatcagca tgttcctgct tatccacaaa tataatgaca     240
gatcctgact cttgataatg gcctagaagc tcaagtaact tcaagaattt cttttcttct     300
tcaatcacaa tcacttgtng ctccacatct gagcaaacca cactcctgcc tccaacttgt     360
acctgccccg ggcgggcgct caagggcgaa                                       390
```

<210> SEQ ID NO 141
<211> LENGTH: 420
<212> TYPE: DNA
<213> ORGANISM: Homo sapiens
<220> FEATURE:
<221> NAME/KEY: misc_feature
<222> LOCATION: (1)...(420)
<223> OTHER INFORMATION: n = A,T,C or G

<400> SEQUENCE: 141

```
gacactcagg gaaaagcatn ngncaaanag agcttaaaat gcatcgccaa cggggtcacc      60
tccaaggtct tcctcgccat tcggaggtgc tccactttcc aaaggatgat tgctgaggtg     120
caggaagagt gctacagcaa gctgaatgtg cgcancatcg ccaagcggaa cccngaagcc     180
atcactgagg tcgtgcagct gcccaatcac ttctccaaca natactataa cagacttgnn     240
cgaagcctgc tggaatgnga tgaanacaca gggcagcaca atcaggagac agcctgatgg     300
anaaaantgg gcctancatg gccaggcctc ttccacatcc tngcangaca gaccactgtg     360
cccaaacaca cccnctgagc tgacttnnac aggagacgca cnaaggagcc cggcagangc     420
```

<210> SEQ ID NO 142
<211> LENGTH: 371
<212> TYPE: DNA
<213> ORGANISM: Homo sapiens

<400> SEQUENCE: 142

```
gggttcgaca atgctgatcc gcaattagaa gacactggta agctgtgtta cactgggctt      60
cattgaaatc ttcaaggata tagccagctc ctgctcgaag ctgggattct gtatactgct     120
tgttgaaagg aggaatttcc aaaaattcct cctcttcttc actgcttcct gtaggaccat     180
ctggcagttt ggagcggctg gccaacttgt cactggttgt ggccatggta aggagaaatg     240
cgtagcccag aaacaaggtc ttgttgagag gcaaaggccc tctctgctct tccagggcag     300
agggttcacc ggtgttgtct ccactctcac aggggctcac aaactctcct gccccctactt     360 gcaccaggtt t                                                          371
```

<210> SEQ ID NO 143
<211> LENGTH: 270
<212> TYPE: DNA
<213> ORGANISM: Homo sapiens
<220> FEATURE:
<221> NAME/KEY: misc_feature
<222> LOCATION: (1)...(270)
<223> OTHER INFORMATION: n = A,T,C or G

<400> SEQUENCE: 143

```
ggtggctgtg atnacctttn ttagtttaca aataaaaaag ntaaaagaa atactgtgtt       60 tagggtaagg taacannttc atctaatcag aggagagtga agangaggcn ctgccttcta     120
ggngctgtga ccttctcctt ttcgngattc ttcnccacct tgggnaacat cttccccgct     180
atgctggaan tacttcggng ttctgcggtg gccatgntga acatctgatg aactgaaant     240
ncatccnaat gcacacgaag anatagncna                                      270
```

<210> SEQ ID NO 144
<211> LENGTH: 259
<212> TYPE: DNA
<213> ORGANISM: Homo sapiens
<220> FEATURE:
<221> NAME/KEY: misc_feature
<222> LOCATION: (1)...(259)
<223> OTHER INFORMATION: n = A,T,C or G

<400> SEQUENCE: 144

```
ttctctttgc tttttataat tttaaagnaa ataacacatt taactgtatt taagtctgtg      60
caaataatcc ttcagaagaa atatccaaga ttctgtttgc agaggtcatt ttgtctctca     120
aagatgatta aatgagtttg tcttcagata aagtgctcct gtccagnaga actcaaaagg     180
ccttcaagct gttcagtaag tgtaggttca gataagactc cgncatacga attccagctt     240
```

```
cccgtgccca ctgtacctc                                                    259

<210> SEQ ID NO 145
<211> LENGTH: 433
<212> TYPE: DNA
<213> ORGANISM: Homo sapiens
<220> FEATURE:
<221> NAME/KEY: misc_feature
<222> LOCATION: (1)...(433)
<223> OTHER INFORMATION: n = A,T,C or G

<400> SEQUENCE: 145
accacatnta ccatagtgta attagttttta attttcacat gaatcaaagg tttcctttca       60
tgtctattta cagtccaatt gtgccaaact cttacttgtg tgctgactaa caaggcattt      120
aggtgtgcag catcctagag tgctccaggg cagtgtcagc gttctcggga gtaaaaggtg      180
ccacttggta gcaatgatat tccagaatta aatgggtttt gttgccatg gagactgcat       240 ttatataaat gtagcctgta gcttaagtta actaaaccta atgctgctgt taaaaacagt     300
ttattttaat attaaaatac agttgattag caacagcggt gctgtatttt aagagacact      360
ttattggaag tgcaatcata gttatttgtt ttcacaattt tacagngcat tctaattact      420
gatgggtgca att                                                          433

<210> SEQ ID NO 146
<211> LENGTH: 576
<212> TYPE: DNA
<213> ORGANISM: Homo sapiens

<400> SEQUENCE: 146
acctcaggcc tgtgcacctc tttgcttgaa atatggcaag acttggaaaa atgtttgccc       60
ttagaatcta tctcactact ttagttagtt gtctcctttg ggcctgggca cagttctggc      120
cctgatctgg aacagactcc ttttctaaa actggaccttt gaccacatca aaagtttgta     180
aaacaatctc catggtaatt aaacttgcat tcaacaccat atggtaacag aagatggcaa      240
aggataagat tcagatctta gatctttcca gtagggcat gttagatgat agaaggatta       300
gttgcaagct ggatctgagc tcaggcttgg gcatgaagga aactgtctcc catgtggttt      360
ggaagagtta ggggctccct gagctctatt gtgaactata cgggtttcat ccaaggaatg     420
gtatgatgtg ggcataaaac cattcttcag acaactgaag atggtcccct tctgtagcca     480
gaaacactag ctgtcctgca ttgccatttc ctttacccca gcggcctgc agaaggaaag       540 gccataatta attaaaaggc ttaatgaagt tttgga                                576

<210> SEQ ID NO 147
<211> LENGTH: 300
<212> TYPE: DNA
<213> ORGANISM: Homo sapiens

<400> SEQUENCE: 147
ccagccccca ggaggaaggt gggtctgaat ctagcaccat gacggaacta gagacagcca       60
tgggcatgat catagacgtc tttacccgat attcgggcag cgagggcagc acgcagaccc      120
tgaccaaggg ggagctcaag gtgcttatgg agaaaggagc taccaggctt ctgcagagtg      180
gaaaagacaa ggatgccgtg gataaattgc tcaaggacct agacgccaat ggagatgccc      240
aggtggactt cagtgagttc atcgtgttcg tggctgcaat cacgtctgcc tgtcacaagt      300

<210> SEQ ID NO 148
```

```
<211> LENGTH: 371
<212> TYPE: DNA
<213> ORGANISM: Homo sapiens

<400> SEQUENCE: 148
acataatcct cataatggtt ggggcagcta taatttacta caagaatcag atgtttcaca        60
tctagacctc gggcagcaac agaggtagcc acaagaagtt tgcaggtccc attcttaaag       120
tcatttatga tgctatctct gtcatattga tcaaatggcc tccatgaaga gacatgcaag       180
gataagatgc tctcattaaa tccttaagaa gaccatcagc atgttcctgc ttatccacaa       240
atataatgac agatcctgac tcttgataat ggcctagaag ctcaagtaac ttcaagaatt       300
tcttttcttc ttcaatcaca atcacttgtt gctccacatc tgagcaaacc acactcctgc       360
ctccaacttg t                                                            371

<210> SEQ ID NO 149
<211> LENGTH: 585
<212> TYPE: DNA
<213> ORGANISM: Homo sapiens
<220> FEATURE:
<221> NAME/KEY: misc_feature
<222> LOCATION: (1)...(585)
<223> OTHER INFORMATION: n=A,T,C or G

<400> SEQUENCE: 149
cgaggtacan cactgctaaa tttgacactn anggaaaagc attcgtcaaa gagagcttaa        60
aatgcatcgc caacggggtc acctccaagg tcttcctcgc cattcggagg tgctccactt       120
tccaaaggat gattgctgag gtgcaggaag agtgctacag caagctgaat gtgtgcagca       180
tcgccaagcg gaaccctgaa gccatcactg aggtcgtcca gctgcccaat cacttctcca       240
acagatacta taacagactt gtccgaagcc tgctggaatg tgatgaagac acagtcagca       300
caatcagaga cagcctgatg gagaaaattg ggcctaacat ggccagcctc ttccacatcc       360
tgcagacaga ccactgtgcc caaacacacc cacgagctga cttcaacagg agacgcacca       420
atgagccgca gaagctgaaa gtcctcctca ggaacctccg aggtgaggag gactctccct       480
cccacatcaa acgcacatcc catgagagtg cataaccagg gagaggntat tcacaacctc       540
ccaaactagt atcattttag ggggngttga cacaccagtt ttgag                      585

<210> SEQ ID NO 150
<211> LENGTH: 642
<212> TYPE: DNA
<213> ORGANISM: Homo sapiens
<220> FEATURE:
<221> NAME/KEY: misc_feature
<222> LOCATION: (1)...(642)
<223> OTHER INFORMATION: n=A,T,C or G

<400> SEQUENCE: 150
acttncgggt tcgacaatgc tgatccgcaa ttagaagaca ctggtaagct gtgttacact        60
gggcttcatt gaaatcttca aggatatagc cagctcctgc tcgaagctgg gattctgtat       120
actgcttgtt gaaaggagga atttccaaaa attcctcctc ttcttcactg cttcctgtag       180
gaccatctgg cagtttggag cggctggcca acttgtcact ggttgtggcc atggtaagga       240
gaaatgcgta gcccagaaac aaggtcttgt tgagaggcaa aggccctctc tgctcttcca       300
gggcagaggg ttcaccggtg ttgtctccac tctcacaggg gctcacaaac tctcctgccc       360
ctactgcacc aggttttact gtggcagact tgcgacctcg cttggcaggg gaccgttcct       420
cttcagaagt gataagtttt cttttgcctg agagaactcc catggaggca cgaggacttt       480
```

```
ctgtgatctt tcgggtaggg gttgtgctgc tactggaggc agtanggggtg gctggggagc    540 tgacgttact gcgccgtttc cgcttccttc caccaaattg ctaagctgat atctgctgcc    600
tttgtaagaa gnggtactgc ttcatanggg ccaagcccat ac                       642
```

<210> SEQ ID NO 151
<211> LENGTH: 322
<212> TYPE: DNA
<213> ORGANISM: Homo sapiens
<220> FEATURE:
<221> NAME/KEY: misc_feature
<222> LOCATION: (1)...(322)
<223> OTHER INFORMATION: n=A,T,C or G

<400> SEQUENCE: 151

```
nttggacaac atcttccccg ctatgctgga attacttcgg tgttctgcgg tggccatggt     60
gaacatctga tgaactgaaa ttccatcgga atgcacagga agatatagtt gatcttcaaa    120
aatgtccttt ccaggaccac catactgggg aagttctttc gggtgcctgc naatgggctg    180
caccctgggg ctgggcccga gctctagctc tgtcatgcca tcgccactga atcggttttn    240
cagatgatta gtctcttcat gccccgtcca ttttttcggtt tttctccagt gttcagaaat    300
tcaaatgatt aacttctggg aa                                             322
```

<210> SEQ ID NO 152
<211> LENGTH: 262
<212> TYPE: DNA
<213> ORGANISM: Homo sapiens

<400> SEQUENCE: 152

```
acaaagtctt ctctttgctt tttataattt taaagcaaat aacacattta actgtattta     60
agtctgtgca aataatcctt cagaagaaat atccaagatt ctgtttgcag aggtcatttt    120
gtctctcaaa gatgattaaa tgagtttgtc tttagaataa agtgctcctg tccagcagaa    180
ctcaaaaggc cttcaagctg ttcagtaagt gtagttcaga taagactccg tcatacgaat    240
tccagcttcc cgtgcccact gt                                             262
```

<210> SEQ ID NO 153
<211> LENGTH: 284
<212> TYPE: DNA
<213> ORGANISM: Homo sapiens
<220> FEATURE:
<221> NAME/KEY: misc_feature
<222> LOCATION: (1)
<223> OTHER INFORMATION: n=A,T,C or G

<400> SEQUENCE: 153

```
ctcgggagta aaaggtgcca cttggtagca atgatattcc agaattaaat gggttttttgt     60 tgccatggag actgcattta tataaatgta gcctgtagct taagttaact aaacctaatg    120
ctgctgttaa aaacagttta ttttaatatt aaaatacagt tgattagcaa cagcggtgct    180
gtattttaag agacacttta ttggaagtgc aatcatagtt atttgttttc acaattttac    240
ngtgcattct aattactgat gggngcaatt acttttaatc gngg                     284
```

<210> SEQ ID NO 154
<211> LENGTH: 531
<212> TYPE: DNA
<213> ORGANISM: Homo sapiens
<220> FEATURE:
<221> NAME/KEY: misc_feature
<222> LOCATION: (1)...(531)

<223> OTHER INFORMATION: n=A,T,C or G

<400> SEQUENCE: 154

| | |
|---|---|
| acccaccta aatttgaact cttatcaaga ggctgatgaa tctgaccatc aaataggata | 60 |
| ggatggacct ttttttgagt tcattgtata aacaaatttt ctgatttgga cttaattccc | 120 |
| aaaggattag gtctactcct gctcattcac tctttcaaag ctctgtccac tctaactttt | 180 |
| ctccagtgtc atagataggg aattgctcac tgcgtgccta gtctttcttc acttacctgg | 240 |
| cctctgatag aaacagttgc ccctctcatt tcataaggtc gaggacttgt gaccctggat | 300 |
| ggttctaaat ggaaaagca ccgccagatt gtgaaacctg gcttcaacat cagcattctg | 360 |
| aaaatattca tcaccatgat gtctgagagt gttcggatga tgctgaacaa atgggaggaa | 420 |
| cacattgccc aaaactcacg tctggagctc tttcaacatg tctccctgat gaccctggac | 480 |
| agcatcatga agtgtgcctt cagccaccag ggcagcatcc agttngacag t | 531 |

<210> SEQ ID NO 155
<211> LENGTH: 353
<212> TYPE: DNA
<213> ORGANISM: Homo sapiens
<220> FEATURE:
<221> NAME/KEY: misc_feature
<222> LOCATION: (1)...(353)
<223> OTHER INFORMATION: n=A,T,C or G

<400> SEQUENCE: 155

| | |
|---|---|
| tcttgacaag actgagagag ttacatgttg ggaaaaaaaa agaagcatta acttagtaga | 60 |
| actgaaccag gagcattaag ttctgaaatt ttgaatcatc tctgaaatga agcaggtgta | 120 |
| gcctgccctc tcatcaatcc gtctgggtgc cagaactcaa ggttcagtgg acacatcccc | 180 |
| ctgttagaga ccctcatggg ctaggacttt tcatctagga tagattcaag acctttacct | 240 |
| canaattatg taaactgtga ttgtgtttta gaaaaattat tatttgctaa aaccatttaa | 300 |
| gtctttgtat atgtgtaaat gatcacaaaa atgtatttta taaaatgttc tgt | 353 |

<210> SEQ ID NO 156
<211> LENGTH: 169
<212> TYPE: DNA
<213> ORGANISM: Homo sapiens

<400> SEQUENCE: 156

| | |
|---|---|
| agtttgttct actacatttg tggtccacta gttcactttg ctgtgttgat aagcgttacc | 60 |
| accaattgca ctttctatag cctctttac aatgttgctc acttcatcaa caacaaaagc | 120 |
| agtctcctcc gcagcctggt agtcttccat cttttcctccg gcgcgtccc | 169 |

<210> SEQ ID NO 157
<211> LENGTH: 402
<212> TYPE: DNA
<213> ORGANISM: Homo sapiens
<220> FEATURE:
<221> NAME/KEY: misc_feature
<222> LOCATION: (1)...(402)
<223> OTHER INFORMATION: n=A,T,C or G

<400> SEQUENCE: 157

| | |
|---|---|
| gttaactacc cgctccgaga cgggattgat gacgagtcct atgaggccat tttcaagccg | 60 |
| gtcatgtcca agtaatgga gatgttccag cctagtgcgg tggtcttaca gtgtggctca | 120 |
| gactccctat ctggggatcg gttaggntgc tttaatctac tatcaaagga cacgccaagt | 180 |
| gtgtggaatt tgtcaagagc tttaacctgc ctatgctgat gctgggaggc ggtggttaca | 240 |

```
ccattcgtaa cgttgcccgg tgctggacat atgagacagc tgtggccctg gatacggaga      300
tccctaatga gcttccatac aatgactact ttgaatactt tggaccagat ttcaagctcc      360
acatcagtcc ttccaacatg actaaccaga acacgaatga gt                         402
```

<210> SEQ ID NO 158
<211> LENGTH: 546
<212> TYPE: DNA
<213> ORGANISM: Homo sapiens

<400> SEQUENCE: 158

```
actttgggct ccagacttca ctgtccttag gcattgaaac catcacctgg tttgcattct       60
tcatgactga ggttaactta aaacaaaaat ggtaggaaag cttttcctatg cttcgggtaa     120 gagacaaatt tgcttttgta gaattggtgg ctgagaaagg cagacagggc ctgattaaag     180
aagacatttg tcaccactag ccaccaagtt aagttgtgga acccaaaggt gacggccatg     240
gaaacgtaga tcatcagctc tgctaagtag ttaggggaag aaacatattc aaaccagtct     300
ccaaatggat cctgtggtta cagtgaatga ccactcctgc tttattttc ctgagattgc      360 cgagaataac atggcactta tactgatggg cagatgacca gatgaacatc atcatcccaa     420
gaatatggaa ccaccgtgct tgcatcaata gattttccc tgttatgtag gcattcctgc      480
catccattgg cacttggctc agcacagtta ggccaacaag gacataatag acaagtccaa     540
aacagt                                                                546
```

<210> SEQ ID NO 159
<211> LENGTH: 145
<212> TYPE: DNA
<213> ORGANISM: Homo sapiens
<220> FEATURE:
<221> NAME/KEY: misc_feature
<222> LOCATION: (1)...(145)
<223> OTHER INFORMATION: n=A,T,C or G

<400> SEQUENCE: 159

```
acttttgcta taagtttcct aaaaatattt aatactttt ttttcaatt taaattaaat        60 ctnttgatga acagggggg gntggcaaaa tttccaagcn ctggactgga attttganan      120
aggcatttac ngaccctnat aactt                                            145
```

<210> SEQ ID NO 160
<211> LENGTH: 405
<212> TYPE: DNA
<213> ORGANISM: Homo sapiens

<400> SEQUENCE: 160

```
tgtaaatcgc tgtttggatt tcctgatttt ataacagggc ggctggttaa tatctcacac       60
agtttaaaaa atcagcccct aatttctcca tgtttacact tcaatctgca ggcttcttaa     120
agtgacagta tcccttaacc tgccaccagt gtcccccctc cggccccgt cttgtaaaaa      180 ggggaggaga attagccaaa cactgtaagc ttttaagaaa aacaaagttt taaacgaaat     240
actgctctgt ccagaggctt taaaactggt gcaattacag caaaaaggga ttctgtagct     300
ttaacttgta aaccacatct ttttgcact ttttttataa gcaaaaacgt gccgtttaaa      360
ccactggatc tatctaaatg ccgatttgag ttcgcgacac tatgt                      405
```

<210> SEQ ID NO 161
<211> LENGTH: 443
<212> TYPE: DNA

```
<213> ORGANISM: Homo sapiens
<220> FEATURE:
<221> NAME/KEY: misc_feature
<222> LOCATION: (1)...(443)
<223> OTHER INFORMATION: n=A,T,C or G

<400> SEQUENCE: 161 tttgcttta  atgaaggaca  agggattaag  acncatagag  actggccana  caaatgggaa      60
accgaccaga  ccagcccatg  accaaaatat  cacaggcaga  ccacccacaa  atgcagaggc     120
ctcagagtcc  acagtgggcg  gttggaaccc  agggccccag  ggaatctttc  agctgcattc     180
cggctgtgat  cggcgggcaa  caggtagagg  tgctggaggg  ggctgagtcg  tgattttcgg     240
tgtctgtcat  attcgatcaa  gtgtgtcata  gagcttcctg  tttcatctcc  cagttattca     300
aggagaggct  ggtggctcca  ccttcccagg  aactgtgctg  tgaagatctg  aagacaggca     360
cgggctcagg  caccgcttgt  ctggaatgtc  aatttgaaac  ttaaaaagca  gcgaccatcc     420
agtcatttat  ttccctccat  tcc                                                443

<210> SEQ ID NO 162
<211> LENGTH: 228
<212> TYPE: DNA
<213> ORGANISM: Homo sapiens
<220> FEATURE:
<221> NAME/KEY: misc_feature
<222> LOCATION: (1)...(228)
<223> OTHER INFORMATION: n=A,T,C or G

<400> SEQUENCE: 162
tcgttatcaa  aatggaagac  accaaaccat  tactggcttc  taagctgaca  gaaaaggagg      60
aagaaatcgt  ggactagtgg  agtaaatttt  atgcttnctc  aggggaacat  gaaaaatgcg     120
gacagtatat  tcagaaaggc  tattccnagc  tcaagatata  tnattgtgaa  ctanaaaata     180
tagcanaatt  tgagggcctg  acagacttct  canatacntt  caagttgt                   228

<210> SEQ ID NO 163
<211> LENGTH: 580
<212> TYPE: DNA
<213> ORGANISM: Homo sapiens
<220> FEATURE:
<221> NAME/KEY: misc_feature
<222> LOCATION: (1)...(580)
<223> OTHER INFORMATION: n=A,T,C or G

<400> SEQUENCE: 163
acccaaggct  acacatcctt  ctgtgaaaca  gtctcacgga  gactctcaga  atcccaagaa      60
ttttcttcaa  ccttcttttg  ttttgattct  gaagggaaca  tctgatctgc  tctcaatgtt     120
tgttcattct  tcaattccaa  ggctttattt  ggaacagact  ttgcatttca  atggcaggct     180
cgaaggcaga  tggcttctcg  ggaggctctg  ctttgaaagt  ttgcntgtcc  atcaattcta     240
aggctttagn  tggaatagaa  actttcattc  tgcagggagc  cttcagaaaa  ccatcattat     300
caggagactc  ttctaatttt  ccatttattt  tatctatttc  ttttgatgc   gcagccttgg     360
gtanacacac  atccttctgt  gaaacagtct  cacagagact  ctcagaatcc  caagaacttt     420
cttcatagtc  cttttgtttg  gattctgatg  ggagtatctc  atctgctctc  aatgtttgtt     480
cattcttcaa  ttccaaggct  ttatttggaa  cagacttttg  catttcaatg  gcaggctcga     540
aggcagatgg  cttctcggga  ggctctgctt  tgaaaagttg                             580

<210> SEQ ID NO 164
<211> LENGTH: 140
```

```
<212> TYPE: DNA
<213> ORGANISM: Homo sapiens
<220> FEATURE:
<221> NAME/KEY: misc_feature
<222> LOCATION: (1)...(140)
<223> OTHER INFORMATION: n=A,T,C or G

<400> SEQUENCE: 164
acttatatct tttggncttg ggcttctcaa agttcacgac agacataggc actctcacag    60
tatcaagccc atttaccgnc acctcacacc aatactcgcc ccaccgngng ataggntctg   120
ctggnaactt taatgnatgn                                              140

<210> SEQ ID NO 165
<211> LENGTH: 370
<212> TYPE: DNA
<213> ORGANISM: Homo sapiens
<220> FEATURE:
<221> NAME/KEY: misc_feature
<222> LOCATION: (1)...(370)
<223> OTHER INFORMATION: n=A,T,C or G

<400> SEQUENCE: 165
acatggagcc actgccacca gtggtgatgg aaagcactgc cttcttactc cggaagggtc    60
ctttgtcata catggcagcg taagtgtaag caaactctcc tatgaacact cgctcaaacc   120
agcctttcag aatggcaggg actccaaacc actgcnnggg ggaactggaa atcacaagg    180 tctgcggctt ccagcttctt ttgttcagcc acaatatctg gctcanatg gncttcttta   240 taagccagaa cagactcggn aggatactga aagttcgcag ggnccttcan tttacctgng   300 atgnccttn tggaaatgat gggattgaag ntcatggnat aaaggnccga ctncaccacc   360
tccattcttt                                                         370

<210> SEQ ID NO 166
<211> LENGTH: 258
<212> TYPE: DNA
<213> ORGANISM: Homo sapiens

<400> SEQUENCE: 166
gtcaaaagtc atgatttta tcttagttct tcattactgc attgaaaagg aaaacctgtc    60
tgagaaaatg cctgacagtt taatttaaaa ctatggtgta agtctttgac aagaaaaaaa   120
aacaaacaaa cacttctttc catcagtaac actggcaatc ttcctgttaa ccactctcct   180
tagggatggt atctgaaaca acaatggtca ccctcttgag attcgtttta agtgtaattc   240
cataatgagc agaggtgt                                                258

<210> SEQ ID NO 167
<211> LENGTH: 345
<212> TYPE: DNA
<213> ORGANISM: Homo sapiens
<220> FEATURE:
<221> NAME/KEY: misc_feature
<222> LOCATION: (1)...(345)
<223> OTHER INFORMATION: n=A,T,C or G

<400> SEQUENCE: 167
ggtcagccaa acacccagga tctctgtaaa actgaagaac aggncaatgc caccaacaaa    60
tctcaaaacc tctccagcat attctcctat gattggagca catggngagc acnantggtc   120
acttttaaca canctagcca gacaggngnc atttgggtta acacttcgga acccacagca   180 ntttananntt ctctggatgt catttcgagc acttgtattt attggtcann tttctgtatc   240
```

```
tngcgcttgg ttagccctga accaggagca acagggncag cttctggagg ntggttggaa        300
caatacggca agtgntngaa atgacatcca acctncngaa atgac                        345

<210> SEQ ID NO 168
<211> LENGTH: 61
<212> TYPE: DNA
<213> ORGANISM: Homo sapiens

<400> SEQUENCE: 168
gatagtgtgg tttatggact gaggtcaaaa tctaagaagt ttcgcagacc tgacatccag        60
t                                                                        61

<210> SEQ ID NO 169
<211> LENGTH: 344
<212> TYPE: DNA
<213> ORGANISM: Homo sapiens

<400> SEQUENCE: 169
acattggtgc tataaatata aatgctactt atgaagcatg aaattaagct tcttttttct        60
tcaagttttt tctcttgtct agcaatctgt taggcttctg aaccaagacc aaatgtttac       120
gttcctctgc tgcataccaa cgttactcca acaataaaaa aatctatcat ttctgctctg       180
tgctgaggaa tggaaaatga aacccccacc ccctgacccc taggactata cagtggaaac       240
tgttcattgc tgatgaatgc agcagtcacc aaaaaataca cccaatcttc cagataaccct      300 cagtgcactt taggaaatca aaaattaccct ggaagcaatt tagt                       344

<210> SEQ ID NO 170
<211> LENGTH: 114
<212> TYPE: DNA
<213> ORGANISM: Homo sapiens

<400> SEQUENCE: 170
agcagtgtgt cctccatgaa taaacaggag ttctggaggc ccatcttctg catcttctgc        60
tgattgttct tccccaattt tacttaaatc ccacacattc aggcggcggt cagt             114

<210> SEQ ID NO 171
<211> LENGTH: 150
<212> TYPE: DNA
<213> ORGANISM: Homo sapiens
<220> FEATURE:
<221> NAME/KEY: misc_feature
<222> LOCATION: (1)...(150)
<223> OTHER INFORMATION: n=A,T,C or G

<400> SEQUENCE: 171
actgagagca tttataatct gaccaaattc ataggcatta ttaggcttgg ctatcggaag        60
tttctcaggg tcttctggng acctgctgct tttgcctccc ttctcanaag caaggcatcc       120
catggagacc tccctgcag ggcttccagg                                         150

<210> SEQ ID NO 172
<211> LENGTH: 435
<212> TYPE: DNA
<213> ORGANISM: Homo sapiens
<220> FEATURE:
<221> NAME/KEY: misc_feature
<222> LOCATION: (1)...(435)
<223> OTHER INFORMATION: n=A,T,C or G

<400> SEQUENCE: 172
atttgttttc cactgcctca cactagtgag ctgtgccaag tagtagtgtg acacctgtgt        60
```

```
tgtcatttcc cacatcacgt aagagcttcc aaggaaagcc aaatcccaga tgagtctcag    120
agagggatca atatgtccat gattatcttc tggtttaggt ctacagtcaa tgtgatggtg    180
gtctttgctt cccagtctgc cagaatatct ttgtgcttct ctaatcattg gctttaaagc    240
taatcaatgt gttggcagca tctctgtcac tcttgtttaa cacgtgaaga aatcaggtag    300
atttttttct gtggcattgt tttcggacct aaaatcaggt atgctgacta tttccaaggg    360 gttttcagt tgcttcattt gcttgtaaag cagggaatcc tcttgntgct tttcttttc    420 tcgatgagcc cgtgt    435

<210> SEQ ID NO 173
<211> LENGTH: 622
<212> TYPE: DNA
<213> ORGANISM: Homo sapiens
<220> FEATURE:
<221> NAME/KEY: misc_feature
<222> LOCATION: (1)...(622)
<223> OTHER INFORMATION: n=A,T,C or G

<400> SEQUENCE: 173
actgntttcc cccaagtcca tgacatgtat acataattaa tggtttgcct ccttgattgt    60
tttctccaac atccagacat agaggctgac caacgctttt aatgtatcca gatataacag    120
gattaaggtc tggcacatac acctctggat aaatgttgtt cagataccat gtaaaatttt    180
tacactgaag gcggtgtttt atttcaaatc tttttgaaag atcaccaaat gcttttgtt    240 taacaatttt tgctgcatct gtatttctcc tataaaatat ttccttgtat tcatccatcc    300
agacttctgc aaggcgaact tggtttctag caatcacctg agtgccttt ggaaagctat    360 gagggctttt gctgcgaaaa acatgtccaa caacagagca aggcataatc tccaactgcc    420
caccacattg ccatactctg aaagacattt ctatattttc acctcccag atttccattt    480 cttcatcata gcttccaata tactcaaaat attcttttga tatggaaaaa agtcctcctg    540
caaaagtggg tgttttaatt gggtagggtt catctttcct tctttgcttc tcatgatcag    600
gaagcgactt ccacccaatg aa    622

<210> SEQ ID NO 174
<211> LENGTH: 362
<212> TYPE: DNA
<213> ORGANISM: Homo sapiens

<400> SEQUENCE: 174
acggtgcagt tgacccactg ttggctctcc ttgcagttcc tgatatgtca tctttagcat    60
gtggctactt acgtaatctt acctggacac tttctaatct ttgccgcaac aagaatcctg    120 caccccgat agatgctgtt gagcagattc ttcctacctt agttcagctc ctgcatcatg    180
atgatccaga agtgttagca gatacctgct gggctatttc ctaccttact gatggtccaa    240
atgaacgaat tggcatggtg gtgaaaacag gagttgtgcc ccaacttgtg aagcttctag    300
gagcttctga attgccaatt gtgactcctg ccctaagagc catagggaat attgtcactg    360
gt    362

<210> SEQ ID NO 175
<211> LENGTH: 486
<212> TYPE: DNA
<213> ORGANISM: Homo sapiens
<220> FEATURE:
<221> NAME/KEY: misc_feature
<222> LOCATION: (1)...(486)
```

<223> OTHER INFORMATION: n=A,T,C or G

<400> SEQUENCE: 175

```
acagntnctc tactacactc agcctcttat gtgccaagtt tttctttaag caatgagaaa      60
ttgctcatgt tcttcatctt ctcaaatcat cagaggccga agaaaaacac tttggctgtg     120
tctaaaactt gacacagtca atagaatgaa gaaaattaga gtagttatgt gattatttca     180
gctcttgacc tgtcccctct ggctgcctct gagtctgaat ctcccaaaga gagaaaccaa     240
tttctaagag gactggattg cagaagactc ggggacaaca tttgatccaa gatcttaaat     300
gttatattga taaccatgct cagcaatgag ctattagatt cattttggga aatctccata     360
atttcaattt gtaaactttg ttaagacctg tctacattgt tatatgtgtg tgacttgagt     420
aatgttatca acgttttgt aaatatttac tatgttttc tattagctaa attccaacaa      480
ttttgt                                                                486
```

<210> SEQ ID NO 176
<211> LENGTH: 461
<212> TYPE: DNA
<213> ORGANISM: Homo sapiens

<400> SEQUENCE: 176

```
accctggcca ctcctttcct tttggctggc caatgtctcc tctgtaggct ccagaaggct      60
ctcagggatg caggcggcct cctgcagggt tgagttgcaa tgggaacaaa gacagctgtg    120
gtcccatagc accctcatct ggtgacatcc tgctactgac agtcaaaaga agccttccca    180
gatgaaattt tagtcctctg cgcagccatg ctcttcttcc agcaaaagag ccatgtgcag    240
tcgggtctgc tccccatggg ggctttgatg tgggcccagc agtggatcag ccttccagac    300
acgctcaact ctgcacactc ttcctgccgc ctcaggcttt ccaggaccct cccgagcctt    360
atcagagtcc ttaccctcag ggctactgat accttgctgg gtgaccttgg acagattcac    420
ttacctggac tcagtttcat aatatgaaaa tgatagggtt g                         461
```

<210> SEQ ID NO 177
<211> LENGTH: 234
<212> TYPE: DNA
<213> ORGANISM: Homo sapiens

<400> SEQUENCE: 177

```
acacattttg taattacctt ttttgttgtt ttgtagcaac catttgtaaa acattccaaa      60
taattccaca gtcctgaagc agcaatcgaa tcccttctc acttttggaa ggtgactttt     120
caccttaatg catattcccc tctccataga ggagaggaaa aggtgtaggc ctgccttacc    180
gagagccaaa cagagcccag ggagactccg ctgtgggaaa cctcattgtt ctgt          234
```

<210> SEQ ID NO 178
<211> LENGTH: 657
<212> TYPE: DNA
<213> ORGANISM: Homo sapiens
<220> FEATURE:
<221> NAME/KEY: misc_feature
<222> LOCATION: (1)...(657)
<223> OTHER INFORMATION: n=A,T,C or G

<400> SEQUENCE: 178

```
gagctcggan ccctagtaac ggccgccagg gtgctggnat ngcccttgc gagcgngncg      60
cccgggcagg nactttnatc cccctcatc ttcctgtagc tcatttgtnt ctctcatttt    120
ttggcatatt tttcaagtca cacttaaaaa ctcttccatg tattcacttc tcatcacttg    180
```

```
gtctacatgc cgaacctaag gtcaggattc caaaaagatg agtatcctct caaacgcctc    240
ctaagcctct ggtatacatg actttggctg tgcacttcat ttagacttca ccttttttgtt   300 tgctgttgtt ttttacacta gattcctttg tcttcattaa agataatgaa agattcacat    360
cacagtgcag ctcttcgctt tgtcctttcg taagtccgta gcaactgccg agagttctgg    420
tctgctaggc atgtgtgaaa tccgctttgt ggctctctgt gatttgttcc gcttaacgtt    480
tttatttgtc ttatttacac atgccaaggt ggcaacgtga aaaatgtctc tgacgctatt    540
ttccgactgt aaagctgagc attcgatata agtagctgct ccaatctgtt tggccatact    600 tgcccctgg  tcataggaca ctggcgtctg cctgtgattg gagagctcta ctaatgt       657
```

<210> SEQ ID NO 179
<211> LENGTH: 182
<212> TYPE: DNA
<213> ORGANISM: Homo sapiens
<220> FEATURE:
<221> NAME/KEY: misc_feature
<222> LOCATION: (1)...(182)
<223> OTHER INFORMATION: n=A,T,C or G

<400> SEQUENCE: 179

```
acaaaanctt ttaaattttta tattattttg aaactttgct ttgggtttgt ggcaccctgg    60
ccaccccatc tggctgtgac agcctctgca gtccgtgggc tggcagtttg ttgatcttt    120 aagtttcctt ccctacccag tccccatttt ctggtaaggt ttctaggagg tctgttaggt    180
gt                                                                    182
```

<210> SEQ ID NO 180
<211> LENGTH: 525
<212> TYPE: DNA
<213> ORGANISM: Homo sapiens

<400> SEQUENCE: 180

```
acacgctttt ggccccgacc aatgaggcct tcgagaagat ccctagtgag actttgaacc    60
gtatcctggg cgacccagaa gccctgagag acctgctgaa caaccacatc ttgaagtcag   120
ctatgtgtgc tgaagccatc gttgcggggc tgtctgtaga ccctggagg catgacac     180 tggaggtggg ctgcagcggg gacatgctca ctatcaacgg gaaggcgatc atctccaata   240
aagacatcct agccaccaac ggggtgatcc actacattga tgagctactc atcccagact   300
cagccaagac actatttgaa ttggctgcag agtctgatgt gtccacagcc attgaccttt    360
tcagacaagc cggcctcggc aatcatctct ctggaagtga gcggttgacc ctcctggctc    420
ccctgaattc tgtattcaaa gatggaaccc ctccaattga tgcccataca aggaatttgc    480
ttcggaacca cataattaaa gaccagctgg cctctaagta tctgt                   525
```

<210> SEQ ID NO 181
<211> LENGTH: 444
<212> TYPE: DNA
<213> ORGANISM: Homo sapiens

<400> SEQUENCE: 181

```
acaccacaat gtgcatcaag gagacgtgcc gattgattcc tgcagtcccg tccatttcca    60
gagatctcag caagccactt accttcccag atggatgcac attgcctgca gggatcaccg   120
tggttcttag tatttgggt cttcaccaca atcctgctgt ctggaaaaac ccaaaggtct    180
ctgacccctt gaggttctct caggagaatt ctgatcagag acaccctat gcctacttac    240
```

| | |
|---|---|
| cattctcagc tggatcaagg aactgcattg ggcaggagtt tgccatgatt gagtttaaagg | 300 |
| taaccattgc cttgattctg ctccacttca gagtgactcc agaccccacc aggcctctta | 360 |
| ctttccccaa ccattttatc ctcaagccca agaatgggat gtatttgcac ctgaagaaac | 420 |
| tctctgaatg ttagatctca gggt | 444 |

```
<210> SEQ ID NO 182
<211> LENGTH: 441
<212> TYPE: DNA
<213> ORGANISM: Homo sapiens

<400> SEQUENCE: 182
```

| | |
|---|---|
| acaaccttta ttgcttctcc agcatttttcc agaagaatgg tgtcattaga gggccacagg | 60 |
| ggatggggga gtaaaaaata acataaacga actgaacaga aatgcaggag ggtggcaaga | 120 |
| ggggccgaga ttgggtgttc agggcagaga ggtggaagac caggggcagt cagtgcttct | 180 |
| tagctttcag ccaccagagt ggagaattcg tcaaccccaa ttttgccgtc cccatctttg | 240 |
| tctccagcag ccatcagcat cttggtttct ttagcagaca ggtctctggc atctggggag | 300 |
| aagccttttta ggatgaatcc cagctcatcc tcctcgatga agccactttg tccttgtcca | 360 |
| gcatgtgaaa caccttcttc acatcatccg cactcttttt cttcaggccg accatttgga | 420 |
| agaactttt gtggtcgaag g | 441 |

```
<210> SEQ ID NO 183
<211> LENGTH: 339
<212> TYPE: DNA
<213> ORGANISM: Homo sapiens
<220> FEATURE:
<221> NAME/KEY: misc_feature
<222> LOCATION: (1)...(339)
<223> OTHER INFORMATION: n=A,T,C or G

<400> SEQUENCE: 183
```

| | |
|---|---|
| tgtntcatcn taaggggatt gggctctaga tctgtcgacg gcgcattgag gatttgcnat | 60 |
| cggttangtg gtccgcgagt catgaatttt tgctctggag cgttattgtt tgtgaagttt | 120 |
| atccaggaga gaactatgat tgtgtcgatg cgtttactgc aggaagantc acggtctcag | 180 |
| tcacggaggt gtaagggtgg actgactgan tgagacaagg gatatntngt tnttatannc | 240 |
| ttgtgatgaa cctgcctacc gtttatgtct ctttgctaat gggctctcng tnctgtnatt | 300 |
| cncncaagct gcggggggctt ccncggttct gggctctga | 339 |

```
<210> SEQ ID NO 184
<211> LENGTH: 490
<212> TYPE: DNA
<213> ORGANISM: Homo sapiens
<220> FEATURE:
<221> NAME/KEY: misc_feature
<222> LOCATION: (1)...(490)
<223> OTHER INFORMATION: n=A,T,C or G

<400> SEQUENCE: 184
```

| | |
|---|---|
| atatagcaag cttgtacgac cgacacatac ggcgcattgt gctggattgc ttatcttgtc | 60 |
| gcgcgacgtc tatataancg anactacata gtctcggaaa tccactcant ttcaagttcc | 120 |
| caaaanacng ganaaaaacc catgccttat ttaactaanc atcagctcgc ttctccttct | 180 |
| gtaaccgcgc ttntngctcc cagcctatag aagggtaaaa cccacactcg tgcgncagtc | 240 |
| atcnnataac tgattcgccc gggtactgcc gggcggcgct cganaccaat tngcanaatt | 300 |
| cacacattgc ggcgctcnan aagctctaga aggccaatcg ccatattgat ctatacatta | 360 |

```
tggccgtcgt tnacacgtcg tgacgggana ncctggngta ccattaatcg ctgcacantc    420
ccttcgcagc tggggtntac aaaagccgcc catcnctcca cgttgcgncc gatggcaagg    480 acnccctnat                                                          490
```

<210> SEQ ID NO 185
<211> LENGTH: 368
<212> TYPE: DNA
<213> ORGANISM: Homo sapiens
<220> FEATURE:
<221> NAME/KEY: misc_feature
<222> LOCATION: (1)...(368)
<223> OTHER INFORMATION: n=A,T,C or G

<400> SEQUENCE: 185

```
ctnnanatag cangcttgta cgaccgacac aatacggcca ntgtgctgga ttcgcttcag     60
cgccgcccgg gcagtaccgg cgctcatcta tcngatgatg gcgcaccaat gtggggtttt    120 aacctttta tatggctggg gacanaaagc gcggttacnn aaccnataac gagctgatgg     180
tcatttaaaa atgcttgggg ttttcccggt cttttgggga attgaaactg agtgggactt    240
canaaactgt gctactttcg cttatctaag tactcggccg caacacctag ccgaatccgc    300
anatatcatc acnctgggcg gcgtcancat gcntctaaag ggccaattcn cctanatgag    360
tcttatac                                                            368
```

<210> SEQ ID NO 186
<211> LENGTH: 214
<212> TYPE: DNA
<213> ORGANISM: Homo sapiens
<220> FEATURE:
<221> NAME/KEY: misc_feature
<222> LOCATION: (1)...(214)
<223> OTHER INFORMATION: n=A,T,C or G

<400> SEQUENCE: 186

```
ngggagatcg cagcttgtac gactcgtcat ataacgnnca atgtgctgga tcgcttcanc     60
gccgccggcg gtctaatctg gttcggattn tgtgtgtntt gtctntntta canggtgcta    120
tccccttctt cctcctcctc tgccatcctc atccttatc tccttttgg acaagtgtca     180 nancagacag angcagggtg gtggcaccgt tgaa                               214
```

<210> SEQ ID NO 187
<211> LENGTH: 630
<212> TYPE: DNA
<213> ORGANISM: Homo sapiens
<220> FEATURE:
<221> NAME/KEY: misc_feature
<222> LOCATION: (1)...(630)
<223> OTHER INFORMATION: n=A,T,C or G

<400> SEQUENCE: 187

```
cagctgggac gagtcgatca tatacggcgc atgtgttgna tcgctatcgt gtccggcgag     60
tanttattan attactgtta tttctgctcc tactggatat gatctcttga nggcangtct    120
gtgtcgtctg gtcacaccat gttctcaggc tgggcaaata ccttcctata atagtttatg    180
gataatgaat gacgactang tctanaaana cgctagctaa ataacacact cagggaaaga    240
gtcttaaata ttgtgaaggt gttttttanta tacaacnttt gtttacataa taggaaataa    300
tttttagact tttaaacaga cacttgagcc agatttgtta atgttaccat ctatagtgtc    360
ttgaaaatat tcctcttagt ttccaatatg aatgaatcta aaatccatct tttcaattat    420
```

```
gcccaggccc gtggtcaatg cnccctcnac acttcattaa cggattatac cttgggaaac    480
cataatctgg cntaggacga atcgcctggc ncangctaan aactgccctg tattgagggg    540
ttatnnctga ttgcngaggt gcctctccag gtccccaaag ggtcgtactg ttgaanctgg    600
ctctaatntt ntcttgcctn acaggtctcc                                     630
```

<210> SEQ ID NO 188
<211> LENGTH: 441
<212> TYPE: DNA
<213> ORGANISM: Homo sapiens
<220> FEATURE:
<221> NAME/KEY: misc_feature
<222> LOCATION: (1)...(441)
<223> OTHER INFORMATION: n=A,T,C or G

<400> SEQUENCE: 188

```
cnngcaanac anggtcggat tccgntgagg naanaattcc ctnataggc tcgccccta      60 ttcaccaaac caancngaaa ctcttgcggt caaatctaag ctatnncaca accccactct    120
gnagggtatg cgccccgccc ctgcaatgaa atcaatanca tatttggaga cagagagata    180
gagagagaga ggttcctggc cttnnctatt ctgctcttac ttgnnagatn tcaganatag    240
aaaaacctat cctaggtccn nccaatgatn gcggcttncg aatcccgnng tggccantcc    300
ccggatcgga ctaaatcaaa gaagatcctc cgtcntcctg ttcctccaca ctggagtccc    360
attgtatgca tgggtntttc actggctnat cataccnnag gatctgtcca ccttnaactc    420
ttctctngga antccctncc c                                              441
```

<210> SEQ ID NO 189
<211> LENGTH: 637
<212> TYPE: DNA
<213> ORGANISM: Homo sapiens
<220> FEATURE:
<221> NAME/KEY: misc_feature
<222> LOCATION: (1)...(637)
<223> OTHER INFORMATION: n=A,T,C or G

<400> SEQUENCE: 189

```
agggngtata tacccacttg tacnactcga tcatanacgc gcatntctga atcgcttnct    60
ggccgcgatg tactgtgggc acttaagcac tgagtactgt ttgcgtcatg ccnggtcana    120
agatgctgct gcaaagggac tccaacnaaa tacactgtct tcaacaggag ttaacacctc    180
acacttggtg ganaanagaa ctcactggtg gtgatgcaca cgactgnatc catcaagtgc    240
gtttgcctgt tgactgctaa ccaaggctct ggcagtacct gccgggcgg cgctcgaaac    300 caaatctgca aatatcatca cactggcggn cgctcagcat catctanaag gccatcgcct    360
atagtgagtc tatacatcat ggccgcnttt acactcctac tggaaaacct gcgtaccact    420
taatcgcttc acacatcccc tttgcngtn gcttatancn aaaagcccac gatgcctcca    480
cattgcncnc tgatggcatg anccccttac gcgcatancc gcggtntgtg taccncangt    540
accgtnctgc acgctacncn tcttccttct cctcttcccc ttcccgttcc tcaccattcg    600
gggccttagg tcnatatctc gnccacccaa atntagg                             637
```

<210> SEQ ID NO 190
<211> LENGTH: 653
<212> TYPE: DNA
<213> ORGANISM: Homo sapiens
<220> FEATURE:
<221> NAME/KEY: misc_feature
<222> LOCATION: (1)...(653)
<223> OTHER INFORMATION: n=A,T,C or G

<400> SEQUENCE: 190

| aggggtata | tacccacttg | tacgactgna | tcatatacgc | gcatgtctgg | aatcgcttnc | 60 |
|---|---|---|---|---|---|---|
| gtggctgcca | tgtattgaca | ctacttctaa | gaactacaaa | agtgtactg | angatacatt | 120 |
| acacagaang | gctnacattc | tcncagatcc | tcatttntca | tgatatgtgg | acatcangan | 180 |
| cacgtggata | agtgtatcta | aanaatggct | ttcaaaatat | ttccacttta | ttaaggtttg | 240 |
| acatganatt | cataaaatgt | cttaatacta | tttctnaaaa | taacatctaa | tcggaaacta | 300 |
| tgcctnaact | gcacnttttn | tgtgtanata | atcntanttg | tacgcccggc | ggcgccaaag | 360 |
| ccnaatctgc | gattcctcac | ctggcgccgc | tcaacatcat | ctaaaggcca | atcgcctata | 420 |
| ntantctata | catcctggcc | gcgtttacac | gtctaatggg | aaaccggcgt | accacttatc | 480 |
| gcttgcagca | ctccccttcc | cactgggtta | tacnaaagcc | gcncgatgcc | tcccacattc | 540 |
| canctgatgc | aatgacccct | gttcgcctta | ncccgcggtt | tgtgtaccca | ntnaccacnt | 600 |
| cagcgctgcn | cntcttcntt | ctcctcttct | gccnttncgt | tccctcactc | nng | 653 |

<210> SEQ ID NO 191
<211> LENGTH: 663
<212> TYPE: DNA
<213> ORGANISM: Homo sapiens
<220> FEATURE:
<221> NAME/KEY: misc_feature
<222> LOCATION: (1)...(663)
<223> OTHER INFORMATION: n=A,T,C or G

<400> SEQUENCE: 191

| anggngtata | tacccactgt | ncgactcgat | catatacgcg | catgtcggat | cggctccanc | 60 |
|---|---|---|---|---|---|---|
| gcgccggcat | gtactatatc | tacatcaact | gtattatcat | ttanatattg | atnaaagaca | 120 |
| aaatcatact | tccatctgct | cactgatgat | aattactatg | atacatgatc | atgtaaacgt | 180 |
| atcaatataa | caatggaaga | tccctctgac | tatgcaagcc | taattttcca | atcncatgca | 240 |
| ctctcatagc | tcaaanatnt | cacngacatc | ctgatgaaac | tatnatacan | tttccacaca | 300 |
| aatcacttcg | ctttagatct | ctccattatt | cttgcttttc | cccctaaca | actacaaatc | 360 |
| ctcntgggat | gggaagaata | tatatcatct | actaaaaata | atatataatc | ccctgcanat | 420 |
| ttgtggnaaa | tcnggtgtct | caanagccac | aggagnacaa | gggggnacca | actaggactt | 480 |
| ttgtatgctt | atctctgtac | tcgcgcacac | ctaagcgatt | ctgcnattct | ccctggcggc | 540 |
| gtcacanctc | tanaggccat | cncnatatga | tctatacatc | ntggcgtctt | tacactctga | 600 |
| cggaaaccgg | gtnccantta | ccctggacca | tcccttcgcn | ctgntataca | aagcccccga | 660 |
| ncc | | | | | | 663 |

<210> SEQ ID NO 192
<211> LENGTH: 361
<212> TYPE: DNA
<213> ORGANISM: Homo sapiens
<220> FEATURE:
<221> NAME/KEY: misc_feature
<222> LOCATION: (1)...(361)
<223> OTHER INFORMATION: n=A,T,C or G

<400> SEQUENCE: 192

| antttttata | tacccactgg | tacaactcga | ncctatacgg | cgcanttncg | gaatcanctt | 60 |
|---|---|---|---|---|---|---|
| cancggcgcc | ggcatgtacc | ggtnatcatc | atcngatgat | ggcgctcnaa | tgtgggtttt | 120 |
| acctnttata | cggctgagat | canatcgcgt | acataacaaa | nncaactgat | ggtnaatnta | 180 |

| aatncggttg ggttctcccn ntctgttggg gaacttgana ctgagtgnga cntccatana | 240 |
| cgtgctattn tcggctancn antcctcagc gnacacctat ngnagtgcgc naattcatcc | 300 |
| atgntggcct cgactnttcc aaaangcent ncgcccacnt gntcgcnana cantctcggc | 360 |
| c | 361 |

<210> SEQ ID NO 193
<211> LENGTH: 314
<212> TYPE: DNA
<213> ORGANISM: Homo sapiens
<220> FEATURE:
<221> NAME/KEY: misc_feature
<222> LOCATION: (1)...(314)
<223> OTHER INFORMATION: n=A,T,C or G

<400> SEQUENCE: 193

| agggngnata taccaactgg tncgactcga tcctatacgc gcatttcgga ttcgcttcaa | 60 |
| cggcgccggc atgtaccaaa cctcaatccc aaccgtctca nttngacggg ctcagttctg | 120 |
| tcacagccac cccacatttc ttttgttttg tctgccactt caaagaatt ccaaataaga | 180 |
| attctgctgc agctccgtac aaggatatgg gcagcacagc acacacagag tngtgctcct | 240 |
| cacacttctc tggnaatgtc tcgtgaatat ctcaacagtc angaagtggg gcgttatcaa | 300 |
| aaacaatcag ggcc | 314 |

<210> SEQ ID NO 194
<211> LENGTH: 550
<212> TYPE: DNA
<213> ORGANISM: Homo sapiens
<220> FEATURE:
<221> NAME/KEY: misc_feature
<222> LOCATION: (1)...(550)
<223> OTHER INFORMATION: n=A,T,C or G

<400> SEQUENCE: 194

| aggngngata tacccactgg tncgactcga tcctatacgc gcatgtcgga ncgctatgtg | 60 |
| gtcncgcaag tacctcttct gcagtgatgg tctgtntcct ctatgatnag tgatcgaata | 120 |
| atcatcgaat tcancgaaag ttattcgagt gatatntgtg gcttgtagaa tctatgctcc | 180 |
| atggtgtggt cactgtcaag attaacacag aatggaagan ncngcactgc ataaaagatg | 240 |
| ttgtcaaatt gggtgcgttg atcngatagc tcntcccaag aggtcantgg tgttcaggat | 300 |
| tncnacataa gatnttggat caccngacga ccagangata ccgtgcaaa ctgtgaancn | 360 |
| ngtaatctgc ctatncctgc cctctcggan gatccctcgg ggacgacgag atcattctgg | 420 |
| aaacagcnan tgatagtcca gtnnangatt gatgancgac ganacgcntg atanatgtct | 480 |
| gacgtgagat tnggatgtga atcttcccnt gtgtgacctg cnccntaccn aanggtgcgn | 540 |
| ctccactcnn | 550 |

<210> SEQ ID NO 195
<211> LENGTH: 452
<212> TYPE: DNA
<213> ORGANISM: Homo sapiens
<220> FEATURE:
<221> NAME/KEY: misc_feature
<222> LOCATION: (1)...(452)
<223> OTHER INFORMATION: n=A,T,C or G

<400> SEQUENCE: 195

| nngcgggnat dataccaact ggtacgaact cganctctat nacggcgctn tttcnngatc | 60 |
| tgctatgtgg tctcggcaat gtacattata acngggcana catataatct acntctgtct | 120 |

```
ttntctcccc cngagagcgc aancatctcc aaatcgggtt ctgggtcatc caatggtctc    180
cantaatcac acaactcata tatatttatg gaangtgtct gtcatcgtcc ccacgangga    240
agtnncgtcg ctgtntgtct gtcactaggt gngtactctc cagtacttga aanctggtna    300
nggctgtctg tngtactggc cggcgccctc gaaancgaat ctgtnnatat catcacatng    360
cgncgcccga ncatcactna gggncanttc gcctatactg atcgtntgcg anncctgcgn    420
cncttacacg tcgnacggga naccggcctt cc                                 452

<210> SEQ ID NO 196
<211> LENGTH: 429
<212> TYPE: DNA
<213> ORGANISM: Homo sapiens
<220> FEATURE:
<221> NAME/KEY: misc_feature
<222> LOCATION: (1)...(429)
<223> OTHER INFORMATION: n=A,T,C or G

<400> SEQUENCE: 196
gcgggnnnat dataccagct ngtacgactc gatcctataa cggcgcatgt gngtatcggc    60
tacgtgtctc ggcgatgtac atataacggg gcaacatata atnatacant ctgtcttttt    120
ctcccccgga aacggcaacc atctccaata tcggtctggg tctccaatgg tctccaacta    180
aatcacacaa gtcaaatata nttanggaaa gtgtctgtct cntccccaga aggagtancg    240
ttagctgttg tctgtcatta ggttggtacc tccagtnaca tgaaaactgg tgagggtgtc    300
cttgtacaag ctctgcctca ccagatccta tactattagg gggcccacgg ttatctatct    360
taagggtctn aaaacctgga cttcatctgc tccggcggan gaatgtcccg cttacttacg    420 ntgttccac                                                           429

<210> SEQ ID NO 197
<211> LENGTH: 471
<212> TYPE: DNA
<213> ORGANISM: Homo sapiens
<220> FEATURE:
<221> NAME/KEY: misc_feature
<222> LOCATION: (1)...(471)
<223> OTHER INFORMATION: n=A,T,C or G

<400> SEQUENCE: 197
atgatacgca gctngtacga gccgtcacta tnacggcnca ttgtgtggat tcngctntga    60
tcggcgcccg ggcatgtcca tcnagagcgc atcatgggan tgnactcccc atatnntgac    120
caangttcgc gcaaggagcc nagaaccgat actacctgag ctgtcgtctn gttatacacg    180
tttctggcca angancaact ccacatncaa caagttggtg ttgaaatgtt gtttatnagt    240
ccaccaaccg gccgctctgt cccttcccga tgatccgaag ataagcttcc tgtccggaan    300
acgaacggcg tggtgtgngg acatantgat atgtgcgggt caggaagtac tcgncgcaac    360
ncgcaagcna atctgcnata tcatcacctg gcggcgctcg agctgccana ngcccnttcg    420
cctatatgag tctatacatt cctggccgtc tnttacactc ngacgggaaa c            471

<210> SEQ ID NO 198
<211> LENGTH: 643
<212> TYPE: DNA
<213> ORGANISM: Homo sapiens
<220> FEATURE:
<221> NAME/KEY: misc_feature
<222> LOCATION: (1)...(643)
<223> OTHER INFORMATION: n=A,T,C or G
```

```
<400> SEQUENCE: 198
tngtncgacc gtcactatac gcccatgtgt ggatccgntc cacggcgccg ggcangtacg        60
anactatatt gatcctctga tattgaaagt tggtctanca ataaccttta angcaaatca       120
ctcantgagt tttgaccaga agtcaccaca tcatgaatca cagtctatgg caaatgatac       180
cagtgtctct aagtcctatg ctcaaggtaa gagcatgcta ttccgtttta catttactgg       240
aatttactgt tcattcatna ttaaaatctc tagttttcat cctcaactgt ctaanaccag       300
tgtgcacaga cttaagactc tgttctcctc attttctcca acagaaacat tctcagtgtc       360
tactgttcta aaagggaatt tccgaggtgg cacttctcgg aatatcgacc ctcnggctct       420
atcaggcgtt acttcnngca ctcgtcattt gggcttgttc anttgtctta tctgtccagt       480
cacttcattt taagaaaaca attgatcgct ggtcacatgt nattcattgg cagccggtgt       540
gactgctgag tctcgcgcac acnctagcaa tcgnnattct ccatggngcg tcactctcta       600
naggccatcc cctatatgat ctataatctg gcgtctttac act                        643

<210> SEQ ID NO 199
<211> LENGTH: 292
<212> TYPE: DNA
<213> ORGANISM: Homo sapiens
<220> FEATURE:
<221> NAME/KEY: misc_feature
<222> LOCATION: (1)...(292)
<223> OTHER INFORMATION: n=A,T,C or G

<400> SEQUENCE: 199
ncggcnggag ttcgcagttg nacgaccgat cctatacgnc gcatttctga tccgctacnt        60
gtccggcgag tctatgctat ttatttntga ttaaatcaat attttctttc tgaatattaa       120
tcttatctnt acttttatac tattgaccta gctatatgta ttganctttt tgaactccta       180
tcagtntttt tcatgctatc gtatatttc cacttggtac ctntngctga ntcctagata       240
tcgtaaaaca tctctnnatc ntcacacnga gnccagggnt ctgtatngaa tt              292

<210> SEQ ID NO 200
<211> LENGTH: 275
<212> TYPE: DNA
<213> ORGANISM: Homo sapiens
<220> FEATURE:
<221> NAME/KEY: misc_feature
<222> LOCATION: (1)...(275)
<223> OTHER INFORMATION: n=A,T,C or G

<400> SEQUENCE: 200
atacgcaagc ttggtaccga gctnggatcc ctattaaccg gccgcaatat tctggaattc        60
tgcttancgt ggtcncggcc gaagtactat gctatnttac tttttttggga tataaaatca     120 atatatttct ttctnaagta tataaatctt atccncgtat cnttcnatac ctntctgaca       180
ntaagcttat angtatntga tctntgttga actcctatca agtgntttcn catgctatcg       240
tganntcttc cacnttggta cctttttacgc tgaat                                275

<210> SEQ ID NO 201
<211> LENGTH: 284
<212> TYPE: DNA
<213> ORGANISM: Homo sapiens
<220> FEATURE:
<221> NAME/KEY: misc_feature
<222> LOCATION: (1)...(284)
<223> OTHER INFORMATION: n=A,T,C or G

<400> SEQUENCE: 201
```

```
cgnnnatcca gtgtanaccg tcnttacgcg cattctgatc gttcacgccc gcgtctttat    60
atctatctcg actgattcac ctgtcattgt aaanaattcg tgtcagctgt ctaccnctta   120
nacatcatct aatcnaacta ncctgataaa tttcttcaat agggatanac ntntagtaca   180
tacgnttcca ttgagntacn tccgcggacc cncatcgcaa acnncatgcg gtcagtcnna   240
gcatcctcta tcttaatccg tccttaccnt ntgaacgctc cact                    284
```

<210> SEQ ID NO 202
<211> LENGTH: 448
<212> TYPE: DNA
<213> ORGANISM: Homo sapiens
<220> FEATURE:
<221> NAME/KEY: misc_feature
<222> LOCATION: (1)...(448)
<223> OTHER INFORMATION: n=A,T,C or G

<400> SEQUENCE: 202

```
atgatacgca agcttgtacg actcggatca tataacggcc gcaatgtgct ggaattccgc    60
ttcgacggac gccgggcatg tacttttata atnctactcc tcagaccttg catctcnacc   120
gctnggtcca gtttgtaaaa acnnacttcc gtngtgcagc cctggttctg ancantctct   180
atcacnctct atcctcncat ccncaanact anatcgcgtg aattcatatt tattcatttt   240
ccataatgat gggggaanga ctatcnctna tnatgcttan cacnctngct gcanttcgnc   300
natctcgcna ngcntgaaac gattactctg tcgcgaaccc tctangntga attctgcnaa   360
atatctntna cnctggcngg cgctcnangn atgcctctcg anggccaatc cgccnngcat   420
gattctaatt anatccntng gtcccntt                                      448
```

<210> SEQ ID NO 203
<211> LENGTH: 321
<212> TYPE: DNA
<213> ORGANISM: Homo sapiens
<220> FEATURE:
<221> NAME/KEY: misc_feature
<222> LOCATION: (1)...(321)
<223> OTHER INFORMATION: n=A,T,C or G

<400> SEQUENCE: 203

```
gggtgcnaga tcgcagtngt acgaatcgnt catatacggc gcatgtgntg antcgctacg    60
tgtccggcga ngtaccatat aatcgaanta ncatagttct ggangcccnc tcattttcaa   120
tttcccaaaa nacgggaaaa ccnaagcctt atttaactaa ctatctgctc gcttctcgct   180
tctgtaccgc gctatntgct nccagcctat aanaagggta aaacccacac tcggtgcgtc   240
agtctccnat atantgagtc nccgggtact ggccgggcgg tcgttcnaaa ncaattcncg   300
aanttcacta ctggcggcgc c                                             321
```

<210> SEQ ID NO 204
<211> LENGTH: 369
<212> TYPE: DNA
<213> ORGANISM: Homo sapiens
<220> FEATURE:
<221> NAME/KEY: misc_feature
<222> LOCATION: (1)...(369)
<223> OTHER INFORMATION: n=A,T,C or G

<400> SEQUENCE: 204

```
ntgtngtatg tacccagtgg tacgactcga tcctagtacg gcgcagtgtg ctgaatcgtt    60
acttgtcgcg gccaagtatc tataaagcaa actatcacag ttctgaaagt ccatctcant   120
```

```
ttcagttccc aaaagancgg gaaaacccaa gccttattaa actaacaatc agtcgctctc      180
gcttctgtac cgcgcttttg gccccagcc tataaaaggg taaaacccac actcggtgcg       240
ccagtcatcg ataactgaat cgcccggtac tgcccgggcg gcgctcnann ccaaatctgc      300
agatatcaca cactggcggc gctcancatg ctctagaagg ccaattcncc tatantgatt      360
ctattacaa                                                              369
```

<210> SEQ ID NO 205
<211> LENGTH: 2996
<212> TYPE: DNA
<213> ORGANISM: Homo sapien

<400> SEQUENCE: 205

```
cagccaccgg agtggatgcc atctgcaccc accgccctga ccccacaggc cctgggctgg       60
acagagagca gctgtatttg gagctgagcc agctgaccca cagcatcact gagctgggcc      120
cctacaccct ggacagggac agtctctatg tcaatggttt cacacagcgg agctctgtgc      180
ccaccactag cattcctggg accccacag tggacctggg aacatctggg actccagttt       240
ctaaacctgg tccctcggct gccagccctc tcctggtgct attcactctc aacttcacca      300
tcaccaacct gcggtatgag gagaacatgc agcaccctgg ctccaggaag ttcaacacca      360
cggagagggt ccttcagggc ctggtccctg ttcaagagca ccagtgttgg ccctctgtac      420
tctggctgca gactgacttt gctcaggcct gaaaaggatg ggacagccac tggagtggat      480
gccatctgca cccaccaccc tgaccccaaa agccctaggc tggacagaga gcagctgtat      540
tgggagctga gccagctgac ccacaatatc actgagctgg gccctatgc cctggacaac       600 gacagcctct tgtcaatgg tttcactcat cggagctctg tgtccaccac cagcactcct       660
gggaccccca cagtgtatct gggagcatct aagactccag cctcgatatt tggcccttca      720
gctgccagcc atctcctgat actattcacc ctcaacttca ccatcactaa cctgcggtat      780
gaggagaaca tgtggcctgg ctccaggaag ttcaacacta cagagagggt ccttcagggc      840
ctgctaaggc ccttgttcaa gaacaccagt gttggccctc tgtactctgg ctgcaggctg      900
accttgctca ggcagagaa agatggggaa gccaccggag tggatgccat ctgcacccac      960
cgccctgacc ccacaggccc tgggctggac agagagcagc tgtatttgga gctgagccag     1020
ctgacccaca gcatcactga gctgggcccc tacacactgg acaggacag tctctatgtc      1080 aatggtttca cccatcggag ctctgtaccc accaccagca ccggggtggt cagcgaggag     1140
ccattcacac tgaacttcac catcaacaac ctgcgctaca tggcggacat gggccaaccc     1200
ggctccctca gttcaacat cacagacaac gtcatgaagc acctgctcag tcctttgttc      1260
cagaggagca gctgggtgc acggtacaca ggctgcaggt catcgcact aaggtctgtg       1320 aagaacggtg ctgagacacg ggtggacctc ctctgcacct acctgcagcc cctcagcggc     1380
ccaggtctgc ctatcaagca ggtgttccat gagctgagcc agcagaccca tggcatcacc     1440
cggctgggcc cctactctct ggacaaagac agcctctacc ttaacggtta caatgaacct     1500
ggtccagatg agcctcctac aactcccaag ccagccacca cattcctgcc tcctctgtca     1560
gaagccacaa cagccatggg gtaccacctg aagaccctca cactcaactt caccatctcc     1620
aatctccagt attcaccaga tatgggcaag ggctcagcta cattcaactc caccgagggg     1680
gtccttcagc acctgctcag acccttgttc cagaagagca gcatgggccc cttctacttg     1740
ggttgccaac tgatctccct caggcctgag aaggatgggg cagccactgg tgtggacacc     1800
acctgcacct accaccctga ccctgtgggc cccggctgg acatacagca gctttactgg     1860
```

```
gagctgagtc agctgaccca tggtgtcacc caactgggct tctatgtcct ggacagggat    1920
agcctcttca tcaatggcta tgcaccccag aatttatcaa tccggggcga gtaccagata    1980
aatttccaca ttgtcaactg gaacctcagt aatccagacc ccacatcctc agagtacatc    2040
accctgctga gggacatcca ggacaaggtc accacactct acaaaggcag tcaactacat    2100
gacacattcc gcttctgcct ggtcaccaac ttgacgatgg actccgtgtt ggtcactgtc    2160
aaggcattgt tctcctccaa tttggacccc agcctggtgg agcaagtctt tctagataag    2220
accctgaatg cctcattcca ttggctgggc tccacctacc agttggtgga catccatgtg    2280
acagaaatgg agtcatcagt ttatcaacca caagcagct ccagcaccca gcacttctac    2340
ctgaatttca ccatcaccaa cctaccatat tcccaggaca agcccagcc aggcaccacc    2400 aattaccaga ggaacaaaag gaatattgag gatgcgctca accaactctt ccgaaacagc    2460
agcatcaaga gttattttc tgactgtcaa gtttcaacat tcaggtctgt ccccaacagg    2520
caccacaccg gggtggactc cctgtgtaac ttctcgccac tggctcggag agtagacaga    2580
gttgccatct atgaggaatt tctgcggatg acccggaatg gtaccagct gcagaacttc    2640 accctggaca ggagcagtgt ccttgtggat gggtattttc ccaacagaaa tgagcccta    2700 actgggaatt ctgaccttcc cttctgggct gtcatcctca tcggcttggc aggactcctg    2760
ggactcatca catgcctgat ctgcggtgtc ctggtgacca cccgccggcg gaagaaggaa    2820
ggagaataca cgtccagca acagtgccca ggctactacc agtcacacct agacctggag    2880
gatctgcaat gactggaact tgccggtgcc tggggtgcct tccccccagc cagggtccaa    2940
agaagcttgg ctggggcaga aataaaccat attggtcgga cacaaaaaaa aaaaaa        2996
```

<210> SEQ ID NO 206
<211> LENGTH: 914
<212> TYPE: PRT
<213> ORGANISM: Homo sapien

<400> SEQUENCE: 206

```
Met Ser Met Val Ser His Ser Gly Ala Leu Cys Pro Pro Leu Ala Phe
 1               5                  10                  15

Leu Gly Pro Pro Gln Trp Thr Trp Glu His Leu Gly Leu Gln Phe Leu
                20                  25                  30

Asn Leu Val Pro Arg Leu Pro Ala Leu Ser Trp Cys Tyr Ser Leu Ser
            35                  40                  45

Thr Ser Pro Ser Pro Thr Cys Gly Met Arg Arg Thr Cys Ser Thr Leu
        50                  55                  60

Ala Pro Gly Ser Ser Thr Pro Arg Arg Gly Ser Phe Arg Ala Trp Ser
65                  70                  75                  80

Leu Phe Lys Ser Thr Ser Val Gly Pro Leu Tyr Ser Gly Cys Arg Leu
                85                  90                  95

Thr Leu Leu Arg Pro Glu Lys Asp Gly Thr Ala Thr Gly Val Asp Ala
               100                 105                 110

Ile Cys Thr His His Pro Asp Pro Lys Ser Pro Arg Leu Asp Arg Glu
           115                 120                 125

Gln Leu Tyr Trp Glu Leu Ser Gln Leu Thr His Asn Ile Thr Glu Leu
       130                 135                 140

Gly Pro Tyr Ala Leu Asp Asn Asp Ser Leu Phe Val Asn Gly Phe Thr
145                 150                 155                 160

His Arg Ser Ser Val Ser Thr Ser Thr Pro Gly Thr Pro Thr Val
               165                 170                 175
```

```
Tyr Leu Gly Ala Ser Lys Thr Pro Ala Ser Ile Phe Gly Pro Ser Ala
            180                 185                 190

Ala Ser His Leu Leu Ile Leu Phe Thr Leu Asn Phe Thr Ile Thr Asn
            195                 200                 205

Leu Arg Tyr Glu Glu Asn Met Trp Pro Gly Ser Arg Lys Phe Asn Thr
            210                 215                 220

Thr Glu Arg Val Leu Gln Gly Leu Leu Arg Pro Leu Phe Lys Asn Thr
225                 230                 235                 240

Ser Val Gly Pro Leu Tyr Ser Gly Cys Arg Leu Thr Leu Leu Arg Pro
                245                 250                 255

Glu Lys Asp Gly Glu Ala Thr Gly Val Asp Ala Ile Cys Thr His Arg
            260                 265                 270

Pro Asp Pro Thr Gly Pro Gly Leu Asp Arg Glu Gln Leu Tyr Leu Glu
            275                 280                 285

Leu Ser Gln Leu Thr His Ser Ile Thr Glu Leu Gly Pro Tyr Thr Leu
            290                 295                 300

Asp Arg Asp Ser Leu Tyr Val Asn Gly Phe Thr His Arg Ser Ser Val
305                 310                 315                 320

Pro Thr Thr Ser Thr Gly Val Val Ser Glu Glu Pro Phe Thr Leu Asn
                325                 330                 335

Phe Thr Ile Asn Asn Leu Arg Tyr Met Ala Asp Met Gly Gln Pro Gly
            340                 345                 350

Ser Leu Lys Phe Asn Ile Thr Asp Asn Val Met Lys His Leu Leu Ser
            355                 360                 365

Pro Leu Phe Gln Arg Ser Ser Leu Gly Ala Arg Tyr Thr Gly Cys Arg
            370                 375                 380

Val Ile Ala Leu Arg Ser Val Lys Asn Gly Ala Glu Thr Arg Val Asp
385                 390                 395                 400

Leu Leu Cys Thr Tyr Leu Gln Pro Leu Ser Gly Pro Gly Leu Pro Ile
                405                 410                 415

Lys Gln Val Phe His Glu Leu Ser Gln Gln Thr His Gly Ile Thr Arg
            420                 425                 430

Leu Gly Pro Tyr Ser Leu Asp Lys Asp Ser Leu Tyr Leu Asn Gly Tyr
            435                 440                 445

Asn Glu Pro Gly Pro Asp Glu Pro Pro Thr Thr Pro Lys Pro Ala Thr
            450                 455                 460

Thr Phe Leu Pro Pro Leu Ser Glu Ala Thr Thr Ala Met Gly Tyr His
465                 470                 475                 480

Leu Lys Thr Leu Thr Leu Asn Phe Thr Ile Ser Asn Leu Gln Tyr Ser
                485                 490                 495

Pro Asp Met Gly Lys Gly Ser Ala Thr Phe Asn Ser Thr Glu Gly Val
            500                 505                 510

Leu Gln His Leu Leu Arg Pro Leu Phe Gln Lys Ser Ser Met Gly Pro
            515                 520                 525

Phe Tyr Leu Gly Cys Gln Leu Ile Ser Leu Arg Pro Glu Lys Asp Gly
            530                 535                 540

Ala Ala Thr Gly Val Asp Thr Thr Cys Thr Tyr His Pro Asp Pro Val
545                 550                 555                 560

Gly Pro Gly Leu Asp Ile Gln Gln Leu Tyr Trp Glu Leu Ser Gln Leu
                565                 570                 575

Thr His Gly Val Thr Gln Leu Gly Phe Tyr Val Leu Asp Arg Asp Ser
            580                 585                 590
```

```
Leu Phe Ile Asn Gly Tyr Ala Pro Gln Asn Leu Ser Ile Arg Gly Glu
            595                 600                 605

Tyr Gln Ile Asn Phe His Ile Val Asn Trp Asn Leu Ser Asn Pro Asp
        610                 615                 620

Pro Thr Ser Ser Glu Tyr Ile Thr Leu Leu Arg Asp Ile Gln Asp Lys
625                 630                 635                 640

Val Thr Thr Leu Tyr Lys Gly Ser Gln Leu His Asp Thr Phe Arg Phe
            645                 650                 655

Cys Leu Val Thr Asn Leu Thr Met Asp Ser Val Leu Val Thr Val Lys
            660                 665                 670

Ala Leu Phe Ser Ser Asn Leu Asp Pro Ser Leu Val Glu Gln Val Phe
            675                 680                 685

Leu Asp Lys Thr Leu Asn Ala Ser Phe His Trp Leu Gly Ser Thr Tyr
        690                 695                 700

Gln Leu Val Asp Ile His Val Thr Glu Met Glu Ser Ser Val Tyr Gln
705                 710                 715                 720

Pro Thr Ser Ser Ser Thr Gln His Phe Tyr Leu Asn Phe Thr Ile
            725                 730                 735

Thr Asn Leu Pro Tyr Ser Gln Asp Lys Ala Gln Pro Gly Thr Thr Asn
            740                 745                 750

Tyr Gln Arg Asn Lys Arg Asn Ile Glu Asp Ala Leu Asn Gln Leu Phe
            755                 760                 765

Arg Asn Ser Ser Ile Lys Ser Tyr Phe Ser Asp Cys Gln Val Ser Thr
        770                 775                 780

Phe Arg Ser Val Pro Asn Arg His His Thr Gly Val Asp Ser Leu Cys
785                 790                 795                 800

Asn Phe Ser Pro Leu Ala Arg Arg Val Asp Arg Val Ala Ile Tyr Glu
            805                 810                 815

Glu Phe Leu Arg Met Thr Arg Asn Gly Thr Gln Leu Gln Asn Phe Thr
            820                 825                 830

Leu Asp Arg Ser Ser Val Leu Val Asp Gly Tyr Phe Pro Asn Arg Asn
        835                 840                 845

Glu Pro Leu Thr Gly Asn Ser Asp Leu Pro Phe Trp Ala Val Ile Leu
850                 855                 860

Ile Gly Leu Ala Gly Leu Leu Gly Leu Ile Thr Cys Leu Ile Cys Gly
865                 870                 875                 880

Val Leu Val Thr Thr Arg Arg Arg Lys Lys Glu Gly Glu Tyr Asn Val
            885                 890                 895

Gln Gln Gln Cys Pro Gly Tyr Tyr Gln Ser His Leu Asp Leu Glu Asp
            900                 905                 910

Leu Gln

<210> SEQ ID NO 207
<211> LENGTH: 2627
<212> TYPE: DNA
<213> ORGANISM: Homo sapiens

<400> SEQUENCE: 207
ccacgcgtcc gcccacgcgt ccggaaggca gcggcagctc cactcagcca gtacccagat      60
acgctgggaa ccttccccag ccatggcttc cctggggcag atcctcttct ggagcataat     120
tagcatcatc attattctgg ctggagcaat tgcactcatc attggctttg gtatttcagg     180
gagacactcc atcacagtca ctactgtcgc ctcagctggg aacattgggg aggatggaat     240
cctgagctgc acttttgaac ctgacatcaa actttctgat atcgtgatac aatggctgaa     300
```

-continued

| | |
|---|---|
| ggaaggtgtt ttaggcttgg tccatgagtt caaagaaggc aaagatgagc tgtcggagca | 360 |
| ggatgaaatg ttcagaggcc ggacagcagt gtttgctgat caagtgatag ttggcaatgc | 420 |
| ctctttgcgg ctgaaaaacg tgcaactcac agatgctggc acctacaaat gttatatcat | 480 |
| cacttctaaa ggcaagggga atgctaacct tgagtataaa actggagcct tcagcatgcc | 540 |
| ggaagtgaat gtggactata atgccagctc agagaccttg cggtgtgagg ctccccgatg | 600 |
| gttcccccag cccacagtgg tctgggcatc ccaagttgac cagggagcca acttctcgga | 660 |
| agtctccaat accagctttg agctgaactc tgagaatgtg accatgaagg ttgtgtctgt | 720 |
| gctctacaat gttacgatca acaacacata ctcctgtatg attgaaaatg acattgccaa | 780 |
| agcaacaggg gatatcaaag tgacagaatc ggagatcaaa aggcggagtc acctacagct | 840 |
| gctaaactca aaggcttctc tgtgtgtctc ttctttcttt gccatcagct gggcacttct | 900 |
| gcctctcagc ccttacctga tgctaaaata atgtgccttg ccacaaaaa agcatgcaaa | 960 |
| gtcattgtta acagggat ctacagaact atttcaccac cagatatgac ctagttttat | 1020 |
| atttctggga ggaaatgaat tcatatctag aagtctggag tgagcaaaca agagcaagaa | 1080 |
| acaaaaagaa gccaaaagca gaaggctcca atatgaacaa gataaatcta tcttcaaaga | 1140 |
| catattagaa gttgggaaaa taattcatgt gaactagaca agtgtgttaa gagtgataag | 1200 |
| taaaatgcac gtggagacaa gtgcatcccc agatctcagg gacctccccc tgcctgtcac | 1260 |
| ctggggagtg agaggacagg atagtgcatg ttctttgtct ctgaattttt agttatatgt | 1320 |
| gctgtaatgt tgctctgagg aagcccctgg aaagtctatc ccaacatatc cacatcttat | 1380 |
| attccacaaa ttaagctgta gtatgtaccc taagacgctg ctaattgact gccacttcgc | 1440 |
| aactcagggg cggctgcatt ttagtaatgg gtcaaatgat tcacttttta tgatgcttcc | 1500 |
| aaaggtgcct tggcttctct tcccaactga caaatgccaa agttgagaaa atgatcata | 1560 |
| attttagcat aaacagagca gtcggcgaca ccgattttat aaataaactg agcaccttct | 1620 |
| ttttaaacaa acaaatgcgg gtttatttct cagatgatgt tcatccgtga atggtccagg | 1680 |
| gaaggacctt tcaccttgac tatatggcat tatgtcatca caagctctga ggcttctcct | 1740 |
| ttccatcctg cgtggacagc taagacctca gttttcaata gcatctagag cagtgggact | 1800 |
| cagctggggt gatttcgccc cccatctccg ggggaatgtc tgaagacaat tttggttacc | 1860 |
| tcaatgaggg agtggaggag gatacagtgc tactaccaac tagtggataa aggccaggga | 1920 |
| tgctgctcaa cctcctacca tgtacaggac gtctccccat tacaactacc caatccgaag | 1980 |
| tgtcaactgt gtcaggacta agaaaccctg gttttgagta gaaaagggcc tggaaagagg | 2040 |
| ggagccaaca aatctgtctg cttcctcaca ttagtcattg gcaaataagc attctgtctc | 2100 |
| tttggctgct gcctcagcac agagagccag aactctatcg ggcaccagga taacatctct | 2160 |
| cagtgaacag agttgacaag gcctatggga aatgcctgat gggattatct tcagcttgtt | 2220 |
| gagcttctaa gtttctttcc cttcattcta ccctgcaagc caagttctgt aagagaaatg | 2280 |
| cctgagttct agctcaggtt ttcttactct gaatttagat ctccagaccc ttcctggcca | 2340 |
| caattcaaat taaggcaaca acatataccc ttccatgaag cacacacaga cttttgaaag | 2400 |
| caaggacaat gactgcttga attgaggcct tgaggaatga agctttgaag gaaaagaata | 2460 |
| ctttgtttcc agcccccttc ccacactctt catgtgttaa ccactgcctt cctgaccttt | 2520 |
| ggagccacgg tgactgtatt acatgttgtt atagaaaact gattttagag ttctgatcgt | 2580 |
| tcaagagaat gattaaatat acatttccta caccaaaaaa aaaaaaa | 2627 |

<210> SEQ ID NO 208
<211> LENGTH: 282
<212> TYPE: PRT
<213> ORGANISM: Homo sapiens

<400> SEQUENCE: 208

Met Ala Ser Leu Gly Gln Ile Leu Phe Trp Ser Ile Ile Ser Ile Ile
                 5                  10                  15
Ile Ile Leu Ala Gly Ala Ile Ala Leu Ile Ile Gly Phe Gly Ile Ser
             20                  25                  30
Gly Arg His Ser Ile Thr Val Thr Thr Val Ala Ser Ala Gly Asn Ile
         35                  40                  45
Gly Glu Asp Gly Ile Leu Ser Cys Thr Phe Glu Pro Asp Ile Lys Leu
     50                  55                  60
Ser Asp Ile Val Ile Gln Trp Leu Lys Glu Gly Val Leu Gly Leu Val
 65                  70                  75                  80
His Glu Phe Lys Glu Gly Lys Asp Glu Leu Ser Glu Gln Asp Glu Met
                 85                  90                  95
Phe Arg Gly Arg Thr Ala Val Phe Ala Asp Gln Val Ile Val Gly Asn
            100                 105                 110
Ala Ser Leu Arg Leu Lys Asn Val Gln Leu Thr Asp Ala Gly Thr Tyr
        115                 120                 125
Lys Cys Tyr Ile Ile Thr Ser Lys Gly Lys Gly Asn Ala Asn Leu Glu
    130                 135                 140
Tyr Lys Thr Gly Ala Phe Ser Met Pro Glu Val Asn Val Asp Tyr Asn
145                 150                 155                 160
Ala Ser Ser Glu Thr Leu Arg Cys Glu Ala Pro Arg Trp Phe Pro Gln
                165                 170                 175
Pro Thr Val Val Trp Ala Ser Gln Val Asp Gln Gly Ala Asn Phe Ser
            180                 185                 190
Glu Val Ser Asn Thr Ser Phe Glu Leu Asn Ser Glu Asn Val Thr Met
        195                 200                 205
Lys Val Val Ser Val Leu Tyr Asn Val Thr Ile Asn Asn Thr Tyr Ser
    210                 215                 220
Cys Met Ile Glu Asn Asp Ile Ala Lys Ala Thr Gly Asp Ile Lys Val
225                 230                 235                 240
Thr Glu Ser Glu Ile Lys Arg Arg Ser His Leu Gln Leu Leu Asn Ser
                245                 250                 255
Lys Ala Ser Leu Cys Val Ser Ser Phe Phe Ala Ile Ser Trp Ala Leu
            260                 265                 270
Leu Pro Leu Ser Pro Tyr Leu Met Leu Lys
        275                 280

<210> SEQ ID NO 209
<211> LENGTH: 309
<212> TYPE: PRT
<213> ORGANISM: Homo sapiens

<400> SEQUENCE: 209

His Ala Ser Ala His Ala Ser Gly Arg Gln Arg Gln Leu His Ser Ala
                 5                  10                  15
Ser Thr Gln Ile Arg Trp Glu Pro Ser Pro Ala Met Ala Ser Leu Gly
             20                  25                  30
Gln Ile Leu Phe Trp Ser Ile Ile Ser Ile Ile Ile Leu Ala Gly
         35                  40                  45

```
Ala Ile Ala Leu Ile Ile Gly Phe Gly Ile Ser Gly Arg His Ser Ile
        50                  55                  60

Thr Val Thr Thr Val Ala Ser Ala Gly Asn Ile Gly Glu Asp Gly Ile
 65                  70                  75                  80

Leu Ser Cys Thr Phe Glu Pro Asp Ile Lys Leu Ser Asp Ile Val Ile
                 85                  90                  95

Gln Trp Leu Lys Glu Gly Val Leu Gly Leu Val His Glu Phe Lys Glu
                100                 105                 110

Gly Lys Asp Glu Leu Ser Glu Gln Asp Glu Met Phe Arg Gly Arg Thr
            115                 120                 125

Ala Val Phe Ala Asp Gln Val Ile Val Gly Asn Ala Ser Leu Arg Leu
        130                 135                 140

Lys Asn Val Gln Leu Thr Asp Ala Gly Thr Tyr Lys Cys Tyr Ile Ile
145                 150                 155                 160

Thr Ser Lys Gly Lys Gly Asn Ala Asn Leu Glu Tyr Lys Thr Gly Ala
                165                 170                 175

Phe Ser Met Pro Glu Val Asn Val Asp Tyr Asn Ala Ser Ser Glu Thr
            180                 185                 190

Leu Arg Cys Glu Ala Pro Arg Trp Phe Pro Gln Pro Thr Val Val Trp
        195                 200                 205

Ala Ser Gln Val Asp Gln Gly Ala Asn Phe Ser Glu Val Ser Asn Thr
        210                 215                 220

Ser Phe Glu Leu Asn Ser Glu Asn Val Thr Met Lys Val Val Ser Val
225                 230                 235                 240

Leu Tyr Asn Val Thr Ile Asn Asn Thr Tyr Ser Cys Met Ile Glu Asn
                245                 250                 255

Asp Ile Ala Lys Ala Thr Gly Asp Ile Lys Val Thr Glu Ser Glu Ile
            260                 265                 270

Lys Arg Arg Ser His Leu Gln Leu Leu Asn Ser Lys Ala Ser Leu Cys
        275                 280                 285

Val Ser Ser Phe Phe Ala Ile Ser Trp Ala Leu Leu Pro Leu Ser Pro
        290                 295                 300

Tyr Leu Met Leu Lys
305

<210> SEQ ID NO 210
<211> LENGTH: 742
<212> TYPE: DNA
<213> ORGANISM: Homo sapiens
<220> FEATURE:
<221> NAME/KEY: misc_feature
<222> LOCATION: (1)...(742)
<223> OTHER INFORMATION: n=A,T,C or G

<400> SEQUENCE: 210
cattgggtac gggcccctc gagtcgacgt atcgataagc ttgatatcga attcggcacg      60
aggcccgacc gctccctgag agccagcaac gggcagtgat gtttagcccc gaggaaaaat   120
tacatgcgga atggaaagca ggcgctcagg gtggctcctg ctggaatgag agctggagtg   180
caggctccgt ggttcctggg catgcgggtg tggctcagtt ctcaccttgc agatggagtg   240
ggactgttga cccaggccag cctggggact gcctcctcac ctcccctgcg aggctgacct   300
tgtcaccttg cctcttgagc ttgcctctct cctgcccaga ngtccttgga gcaaaatgga   360
ggtcgagagg catttggcac tcacgcctca ccacggacac tggtgcattc ttgggtacct   420
cttggcctca atctattgct ggggganggga ngactgangc ccattgctgg ggccctgaat   480
```

| | |
|---|---:|
| gcagggactg taaccaccca tcccctttctc agggcacctc tccctctcca gcacncttgc | 540 |
| tttgctatta atgctaccta atttcctact gangtggtct agaagctcct ccgccattgc | 600 |
| ccttgccgcc agcaaatttt tatccctagg gttaagataa cagaaggcan ccttgggcct | 660 |
| tgcctgccac attctcaggt ntncactgaa gcacagtatc tatttctcca aaaatagggg | 720 |
| ctgtnaacttt gttactaccc cc | 742 |

<210> SEQ ID NO 211
<211> LENGTH: 946
<212> TYPE: DNA
<213> ORGANISM: Homo sapiens
<220> FEATURE:
<221> NAME/KEY: misc_feature
<222> LOCATION: (1)...(946)
<223> OTHER INFORMATION: n=A,T,C or G

<400> SEQUENCE: 211

| | |
|---|---:|
| ggcacgaggc acatcgctgg atttctcatt gccaagctct attaattcat tcttttttcat | 60 |
| aacctcttat tcttatttca tggatgcaac attttctttg tctctcaggg aataataatt | 120 |
| attcctactt ttaaaggtct aatttcttta ttacttttatt tctctgggag tgagtttttc | 180 |
| ctaaagggat aatgagatgg aaaatgaaaa acaaagttg agacatggag ataccttctg | 240 |
| aaactcaagc attcctctac gtggatgtgc cagagggaaa gaacagaaca aaggagggta | 300 |
| gacactattt aaataaaaat atataagaat attacataac aaacaaaaaa gcccaaatcc | 360 |
| tcaggttgaa aaggaggaga aaatgtcaag caagacaaaa acagatgaag caaccaaaaa | 420 |
| agtgacatag ctggtcacct atattgaaat tcagaacat gagtgataaa ggactcccag | 480 |
| aaaaaaacaa aacccaaact aaaaaacaga aaaaaaggac tttaccaccn aaaacttgan | 540 |
| gaatcaggaa gactcagtct ctcattaaga aaantgctat aggggatggg ggcaaggcct | 600 |
| tcaaagtngc aggggatacc aataacctct ctgaagtttt ggaacttcat actccaaat | 660 |
| ngaattttttg tttgaatagc cccggttagg ggccaattttt aggacttaga aaggacccng | 720 |
| gnaaatcatt cccnncttgc cccccccgaa agaaattaat agaagggggtt tattccccgcc | 780 |
| attannaaaa aaggaatcca ggaattnccg ntttttttcca gtgttangnt ggggntgtan | 840 |
| aaactgaggg cttagcaagg gcggnattaa ccaccnggg tcccacccca aaantggnng | 900 |
| gggtgggccc caaattcggg nttnttncct ttaangcgtt aaaccc | 946 |

<210> SEQ ID NO 212
<211> LENGTH: 610
<212> TYPE: DNA
<213> ORGANISM: Homo sapiens
<220> FEATURE:
<221> NAME/KEY: misc_feature
<222> LOCATION: (1)...(610)
<223> OTHER INFORMATION: n=A,T,C or G

<400> SEQUENCE: 212

| | |
|---|---:|
| ggcacgaggt ttctggctgg agcctcggac actggctcac tgcagttggt ggtgtcgaca | 60 |
| gtggtangag ggcaaccagt aacgggagct tctcctgcca ggcaggaaga cgagtagaag | 120 |
| ggagcggcat gctggaggct ggagcctgag cccctggggc tcgccttgct gtgtttggtg | 180 |
| gtgacgtggg acactgcagc tcggccagag tggtaaaaaa tgtcctggtg tacgcttttc | 240 |
| tggctttgcc cgtctatctg ctccaagcca ggctgganga ngaggaaaag gaatcacctg | 300 |
| tggtacgctg gagcctgcat gtggcgtgac tctgcaactc gcctcgtgtg actgatggca | 360 |
| gccacggaga ctgcagctcg acagggagtg aggcttctca ntggcttgaa agctcagctg | 420 |

| | |
|---|---|
| actcccacga aatttgccgg aaactcaagg ctgtcagtga cnttcgtggc gccaagactt | 480 |
| aancangcgc gttgcatgca tccggccagt gtctgtgcca cgtgccctga cnccaccttg | 540 |
| anataancac ccggaacgcg cnncgcgcag gccgcgcgca cacgnccggg cancaacttg | 600 |
| gctggcttcc | 610 |

```
<210> SEQ ID NO 213
<211> LENGTH: 438
<212> TYPE: DNA
<213> ORGANISM: Homo sapiens
<220> FEATURE:
<221> NAME/KEY: misc_feature
<222> LOCATION: (1)...(438)
<223> OTHER INFORMATION: n=A,T,C or G

<400> SEQUENCE: 213
```

| | |
|---|---|
| ccganagcgg tttaaacggg ccctctagac tcgagcggcc gcccttttttt tttttttttg | 60 |
| aaataaattt ctagattatt tattacataa gcagaccact gaaacattta ttcaaaagta | 120 |
| ttccattgag agtcaaaaac atattgatat gattattatt ggtctgttaa agaaaacaaa | 180 |
| ataaaaagaa caaactggga attatcaata aacaaatcaa aacttagatg taattataac | 240 |
| ctaaagggct cacagggcaa atgtgaagca agcttctgtc tcagagcctg catatggaag | 300 |
| acatgtagta cttagctttg gcatctttct ttcctcctct tggttgagtt taagtattaa | 360 |
| taaaaggtgg actgagaaaa ccttttttta caatcttatg gggtattttt agtggaaacg | 420 |
| ttttagaagt aggaatat | 438 |

```
<210> SEQ ID NO 214
<211> LENGTH: 906
<212> TYPE: DNA
<213> ORGANISM: Homo sapiens
<220> FEATURE:
<221> NAME/KEY: misc_feature
<222> LOCATION: (1)...(906)
<223> OTHER INFORMATION: n=A,T,C or G

<400> SEQUENCE: 214
```

| | |
|---|---|
| gccctctaga tcgngcggcc gccctttttt tttttttttt gaaataaatt tctagattat | 60 |
| ttattacata agcagaccac tgaaacattt attcaaaagt attccattga gagtcaaaaa | 120 |
| catattgata tgattattat tggtctgtta aagaaaacaa aataaaaaga acaaactggg | 180 |
| aattatcaat aaacaaatca aaacttagat gtaattataa cctaaagggc tcacagggca | 240 |
| aatgtgaagc aagcttctgt ctcagagcct gcatatggaa gacatgtagt acttagcttt | 300 |
| gncatctttc tttcctcctc ttgnttgagt ttagtattaa taaaaggtgg actgagaaaa | 360 |
| ccttttttta caatcttatg ggttatttttt agtggaaacg tttagaagta gaatatacat | 420 |
| attaaaactg cncagaacaa atgnggtgca tctcaaatgg nggtccattt tcaaaatatg | 480 |
| aacacatatg ggcagcanttt tttttttttaa aaagtcagaa ggggcctnct catgccccttt | 540 |
| tccacttctt cactcattgg nccttcaacc caagcttaac tactntcctg acctccaaca | 600 |
| tcataaacta gtttccnagc tttgaaactt ttttccaatg agtcntaccg gaatagatgn | 660 |
| tcacagaanc ctcttaaaaa ttttggaccc tgcccgggnt ntaaaaaggg tgcaataaac | 720 |
| ccaccaacat cttggctggg ggggcagggg ccaaaagaan ttcccaaaac cgttttttgat | 780 |
| naaaaaggg gacttttgaa aaaaaaatta aaatttttgc cagnaaagca tgggnccccc | 840 |
| cccttgaana aaccccctgc atnaaaccaa cnttntggga nttttttngg tanggttttt | 900 |

```
ctggct                                                                      906
```

```
<210> SEQ ID NO 215
<211> LENGTH: 312
<212> TYPE: DNA
<213> ORGANISM: Homo sapiens
<220> FEATURE:
<221> NAME/KEY: misc_feature
<222> LOCATION: (1)...(312)
<223> OTHER INFORMATION: n=A,T,C or G

<400> SEQUENCE: 215
ggcacgagga aaccaggttg gctgggtttt gggtgtaaac ttaaaaatga caatcagcat      60
gagctggccg tgggctgtgg gggttgtagg ggcatcttgg taagggaacc ctcgctcagt     120
ccctctctgt tctggtgggg aggacaagga gggccaatag gggccaatag ggaggctgct    180
gctaggangg tttcctaaaa gaacaggtgt agggctaggg ctggttctta gttcaggttg     240
ctctgggcag tgatttatat ccacacacct ttctgcaaag tgtcctaagg aganggcagg    300
gataggagtg tc                                                              312
```

```
<210> SEQ ID NO 216
<211> LENGTH: 341
<212> TYPE: DNA
<213> ORGANISM: Homo sapiens
<220> FEATURE:
<221> NAME/KEY: misc_feature
<222> LOCATION: (1)...(341)
<223> OTHER INFORMATION: n=A,T,C or G

<400> SEQUENCE: 216
taagcctntc gaanataatg aatgagtcan ggagaggctn atgangaaat nccaaacacc       60
tgactaatng gtgccacatg attncaatgg nctanacatg ggttagatct cntcngngga      120
atgagcaata acaccnttaa antcntcaat tgacctagac acttcacact tgaaanatca      180 tcactttttna ngaccacgaa tgatgcttaa gaatcacatt ttgtgnngaa ntggantctg     240
gctacttaca cgaacagatt cttattcctg ttcatgagcc agtagacccg gaanaagact     300
taagagcttc tganctttct cttagctcca nngcttgaan g                           341
```

```
<210> SEQ ID NO 217
<211> LENGTH: 273
<212> TYPE: DNA
<213> ORGANISM: Homo sapiens
<220> FEATURE:
<221> NAME/KEY: misc_feature
<222> LOCATION: (1)...(273)
<223> OTHER INFORMATION: n=A,T,C or G

<400> SEQUENCE: 217
nnccttcncc ccttnacnga catgaacaaa acagcngtct ngaaatttta ttaacattnn       60
aagggttacn ctccctnctt ntgttttccg ntaaanncta nacctgcgcn ggggcggccg     120
atncagccct atagtgagaa gcctaattnc agcacactgg cggccgttac tanngnatcc    180
cgactcggta ncaantttg gngtaaagat ggacatanct ctatccnnga gnactcgtca      240
nccnttctct atnttacatg cnctaacgna gac                                       273
```

```
<210> SEQ ID NO 218
<211> LENGTH: 687
<212> TYPE: DNA
<213> ORGANISM: Homo sapiens
<220> FEATURE:
<221> NAME/KEY: misc_feature
```

```
<222> LOCATION: (1)...(687)
<223> OTHER INFORMATION: n=A,T,C or G

<400> SEQUENCE: 218
ttttcagtgc tgttttgttc tcaattttga tgtcaaaatc tctgggttct tctaanctng      60
ttatgttctt ccancaaatc cttccagttt ttgtaatttt tttctatatc agaagcgcct     120
gancccaatg cccaattnat acaccggtct tctccggaac gcttggtcna aagggtntag     180
tcnattnggc tcctggaagc atctnaaatg ctccaggtta ctcccangnc cctggannac     240
ttcanttgtc tanacgaatc ctggttttcg agcggtcctt gatatcgcaa ggaaatacgg     300
taaaaattat ccaagctctc ttcccactna gganttcgga tctcatcagc cgggtaaagg     360
aaaactcctc angaagtttg gcttcccct ccggtctacc ggctaatgtt aggaattact     420
tctggctctc ttccgataca tcctctcttc aaagtnaaga aggttaaaag aatnttaacn     480
tctcccagtg gctaatggtc aaacaccatc ctcatnagtc agactggggt ttcgaaagga     540
ggatataacc tccttgcnag ttnnaattaa aagggattaa ccanatggac tanccctcnc     600
cccgggattt nctctctcac aggagaaggg gtctcnccnc ttggctcatc cgaagcatag     660
gcaaaccccn gggaattttc agaaacc                                         687

<210> SEQ ID NO 219
<211> LENGTH: 247
<212> TYPE: DNA
<213> ORGANISM: Homo sapiens
<220> FEATURE:
<221> NAME/KEY: misc_feature
<222> LOCATION: (1)...(247)
<223> OTHER INFORMATION: n=A,T,C or G

<400> SEQUENCE: 219
gggcccttcn cctttnaatc gagagatcca aggttcaagg catgaaatac cagnctataa      60
aatgtctcaa gacntaaata atacggatng ngatagagag gttgaataat aaatgaanaa     120
anatgaaagn nattatgngg gaatacnaaa aaancngact aanggcggca ctgctgggca     180
tggnnaaatc ggattaattc ctcataggac agccnaaccc cttaaaatct cantttccgt     240 nacccga                                                               247

<210> SEQ ID NO 220
<211> LENGTH: 937
<212> TYPE: DNA
<213> ORGANISM: Homo sapiens
<220> FEATURE:
<221> NAME/KEY: misc_feature
<222> LOCATION: (1)...(937)
<223> OTHER INFORMATION: n=A,T,C or G

<400> SEQUENCE: 220
cgggctcgag tgcggccgca agcttttttt actatagacc aatattaaag tcagttaagt      60
tccaaataca ganttggaaa actaaagtaa aatatttaat gggagaatat ctgcatctga     120
atatgtcaac tgtttgctat ttttcagcta tttaatcctt ctacctgtat ctcagaaaca     180
aatttaaaaa ttaatagatt tgacagcaaa atcattcagc actttactta ctccatcagc     240
aaggtattta tgtagtcatt tccatccatg tggccaaact gaaatccct aaccaccacc     300 aaccaaaaat aaataaataa aaggagaggg ggtgggggga gagagagaga gaaagctcat     360
taaatagtaa aaaagtaaat aaaacaatga agttaaattc aggcctcagt aggcccagaa     420
actgtaaaca tttcacatgt aaatcatata caataaacac tgctaaaagt gtaaattcta     480
```

```
ctggcttctg agatacaaat acacgagtag aggaaattct aagacatttc tacttggttt    540
atgcatattt aaaattcagg gaaatatcag ctattctacc tgaaatatgt ttaagaaaaa    600
ttcctatttt ctctaaaaaa aggaataatc agaagacgct acatactatg taagaaaact    660
atacaatgac ccatcattag aagattcaga ataggaaaga aataataatt cactaataaa    720
atatatttat attgactgtc tttttttatg atagcaacaa tgattcagca taaagtaaaa    780
atatatgtat ttccgatgcc atttttattt cagttattct tttgagtttc tgttagaata    840
attatctgcc tatctctgac ttctgancag tcatttatgt ccaattataa gtacatgtgc    900
atattttatt accttaaacg cctctcaaat cctttca                              937

<210> SEQ ID NO 221
<211> LENGTH: 353
<212> TYPE: DNA
<213> ORGANISM: Homo sapiens
<220> FEATURE:
<221> NAME/KEY: misc_feature
<222> LOCATION: (1)...(353)
<223> OTHER INFORMATION: n=A,T,C or G

<400> SEQUENCE: 221
ggctatnnna tnnttntaan atcntgncnn ccttgacgct gttantaaan aaaaacaaac     60
gaatatcctt tttttgctcc ccctgtnca gatactaatc tcacactaat acttacagta    120
taactnttcc tttcaactac caatattaag ttccaagcca cctgggctta agtatcccaa    180
caacttaggt aatttgttgc taaccaccat actatatgct aattataaca ctctaagccc    240
caaggaattt ttgttcagat ttcttatant ttccacttat aaatatnatt ccncctctat    300
gggtatatnn nncctctagn cccatatnnc ccacngggat tgttgagggg ggc           353

<210> SEQ ID NO 222
<211> LENGTH: 813
<212> TYPE: DNA
<213> ORGANISM: Homo sapiens
<220> FEATURE:
<221> NAME/KEY: misc_feature
<222> LOCATION: (1)...(813)
<223> OTHER INFORMATION: n=A,T,C or G

<400> SEQUENCE: 222
ggcacgaggc tttactaagg ccagactcac tatccccgct tctgttctgt ggtacactgt     60
tcactcctca gtccatccta acctgacttc ctggccactg cagctcttcc gataagggtc    120
agcagtggct tagttattgc taaataataa gcgcacatgc actccctctt tcctgaaaca    180
ttgtccctcc ttggtttctg ttccttccta ggtctcctat cactcctcct tagtcttctg    240
tgcggacttc tgttccttct gcccttaaaa agttggtatt ttccaggatt ctgtcctagg    300
cccacttact tctcattctg cacgttcttg ttggatgatt ctatcacatc cctaacttct    360
gctgcccagt atgcacttaa aattcccaaa tctgtatatc tggatctggc ctgtgtctct    420
agcctagaag tgtgctttat cccagaagca cctcaaacac tgcactttgg aaattaagct    480
tactgagtct cgagtctcaa gtcccaaact gacttctttt tctctatttt ggttagtgac    540
aacactattt attcagtcat gcaaaccaga gccctgagaa ccatcttaca ttctctttct    600 cccttactc agttcttgct tctgttcttt ctcctccncc tctcctgcct gtgggcctag     660
nggncattaa ctggttggca ctgctttact ttcnattttt ttggctganc taacccnaag    720
ancctnttgt aggggccttt ctntcaggcn tnacttctnn caagancccc cgaaaccaga    780
tccnggggan tgctatggnn tggaaatatt ttg                                 813
```

<210> SEQ ID NO 223
<211> LENGTH: 882
<212> TYPE: DNA
<213> ORGANISM: Homo sapiens
<220> FEATURE:
<221> NAME/KEY: misc_feature
<222> LOCATION: (1)...(882)
<223> OTHER INFORMATION: n=A,T,C or G

<400> SEQUENCE: 223

```
tcacactact gagaagcagg gaaacccact gaaagggcac gtttcttaac ctcagaatgg      60
ggctactagc ctctaaagca ggaattgcgt tttgtttagt atttccatgg tctgctgcaa     120
ggcgtggcct ttacccaatg gataaatgcg tacaaggctc ttgtgagcag tcaagtttct     180
cgaggtttac agttgaaggg aagtgggatt gttttcctgc gcatttaaat gaaggtaggt     240
gggtgatcac cttctcttaa atgtgtgaag ggatgagata agagataggg catcttaatt     300
gccactgatg gccttcaggt gaggacaggc atgagccaac tgaagctttg acaattgtgc     360
tgaacccaaa acttcaaaaa caagaaaaaa catagactgg ctgaaatgat ctaagtcaac     420
agagcatggc cagcgcttca tacaaggcag gaccacaggg gaacactgac agcccaggag     480
gcactgagac agaggcagtg ggaagaagtg acagacccca gggactcccc accaacagca     540
gctgctgttg attaggaacc cccagtagac tgtcaggcac ctggtagtgg agaggctacc     600
aaggcccgga ctggagagga gccaaaggaa gaaacagtgc agtgcttaga cccctctggg     660
tctgcccgtg tccataccccc tagggagatt ccattccaga agtggacata ttcccacaga     720
gtgcctgggg ctcactcatc acagctgccc ctncatgaag gcattctcac tgcagcctta     780
ncagggaaca gggtcatttg cattaggcan cttgctgtcc tagaaggcnt cgggngtccc     840
tacactgccc atgttcccaa ngnggttcaa nctcnaaaan tn                       882
```

<210> SEQ ID NO 224
<211> LENGTH: 660
<212> TYPE: DNA
<213> ORGANISM: Homo sapiens
<220> FEATURE:
<221> NAME/KEY: misc_feature
<222> LOCATION: (1)...(660)
<223> OTHER INFORMATION: n=A,T,C or G

<400> SEQUENCE: 224

```
gattaaactc aatcattcac ccgggctcga gtgcggccgc aagctttttt tttttttttt      60
tttttttttt ttttggncct ctgggcttgt gcccggaagg ggantgctgg gccacntggg     120
tgtccgtgtt tgattttctg ggacctgccc ccccgtntcc cgcccggnt gccgcgtctc     180
actcccgcc gcggtgcnag gggcccccgtg tgccgcgcac ccttccaccc gtgttttgct     240
gttttttttga ctntgggcgt cccaggggtg cancggccgt ggggcccctgg tttgctttca     300
cctcttcatc tgctcactgg ccgcnantgn gtcttnttca aacaaacgtn tgaaggncaa     360
ncccctgggct cctgtgaacc cggccgtctt tgccggcaaan tctgaggctc cttcgttatt     420
ctggatccgg cctntggtcg gangcgtgct ctgcaggcac tgctcccatt gctggcancc     480
ttttctcccc gtggccgccc ggccgcccat naaaggcgtt gcaaacgccc gccctcgcca     540
gcgcaaagtc aaacnccggt ggcccgcgga cccccggcg gncgggaaca ccccancagg     600
cgggcaccac aanaagcgcg gncctccggc gtctaaaact nccatgtggc nccccccgn     660
```

<210> SEQ ID NO 225

```
<211> LENGTH: 438
<212> TYPE: DNA
<213> ORGANISM: Homo sapiens
<220> FEATURE:
<221> NAME/KEY: misc_feature
<222> LOCATION: (1)...(438)
<223> OTHER INFORMATION: n=A,T,C or G

<400> SEQUENCE: 225
aaaaaaaaag gaaaagtacc cagtgctctc agcttctgag cctcctctac agccctgttg    60
gnttttaaac ctgtgccctg tgtctgtgtc cccacttaat atatatagta cacagctgga   120
gagatggctc agccaggaga gggacccata ggtctgtgaa ttccagagga naggcaggna   180
tttataggtg gntctgtcag gtgaaatcng aggagccaaa gctattgtat gtgcatatgt   240
cagccgggct ctgtgggagg tggtgtaaga cctatggnat gggacangtg tncacgctgg   300
gatctctggc cggttccgaa aagtgaggat caggtagtgg gtggctgatt gcacaagttt   360
anaacccagg attagggaca cacaggtcag cacctgcttc tcagcatcct gactgggtgt   420
gatgggcata ctcaaggc                                                 438

<210> SEQ ID NO 226
<211> LENGTH: 480
<212> TYPE: DNA
<213> ORGANISM: Homo sapiens
<220> FEATURE:
<221> NAME/KEY: misc_feature
<222> LOCATION: (1)...(480)
<223> OTHER INFORMATION: n=A,T,C or G

<400> SEQUENCE: 226
aaaattaaaa ccaaaaggat cttagaggtc ctttacttca gtggttctca atgtcagagg    60
atgttatgat acctaatcaa aatctccagg ggaactgttt tgaactcaac agactctctc   120
ctgttctgag agactctggc aaagttggga gagctgccag gtactgtcca catgaccctg   180
actgcccatg attcaattac cttgaatggc ttatccagtc caataccttc atttcttaca   240
tgaggaaact gaagcacgta tcacatagtg atacaatgaa aacttggcct taatcgattt   300
tcagtgctgc cagtacaatg tcttgagcat atcaatttct tccaacccctt gacaacataa   360 ggtacgacca tcaaattttt tatttctgct aatttattag accaaaaaaa aagggnatct   420
cncccattgt tttacaggga tgattttatt ncagaggatt tcatcntggn gctgattcnt   480

<210> SEQ ID NO 227
<211> LENGTH: 423
<212> TYPE: DNA
<213> ORGANISM: Homo sapiens
<220> FEATURE:
<221> NAME/KEY: misc_feature
<222> LOCATION: (1)...(423)
<223> OTHER INFORMATION: n=A,T,C or G

<400> SEQUENCE: 227
cattgtgttg ggctctgctt agcacatcac atcggagcac agaggtgacc tgttctgcca    60
cagggatgtt caccttagtc acctgattga ttcctcttca ctttggtcac gtgattcctc   120
caggaggatg ttcaccttgg tcgcctgatt cctccaggag gatgttcacc ttggtcgcct   180
gaccacacag gcatctatca ggctttctca ctgcagccac tatgtcccca taatggatga   240
gtgtcttgtg gagagatagt ccaaatgaca ctgataccttt tgcctcata cggcctcacc   300 ccccaacaat cnaccactaa tgactgcctc atagcagttt ttccatttcc acagttcctt   360
ctatatgtat taattgtcat tctactataa agaanacttt ttcttttaaa aaaaaaaaa    420
```

```
aag                                                             423

<210> SEQ ID NO 228
<211> LENGTH: 249
<212> TYPE: DNA
<213> ORGANISM: Homo sapiens

<400> SEQUENCE: 228
cattgtgttg ggctgtagta aaatatgtgt ctggtaagat atgtgaagaa ataaaataag    60
atcaattaaa tctggcccat tgaatgacac attaattgta tattaatatg taatgttaaa   120
gatattagga gatggtggga cattatggca aactaaattt gggaggaggt tgaattgtat   180
aatttatgaa atcctaaagt ctagtacatt aacactctct actgtcaact tttcaaagca   240
gtgagaaac                                                           249

<210> SEQ ID NO 229
<211> LENGTH: 436
<212> TYPE: DNA
<213> ORGANISM: Homo sapiens

<400> SEQUENCE: 229
cattgtgttg ggatgttatc tgaccatcac aatatgattt ataatatgga ggcatgaagt    60
catttctcat tggggcagga gtgtggcaag ggggaagaag agctttacca attaactcaa   120
gattatttgg tgacatttct cttacctttt aggtgaggag aaagagacag aggatggaga   180
attggtgctt ttagtatgct gatacattaa gctgcctgga agcagatgct aaatcctatt   240 gaaataatt ttatttgcgt tttgcttagg gcattgttta gcaaaatact acacaaaaag    300
tcttgacctg tgtgtttgaa atggcagatg ttcacagtga ggactgagcc ttggggcaac   360
atcaatcttc acaattctgc acctatttgc tcaataactg gcttggttgg aaaaaaaggg   420
aaaaaaaaaa aaaaag                                                   436

<210> SEQ ID NO 230
<211> LENGTH: 760
<212> TYPE: DNA
<213> ORGANISM: Homo sapiens
<220> FEATURE:
<221> NAME/KEY: misc_feature
<222> LOCATION: (1)...(760)
<223> OTHER INFORMATION: n=A,T,C or G

<400> SEQUENCE: 230
cattgtgttg ggnngtggaa ggaaaantttt gaggcaatga agctaaacat aaaagaggaa    60
aagcanatgt tacctcaatg accacaatct acaaagtcca aatanaaaac ctgggagtat   120
gataggatga aactataacc tccagcaaag agcttaacag caattaaaat aaagacaaat   180
ttctgggatg gatnagacaa agtagcatat attacaaagg aaaatanact agtatcatnt   240
acgtttgatt aagtaactgc tttcaaataa ttgaatcata acaatgatt tctgcggttt     300 taagctcatt attttggttc cctggttttct cctaggatgc agtatagaat ctccatgcct   360
gatgtttatg taccaacaga agctgctgct tctttctttc attatttcct ttttaagtga   420
aagttaatac ctttatatg ttacagaaa gaggcagaaa aagccacact cccactatgc      480
tattaaatgc cctgaggatc aactgaggga tgattatacn catggctgaa tacagtntat   540
tcatttgttt ctttggattg tanataacaa aaggtggtat tctgtaacat cttgtgncaa   600
ttanccaaat gttaaggcga aaatggaatc tttcaaacaa gtgttntaaa caggttttga   660
```

| | |
|---|---|
| ttttccaaaa tttantatta gaaccntttc aattctggaa gttncccaat ttccangttg | 720 |
| tgttttctct tccaattctt ctttccttg naaattcccc | 760 |

<210> SEQ ID NO 231
<211> LENGTH: 692
<212> TYPE: DNA
<213> ORGANISM: Homo sapiens
<220> FEATURE:
<221> NAME/KEY: misc_feature
<222> LOCATION: (1)...(692)
<223> OTHER INFORMATION: n=A,T,C or G

<400> SEQUENCE: 231

| | |
|---|---|
| cattgtgttg gggggtgctn tggggagaac acgcttatgt tganatnggg ctccccgaga | 60 |
| aagcctcatt gacacnttcg aataaggacc cntngggaaa ttcangtgag ttgtggacat | 120 |
| ncntagataa natcaaaggc cttgangaag tccgcctggc accttccngt ctgcgaggag | 180 |
| gttgatacca aatgctaagg ggtccagntg cantgtanta tcgtgagatc agagtgatgg | 240 |
| gcaggtgtgg gcatgcgggc cctcaananag aagtgcccag gatgactcag acttatgcct | 300 |
| atatccattc antcctgttc attattttta ncnttccctc naaggacccc caatttnaac | 360 |
| catttgttat tcanggctat acttataaaa gtcatttgtt ttnagtctgg gtgatattaa | 420 |
| aaccatttgg acgccangca tggtggctcn nggcctataa tcctntccac cttggggaag | 480 |
| ccgaagctgg tnnaatccct naaggtcngg aatttgaaaa ccatcctggg ncaacattgg | 540 |
| gngaaaccct gtctctactn caaaaaacan aaaattttct ggggcctngg ttngcaggtn | 600 |
| gcctgaaaat ttcccancnt tactccggga aggccgaatg ccntaaaaaa nnnacctta | 660 |
| acccccccga angggcggaa agtttccatt tn | 692 |

<210> SEQ ID NO 232
<211> LENGTH: 518
<212> TYPE: DNA
<213> ORGANISM: Homo sapiens
<220> FEATURE:
<221> NAME/KEY: misc_feature
<222> LOCATION: (1)...(518)
<223> OTHER INFORMATION: n=A,T,C or G

<400> SEQUENCE: 232

| | |
|---|---|
| actcaaatgn ccncttgaag gtcacccaga ctcanaangt gtcaagcttt gggtggggtn | 60 |
| gtaatnaata nctcggnctc ctgattagtn ctcctagctc gatcnctggc tgagatnngt | 120 |
| tcgagcaccc ttcctttgat cccgtcaaac nccnggnaaa agcngcctgc gtagtcncct | 180 |
| nagccgaatc tgntttcccg acaccctccg ctcggtcggc tgccctggtn aagcngcntc | 240 |
| ctnaaanaan aaagngaagt ctccccngtc tcncccnant cctngggaaa acngcctgaa | 300 |
| ccaatatgnt ccccccaaggn cnccccaggg cacntaaccc gttaggaggg cccccccctg | 360 |
| gcgttttggn cnnaagcccn gccccngnaa taacccccnct anaaccacgn aaaaatgcaa | 420 |
| agtcccaaag ggtaaagaat ctcccnaccc cccggttccc tcgcaanctt cccctnngna | 480 |
| cttgtgttcc gggaaaaccc ttancccgan cctttcca | 518 |

<210> SEQ ID NO 233
<211> LENGTH: 698
<212> TYPE: DNA
<213> ORGANISM: Homo sapiens
<220> FEATURE:
<221> NAME/KEY: misc_feature
<222> LOCATION: (1)...(698)
<223> OTHER INFORMATION: n=A,T,C or G

<400> SEQUENCE: 233

```
gcacgagttt ctgtctgtct gtctctctct ctctctctct ctctctctgt ctctctctca    60
cagttagaat ttggtctgtt tctttattca atacccccaat atatgttcat tagggttata   120
ctgtatacac tacacataac agttttgttt tttgttttgg atattatttg ataataagaa   180
ttttaccaca tcattaaaaa aagtttcccc aagctataat ttttgataat tgcactcttc   240
cactattcaa atgtttattt aactctttct ctcctggagt aggtttacat tccattttag   300
ctatgatact gctttaagag aaattgtttt aagataaatt tccatagaca ggtcaaagga   360
ggtgaatata tgtaagcttt tcgatgcctg ttactgaatc tcattctgga aaacataact   420
gtcaatgccc tcttttctc atggtaaaaa aatacataac aaaatttacc atcttaatcg    480
tttttaaatg ttacagtacg atagtgttna ctgtatgtac cttgtgcaac agattctctg   540
aaaacttttt catttttcaa aatgaaaact ctgtactcat tgaacaggca gcttcccaac   600
ttccccattc ctcccanncc ctaccctgg  ttaanagtct nacaaaaccc gggaatttta   660
tgaaatttga aacactttta naataccncn tattaggg                           698
```

<210> SEQ ID NO 234
<211> LENGTH: 773
<212> TYPE: DNA
<213> ORGANISM: Homo sapiens
<220> FEATURE:
<221> NAME/KEY: misc_feature
<222> LOCATION: (1)...(773)
<223> OTHER INFORMATION: n=A,T,C or G

<400> SEQUENCE: 234

```
ggcacgagcg cagcttttcg aaagctgtaa tttgttttgt atcaaaagtc ctgcagtata    60
ttagtctcat tgcattttaa agagtttcca agtgatcagt gatggttgtc tgttttttag   120
tattacggtc ttatgtaatg ttcgaaaact agtcagtttg gtgctgtcgt acggggcgga   180
aagatcaggc caggcaaagt actctggccg ccaaagtaaa tgcttaaggc cgccaacgga   240
ttatgtcctg gggttcgatg agggccgtaa ttaggttgag ctggtgtang ctaacctcgc   300
agccatgtcg gagagagatg agagacataa nattttaaag taggggcgta ttttacgaag   360
ttctgancca tttcctttgt tatcggtccc ggcaaaagca actgagataa atgtgttaaa   420
agactcgatg attttttcga cttcagcaac gtactcagcc ttgggttctc gtagttttc    480
aaaggcagct atttgctgag attcatgaaa agtttgactt ganctgcttg tcaatttctg   540
cagcncgggc ttcaactgtt attgaatttg tttgattaag cncaatacgt tgcnggtcac   600
caaggttttc catgttttga ctncacctgg tcgaaccaat ttgaattatg tnttttttgcc  660
tgncctgttc ccccnccttt aaatccatct ctttttnga aacctttgng nggttgaatt   720
cngccgcccg gttcccaacn tttggttcna ccttggaaaa aaanatgggt agt          773
```

<210> SEQ ID NO 235
<211> LENGTH: 849
<212> TYPE: DNA
<213> ORGANISM: Homo sapiens
<220> FEATURE:
<221> NAME/KEY: misc_feature
<222> LOCATION: (1)...(849)
<223> OTHER INFORMATION: n=A,T,C or G

<400> SEQUENCE: 235

```
attgggtacg ggcccccctc gagcagcctc cactgcaatg ccgctgaatc aagagacttt    60
```

-continued

```
tcaatacgct ttatcagtga aaatgatgtg atctgaagag tcctatcttg agcactttgc    120
atgacatcca acgttaatgt ccacaacgtt cttagctgcc caacccctttt atcggcaagc   180 tccaaaggtg tgtgcaaacg ttctacggcg tcatgaaaag ctgaaaaatg ctgtgtcaac    240
actgcaccgc tgcgcatctt caaaagcagc gcccttatag tctccgcatt cgaagacgat    300
aacccgcgta gaatagcctc ataatcactt ttgtagaaat caatcagagc tgtgctagga    360
accttcccat ccaaaacata cgactgtgcg accacgtctg caaaagcaga cgtcacatta    420
tgcatatgcc ctcttaccgt cagccgatca tcctcactca tagcgacgcg agaaagctct    480
tgttccagct cgtgcacggt atccaattca gtaatcctac gcaacgccgt ctgaatcgtg    540
ttcataagtt cagttttaaa gctcaaaact tcgtctctta ntttacccccc tgtgactttc    600 aaactgggcg antcttcacc attttattaa tcgtctttttt ganggangc ccagcgttag    660 atctgcatcg ccagcggaat cgttactccc tcccattcct cctccgggta acgcanntag    720
tttctccgaa gccttaaaat tagccgggga aagggaattt atttgcccca acaanggnat    780
cgcggnnctg gtggttaaaa ggaactgaaa taaaattaaa ncccncttgg gggaaangcc    840
cgcatactg                                                             849
```

<210> SEQ ID NO 236
<211> LENGTH: 310
<212> TYPE: DNA
<213> ORGANISM: Homo sapiens
<220> FEATURE:
<221> NAME/KEY: misc_feature
<222> LOCATION: (1)...(310)
<223> OTHER INFORMATION: n=A,T,C or G

<400> SEQUENCE: 236

```
ggggtgggtt gcttccgaaa nccggggccc ggccaacttg ttggcttggg aatattctgg     60
caagaaaatt tccagggcgg cgccaatttn atcaagcccg ggcggcctta aaccgaaaac    120
tctggcaggg tcaaccccttt tcatgggcgn ttgaaagctt gaagcgcccc aagttactcc   180
caagcttgtt gcgnttgccg ttggggggcgg gggaaaagtt gaaaacacgg gcgntttgtt   240
gcccgccccg cgggcggttt nttacgccat cctgggaaaa ctttcagggt tggctgctta   300 cnaaaacggg                                                            310
```

<210> SEQ ID NO 237
<211> LENGTH: 315
<212> TYPE: DNA
<213> ORGANISM: Homo sapiens
<220> FEATURE:
<221> NAME/KEY: misc_feature
<222> LOCATION: (1)...(315)
<223> OTHER INFORMATION: n=A,T,C or G

<400> SEQUENCE: 237

```
gcacgagtnt ttgttatta natnttgctt tgtttaangg aagaacacaa naatgccctg      60
ctaaagggat tctgtttggt tgcangctgc nagcggggaa aaaatcnaan tgtatnttgc    120
acaacangat ttttttagaan tcagaactat gacatgaagt canncagggc actctacgac   180
tgaatttgcn gtgctgcctt cacangctcc ttnctcgctc tntnctggca ncngtgactc    240
ntacacgtcc tggananantan cctccctana aggaacgact ccgacacccc cccnntaccc   300
ctnaangttc atcng                                                      315
```

<210> SEQ ID NO 238
<211> LENGTH: 510

```
<212> TYPE: DNA
<213> ORGANISM: Homo sapiens
<220> FEATURE:
<221> NAME/KEY: misc_feature
<222> LOCATION: (1)...(510)
<223> OTHER INFORMATION: n=A,T,C or G

<400> SEQUENCE: 238
ngcacgagtn tttgttattt atatattgct ttgtttaaag gaagaacaca aaaatgccct    60
gctaaaggga ttctgtttgg ttgcaggctg cnngcgggga aaaaatcaaa gtgtattttg   120
cagaaaatga tttttttanaa gtcagaacta tgacatgaag tcaagcaggg cactctagga   180
ctgaatttgc tgtgctgcct tcatatgctc cttgctcgct cttttctggc agctgtgact   240
cncacaggtc atggaganta tcattcccta aaaggaacaa cnccgatatt catctttatc   300
cattaagtnc atctgtccca ttctatgtng tggatgctaa cttttgatca ttgatngtga   360
tnccatggac atntancatc anctttcana ncctnggatc tttgacnagt cttattantn   420
agantccaac tantacgatg ccganttana aatgctggnt ntccaattcc tactcaaata   480
nccnacatga acttccantc cccttgcnna                                     510

<210> SEQ ID NO 239
<211> LENGTH: 209
<212> TYPE: DNA
<213> ORGANISM: Homo sapiens

<400> SEQUENCE: 239
ggtgcttttc ccttctactc gtcttcctgc ctggcaggag aagctcccgc tactggttgc    60
ccttctacca ctgtcgacac caccaactgc agtgagccag tgtccgaggc tccagccaga   120
aacaggtagc agccatgccg gataccaaac gcccacactt aagagcctga aatgacctga   180
cgccacctcc gcatgcttta cctactgag                                     209

<210> SEQ ID NO 240
<211> LENGTH: 610
<212> TYPE: DNA
<213> ORGANISM: Homo sapiens
<220> FEATURE:
<221> NAME/KEY: misc_feature
<222> LOCATION: (1)...(610)
<223> OTHER INFORMATION: n=A,T,C or G

<400> SEQUENCE: 240
ggcacgaggt ttctggctgg agcctcggac actggctcac tgcagttggt ggtgtcgaca    60
gtggtangag ggcaaccagt aacgggagct tctcctgcca ggcaggaaga cgagtagaag   120
ggagcggcat gctggaggct ggagcctgag cccctgggc tcgccttgct gtgtttggtg    180
gtgacgtggg acactgcagc tcggccagag tggtaaaaaa tgtcctggtg tacgcttttc   240
tggctttgcc cgtctatctg ctccaagcca ggctgganga ngagganaag gaatcacctg   300
tggtacgctg gagcctgcat gtggcgtgac tctgcaactc gcctcgtgtg actgatggca   360
gccacggaga ctgcagctcg acagggagtg aggcttctca ntggcttgaa agctcagctg   420
actcccacga aatttgccgg aaactcaagg ctgtcagtga cnttcgtggc gccaagactt   480
aancangcgc gttgcatgca tccggccagt gtctgtgcca cgtgccctga cnccaccttg   540
anataancac ccggaacgcg cnncgcgcag gccgcgcgca cacgnccggg cancaacttg   600
gctggcttcc                                                          610

<210> SEQ ID NO 241
```

```
<211> LENGTH: 474
<212> TYPE: DNA
<213> ORGANISM: Homo sapiens
<220> FEATURE:
<221> NAME/KEY: misc_feature
<222> LOCATION: (1)...(474)
<223> OTHER INFORMATION: n=A,T,C or G

<400> SEQUENCE: 241
ggcacgaggt ttctggctgg agcctcggac actggctcac tgcagttggt ggtgtcgaca      60
gtggtangag ggcaaccaat aacgggagct tctcctgcca ggcaggaaga cgantagaan    120
ggancggcat gctggangct ggancctgan ccctgggc tcccttgctg tgtttggtgg      180
tgacgtggga cactgcagct cggccagant ggtaaaaatg tcctggtgta cgcttttctg    240
gctttgcccg tctatctgct ccaagccacg ctggaagang agganaagga ntcacctgtg    300
gtacgccgga gcctgcatgt gggngtgact ctgcaactcg cctcgtgtga ctgatggcac    360
ccacggacac tgccactcta cagngaatga ggcttctccn tggactngaa agctcanctt    420
nactcccncc aagtttgncg gaactcaagg ctntcactna acttcgtggc gcca          474

<210> SEQ ID NO 242
<211> LENGTH: 415
<212> TYPE: DNA
<213> ORGANISM: Homo sapiens
<220> FEATURE:
<221> NAME/KEY: misc_feature
<222> LOCATION: (1)...(415)
<223> OTHER INFORMATION: n=A,T,C or G

<400> SEQUENCE: 242
ngcggggnnt tccaccagct cgtgtgcaca agtngcgcca cacaaacatg cgcaggcact      60
gcatgtcatc natgtgcttc gccgtggttc tggaacagcg agtagaagat ggcgttcggg    120
tcgcgaccaa attcgacgtc ntggatgctc ttgcgcaaga angtcacgta cgggatcggc    180
ccgatggatc cgctnaagcg ccgaaaggcc ctgacttgca aaccgcggct cacagaaccg    240
gcaccaccgg cgccctccgc cnacaaaagt cgagcggcct ccgacacaca ctccctcaca    300
tccccgtcnc gcacttcggc ngtttctagc tccgccacgg ttgtcagcgg caccgcgggc    360
gccnagctgc cggcggcatc cgttgcacac agcacacacg gatccgctct cgtgc          415

<210> SEQ ID NO 243
<211> LENGTH: 841
<212> TYPE: DNA
<213> ORGANISM: Homo sapiens
<220> FEATURE:
<221> NAME/KEY: misc_feature
<222> LOCATION: (1)...(841)
<223> OTHER INFORMATION: n=A,T,C or G

<400> SEQUENCE: 243
aacgaggtgt cgatgagcgc gaacaatcgc cctccttcat ctctacctga tggtgaactt      60
cgctcctaca gccgagccaa tgaagacgaa tggctgctgc cgaggatggg agtctcacta    120
gagcacgcgg cgctggacaa ctcatcgact tgtacgcttc cggtagctta gcccattcag    180
ctccactgac gacagagacg gagctggcca ctgccatctc gacgcagcgg gacaaggagc    240
agcttcgggc gccgtatgca tcactcgaag agaaccagga gcagcggaa gcaggangcg     300 ctgcacggta caggcacttt cggcgcttca gcggatccat cgggccgatc cgtacgtca    360 ccttcttgcg caagaacatc caggacgtcg aattcggtcg cgaaccgaat gccatcttct    420
actcgctctt ccaggacccg gcgaagcaca ttgatgacat gcagtgcctt gcgcatgttt    480
```

```
gtgcggcgct accttggtgc acacgaacga nggcaaccaa cccgcccag gtgccgctct    540 atgcattcct gttctgttcc ggtgtgcatg gccggatgtg gaccgtganc ttggtgaatc    600
ggctggtgca tgaagactta ccgctctcnt caagggcgaa cgcncctcan ttcgganaag    660
gaacaaaacc ccccnnaag aacggcantt gcancntttt ccccgctgc cggctcttct     720 ccattcgggn attctctntc tccnaaaant ccgcnaaatc ttctttcggt ttctcccctg   780
tttttatttg cccttcccgc cacttgggtt gttttacatc ctacaancct tttttttctc  840
c                                                                    841

<210> SEQ ID NO 244
<211> LENGTH: 761
<212> TYPE: DNA
<213> ORGANISM: Homo sapiens
<220> FEATURE:
<221> NAME/KEY: misc_feature
<222> LOCATION: (1)...(761)
<223> OTHER INFORMATION: n=A,T,C or G

<400> SEQUENCE: 244
aacgaggtgt cgatgagcgc gaacaatcgc cctccttcat ctctacctga tggtgaactt    60
cgctcctaca gccgagccaa tgaagacgaa gtggctgctg ccgaggatgg gagtctcact   120
agagcacgcg gcgctggaca actcatcgac ttgtacgctt ccggtagctt agcccattca   180
gctccactga cgacagagac ggagctggcc actgccatct cgacgcagcg ggacaaggag   240 canct tcggg cgccgtatgc atcactcgaa gagaaccagg agcagccgga agcaggaggc   300
gctgcacggt acaggcactt tcggcgcttc agcggatcca tcgggccgat cccgtacgtc   360
accttcttgc gcaagaaaca tccaggacgt cgaattcggt cgcgacccga atgccatctt   420
ctactcgctc ttccaggacc cggcgaagca catttgatga actgcagtgc ctgcgcatgt   480
ttgttgcggg gctacctggt tgcacncgan cganggcaac aacccgcgcc angttgccgc   540
tctatgcatt ccctgtctgt ccggtgttgc atggccggat gtggancgtg ancttgtgaa   600
tccgctgggt gcatgaagga cttaccgctc tcgtcaaggg cgaacgcgcc atcaattccg   660
gaaaaggaac naaaacccc ccccaangac ggnaatttgc anctttttccc ncncctgccg   720 gctcttctcc antncgggct tctctttctc anaaaattcc c                        761

<210> SEQ ID NO 245
<211> LENGTH: 710
<212> TYPE: DNA
<213> ORGANISM: Homo sapiens
<220> FEATURE:
<221> NAME/KEY: misc_feature
<222> LOCATION: (1)...(710)
<223> OTHER INFORMATION: n=A,T,C or G

<400> SEQUENCE: 245
aacgaggtgt cgatgagcgc gaacaatcgc cctccttcat ctctacctga tggtgaactt    60
cgctcctaca gccgagccaa tgaagacgaa gtggctgctg ccgaggatgg gagtctcact   120
agagcacgcg gcgctggaca actcatcgac ttgtacgctt ccggtagctt agcccattca   180
gctccactga cgacagagac ggagctggcc actgccatct cgacgcagcg ggacaaggag   240
cagcttcggg cgccgtatgc atcactcgaa gagaaccagg agcagccgga agcaggaggc   300
gctgcacggt acaggcactt tcggcgcttc agcggatcca tcgggccgat cccgtacgtc   360
accttcttgc gcaagaacat ccaggacgtc aaattcggtc gcgaccgaat gccatcttct   420
```

```
actcgctctt ccaggaaccg gcgaagcaca ttgataacat catgcctgcc catgtttgtt    480
gcggccctcc tggttgcnca cgaancgaag ggcaacaaac ccgcgccagg tngccgctct    540
tatgcattcc ttgtctgttc cggtnntgca tggcccggan nttggaaccg tnancttggt    600
nnaatcggct ggtgcattga aggaacttac cgctctcgtc aagggccgaa cgcncccttc    660
agttcggana aaggancgaa accccccccn naaggaacgg ccnttgcnng              710

<210> SEQ ID NO 246
<211> LENGTH: 704
<212> TYPE: DNA
<213> ORGANISM: Homo sapiens
<220> FEATURE:
<221> NAME/KEY: misc_feature
<222> LOCATION: (1)...(704)
<223> OTHER INFORMATION: n=A,T,C or G

<400> SEQUENCE: 246
aacgaggtgt cgatgagcgc gaacaatcgc cctccttcat ctctacctga tggtgaactt     60
cgctcctaca gccgagccaa tgaanacgaa ntggctgctg ccgaggatgg gagtctcact    120
aaagcacgcg gcgctggaca actcatcgac ttgtacgctt ccggtagctt agcccattca    180
gctccactga cgacaganac ggagctggcc actgccatct cgacgcagcg ggacaaggga    240
gcagcttcgg gcgccgtatg catcactcga agagaacagg agcagccgga agcaggaggc    300
gctgcccggt acaggcactt cggcgcttc ancggatcca tcgggccgat ccgtacgtc     360 accttcttgc gcaanaacat ccaggacgtc gaattcggtc gcgacccgaa ttgccatctt    420
ctactcgctc ttccagggac cggcgaagca cattgatnaa attgcattgc ctgcgcatgt    480
ttgtgcgggg cttcctggtg ccccgancga agggcnacaa ccccgcgcca gggtgccnct    540
ctatgcattc ctntctgttc cggtgttgcn tgggcgggat ttgaaccgtg aancttggtg    600
aatccgnttg gtgcattaag aacntaaccg ttcntcgtca ggggcnnacc ggncccttnc    660
aatttcggaa aaangaacca aaancccccc ccnccaagga aacn                    704

<210> SEQ ID NO 247
<211> LENGTH: 618
<212> TYPE: DNA
<213> ORGANISM: Homo sapiens
<220> FEATURE:
<221> NAME/KEY: misc_feature
<222> LOCATION: (1)...(618)
<223> OTHER INFORMATION: n=A,T,C or G

<400> SEQUENCE: 247
ggccgccagt gtgatggata tcgaattcaa cgaggtgtcg atgagcgcga acaatcgccc     60
tccttcatct ctacctgatg gtgaacttcg ctcctacagc cgagccaatg aagacgaagt    120
ggctgctgcc gaggatggga gtctcactag agcacgcggc gctggacaac tcatcgactt    180
gtacgcttcc ggtagcttag cccattcagc tccactgacg acagacggg agctggccac    240 tgccatctcg acgcagcggg acaaggagca gcttcgggcg ccgtatgcat cactcgaaga    300
gaaccaggaa gcagccggaa gcaggaggcg ctgcacggta caggcacttt cggcgcttca    360
gcggatccat cgggccgatc ccgtacgtca ccttcttgcg caagaacatc caggacgtcg    420
aattcggtcg cgacccgaat tgccatcttct actcgctctt ccaggacccg gcgaaagcac    480
attgatgaca tgcagtgcct gcgcatgttt gtngcggcgc tacctggtgc acacgagcga    540
nggcaacaaa cccgcgccca ggtgccgctc tatgcattcc tgttctgtcc gggtgtgcat    600
ggcccggatg tggaaccc                                                 618
```

<210> SEQ ID NO 248
<211> LENGTH: 622
<212> TYPE: DNA
<213> ORGANISM: Homo sapiens
<220> FEATURE:
<221> NAME/KEY: misc_feature
<222> LOCATION: (1)...(622)
<223> OTHER INFORMATION: n=A,T,C or G

<400> SEQUENCE: 248

```
gcacgagagc ggatccgtgt gtgctgtgtg caacggatgc cgccggcagc ttggcgcccg      60
cggtgccgct gacaaccgtg gcggagctag aaactgccga agtgcgcgac ggggatgtga     120
gggagtgtgt gtcggaggcc gctcgacttt tgttggcgga gggcgccggt ggtgccggtt     180
ctgtgagccg cggttttgcaa gtcagggcct ttcggcgctt cagcggatcc atcgggccga   240
tcccgtacgt gaccttcttg cgcaagagca tccacnacgt cgaatttggt cgcgaaccga    300
acgccatctt ctactcgctc ttccagaacc cggcgaagca cattgacaac atgcnntgcc    360
tgcgcatgtt tgtgcggcgc tncctgntgc acacgaccga gggtaccaac ccgcgccagg    420
ntgccnctct acgcattcct gtctgcccgg tgtgcgtggc cnggatgtgg accntgagcn    480
ggngantccg ctggtgcntg aagacnttgc cgctctcgtc aaggccnacc gccentcgcg    540
gcggaaaaag gancaaaanc ccccgccaa gaaccggcnc tgcaccgttn tcgcgcccct     600
gctgggctct tctccnttac gg                                             622
```

<210> SEQ ID NO 249
<211> LENGTH: 517
<212> TYPE: DNA
<213> ORGANISM: Homo sapiens
<220> FEATURE:
<221> NAME/KEY: misc_feature
<222> LOCATION: (1)...(517)
<223> OTHER INFORMATION: n=A,T,C or G

<400> SEQUENCE: 249

```
cattcgagct cggtaccggg gatccgattg gtaaagggga tgcggaacag ccagctggtg      60
ttttcggtgc ggccggggca gcccacatcg ctgtggtcgt tggcgtactg gatgcgatgt     120
gccgggacaa acgcgttttc caccacgatg tcatgactgc ctgtgccgcg caggcccagc    180
acatcccagt tgtcctcaat gcggtagtcc gccttgggca ccagaaaagt cacatgctcc    240
aggccaggcg tgccatcacg cttgggcagc agaccgccta gaaacagcca gtcgcaatgc    300
ttggagccgg tggaaaagct ccagcgaccg ttgaacctga atccgccttc cacgggctcg    360
gccttgccag taggcatata ggtcgaggcg atgcgcacgc cgttatcctt gccccacaca    420
tcctgctggg cctggtcggg gaaaaancgc cagctgccaa ggggtgaacg ccgaccaccc    480
cgtaaatcca ggccgtggac atgcagccct ttaccaa                             517
```

<210> SEQ ID NO 250
<211> LENGTH: 215
<212> TYPE: DNA
<213> ORGANISM: Homo sapiens
<220> FEATURE:
<221> NAME/KEY: misc_feature
<222> LOCATION: (1)...(215)
<223> OTHER INFORMATION: n=A,T,C or G

<400> SEQUENCE: 250

```
nntncattgg gccgacgtcg catgctcccg gccgccatgg ccgcgggatt accgcttgtg      60
```

```
accgcttgtg accgcttgtg accgcttgtg accgcttgtg accgcttgtg accgcttgtg    120
accgcttgtg accgcttgtg accgcttgtg accgcttgtg accgcttgtg accgcttgtg    180
accgcttgtn acnggggtg tctgggggac tatga                                215
```

<210> SEQ ID NO 251
<211> LENGTH: 231
<212> TYPE: DNA
<213> ORGANISM: Homo sapiens
<220> FEATURE:
<221> NAME/KEY: misc_feature
<222> LOCATION: (1)...(231)
<223> OTHER INFORMATION: n=A,T,C or G
<400> SEQUENCE: 251

```
ngcgcccacc tngtgattga tggtcgttta ctatcaagta tgtacatctt gctctagaca     60
actccnattc agtggaagaa attgggaaag tatcccggat aagtaatagg nattaggtct    120
nccttantgc ttggtgggat attccncaac tgntccngat cggatcagnc tcgtgtcngn    180
gaatgtgctc gatcgtnatt ctactnctga gcttctatcc nnacgtggcc t             231
```

<210> SEQ ID NO 252
<211> LENGTH: 389
<212> TYPE: DNA
<213> ORGANISM: Homo sapiens
<220> FEATURE:
<221> NAME/KEY: misc_feature
<222> LOCATION: (1)...(389)
<223> OTHER INFORMATION: n=A,T,C or G
<400> SEQUENCE: 252

```
atgtatcanc nctgttggtg ttncatcttt tgcagtcngt tctaagggcn gataantatc     60
agagatgcta atgcatnttc tgccaggcca ncattggtgg cctatgcgta ctcttcttat    120
cttcctgaag agtcatctct ggnggatgtg ttccccccctc tccacagtgt ttgcaagcgt    180
tacccacgcn tgtcggngcc gggaaggtcn ncacatccgg gnagacttcc ccncgtntga    240
atcgtntctn gaatctccgg cgtcntccct naacctcttg actnggacaa ngncccgtnt    300 tccctntgt gaactngtan ccgccccct ttccccctc agcctaancg ggaangaaga      360
cngggtcnat ctngggcncc acaagaant                                      389
```

<210> SEQ ID NO 253
<211> LENGTH: 289
<212> TYPE: DNA
<213> ORGANISM: Homo sapiens
<220> FEATURE:
<221> NAME/KEY: misc_feature
<222> LOCATION: (1)...(289)
<223> OTHER INFORMATION: n=A,T,C or G
<400> SEQUENCE: 253

```
ngggccnna tgagcgcgcg taatacnatc actatngggc gaattgggta cgggcccccc      60
tcnagcggcc gccttttntt ntttttttnt tnttttttnt caaaacaccc tccnccntgg    120
atgganacgt naccttctc taaccanatc ttcacaatnc nantctcagg cagccgcctc    180
aaanccgatg tcangttggn atntcaantn caatcttatt ttgngaatta anctganatt    240
gtggatggtn naccaatcan atacttggna tccgttgaac ccctgtgga               289
```

<210> SEQ ID NO 254
<211> LENGTH: 410
<212> TYPE: DNA
<213> ORGANISM: Homo sapiens

```
<220> FEATURE:
<221> NAME/KEY: misc_feature
<222> LOCATION: (1)...(410)
<223> OTHER INFORMATION: n=A,T,C or G

<400> SEQUENCE: 254
attgtgttgg gaacttgtag acagctatat caattgcagt gctatttctc tgaggtattg     60
aatctcantt attataattt tgaaatccaa ttggcttgga cttcattatt ttccaactaa    120
aaagatgatt gaaggattta tttgaaatgt gtaaagagta atatagattt tatgcttatg    180
tttccttgaa aaaagtaggt aaaattcttc tggaagtgtt actcctaaaa tacaaatgaa    240
catgtcaaga attacataaa ttctttaaac tatccttaan aannaatggc tctatgtann    300
gagngaccct tacagactat taagaattaa cttgcatggc anagactcat ttanattcat    360
gaaatggntc tcactttctt ggtaagatct ggcttggacg ttttggtaa                410

<210> SEQ ID NO 255
<211> LENGTH: 668
<212> TYPE: DNA
<213> ORGANISM: Homo sapiens
<220> FEATURE:
<221> NAME/KEY: misc_feature
<222> LOCATION: (1)...(668)
<223> OTHER INFORMATION: n=A,T,C or G

<400> SEQUENCE: 255
tttttttttt ttttcctgtg ccaggcacta taccactgtg ctaggtgcct tctttgcatt     60
acttcatttc ctcataagct ttctgaggan acagaaagct tgaggttcac gtagctagca    120
tctacataaa ttagttgcta aaaacataca atacgtcttc cggcaggctg tcattagtaa    180
ctgatactac tagttgataa tctcataaac ctagcanaan ctaccattta agctgaaaca    240
actgtcaata tcactaanta aaacttaaat ccataaatca actatattct aaaatctgac    300
ttcagttcaa ttaaaaaatc actagttgtt acctacctcc ttctgaaagc cagtacaagt    360
taaatgaaca actcccgagt ttaacaaaca agtggcatct aaaaaaaaga tttaaaaaat    420
aatccactta catatattta aaatggcatt aataaaacaa aatttatcca ataacnaant    480
ggcaaaggaa ggtgtccaat tattacatgt tataaatctt taaattaaac ttttcttngg    540
tttttcntcc ctanaataaa tacaanccctt tcccgccna accagaaaaa agcaaaaaac    600
aaaacccaaa aactcccagc ncngcttaaa aaacncaaaa aaataaaaan ctctattaaa    660 tgcccnaa                                                             668

<210> SEQ ID NO 256
<211> LENGTH: 487
<212> TYPE: DNA
<213> ORGANISM: Homo sapiens
<220> FEATURE:
<221> NAME/KEY: misc_feature
<222> LOCATION: (1)...(487)
<223> OTHER INFORMATION: n=A,T,C or G

<400> SEQUENCE: 256
cgnaaccgtn cnttttttnat gtgcgcccgc cncagnacca gngccgctac aggcgaaggc     60
cggaagcacg ggagaggntt nggaaaaaaa agagtgctta caaagagcat attcgcagag    120
ttgggatgag tgaagggggac cagaagggngc agccgtaggg acgcgtgaaa ggangcngcg    180
gagaaatgac agcaagaagg gganaagcac acgaaaaggc agtatcctcc tcccccttt    240 tcgaggactg ccgcatcttt gttttctgcc cattccagtc accgaanaag atcccaaana    300
```

| | |
|---|---|
| aagaagaaaa gaancagagg tgcacttcgc ttcatatttc nctcgctttc ttttctgnct | 360 |
| tcacnagttc tgcaggattg cccttgtcct cttccgagca catctacgca cgnatgaggc | 420 |
| tcggcaggtc aagccnacaa aacnctcgca ctcctctttt tctttgcnng tctgngtggt | 480 |
| anggngg | 487 |

<210> SEQ ID NO 257
<211> LENGTH: 502
<212> TYPE: DNA
<213> ORGANISM: Homo sapiens
<220> FEATURE:
<221> NAME/KEY: misc_feature
<222> LOCATION: (1)...(502)
<223> OTHER INFORMATION: n=A,T,C or G

<400> SEQUENCE: 257

| | |
|---|---|
| cctttgaaag nccngctnaa ttcngnganc ccccngatca gcaccaggga gctacaacna | 60 |
| aggccggaag cagggdattt ngccggaaaa aaaagagtgc ttacaaagag nttatccnca | 120 |
| nagatgggat gagtgaaggg gacgagaagg tgcagcggta gggacgcgtg aaaggaggca | 180 |
| gcggagaaat gacagcaaga aggggagaag cacacgaaaa ggcagtatcc tcctcccccc | 240 |
| ttttcgagga ctgccgcatc tttgttttct gcccattcca gtcaccgaaa aagatcccaa | 300 |
| agaaagaaga aaagaaacag aggtgcactt cgcttcatat ttcgctcgct ttcttttctg | 360 |
| tcttcacaag tctgcaggat tgcccttgtc ctcttccgag cacatctacg cacgtatgag | 420 |
| gctcggaggn caagccaaaa aaacgcttgc actcctcttt ttctttgcgt gtctgtgtgt | 480 |
| atgtggaatt ccgcggcncc gc | 502 |

<210> SEQ ID NO 258
<211> LENGTH: 510
<212> TYPE: DNA
<213> ORGANISM: Homo sapiens
<220> FEATURE:
<221> NAME/KEY: misc_feature
<222> LOCATION: (1)...(510)
<223> OTHER INFORMATION: n=A,T,C or G

<400> SEQUENCE: 258

| | |
|---|---|
| actcgncact cgatncanta caagagnnta tgnattcgaa ngtgccccg catcagcacc | 60 |
| agggagctac aacgaaggcc ggaagcaggg gagagggccg gaaaaaaaag agtgcttaca | 120 |
| aagagcatat ccgcagagtt gggatgagtg aaggggacga aaggtgcag cggtagggac | 180 |
| gcgtgaaagg aggcagcgga gaaatgacag caagaagggg agaagcacac gaaaggcag | 240 |
| tatcctcctc cccctttc gaggactgcc gcatctttgt tttctgccca ttccagtcac | 300 |
| cgaaaaagat cccaaagaaa gaanaaaga acagaggtg cacttcgctt catatttcgc | 360 |
| tcgctttctt ttctgtcttc caagtctgca ggattgccct tgtcctcttc cgagcacatc | 420 |
| tacgcacgta tgaagctcgg aggtcnngnc aaaaaaacgc ttgcactcct ctttttcttt | 480 |
| gcnagtctgt gtgcatgngg gaaatnctna | 510 |

<210> SEQ ID NO 259
<211> LENGTH: 292
<212> TYPE: DNA
<213> ORGANISM: Homo sapiens
<220> FEATURE:
<221> NAME/KEY: misc_feature
<222> LOCATION: (1)...(292)
<223> OTHER INFORMATION: n=A,T,C or G

<400> SEQUENCE: 259

```
gannngagtc acgaaaaggc agtatcctcc tcccccnttt tcgaggactg ccgcatcttt    60
gttttctgcc cattccagtc accgaaaaag atcccaaaga aagaagaaaa gaaacagagg   120
tgcacttcgc ttcatatttc gctcgctttc ttttctgtct tcacaagtct gcaggattgc   180
ccttgtcctc ttccgagcac atctacgcac gtatgaggct cggaggtcaa gccaaaaaaa   240
cgcttgcact cctctttttc tttgcgtgtc tgtgtgtatg tggaattcct tg           292
```

<210> SEQ ID NO 260
<211> LENGTH: 582
<212> TYPE: DNA
<213> ORGANISM: Homo sapiens
<220> FEATURE:
<221> NAME/KEY: misc_feature
<222> LOCATION: (1)...(582)
<223> OTHER INFORMATION: n=A,T,C or G

<400> SEQUENCE: 260

```
gcacgaggtt gggtggtact gtgtataata actccagatc cttgaccaag tttggagagt    60
cacttatggc catttgaaac caaatgaagg atcaaaggac taattatttt gaatacctct   120
gagtgttttc cccaagcttg agaagagttt cattcagcta taaaatgctc attgtgcaaa   180
tgagtggttt ccatgctgta taattaaagc attgccttta ataatatttt attaccttta   240
gcttgtcttt ttaatttgag gaaaatccaa acaatttaaa gtaaaacgtg ataaagacag   300
tttttcngga gananaaggg nagatcgcta tgtttattcc acttaatatc tatatcaaat   360
atttgtatca aaagcagact ctcacttta aaatattctt ctaatggcna gaatcttttn   420
cctagattga gagtcagagc tcacatagna tnactgctgg taaatagaca cttagactat   480
agagctnagc tnaagttcca actanccaac tgcatttctg aatatgcttt ttattnaaag   540
gccagnnctt ttgccttttt nccncccta tnccttctat tg                      582
```

<210> SEQ ID NO 261
<211> LENGTH: 783
<212> TYPE: DNA
<213> ORGANISM: Homo sapiens
<220> FEATURE:
<221> NAME/KEY: misc_feature
<222> LOCATION: (1)...(783)
<223> OTHER INFORMATION: n=A,T,C or G

<400> SEQUENCE: 261

```
gcacgaggca aaatacagag ggtatttac catggacagg caacccattt ttccaggaca     60
actctttgca gcagagagct attctcttc ttttgcctta cactctcaac ctcactcttc   120
gagtgtctgc atcctanttt tccatggcca taagataagg aaccatgagt gttactctag   180
atgaggctgt ttcattgtgg gagctcatcc aggatccaag gtagattcat cagaagggta   240
agtataggag tgggaaccca aatctctact tttattttga ggccttctct cctcaatttt   300
aaattgtaaa atcaaactta aaactgggta tctgatggcc agttaaaaga ctgggtatct   360
gattgccagt taagagatgg tcatttatgc tcaccaccat tctcaagacg caggtgaggt   420
gacangcttg ctgggaatg ctgancgaat cccccaatgc cttcaggatt ctgggaatgg   480
tggctctgnt ttaaactggn tgacttttac aaagagccta cccgtcatgg ggggactggg   540
aagaaaaccc anangcagnt tctggcccan ggttacaccc ccanggntac cttgaaggnt   600
ttttggacat acctnttncc cccctnttac tgnttcatta gggcntcnnc aacccaantt   660 tccaagtttnt ggcccttcna aaantttttt ntttccntt tccanggacc ccctggntt    720
```

| | |
|---|---|
| cctggnnccc cctttttata nccaaccttg ccnggnattt tttcncnttn aagggaaat | 780 |
| aat | 783 |

<210> SEQ ID NO 262
<211> LENGTH: 741
<212> TYPE: DNA
<213> ORGANISM: Homo sapiens
<220> FEATURE:
<221> NAME/KEY: misc_feature
<222> LOCATION: (1)...(741)
<223> OTHER INFORMATION: n=A,T,C or G

<400> SEQUENCE: 262

| | |
|---|---|
| tgaaccctan tgggcccggc cccctcgagt cgacggtatc gataagcttg atatcgaatt | 60 |
| cggcacgagt gtatattctg ttattatacc ccagattnaa gtgtatattc ttaggcagta | 120 |
| gttctggtta acatccttac tacataaaat ccacttacta tttaagtatt attctaacag | 180 |
| gaggtagaat agctgcctta aaaaatgtag tgatcgaatg gcagttttc tgctgaatgg | 240 |
| aaattactga cacaaaattt ggttttggga gacattttcc tccttgttgt tgagttttcc | 300 |
| cattcacgga tagggcataa agcttggttt atagttgagg ggtgcaaaag ggaatagga | 360 |
| ttgggaaaat acagtgttcc agcaaaggtc tgacaaggta catcttggag aggattccta | 420 |
| ttctgctang tggcactgta ngtcttgaaa tactgtgtac tttccagaca aaggatagag | 480 |
| aaaagacct tcactgggtg ggggagaaga aaaccttgt tcctagaaaa atcacaaaaa | 540 |
| aggcatcctt tanccctatat tcccagnttt actggngcat ttgcttgatg tgactgacnc | 600 |
| ngattatttc ctttnactgg naaaaattcc tgccnctttg gatatnaang ggggnaccng | 660 |
| gaaaatnggg ggcnttgggg aaggaaanaa aaaaaattgg agggaccnaa ctttggaaaa | 720 |
| tgggntgctt nangccttaa g | 741 |

<210> SEQ ID NO 263
<211> LENGTH: 437
<212> TYPE: DNA
<213> ORGANISM: Homo sapiens
<220> FEATURE:
<221> NAME/KEY: misc_feature
<222> LOCATION: (1)...(437)
<223> OTHER INFORMATION: n=A,T,C or G

<400> SEQUENCE: 263

| | |
|---|---|
| ggcacgagag aatgtgttca cagacactat tttatannta tctgatgtgt actgtgtctg | 60 |
| gtggatgtga aagccatact tcttaaatct gatttgaaaa gcaaatctga ttatcacagc | 120 |
| cataattaaa tttggccagc cttccttcct ccctccctcc ttcacttcct tccttccttc | 180 |
| cgcctcgtgc cgaattcggc acgagcctga cctcactacc aaaaaaaaaa aaattcaaag | 240 |
| tgcctgaggt ttccaggcat tcttagctct atttacttac ttcccacctc aaatggcctt | 300 |
| agaattcaaa ttctgnanaa aatggattgc catanataat ccaatgaaaa tgggtcatat | 360 |
| tttgccatta atagaatcac agtcnacaag ggactaatag aattagtcac ttangtatcn | 420 |
| ttagatttgg gagacnn | 437 |

<210> SEQ ID NO 264
<211> LENGTH: 706
<212> TYPE: DNA
<213> ORGANISM: Homo sapiens
<220> FEATURE:
<221> NAME/KEY: misc_feature
<222> LOCATION: (1)...(706)
<223> OTHER INFORMATION: n=A,T,C or G

<400> SEQUENCE: 264

```
gcacgagcac cccaaggttt taggacaaaa tgggatgagt gaattcatgg cttgacagac      60
tgaacagaaa aatgaggctc cgtgctccat attcatgtgc atctgcccct catggtgaca     120
tgctaattgg ttggccggtg cacaagacaa ggaagtgcag gtttcctgtt gctcacacag     180
tgcttcctgt ctgctgtggc aggagccggg aggaagggag cgagccaaga ggggctgctgc    240
ccaccggaaa cgatggcgcg aggccgcaga gctaaatggg ggcctctcca gggagtgctc     300
tgttcacggc tccatcgctg ttagtaagta tcttgtgatt tcggaattta aatgaggttg     360
tgtttaacct gcataacatc tggctttttaa aatctgactt tattttcctt ttatttctgt    420
gcatcggctc aggcacactt agtggtggct taggtgttga agtcaggtta ccaaacagca     480
cgccctctct ttattctcag gctgcgtgtt tcattgattc tgaaggtcag atggctgtgt     540
tcaagttctg ttagtatatt ggtgtcagaa atgaaaagat gatgtaaccc tttataactt     600
cttaaaggct catatcatgt caggaaatta acctgtacga gttatggaca aatgcccatc     660
ctgatgattt tcanccatga aaatgaatna aaggggganaa gggcca                   706
```

<210> SEQ ID NO 265
<211> LENGTH: 717
<212> TYPE: DNA
<213> ORGANISM: Homo sapiens

<400> SEQUENCE: 265

```
ggcacgagca gcattacggt ttatacacat gtccacaact cagcattgct ttcaaaatag      60
gaacacttta ttagtaaaga ggaagaaatt gcctaaacag actcagtgtc tttcccataa     120
caatcatctg ccaagccgca ggcctaacca ggaaatccca tttccttttg gcgttgtgtc     180
ctccaccaac agatacaacc ctgatgccaa atgttgtatg gtttgtaggt gttgtgagcc     240
aatgagggca tgcctagggc caaaggctgc cctttggaat gagggcaagg tcgtagactc     300
catcaaacaa caaatgcatc ctcctccaaa atcaaatgct caacacatgc agcctttcgt     360
atgcccatct ccccttttact cattttcatg gctgaaaatc atcaggatgg gcatttgtcc    420
ataactccta caggttaatt tcctgacatg atatgagcct ttaagaagtt ataaagggtt     480
acatcatctt ttcatttctg acaccaatat actaacagaa cttgaacaca gccatctgac    540
cttcagaatc aatgaaacac gcagcctgag aataaagaga gggcgtgctg tttggtaacc     600
tgacttcaac acctaagcca ccactaagtg tgcctgagcc gatgcacaga aataaaagga    660
aaataaagtc agattttaaa aagccagatg ttatgcaggg taaacacaac ctcatta       717
```

<210> SEQ ID NO 266
<211> LENGTH: 362
<212> TYPE: DNA
<213> ORGANISM: Homo sapiens
<220> FEATURE:
<221> NAME/KEY: misc_feature
<222> LOCATION: (1)...(362)
<223> OTHER INFORMATION: n=A,T,C or G

<400> SEQUENCE: 266

```
ggcacgaggt tagatttaac ttccacagat gactcagcag aggataacta ctaatcagag      60
tacaacatca aaactgtaac cagtataatc actggattat gagcaactca aaatagctcc     120
agtttccaaa gggccataaa ctgcacatat cagtactatg tgcaattaac acataattta     180
ttatgaaaat gtggacatgc caggtaagta aggggattta ggttgacttt ttataatact     240
```

```
ttaaatttga aatgccattt ctgtggattg gatgacatct tccaggtgct ntaatnctgg    300
gntacctnct gatanatcct gananaaaga ggtancacca gcgtctatca nacctcaata    360
ca                                                                  362
```

<210> SEQ ID NO 267
<211> LENGTH: 692
<212> TYPE: DNA
<213> ORGANISM: Homo sapiens
<220> FEATURE:
<221> NAME/KEY: misc_feature
<222> LOCATION: (1)...(692)
<223> OTHER INFORMATION: n=A,T,C or G

<400> SEQUENCE: 267

```
ggcacgaggt tagatttaac ttccacagat gactcagcag aggataacta ctaatcagag     60
tacaacatca aaactgtaac cagtataatc actggattat gagcaactca aaatagctcc    120
agtttccaaa gggccataac tggccctttt aanactttnn gcaattaaca cataattttat    180 tatgaaaatg tggacatgcc aggtaagtaa ggggatttag gttgacttttt tataatactt    240 taaatttgaa atgccatttc tgtggattgg atgacatctt ccaggtgctt taatttggtt    300
tacctcctga tagatcctga cagaaagagg nagcaccagc gtctatcaaa cctcaataca    360
gngtgtgaaa cacangagag cctgcttttg tcnacgggg gaaacacatt gttatcacaa    420
cacacaaaag gcaanctncc aatggggnan ncttacctgn cctctcatat tgggggcaan    480
gaaaangggg cccccanatg gctgagtana tcccaaaaaa ccnccactan tggtcagnnt    540
gcttccccan acagccagat gactgaattt agcccaagct gcagtctcaa aaccagcttt    600
ctgacaatca gtaacaagaa catactggtc tgttgcagtg agctcaagtg ttgggtgttc    660
agtcaaaanc catggatgcc aatcatctcc ca                                  692
```

<210> SEQ ID NO 268
<211> LENGTH: 605
<212> TYPE: DNA
<213> ORGANISM: Homo sapiens
<220> FEATURE:
<221> NAME/KEY: misc_feature
<222> LOCATION: (1)..(605)
<223> OTHER INFORMATION: n=A,T,C or G

<400> SEQUENCE: 268

```
cgtgccgaat tcggcacgag ngcacatatc agtactatgt gcaattaaca cataattttat     60 tatgaaaatg tggacatgcc aggtaagtaa ggggatttan gttgactttt tataatactt    120
taaatttgaa atgccatttc tgtggattgg atgacatctt ccaggtgctt taatttggtt    180
tacctcctga tagatcctga cagaaagagg tagcaccagc gtctatcaaa cctcaataca    240
gttgtaaaac acagagagcc tgcttgccta cacatggaga aacattgtta tcacaagaca    300
cagaaggcaa acttccaatc tggcatactt nccgtcctc tcatatttgg ggcaatgaga    360
atggtggacc agatggcttg antagatgcc aaagaacacc canactgggc agcatgcttn    420
cccagacagc cngaagactg aaatttantc ccagctgcag ncttaaaccc ttttttttgac    480 nttccgtaac cagaccatac tttttttttct gatgcttttc ttaacttcat cttttccaat    540
taaattcatt agtnnaaccc taaangggc ccgttttccg aaaaattttc nttnttnttt    600 ccccn                                                               605
```

<210> SEQ ID NO 269
<211> LENGTH: 535

```
<212> TYPE: DNA
<213> ORGANISM: Homo sapiens
<220> FEATURE:
<221> NAME/KEY: misc_feature
<222> LOCATION: (1)...(535)
<223> OTHER INFORMATION: n=A,T,C or G

<400> SEQUENCE: 269
gcacgaggng caaccccagg gtggggtctc tgggatgaac ctggagacct gagcttgcac    60
agcttccttg gtaaattgag gaggcatgga ccacaagatt gccaagctcc tttctatcca   120
aacttgatat tgttagattc catgatccag ttcatcacgg ttgatggctg aatctcatgc   180
actanaaaaa ggtaatataa aaganaaaaa tanaangatn ttcaagtgag tataaanacc   240
tttaatctca ntcttttctag ttcaaagaga cggaacaatg agagatgctg gttcatanag   300
ctgntanatt taacttccac agatgactca ncagaggata actactaatc anagtacaac   360
atcaaaactg taaccagtat aatcactgga ttatgagcaa ctcaaaatag ctccagtttc   420
caaagggcca taaactgcca tatcaantac tatgtgccat taacccataa tttattatga   480
aaatgtggac atgccangtn agtaagggga tttagggtga cttttttatna tactt       535

<210> SEQ ID NO 270
<211> LENGTH: 803
<212> TYPE: DNA
<213> ORGANISM: Homo sapiens
<220> FEATURE:
<221> NAME/KEY: misc_feature
<222> LOCATION: (1)...(803)
<223> OTHER INFORMATION: n=A,T,C or G

<400> SEQUENCE: 270
gcacgagggc aacccagggg tggggtctct gggatgaacc tggagacctg agcttgcaca    60
gcttccttgg taaattgagg aggcatggac cacaagattg ccaagctcct ttctatccaa   120
acttgatatt gttagattcc atgatccagt tcatcacggt tgatggctga atctcatgca   180
ctagaaaaag gtaatataaa agaaaaaaat aaaagatat tcaagtgagt ataaagacct   240
ttaatctcag tcttttctagt tcaaagagac ggaacaatga gagatgctgg ttcatagagc   300
tgttagattt aacttccaca gatgactcag cagaggataa ctactaatca gagtacaaca   360
tcaaaactgt aaccagtata atcactggat tatgagcaac tcaaaatagc tccagtttcc   420
aaagggccat aaactgcaca tatcagtact atgtgcaatt aacacataat ttattatgaa   480
aatgtggaca tgccaggtaa gtaagggat ttaggttgac tttttataat actttaaatt   540
tgaaatgcca tttctgtgga ttggatgaca tcttccaggt gctttaattt ggtttacctc   600
ctgatagatc ctgacagaaa gaggtagcac cagcgtctat caaacctcaa tacagttgta   660
aaacacagag agcctgnttt gcctacncat ggagaacatt gttatcacaa gacacagaag   720
ggaacttcca tctggctact tacctggctt tattttttggg gcaatganaa tnggggggacc   780 aatggntgan tanatgccaa aaa                                           803

<210> SEQ ID NO 271
<211> LENGTH: 836
<212> TYPE: DNA
<213> ORGANISM: Homo sapiens
<220> FEATURE:
<221> NAME/KEY: misc_feature
<222> LOCATION: (1)...(836)
<223> OTHER INFORMATION: n=A,T,C or G

<400> SEQUENCE: 271
```

```
gcacgagggc aaccccaggg tggggtctct gggatgaacc tggagacctg agcttgcaca    60
gcttccttgg taaattgagg aggcatggac cacaagattg ccaagctcct ttctatccaa   120
acttgatatt gttagattcc atgatccagt tcatcacggt tgatggctga atctcatgca   180
ctagaaaaag gtaatataaa agaaaaaaat aaaagatat tcaagtgagt ataaagacct    240
ttaatctcag tctttctagt tcaaagagac ggaacaatga gagatgctgg ttcatagagc   300
tgttagattt aacttccaca gatgactcag cagaggataa ctactaatca gagtacaaca   360
tcaaaactgt aaccagtata atcactggat tatgagcaac tcaaaatagc tccagtttcc   420
aaagggccat aaactgcaca tatcagtact atgtgcaatt aacacataat ttattatgaa   480
aatgtggaca tgccaggtaa gtaaggggat ttaggttgac tttttataat actttaaatt   540
tgaaatgcca tttctgtgga ttggatgaca tcttccaggt gctttaattt ggtttacctc   600
ctgatagatc ctgacagaaa gangtagcac cagcgtctat caaacctcaa tacagttgta   660
aaacacagag agcctgcttt gnctacacat ggagaaacat tgtatcacaa gacacagnaa   720
ggcaacttcc atctgggata ctacctgtct ctctatttgg ggcatganat ggggacaatg   780
ntgananatg caanacacca atgngagctg nttccnacag cnatatgatt ntccat       836

<210> SEQ ID NO 272
<211> LENGTH: 203
<212> TYPE: DNA
<213> ORGANISM: Homo sapiens
<220> FEATURE:
<221> NAME/KEY: misc_feature
<222> LOCATION: (1)...(203)
<223> OTHER INFORMATION: n=A,T,C or G

<400> SEQUENCE: 272
ggagaattgg gcccgtcang ggtgcattct gcatcacctg anttcnaaat ctnagtcaat    60
cnncgtacta atantatcaa catnatttna acctgatctc cactgcttng tnattttcnn   120
ttcactgncc ctntcactng aacntctntt cacacagcca cccccatta tctggntggc   180 acctccncca aatnccncct naa                                          203

<210> SEQ ID NO 273
<211> LENGTH: 594
<212> TYPE: DNA
<213> ORGANISM: Homo sapiens
<220> FEATURE:
<221> NAME/KEY: misc_feature
<222> LOCATION: (1)...(594)
<223> OTHER INFORMATION: n=A,T,C or G

<400> SEQUENCE: 273
attcgggccn ctggatncgt gctcgagcgg ccgccgctgt gatggatatc tgcanaattc    60
ggcttctgga gagagctttn ttttgatgg ttgcangtac tctcgatgga gttggtgggt    120
gtggttatct ctctctggtt gtctttctgt ataaanttc tgcnctgact ncctanctcn    180 cctcccctg gtccttccct tagngtaaca nctggtaatc cctntcttct ttgctctcct    240
tncttctcct gancgatttc ctctntttgt ccactctcag gnanaccct gntggtcagt    300 gttcatgact tcnngaagnt cgacccgcna aataggncn cacggatnat gttgaancng    360
ggaagggagn gtccaanttc tctgttccan aggctnagcc tagaganaat gatgggagan   420
ggtttactga gatcatngnn tcttctcgaa gatatnnttt agggtggtcc cccataagng   480
aatttctcan cttcaaatct tctaatacat tactgaacan ctgncatttg ttacgccaca   540
nattgnaatt ctccatntct ttttagaaac nattncaagg tcatttattt ccct          594
```

<210> SEQ ID NO 274
<211> LENGTH: 229
<212> TYPE: DNA
<213> ORGANISM: Homo sapiens
<220> FEATURE:
<221> NAME/KEY: misc_feature
<222> LOCATION: (1)...(229)
<223> OTHER INFORMATION: n=A,T,C or G

<400> SEQUENCE: 274
ctactcactg tccggccatt tggncctctg natgcatnct caagcagcnc gccantatga     60
tnnatatctg cacanttcag cttctngaga aaactatgtt ttaaacagtt gcntanactt    120
anaatanaaa tcgagtaagg tntagatnan tctctaacga tngaattatt ntacanaggg    180
gtanncgatn accaggagta nctaganttg ancancancc taggtcnga               229

<210> SEQ ID NO 275
<211> LENGTH: 651
<212> TYPE: DNA
<213> ORGANISM: Homo sapiens
<220> FEATURE:
<221> NAME/KEY: misc_feature
<222> LOCATION: (1)...(651)
<223> OTHER INFORMATION: n=A,T,C or G

<400> SEQUENCE: 275
atatctgntg aatacggntt cctgnaaaaa ggtntnattt agatggttga gtccgactca     60
gcgatgcgac ttggtgggtg tggtcantct cttatggttg agattgttca tgatatcatg    120
ccctgagatg cctggactnn cctcaccgga gatcctagac ggtgntancc cctgagagtc    180
tctctcntcc tgctctccta acttctccta atgatccctc cnattgtcta ctgtccnatt    240
gaacccttct tgcttatgta tncaatcntt nacggtgtcc ctgctnantt tttganacga    300
ngctcataat ggacngggga aggatagtnt gaataatntc ctgtataccc acgccnacnt    360
ctacnctntg atctgacacg gtatactgat ttgtgctgtt cncttcacca ttccantttc    420
taccttccgc tcatatgctc tgtangctac accctctgtg actgctttct cagttacgtg    480
caacaaggtn ttcatatctn gaactcttac accattctag anggatcncc cctcgganaa    540
antttggaan aacaagcaag ancanaatnc ctctctngtg ntacacnanc cggcttncgt    600
atcctcgttn aaggaattcc ccgctttcct gggctttaan tctcctaaac t             651

<210> SEQ ID NO 276
<211> LENGTH: 392
<212> TYPE: DNA
<213> ORGANISM: Homo sapiens
<220> FEATURE:
<221> NAME/KEY: misc_feature
<222> LOCATION: (1)...(392)
<223> OTHER INFORMATION: n=A,T,C or G

<400> SEQUENCE: 276
accccccccg aattacgntg gccnatntaa aagtncatca ngcctccang caacntatcn     60
tttcattacc acccacactc ctgttnnggg anggangtgg naatccttca ccatnctaat    120
gtatgtggtg ctctcatgcn ggtacgtata atctanncgt cccctnaaat cggatgcttc    180
tgtaatcnnc agtcacnaaa ccacanggan caactgaaac angatttggc taacagccaa    240
tgtctgggcc ctcncnaatc cctnnaatat ctcctacacc tgtagtanna atnaactacn    300
ctacnctatt nnacacacgn tttaggttgt annaccaagc ccntattgag tgaaatcgtt    360
tntatngtat naaatgccaa aagntgcggt aa 392

<210> SEQ ID NO 277
<211> LENGTH: 212
<212> TYPE: DNA
<213> ORGANISM: Homo sapiens
<220> FEATURE:
<221> NAME/KEY: misc_feature
<222> LOCATION: (1)...(212)
<223> OTHER INFORMATION: n=A,T,C or G

<400> SEQUENCE: 277
ggtttgcggg natgaanttt gnaanaatna actttagnga taacccaccc accaatncct 60
nctnagtatt tgncaacctn aaaactacag ctctctccag atagactntn ccttnctgat 120
ttcaactctc cttggactgg tcagcctgaa gggtggtaat gactcaccaa cgctactaat 180
nccttnttna ctgtgccttn attttttcgc ct 212

<210> SEQ ID NO 278
<211> LENGTH: 269
<212> TYPE: DNA
<213> ORGANISM: Homo sapiens
<220> FEATURE:
<221> NAME/KEY: misc_feature
<222> LOCATION: (1)...(269)
<223> OTHER INFORMATION: n=A,T,C or G

<400> SEQUENCE: 278
nnntccatcc taataccact cactatcggg ctcgaancgg ccgcccgggc acgtntcttn 60
tgngacagga tctgaatnaa gggtggtttg taacttnact naaaattctg aaatgatcct 120
gcatcagaca gggttctccg tntanaatan agtttccctg ttagttatcn agcctgggca 180
ggggangana gattcgagga cntntgaaat gaaggnatta tttaggatgg gtgactcatt 240
ccnaccnttc ncgctnacca gnccganga 269

<210> SEQ ID NO 279
<211> LENGTH: 266
<212> TYPE: DNA
<213> ORGANISM: Homo sapiens
<220> FEATURE:
<221> NAME/KEY: misc_feature
<222> LOCATION: (1)...(266)
<223> OTHER INFORMATION: n=A,T,C or G

<400> SEQUENCE: 279
gttggtgant cngtttggng tcttcctggt gntnggtgtt tggtgtgttg nnttgttgtn 60
gggtngtntt tntggagaga gttgtagttc gtgagggttg cagtgtactt actatggagc 120
ctaaggangt gngctaactt anantgatna ctttgctcat actgccctgc cctnaatgcc 180
nngcttgcct caccctggtg ccnaaccnna tcgaacacct aacagtctag taggcttctt 240
gctntancag actnctcttg aggatc 266

<210> SEQ ID NO 280
<211> LENGTH: 317
<212> TYPE: DNA
<213> ORGANISM: Homo sapiens
<220> FEATURE:
<221> NAME/KEY: misc_feature
<222> LOCATION: (1)...(317)
<223> OTHER INFORMATION: n=A,T,C or G

<400> SEQUENCE: 280
acactgtnag gtgtntggaa ntgntgtagg catagncttt ntggcacaga gttggagccg 60

```
tgaggcatag cntgtactta ctatggagcc taaggangga gctaacttat antnatnact    120
ttgctcatac tgccctgctc tnaatgccta ngcttgcctc accctgntgc cttacnnnat    180
cgaacaccta cgcggtctat aggcttcttg ctctatcagg actnctcttc nagcttcntc    240
gcctcanttg actcactgtg ctcggtcgtt ctactgngat ccagncgctc atnaacctna    300
cttnggacgc aggtcat                                                   317
```

<210> SEQ ID NO 281
<211> LENGTH: 174
<212> TYPE: DNA
<213> ORGANISM: Homo sapiens
<220> FEATURE:
<221> NAME/KEY: misc_feature
<222> LOCATION: (1)...(174)
<223> OTHER INFORMATION: n=A,T,C or G

<400> SEQUENCE: 281

```
gnggtcatat tatacatcta aggcatggcc aactccacgc cattatnaat tccatcgtac     60
tgtccgcagt cactacttat aacctagatt aatagtgcct ggccccggac ngtctgtgca    120
atctnccgcc ataccaattn cgatccncan accncgatna cactcctcct tact          174
```

<210> SEQ ID NO 282
<211> LENGTH: 169
<212> TYPE: DNA
<213> ORGANISM: Homo sapiens
<220> FEATURE:
<221> NAME/KEY: misc_feature
<222> LOCATION: (1)...(169)
<223> OTHER INFORMATION: n=A,T,C or G

<400> SEQUENCE: 282

```
atcgcagctt gtacgatcgt catataacgc gcatgtgcgg atcgcttcag cgccgcccga     60
ctgtcagaag gangagatct tttttatcac ttgtttgttt gactatanat aanancgact    120
acagcattga tgtgtgtcct caaganttgt ctgggtctga naaagctga                169
```

<210> SEQ ID NO 283
<211> LENGTH: 157
<212> TYPE: DNA
<213> ORGANISM: Homo sapiens
<220> FEATURE:
<221> NAME/KEY: misc_feature
<222> LOCATION: (1)...(157)
<223> OTHER INFORMATION: n=A,T,C or G

<400> SEQUENCE: 283

```
ggntntctaa gatcgcagtt gtacgatcgt catatnacgc gcatgtgcgn atcgcttcac     60
gtcgccnggc tgtccaggan atgcatntca acataatgtg cactctatat ggttattgat    120
taatacgagn tangagcana tatcngatac aacacaa                             157
```

<210> SEQ ID NO 284
<211> LENGTH: 133
<212> TYPE: DNA
<213> ORGANISM: Homo sapiens
<220> FEATURE:
<221> NAME/KEY: misc_feature
<222> LOCATION: (1)...(133)
<223> OTHER INFORMATION: n=A,T,C or G

<400> SEQUENCE: 284

```
ggngtggtgt nagatacgca ngctgggacg aatcgnntca tagtacggcg catgtgttga     60
```

```
tcaattctga aaatccatcc cggcgcgctc ancatgcact anagggcaat cgcctatatg    120
antcgtatta caa                                                      133

<210> SEQ ID NO 285
<211> LENGTH: 194
<212> TYPE: DNA
<213> ORGANISM: Homo sapiens
<220> FEATURE:
<221> NAME/KEY: misc_feature
<222> LOCATION: (1)...(194)
<223> OTHER INFORMATION: n=A,T,C or G

<400> SEQUENCE: 285
ntntgngtga tgatacccaa gctggntacc nactngantc caattaccgg ctcantntgc    60
tngaaacngc ttcgatngnc tcctggcatg tacttgaaac aggntanata tctaatagnn    120
tacngtgtnn ttttcnatca tacagnttnt atattncact ncctnccatt cntttctant    180
ctctctctcc ntat                                                     194

<210> SEQ ID NO 286
<211> LENGTH: 134
<212> TYPE: DNA
<213> ORGANISM: Homo sapiens
<220> FEATURE:
<221> NAME/KEY: misc_feature
<222> LOCATION: (1)...(134)
<223> OTHER INFORMATION: n=A,T,C or G

<400> SEQUENCE: 286
gagggnntat gataccaagc tggtacganc ccgtcactat nacggcccag tgtgtggatc    60
cgctanctgg tcncgcgatg tctacncaca cgngaactgc ctctcgcnaa gatctcctct    120
cctctccnaa gaga                                                     134

<210> SEQ ID NO 287
<211> LENGTH: 119
<212> TYPE: DNA
<213> ORGANISM: Homo sapiens
<220> FEATURE:
<221> NAME/KEY: misc_feature
<222> LOCATION: (1)...(119)
<223> OTHER INFORMATION: n=A,T,C or G

<400> SEQUENCE: 287
tngggtatat ccagttgtac actggncata tacgcgcatt atgatcgttt cacgcccgga    60
gtacggcatc attacganat ggnctcattc gtttacccttt ntcgctggac acaagcgtc    119

<210> SEQ ID NO 288
<211> LENGTH: 170
<212> TYPE: DNA
<213> ORGANISM: Homo sapiens
<220> FEATURE:
<221> NAME/KEY: misc_feature
<222> LOCATION: (1)...(170)
<223> OTHER INFORMATION: n=A,T,C or G

<400> SEQUENCE: 288
gggntgagat acncaagttg gtacgagtcg gatcatatna cggncgccat tttctggaat    60
ccgcttacgt ggtcccggcg aagtactttt tcatgccttg caaaatngcg ttactgcact    120
ancttgctta acctatgagt ggggtctttc atacccntc tntcatggaa                170

<210> SEQ ID NO 289
<211> LENGTH: 126
```

```
<212> TYPE: DNA
<213> ORGANISM: Homo sapiens
<220> FEATURE:
<221> NAME/KEY: misc_feature
<222> LOCATION: (1)...(126)
<223> OTHER INFORMATION: n=A,T,C or G

<400> SEQUENCE: 289
ggccaattgg ggcctctana tgcntgctcg aacgggcgcc aatttnatgg atatctccaa      60
aattcggctt accntggtcg cggncnaagt acttaactca atccatctnt cactcaggat     120 naatgc                                                                126

<210> SEQ ID NO 290
<211> LENGTH: 126
<212> TYPE: DNA
<213> ORGANISM: Homo sapiens
<220> FEATURE:
<221> NAME/KEY: misc_feature
<222> LOCATION: (1)...(126)
<223> OTHER INFORMATION: n=A,T,C or G

<400> SEQUENCE: 290
ggccaattgg ggcctctana tgcntgctcg aacgggcgcc aatttnatgg atatctccaa      60
aattcggctt accntggtcg cggncnaagt acttaactca atccatctnt cactcaggat     120 naatgc                                                                126

<210> SEQ ID NO 291
<211> LENGTH: 27
<212> TYPE: DNA
<213> ORGANISM: Artificial Sequence
<220> FEATURE:
<223> OTHER INFORMATION: PCR primer

<400> SEQUENCE: 291 cacatgtgcatccaggggagtcagttc                                           27

<210> SEQ ID NO 292
<211> LENGTH: 34
<212> TYPE: DNA
<213> ORGANISM: Artificial Sequence
<220> FEATURE:
<223> OTHER INFORMATION: PCR primer

<400> SEQUENCE: 292 cgttagaattcatcaattcctccgaagctcaaac                                    34

<210> SEQ ID NO 293
<211> LENGTH: 702
<212> TYPE: DNA
<213> ORGANISM: Homo sapiens

<400> SEQUENCE: 293
atgcagcatc accaccatca ccaccacatg tgcatccagg ggagtcagtt caacgtcgag      60
gtcggcagaa gtgacaagct ttccctgcct ggctttgaga acctcacagc aggatataac     120
aaatttctca ggcccaattt tggtggagaa cccgtacaga tagcgctgac tctggacatt     180
gcaagtatct ctagcatttc agagagtaac atggactaca cagccaccat atacctccga     240
cagcgctgga tggaccagcg gctggtgttt gaaggcaaca gagcttcac tctggatgcc      300 cgcctcgtgg agttcctctg ggtgccagat acttacattg tggagtccaa gaagtccttc     360
ctccatgaag tcactgtggg aaacaggctc atccgcctct tctccaatgg cacggtcctg     420
```

```
tatgccctca gaatcacgac aactgttgca tgtaacatgg atctgtctaa atacccatg    480 gacacacaga catgcaagtt gcagctggaa agctggggct atgatggaaa tgatgtggag    540
ttcacctggc tgagagggaa cgactctgtg cgtggactgg aacacctgcg gcttgctcag    600
tacaccatag agcggtattt caccttagtc accagatcgc agcaggagac aggaaattac    660
actagattgg tcttacagtt tgagcttcgg aggaattgat ga                       702
```

<210> SEQ ID NO 294
<211> LENGTH: 232
<212> TYPE: PRT
<213> ORGANISM: Homo sapiens

<400> SEQUENCE: 294

```
Met Gln His His His His His His Met Cys Ile Gln Gly Ser Gln
  1               5                  10                  15

Phe Asn Val Glu Val Gly Arg Ser Asp Lys Leu Ser Leu Pro Gly Phe
             20                  25                  30

Glu Asn Leu Thr Ala Gly Tyr Asn Lys Phe Leu Arg Pro Asn Phe Gly
         35                  40                  45

Gly Glu Pro Val Gln Ile Ala Leu Thr Leu Asp Ile Ala Ser Ile Ser
     50                  55                  60

Ser Ile Ser Glu Ser Asn Met Asp Tyr Thr Ala Thr Ile Tyr Leu Arg
 65                  70                  75                  80

Gln Arg Trp Met Asp Gln Arg Leu Val Phe Glu Gly Asn Lys Ser Phe
                 85                  90                  95

Thr Leu Asp Ala Arg Leu Val Glu Phe Leu Trp Val Pro Asp Thr Tyr
            100                 105                 110

Ile Val Glu Ser Lys Lys Ser Phe Leu His Glu Val Thr Val Gly Asn
        115                 120                 125

Arg Leu Ile Arg Leu Phe Ser Asn Gly Thr Val Leu Tyr Ala Leu Arg
    130                 135                 140

Ile Thr Thr Thr Val Ala Cys Asn Met Asp Leu Ser Lys Tyr Pro Met
145                 150                 155                 160

Asp Thr Gln Thr Cys Lys Leu Gln Leu Glu Ser Trp Gly Tyr Asp Gly
                165                 170                 175

Asn Asp Val Glu Phe Thr Trp Leu Arg Gly Asn Asp Ser Val Arg Gly
            180                 185                 190

Leu Glu His Leu Arg Leu Ala Gln Tyr Thr Ile Glu Arg Tyr Phe Thr
        195                 200                 205

Leu Val Thr Arg Ser Gln Gln Glu Thr Gly Asn Tyr Thr Arg Leu Val
    210                 215                 220

Leu Gln Phe Glu Leu Arg Arg Asn
225                 230
```

<210> SEQ ID NO 295
<211> LENGTH: 204
<212> TYPE: PRT
<213> ORGANISM: Homo sapiens

<400> SEQUENCE: 295

```
Met Val Cys Gly Gly Phe Ala Cys Ser Lys Asn Cys Leu Cys Ala Leu
  1               5                  10                  15

Asn Leu Leu Tyr Thr Leu Val Ser Leu Leu Ile Gly Ile Ala Ala
             20                  25                  30

Trp Gly Ile Gly Phe Gly Leu Ile Ser Ser Leu Arg Val Val Gly Val
         35                  40                  45
```

```
Val Ile Ala Val Gly Ile Phe Leu Phe Leu Ile Ala Leu Val Gly Leu
         50                  55                  60
Ile Gly Ala Val Lys His His Gln Val Leu Leu Phe Phe Tyr Met Ile
 65                  70                  75                  80
Ile Leu Leu Leu Val Phe Ile Val Gln Phe Ser Val Ser Cys Ala Cys
                 85                  90                  95
Leu Ala Leu Asn Gln Glu Gln Gln Gly Gln Leu Leu Glu Val Gly Trp
            100                 105                 110
Asn Asn Thr Ala Ser Ala Arg Asn Asp Ile Gln Arg Asn Leu Asn Cys
            115                 120                 125
Cys Gly Phe Arg Ser Val Asn Pro Asn Asp Thr Cys Leu Ala Ser Cys
        130                 135                 140
Val Lys Ser Asp His Ser Cys Ser Pro Cys Ala Pro Ile Ile Gly Glu
145                 150                 155                 160
Tyr Ala Gly Glu Val Leu Arg Phe Val Gly Gly Ile Gly Leu Phe Phe
                165                 170                 175
Ser Phe Thr Glu Ile Leu Gly Val Trp Leu Thr Tyr Arg Tyr Arg Asn
            180                 185                 190
Gln Lys Asp Pro Arg Ala Asn Pro Ser Ala Phe Leu
            195                 200

<210> SEQ ID NO 296
<211> LENGTH: 615
<212> TYPE: DNA
<213> ORGANISM: Homo sapiens

<400> SEQUENCE: 296
atggtttgcg ggggcttcgc gtgttccaag aactgcctgt gcgccctcaa cctgctttac      60
accttggtta gtctgctgct aattggaatt gctgcgtggg gcattggctt cgggctgatt     120
tccagtctcc gagtggtcgg cgtggtcatt gcagtgggca tcttcttgtt cctgattgct     180
ttagtgggtc tgattggagc tgtaaaacat catcaggtgt tgctatttt ttatatgatt      240 attctgttac ttgtatttat tgttcagttt tctgtatctt gcgcttgttt agccctgaac     300
caggagcaac agggtcagct tctggaggtt ggttggaaca atacggcaag tgctcgaaat     360
gacatccaga gaaatctaaa ctgctgtggg ttccgaagtg ttaacccaaa tgacacctgt     420
ctggctagct gtgttaaaag tgaccactcg tgctcgccat gtgctccaat cataggagaa     480
tatgctggag aggttttgag atttgttggt ggcattggcc tgttcttcag ttttacagag     540
atcctgggtg tttggctgac ctacagatac aggaaccaga agaccccccg cgcgaatcct     600
agtgcattcc tttga                                                      615

<210> SEQ ID NO 297
<211> LENGTH: 1831
<212> TYPE: DNA
<213> ORGANISM: Homo sapiens

<400> SEQUENCE: 297
gccgcgccgc ccgcacgtgg cagccccagg ccccggcccc ccacccacgt ctgcgttgct      60
gccccgcctg ggccaggccc aaaggcaagg acaaagcagc tgtcagggaa cctccgccgg     120
agtcgaattt acgtgcagct gccggcaacc acaggttcca agatggtttg cggggggcttc     180 gcgtgttcca agaactgcct gtgcgccctc aacctgcttt acaccttggt tagtctgctg     240
ctaattggaa ttgctgcgtg gggcattggc ttcgggctga tttccagtct ccgagtggtc     300
```

```
ggcgtggtca ttgcagtggg catcttcttg ttcctgattg ctttagtggg tctgattgga    360
gctgtaaaac atcatcaggt gttgctattt ttttatatga ttattctgtt acttgtattt    420
attgttcagt tttctgtatc ttgcgcttgt ttagccctga accaggagca acagggtcag    480
cttctggagg ttggttggaa caatacggca agtgctcgaa atgacatcca gagaaatcta    540
aactgctgtg ggttccgaag tgttaaccca aatgacacct gtctggctag ctgtgttaaa    600
agtgaccact cgtgctcgcc atgtgctcca atcataggag aatatgctgg agaggttttg    660
agatttgttg gtggcattgg cctgttcttc agttttacag atcctgggt gtttggctg      720 acctacagat acaggaacca gaaagacccc cgcgcgaatc ctagtgcatt cctttgatga    780
gaaaacaagg aagatttcct ttcgtattat gatcttgttc actttctgta attttctgtt    840
aagctccatt tgccagttta aggaaggaaa cactatctgg aaaagtacct tattgatagt    900
ggaattatat attttttactc tatgtttctc tacatgtttt tttctttccg ttgctgaaaa    960
atatttgaaa cttgtggtct ctgaagctcg gtggcacctg gaatttactg tattcattgt   1020
cgggcactgt ccactgtggc ctttcttagc attttttacct gcagaaaaac tttgtatggt   1080
accactgtgt tggttatatg gtgaatctga acgtacatct cactggtata attatatgta   1140
gcactgtgct gtgtagatag ttcctactgg aaaaagagtg gaaatttatt aaaatcagaa   1200
agtatgagat cctgttatgt taagggaaat ccaaattccc aatttttttt ggtcttttta   1260
ggaaagatgt gttgtggtaa aaagtgttag tataaaaatg gataatttac ttgtgtcttt   1320
tatgattaca ccaatgtatt ctagaaatag ttatgtctta ggaaattgtg gtttaatttt   1380
tgacttttac aggtaagtgc aaaggagaag tggtttcatg aaatgttcta atgtataata   1440
acatttacct tcagcctcca tcagaatgga acgagtttg agtaatcagg aagtatatct    1500
atatgatctt gatattgttt tataataatt tgaagtctaa aagactgcat ttttaaacaa   1560
gttagtatta atgcgttggc ccacgtagca aaaagatatt tgattatctt aaaaattgtt   1620
aaataccgtt ttcatgaaag ttctcagtat tgtaacagca acttgtcaaa cctaagcata   1680
tttgaatatg atctcccata atttgaaatt gaaatcgtat tgtgtggctc tgtatattct   1740
gttaaaaaat taaaggacag aaacctttct ttgtgtatgc atgtttgaat taaaagaaag   1800
taatggaaga attgatcgat gaaaaaaaaa a                                  1831
```

<210> SEQ ID NO 298
<211> LENGTH: 25
<212> TYPE: DNA
<213> ORGANISM: Artificial Sequence
<220> FEATURE:
<223> OTHER INFORMATION: PCR primer

<400> SEQUENCE: 298
cactgcgctt gtttagccct gaacc                                           25

<210> SEQ ID NO 299
<211> LENGTH: 33
<212> TYPE: DNA
<213> ORGANISM: Artificial Sequence
<220> FEATURE:
<223> OTHER INFORMATION: PCR primer

<400> SEQUENCE: 299
ccgaagaatt catcaaaatc tcaaaacctc tcc                                  33

<210> SEQ ID NO 300
<211> LENGTH: 258

```
-continued

<212> TYPE: DNA
<213> ORGANISM: Homo sapiens

<400> SEQUENCE: 300
atgcagcatc accaccatca ccaccactgc gcttgtttag ccctgaacca ggagcaacag      60
ggtcagcttc tggaggttgg ttggaacaat acggcaagtg ctcgaaatga catccagaga     120
aatctaaact gctgtgggtt ccgaagtgtt aacccaaatg acacctgtct ggctagctgt     180
gttaaaagtg accactcgtg ctcgccatgt gctccaatca taggagaata tgctggagag     240
gttttgagat tttgatga                                                    258

<210> SEQ ID NO 301
<211> LENGTH: 84
<212> TYPE: PRT
<213> ORGANISM: Homo sapiens

<400> SEQUENCE: 301

Met Gln His His His His His His Cys Ala Cys Leu Ala Leu Asn
                  5                  10                  15

Gln Glu Gln Gln Gly Gln Leu Leu Glu Val Gly Trp Asn Asn Thr Ala
             20                  25                  30

Ser Ala Arg Asn Asp Ile Gln Arg Asn Leu Asn Cys Cys Gly Phe Arg
         35                  40                  45

Ser Val Asn Pro Asn Asp Thr Cys Leu Ala Ser Cys Val Lys Ser Asp
     50                  55                  60

His Ser Cys Ser Pro Cys Ala Pro Ile Ile Gly Glu Tyr Ala Gly Glu
 65                  70                  75                  80

Val Leu Arg Phe
```